US008993536B2

(12) United States Patent
Kakehi et al.

(10) Patent No.: US 8,993,536 B2
(45) Date of Patent: Mar. 31, 2015

(54) LOW-MOLECULAR POLYSULFATED HYALURONIC ACID DERIVATIVE AND MEDICINE CONTAINING SAME

(75) Inventors: Kazuaki Kakehi, Nara (JP); Hiroaki Asai, Tokushima (JP); Naohiro Hayashi, Tokushima (JP); Satoshi Shimizu, Osaka (JP); Fumitaka Goto, Osaka (JP); Yasuo Koga, Osaka (JP); Takahiro Tomoyasu, Osaka (JP); Takao Taki, Osaka (JP); Yusuke Kato, Osaka (JP); Satoru Nakazato, Osaka (JP); Junji Takaba, Osaka (JP); Atsushi Azuma, Osaka (JP); Wakako Hirano, Osaka (JP); Kazunari Izumi, Osaka (JP); Minoru Kashimoto, Osaka (JP); Yoko Sakamoto, Osaka (JP); Takashi Hayashi, Osaka (JP); Masaru Nishida, Osaka (JP)

(73) Assignees: Otsuka Chemical Co., Ltd., Osaka-shi (JP); Otsuka Pharmaceutical Co., Ltd., Chiyoda-ku (JP)

( * ) Notice: Subject to any disclaimer, the term of this patent is extended or adjusted under 35 U.S.C. 154(b) by 469 days.

(21) Appl. No.: 13/143,129

(22) PCT Filed: Feb. 1, 2010

(86) PCT No.: PCT/JP2010/000583

§ 371 (c)(1),
(2), (4) Date: Jul. 1, 2011

(87) PCT Pub. No.: WO2010/087207

PCT Pub. Date: Aug. 5, 2010

(65) Prior Publication Data

US 2011/0281819 A1 Nov. 17, 2011

(30) Foreign Application Priority Data

Feb. 2, 2009 (JP) ................................ 2009-021820

(51) Int. Cl.

| | |
|---|---|
| ***A61K 31/728*** | (2006.01) |
| ***A61P 11/06*** | (2006.01) |
| ***A61P 17/00*** | (2006.01) |
| ***A61P 37/08*** | (2006.01) |
| ***C08B 37/08*** | (2006.01) |

(52) U.S. Cl.

CPC ........... *A61K 31/728* (2013.01); *C08B 37/0072* (2013.01)

USPC ............................................... 514/54; 536/53

(58) Field of Classification Search

USPC ............................................... 514/54; 536/53

See application file for complete search history.

(56) References Cited

U.S. PATENT DOCUMENTS

| | | | | |
|---|---|---|---|---|
| 5,872,109 | A | 2/1999 | Akima et al. | |
| 6,689,748 | B1 | 2/2004 | Theoharides | |
| 2006/0211651 | A1 * | 9/2006 | Miyasaka et al. | 514/54 |
| 2008/0182820 | A1 | 7/2008 | Viskov | |

FOREIGN PATENT DOCUMENTS

| | | | | |
|---|---|---|---|---|
| EP | 0889055 A1 * | 1/1999 | | C08B 37/08 |
| JP | 8 277224 | 10/1996 | | |
| JP | 10 195107 | 7/1998 | | |
| JP | 11 147901 | 6/1999 | | |
| JP | 11 269077 | 10/1999 | | |
| JP | 11 335288 | 12/1999 | | |
| JP | 2006 517185 | 7/2006 | | |
| WO | WO 00/69917 A1 | 11/2000 | | |
| WO | 2004 011662 | 2/2004 | | |

OTHER PUBLICATIONS

The Merck Manual, 1992, pp. 318-319, 326-327 and p. 2409.*

Extended European Search Report issued Aug. 28, 2012, in European Patent Application No. 10735677.6.

Suzuki, A., et al. "Preparation and inhibitory activity on hyaluronidase of fully O-sulfated hyaluro-oligosaccharides." Glycobiology, vol. 11, No. 1. pp. 57-64 (2001).

Takagaki, K., et al. "Domain Structure of Chondroitin Sulfate E Octasaccharides Binding to Type V Collagen." The Journal of Biological Chemistry, vol. 277, No. 11. pp. 8882-8889 (2002).

Jobe, K.L., et al. "Interleukin-12 release from macrophages by hyaluronan, chondroitin sulfate A and chondroitin sulfate C oligosaccharides." Immunology Letters, 89. pp. 99-109 (2003).

International Search Report issued Apr. 20, 2010 in PCT/JP10/00583 filed Feb. 1, 2010.

* cited by examiner

*Primary Examiner* — Ganapathy Krishnan

(74) *Attorney, Agent, or Firm* — Oblon, McClelland, Maier & Neustadt, L.L.P.

(57) ABSTRACT

A low-molecular-weight polysulfated hyaluronic acid derivative useful for treatment of an allergic disease. An agent for treatment of an allergic disease selected from pollinosis, allergic rhinitis, allergic conjunctivitis, atopic dermatitis, and asthma, represented by the following general formula (IA) or (IB);

(IA)

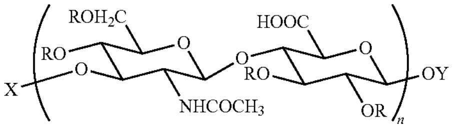

(IB)

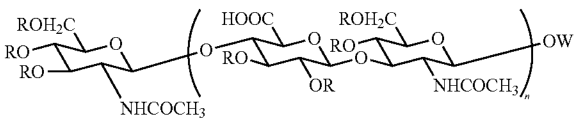

wherein n represents a number of 0 to 15; R's each independently represent a hydrogen atom or an $SO_3H$ group etc.

20 Claims, 103 Drawing Sheets

Ex. 41

Immediate-type nasal airway resistance

Delayed nasal airway resistance

N=3

N=3

LOW-MOLECULAR POLYSULFATED HYALURONIC ACID DERIVATIVE AND MEDICINE CONTAINING SAME

TECHNICAL FIELD

The present invention relates to a low-molecular-weight polysulfated hyaluronic acid derivative (HAPS) useful for prevention and/or treatment of an allergic disease.

BACKGROUND ART

Hyaluronic acid is a linear polymeric polysaccharide in which β-D-N-acetylglucosamine and β-D-glucuronic acid are alternately bonded, is a relatively easily available mucopolysaccharide, and exhibits specific physicochemical properties and physiological properties, and hence, hyaluronic acid itself or various derivatives thereof are used as pharmaceuticals and cosmetics.

It has been known, for example, that polysulfated hyaluronic acid, which is a derivative of hyaluronic acid, has an activity of inhibiting a kallikrein-kinin system (Patent Document 1) and an activity of inhibiting phospholipase A2 (Patent Document 2), can be used as a therapeutic agent for an allergic disease (Patent Document 3), and exhibits a strong anti-inflammatory action to inflammation mediated by selectin, which is one of the adhesion molecules (Patent Document 4).

In addition, it has been reported that polysulfated oligohyaluronates having a low molecular weight such as a viscosity-average molecular weight of 10,000 or less can be used as an active ingredient for cosmetics having excellent skin permeability (Patent Document 5), and polysulfated hyaluronan oligosaccharides ranging from a tetrasaccharide to an eicosasaccharide have an anti-coagulant activity and an anti-hyaluronidase activity, and can be used as an anti-cancer agent (Non-Patent Document 1).

Patent Documents

[Patent Document 1] JP-A-1999-147901

[Patent Document 2] JP-A-1999-269077

[Patent Document 3] JP-A-1999-335288

[Patent Document 4] JP-A-1996-277224

[Patent Document 5] JP-A-1998-195107

Non-Patent Documents

[Non-Patent Document 1] Glycobiology, vol. 11, No. 1, pp. 57-64, 2001

SUMMARY OF THE INVENTION

However, the above-mentioned polysulfated hyaluronic acid and polysulfated hyaluronan oligomer themselves have a stimulating action such as a vascular permeability increasing activity, and hence, some of them are not suitable for clinical applications. The fact is that a few of them meet all requirements such as a pharmacological activity and safety.

The present invention relates to the provision of a low-molecular-weight hyaluronic acid derivative free of such problems and useful for the prevention and/or treatment of an allergic disease.

The inventors of the present invention have intensively studied to develop a compound useful for prevention and/or treatment of an allergic disease, and as a result, the inventors have found that low-molecular-weight polysulfated hyaluronic acid derivatives represented by the following general formulae (IA) and (IB) has an anti-allergy action and an anti-inflammatory action and does not have a vascular permeability increasing activity, and hence is useful as a pharmaceutical.

That is, the present invention relates to the following items (1) to (15):

(1) an agent for prevention and/or treatment of an allergic disease selected from pollinosis, allergic rhinitis, allergic conjunctivitis, atopic dermatitis, and asthma, containing a low-molecular-weight polysulfated hyaluronic acid derivative represented by the following general formula (IA) or (IB), or a pharmaceutically acceptable salt thereof as an active ingredient:

(IA)

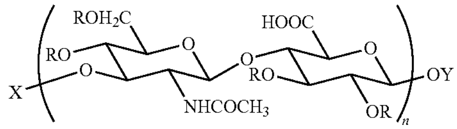

wherein n represents a number of 0 to 15; X represents the following formula (a) or (b);

(a)

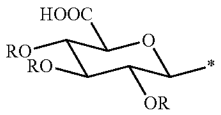

(b)

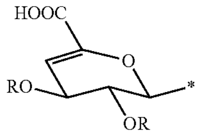

Y represents the following formula (c), (d) or (e);

(c)

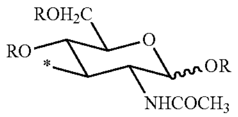

(d)

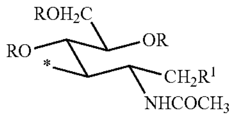

(e)

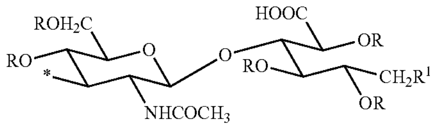

R's each independently represent a hydrogen atom or an $SO_3H$ group (provided that $SO_3H$ groups account for 80 to 100% of the total number of R's); $R^1$ represents —OH, —$OSO_3H$, or —$NZ_1Z_2$ (wherein $Z_1$ and $Z_2$ each independently represent a hydrogen atom, —$SO_3H$, an optionally substituted lower alkyl group, an optionally substituted aryl group, an optionally substituted aralkyl group, or an optionally substituted heteroaryl group, or —$NZ_1Z_2$ collectively represents an amino acid residue or a peptide residue); and *'s each represent a bonding site with an oxygen atom);

(IB)

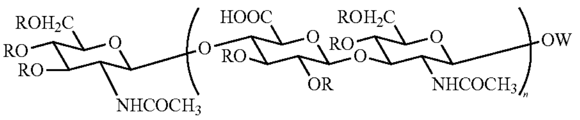

wherein n represents a number of 0 to 15; W represents the following formula (f) or (g);

(f)

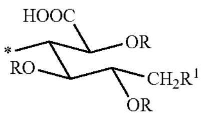

(g)

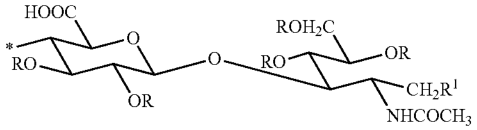

R's each independently represent a hydrogen atom or an $SO_3H$ group (provided that $SO_3H$ groups account for 80 to 100% of the total number of R's); $R^1$ represents —OH, —$OSO_3H$, or —$NZ_1Z_2$ (wherein $Z_1$ and $Z_2$ each independently represent a hydrogen atom, —$SO_3H$, an optionally substituted lower alkyl group, an optionally substituted aryl group, an optionally substituted aralkyl group, or an optionally substituted heteroaryl group, or —$NZ_1Z_2$ collectively represents an amino acid residue or a peptide residue); and *'s each represent a bonding site with an oxygen atom).

(2) the agent for prevention and/or treatment according to the above item (1), wherein Y in the general formula (IA) represents the formula (d) or (e);

(3) the agent for prevention and/or treatment according to the above item (2), wherein X represents the formula (a);

(4) the agent for prevention and/or treatment according to the above item (3), wherein n represents 3, 4, or 5;

(5) the agent for prevention and/or treatment according to the above item (3), wherein n represents 4 or 5;

(6) the agent for prevention and/or treatment according to the above item (1), wherein the low-molecular-weight polysulfated hyaluronic acid derivative is represented by the general formula (IB);

(7) the agent for prevention and/or treatment according to the above item (6), wherein n represents 3, 4, or 5;

(8) the agent for prevention and/or treatment according to the above item (6), wherein n represents 4 or 5;

(9) use of the low-molecular-weight polysulfated hyaluronic acid derivative or the pharmaceutically acceptable salt thereof according to any one of the above items (1) to (8) for producing an agent for prevention and/or treatment of an allergic disease selected from pollinosis, allergic rhinitis, allergic conjunctivitis, atopic dermatitis, and asthma;

(10) a method for prevention and/or treatment of an allergic disease selected from pollinosis, allergic rhinitis, allergic conjunctivitis, atopic dermatitis, and asthma, the method including administering, to a human or an animal, an effective dose of the low-molecular-weight polysulfated hyaluronic acid derivative or the pharmaceutically acceptable salt thereof according to any one of the above items (1) to (8);

(11) a low-molecular-weight polysulfated hyaluronic acid derivative represented by the following general formula (IA') or (IB), or a pharmaceutically acceptable salt thereof:

(IA')

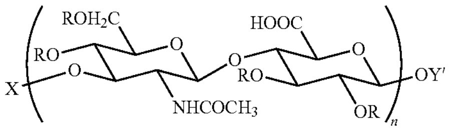

wherein n represents a number of 0 to 15; X represents the following formula (a) or (b);

(a)

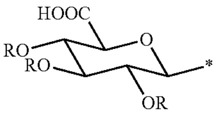

(b)

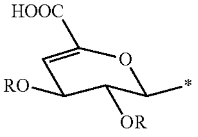

Y' represents the following formula (d) or (e);

(d)

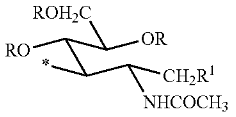

(e)

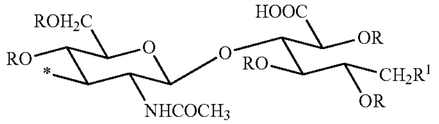

R's each independently represent a hydrogen atom or an $SO_3H$ group (provided that $SO_3H$ groups account for 80 to 100% of the total number of R's); $R^1$ represents —OH, —$OSO_3H$, or —$NZ_1Z_2$ (wherein $Z_1$ and $Z_2$ each independently represent a hydrogen atom, —$SO_3H$, an optionally substituted lower alkyl group, an optionally substituted aryl group, an optionally substituted aralkyl group, or an optionally substituted heteroaryl group, or —$NZ_1Z_2$ collectively represents an amino acid residue or a peptide residue); and *s each represent a bonding site with an oxygen atom;

(IB)

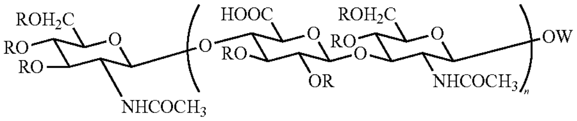

wherein n represents a number of 0 to 15; W represents the following formula (f) or (g);

(f)

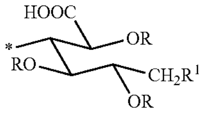

(g)

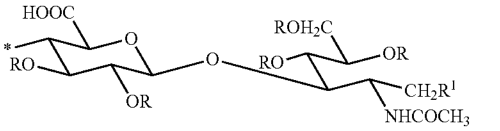

R's each independently represent a hydrogen atom or an $SO_3H$ group (provided that $SO_3H$ groups account for 80 to 100% of the total number of R's); $R^1$ represents —OH, —$OSO_3H$, or —$NZ_1Z_2$ (wherein $Z_1$ and $Z_2$ each independently represent a hydrogen atom, —$SO_3H$, an optionally substituted lower alkyl group, an optionally substituted aryl group, an optionally substituted aralkyl group, or an optionally substituted heteroaryl group, or —$NZ_1Z_2$ collectively represents an amino acid residue or a peptide residue); and *'s each represent a bonding site with an oxygen atom);

(12) the low-molecular-weight polysulfated hyaluronic acid derivative or pharmaceutically acceptable salt thereof according to the above item (11), wherein X in the general formula (IA') represents the formula (a);

(13) the low-molecular-weight polysulfated hyaluronic acid derivative or pharmaceutically acceptable salt thereof according to the above item (11), which is represented by the general formula (IB);

(14) the low-molecular-weight polysulfated hyaluronic acid derivative or pharmaceutically acceptable salt thereof according to the above item (12) or (13), wherein n represents 3, 4, or 5; and

(15) a pharmaceutical composition containing the low-molecular-weight polysulfated hyaluronic acid derivative or the pharmaceutically acceptable salt thereof according to the above item (11), (12), (13), or (14) and a pharmaceutically acceptable excipient.

EFFECTS OF THE INVENTION

The low-molecular-weight polysulfated hyaluronic acid derivative or the pharmaceutically acceptable salt thereof of the present invention has an excellent anti-allergy action and an excellent anti-inflammatory action and does not have a vascular permeability increasing activity, and hence can be used as an agent for prevention and/or treatment of allergic diseases such as pollinosis, allergic rhinitis, allergic conjunctivitis, atopic dermatitis, and asthma, the agent exerting a few side effects and being excellent in safety. In addition, of the low-molecular-weight polysulfated hyaluronic acid derivatives or the pharmaceutically acceptable salts thereof of the present invention, in particular, a compound group represented by the general formula (IA) wherein Y represents the formula (d) or (e) and a compound group represented by the general formula (IB) have advantages that the compounds of the groups are highly stable in aqueous solutions, and hence, easily formed into preparations.

DETAILED DESCRIPTION OF THE INVENTION

Figure 1:
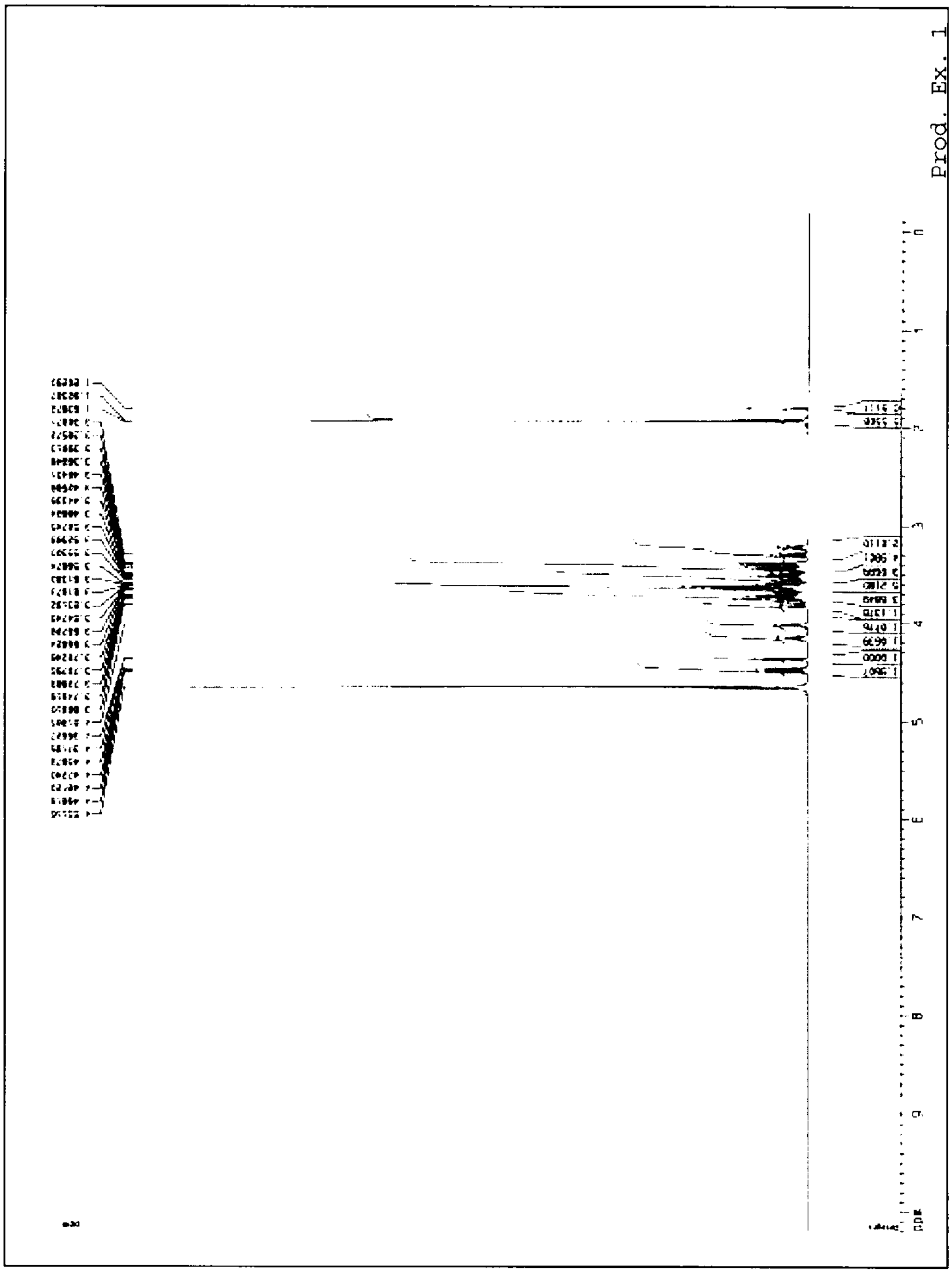
FIG. 1 is a $^1$H-NMR chart of a compound obtained in Production Example 1.

The low-molecular-weight polysulfated hyaluronic acid derivative of the present invention is a derivative in which all hydroxyl groups in a hyaluronan oligomer are excessively sulfated, and the degree of its sulfation (or degree of its substitution) is, for example, $SO_3H$ groups accounting for 80 to 100% of the total number (in the while oligomer) of R's in the general formulae (IA) and (IB), and the $SO_3H$ groups preferably account for 90 to 100%. $SO_3H$ groups in the oligomer may be unevenly distributed, however in general, the oligomer in which $SO_3H$ groups are evenly distributed in its whole molecule is preferred from the viewpoints of its preparation and use.

A compound represented by the general formula (IA) wherein Y represents the formula (d) or (e) (i.e., a compound represented by the general formula (IA')), and a compound represented by the general formula (IB) are novel compounds that have not been disclosed in any document.

Examples of the "lower alkyl" of the optionally substituted lower alkyl group, the optionally substituted aryl group, the optionally substituted aralkyl group, and the optionally substituted heteroaryl group represented by $Z_1$ and $Z_2$ in the above general formulae (IA) and (IB) include linear or branched alkyl groups having 1 to 6 carbon atoms (hereinafter, abbreviated as "$C_{1-6}$") such as methyl, ethyl, n-propyl, isopropyl, n-butyl, isobutyl, sec-butyl, tert-butyl, n-pentyl, and n-hexyl groups. Among these, a $C_{1-4}$ alkyl group is preferable, methyl, ethyl, n-propyl, isopropyl, n-butyl, isobutyl, sec-butyl, and tert-butyl groups are more preferable, and methyl and ethyl groups are even more preferable.

Examples of the "aryl group" include $C_{6-14}$, monocyclic to tricyclic, aromatic hydrocarbon ring groups such as phenyl, naphthyl, and anthracenyl groups. Among these, a phenyl group is preferable.

Examples of the "heteroaryl group" include saturated or unsaturated, monocyclic or polycyclic heterocyclic groups having at least one hetero atom selected from a nitrogen atom, a sulfur atom, and an oxygen atom.

Specific examples of the group include:

3- to 6-membered, unsaturated, monocyclic heterocyclic groups having 1 to 4 nitrogen atoms such as pyrrolyl, pyrrorynyl, imidazolyl, pyrazolyl, pyridyl, pyrimidinyl, pyrazinyl, pyridazinyl, triazolyl, tetrazolyl, and tetrahydropyridyl groups;

3- to 7-membered, saturated, monocyclic heterocyclic groups having 1 to 4 nitrogen atoms such as pyrrolidinyl, imidazolizinyl, piperidyl, piperadinyl, and homopiperidyl groups;

unsaturated, fused heterocyclic groups having 1 to 5 nitrogen atoms such as indolyl, isoindolyl, isoindolinyl, benzimidazolyl, quinolyl, isoquinolyl, imidazopyridyl, indazolyl, benzotriazolyl, tetrazolopyrizinyl, quinoxalinyl, pyridine tetrahydropyridyl, tetrahydroisoquinolyl, indolinyl, and dihydropyrolopyridyl groups;

saturated, fused heterocyclic groups having 1 to 5 nitrogen atoms such as pyrrolidinopiperazinyl, quinuclidinyl, and pyrrolidinopiperidyl groups;

3- to 6-membered, unsaturated monocyclic heterocyclic groups having an oxygen atom such as pyranyl and furyl group;

3- to 6-membered, saturated monocyclic heterocyclic groups having an oxygen atom such as 1H-tetrahydropyranyl and tetrahydrofuranyl groups;

3- to 6-membered, unsaturated monocyclic heterocyclic groups having one or two sulfur atoms such as a thienyl group;

3- to 6-membered, unsaturated monocyclic heterocyclic groups having one or two oxygen atoms and one to three nitrogen atoms such as oxazolyl, isooxazolyl, oxadiazolyl, and oxadilinyl groups;

3- to 6-membered, saturated monocyclic heterocyclic groups having one or two oxygen atoms and one to three nitrogen atoms such as a morpholinyl group;

saturated, fused heterocyclic groups having one or two oxygen atoms and one to three nitrogen atoms such as benzofurazanyl, benzoxazolyl, and benzoxadiazolyl groups;

3- to 6-membered, unsaturated monocyclic heterocyclic groups having one or two sulfur atoms and one to three nitrogen atoms such as thiazolyl and thiadiazolyl groups;

3- to 6-membered, saturated monocyclic heterocyclic groups having one or two sulfur atoms and one to three nitrogen atoms such as a thiazolizinyl group;

unsaturated, fusedheterocyclic groups having one or two sulfur atoms and one to three nitrogen atoms such as benzothiazolyl, benzothiazolyl, and thiazolotetrahydropyridyl groups; and unsaturated, fused heterocyclic groups having one or two oxygen atoms such as benzofuranyl, benzodioxolyl, and chromanyl groups.

The above-mentioned "lower alkyl group" may be substituted by, for example, a halogen atom, a carboxy group, an aryl group, a lower alkoxyl group, or an acyl group, and the above-mentioned "aryl group" and "heteroaryl group" may each be substituted by, for example, a halogen atom, a carboxy group, a lower alkyl group, a lower alkoxyl group, or an acyl group.

In this case, examples of the aryl group include phenyl and naphthyl groups, and examples of the lower alkyl group include the above-mentioned $C_{1-6}$ alkyl groups.

Further, examples of the halogen atom include fluorine, chlorine, bromine, and iodine.

Further, examples of the lower alkoxyl group include linear or branched $C_{1-6}$ alkoxyl groups such as methoxy, ethoxy, n-propoxy, isopropoxy, n-butoxy, isobutoxy, sec-butoxy, tert-butoxy, n-pentoxy, and n-hexoxy. Among these, a $C_{1-4}$ alkoxyl group is preferable, methoxy, ethoxy, n-propoxy, isopropoxy, n-butoxy, isobutoxy, sec-butoxy, and tert-butoxy groups are more preferable, and methoxy and ethoxy groups are even more preferable.

Examples of the acyl group include CHO, $C_{1-6}$ alkyl-carbonyl, $C_{1-6}$ alkoxy-carbonyl, aryl carbonyl, aryl-$C_{1-6}$ alkylene-carbonyl, heteroaryl carbonyl, and heteroaryl-$C_{1-6}$ alkylene-carbonyl groups.

In this case, examples of the $C_{1-6}$ alkyl, $C_{1-6}$ alkoxy, aryl, and heteroaryl groups are the same as those described above. Further, examples of the $C_{1-6}$ alkylene groups include linear or branched $C_{1-6}$ alkylene groups such as methylene, ethylene, trimethylene, tetramethylene, pentamethylene, hexamethylene, propylene, methylmethylene, ethylethylene, 1,2-dimethylethylene, and 1,1,2,2-tetramethylethylene groups. Among these, methylene, ethylene, and trimethylene groups are preferable.

Further, examples of the "aralkyl group" include aryl-$C_{1-6}$ alkyl groups. In this case, examples of the aryl and $C_{1-6}$ alkyl groups are the same as those described above. However, suitable aralkyl groups are, for example, benzyl and phenethyl groups.

The aralkyl group may be substituted by, for example, anyone of the exemplary groups by which the above-mentioned aryl group and lower alkyl group may be substituted.

The "optionally substituted lower alkyl group" which is represented by each of $Z_1$ and $Z_2$ is preferably, for example, a trifluoromethyl, benzyl, 2-, 3-, or 4-methylbenzyl, 2-, 3-, or 4-methoxybenzyl, methoxymethyl, or methoxycarbonylmethyl group, the "optionally substituted aryl group" which is represented by each of $Z_1$ and $Z_2$ is preferably, for example, a 2-, 3-, or 4-methylphenyl, 2-, 3-, or 4-methoxyphenyl, 2-, 3-, or 4-fluorophenyl, 2-, 3-, or 4-trifluoromethyl, or 2-, 3-, or 4-carboxyphenyl group, the "optionally substituted aralkyl group" which is represented by each of $Z_1$ and $Z_2$ is preferably, for example, a benzyl, 2-, 3-, or 4-methylbenzyl, or 2-, 3-, or 4-methoxybenzyl group, and the "optionally substituted heteroaryl group" which is represented by each of $Z_1$ and $Z_2$ is preferably, for example, a 2-, 3-, or 4-methylpyridyl, 2-, 3-, or 4-methoxypyridyl, 2-, 3-, or 4-fluoropyridyl, 2-, 3-, or 4-trifluoropyridyl, or 2-, 3-, or 4-carboxypyridyl group.

Examples of an amino acid residue or a peptide residue when $—NZ_1Z_2$ collectively represents the amino acid residue or the peptide residue include: amino acid residues such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, β-alanine, sarcosine, phenylglycine, N-ethylglycine, N-n-propylglycine, N-isopropylglycine, N-n-butylglycine, N-tert-butylglycine, N-n-pentylglycine, and N-n-hexylglycine; and peptide residues such as sarcosylglycine, glycylglycine, glycylsarcosine, sarcosylsarcosine, alanylglycine, β-alanylphenylalanine, glycylphenylalanine, phenylalanylglycine, phenylalanylphenylalanine, glycylglycylglycine, N-ethylglycylglycine, N-n-

Reaction-1 below. The above-mentioned suitable salts may be used as material compounds and target compounds.

Further, in the following formulae, substituents represented by $Z_3$ and $Z_4$ correspond to $Z_1$ and $Z_2$, respectively, and the meanings of the respective substituents are as described above.

[Reaction-1]

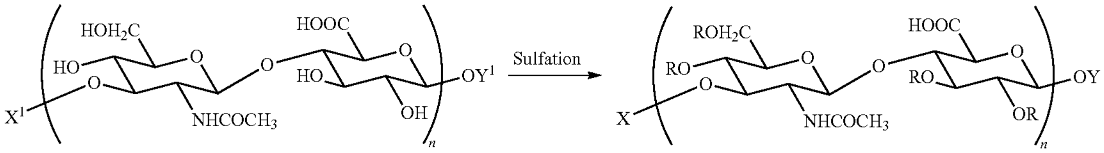

(IIA) (IA)

or

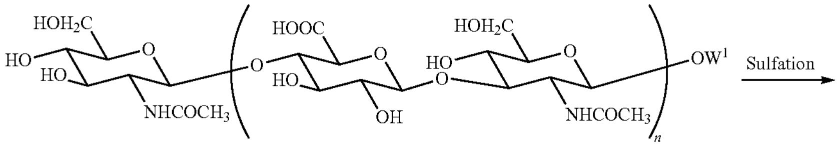

(IIB)

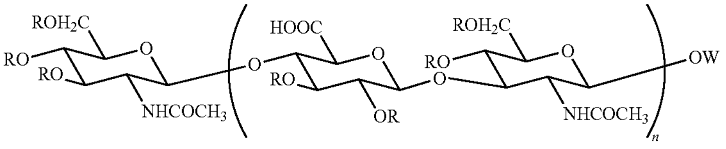

(IB)

propylglycylglycine, sarcosylglycylglycine, N-ethylglycylglycylglycine, and phenylalanylglycylglycine. The amino acid residue or the peptide residue may be amidated at its terminal carboxyl group.

In the compounds represented by the general formulae (IA) or (IB), n represents a number of 0 to 15, preferably 3 to 9, more preferably 3, 4, or 5, or even more preferably 4 or 5.

The compounds represented by the above general formulae (IA) or (IB) includes various stereoisomers, optical isomers, and solvates such as a hydrate.

Further, a suitable salt of the low-molecular-weight polysulfated hyaluronic acid derivative of the present invention is a pharmaceutically acceptable salt. Examples of the salt include: metal salts including alkali metal salts (such as a sodium salt and potassium salt) and alkali earth metal salts (such as a magnesium salt and calcium salt); salts with inorganic bases such as an ammonium salt, and hydroxides, carbonates, or hydrogen carbonates of alkali metals (such as sodium and potassium) and alkali earth metals (such as magnesium and calcium); and salts with organic bases such as organic amines (such as trimethylamine and triethylamine), pyridine, quinoline, piperidine, imidazole, picoline, dimethylaminopyridine, dimethylaniline, and N-methylmorpholine.

The low-molecular-weight polysulfated hyaluronic acid derivative or the pharmaceutically acceptable salt thereof of the present invention preferably has an average molecular weight of 1,500 to 13,500, though the average molecular weight varies depending on the kind of salts.

A compound represented by the general formula (IA) or (IB) of the present invention can be produced by, for example, sulfating a low-molecular-weight hyaluronic acid derivative represented by the general formula (IIA) or (IIB) as shown in

[In the formulae, $X^1$ represents the following ($a^1$) or ($b^1$);

($a^1$)

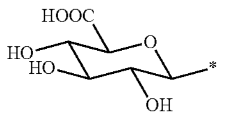

($b^1$)

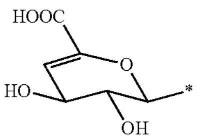

$Y^1$ represents the following ($c^1$), ($d^1$) or ($e^1$);

($c^1$)

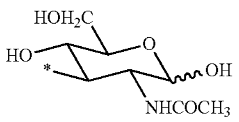

($d^1$)

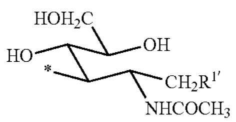

($e^1$)

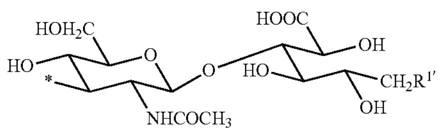

$W^1$ represents the following ($f^1$) or ($g^1$);

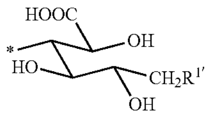

($f^1$)

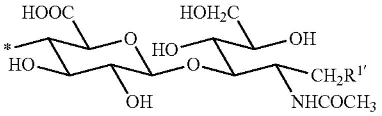

($g^1$)

$R^{1'}$ represents —OH or —$NZ_3Z_4$ (wherein $Z_3$ and $Z_4$ each independently represent a hydrogen atom, an optionally substituted lower alkyl group, an optionally substituted aryl group, an optionally substituted aralkyl group, or an optionally substituted heteroaryl group, or —$NZ_3Z_4$ collectively represents an amino acid residue or a peptide residue); and n, X, Y, W, R, and * are each the same as described above.]

The reaction can be performed by a known sulfation reaction, for example, dissolving a compound (IIA) or (IIB) and a sulfating agent in an appropriate solvent and allowing them to react under heating.

Examples of the solvent used in the subject invention include: N,N-dimethylformamide, dimethyl sulfoxide, N-methylpyrrolidone, N,N-dimethylacetamide, 1,1,3,3-tetramethylurea, pyridine, and N,N-dimethylacrylamide; ionic liquids such as 1-ethyl-3-methylimidazolium hexaflurophosphate, 1-butyl-1-methylpyrrolidinium tetrafluoroborate, and 1-butylpyridinium chloride; and mixed solvents thereof.

The sulfating agent is not particularly limited, and preferably used are complexes of sulfuric anhydride with pyridine, picoline, 2,6-lutidine, trimethylamine, triethylamine, N,N-dimethylformamide, dioxane, and the like, or sulfuric acid-dicyclohexylcarbodiimide, chlorosulfone, and the like. In general, the sulfating agent is preferably used in 1 to 100 equivalents with respect to the amount of the compound (IIA) or (IIB). Further, an acid catalyst, such as trifluoroacetic acid, trifluoromethanesulfonic acid, or the like may be added to the reaction system.

The reaction temperature and the reaction time are not particularly limited, and for example, are from 0 to 120° C. and from 30 minutes to 20 days, respectively.

A compound represented by the general formula (IIA) wherein $Y^1$ represents the formula ($d^1$) or ($e^1$) and $R^{1'}$ represents —OH, or a compound represented by the general formula (IIB) where $R^{1'}$ represents —OH can be prepared by a reduction shown in below Reaction-2. The starting compounds and target compounds may be the above-mentioned suitable salts.

[Reaction-2]

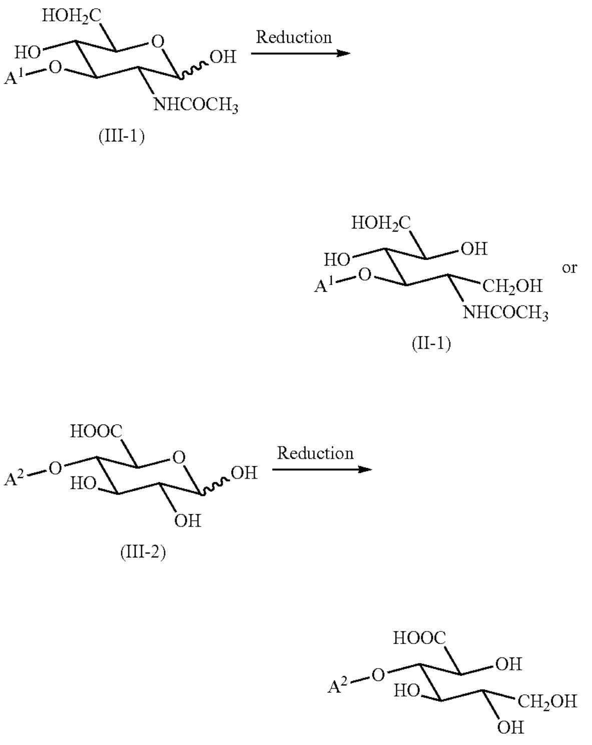

(III-1)

(II-1)

or (III-2)

(II-2)

[In the formulae, $A^1$ represents the following (h) or (i);

(h)

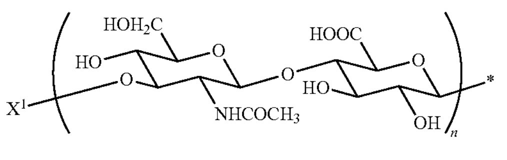

(i)

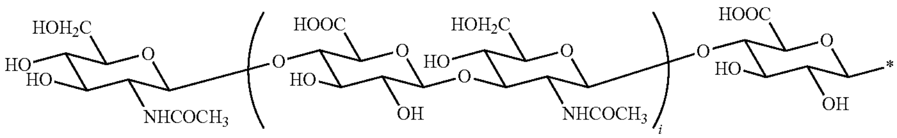

$A^2$ represents the following (j) or (k); and

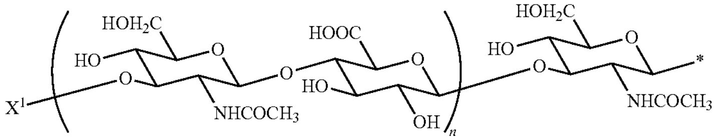

(j)

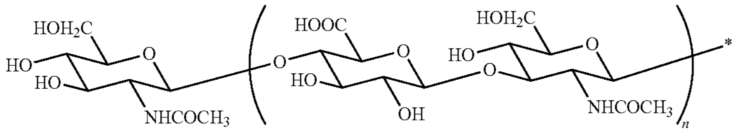

(k)

n, $X^1$, and * are each the same as described above.]

That is, the compound (II-1) or (II-2) can be prepared by subjecting a compound (III-1) or (III-2) to, for example, a reduction in an appropriate solvent in the presence of a reducing agent.

Examples of the solvent to be used in the reaction include: water; lower alcohols such as methanol, ethanol, isopropanol, butanol, tert-butanol, and ethylene glycol; acetonitrile; fatty acids such as formic acid and acetic acid; ethers such as diethyl ether, tetrahydrofuran, dioxane, monoglyme, and diglyme; aromatic hydrocarbons such as benzene, toluene, and xylene; halogenated hydrocarbons such as dichloromethane, dichloroethane, chloroform, and carbon tetrachloride; N,N-dimethylformamide; and mixed solvents thereof.

Examples of the reducing agent include sodium borohydride, lithium borohydride, potassium borohydride, tetrabutylammonium borohydride, zinc borohydride, lithium tri(sec-butyl)borohydride, borane analogs, diisobutyl aluminum hydride, and lithium aluminum hydride.

The reducing agent is generally used in an amount of about 0.1- to 60-fold per mole of the compound (III-1) or (III-2).

Zinc chloride, cobalt(II) chloride, samarium(III) chloride, cerium(III) chloride, titanium(III) chloride, iron(II) chloride, iron(III) chloride, nickel(II) chloride, or the like may be added to the reaction system in the presence of an amine such as pyridine, trimethylamine, triethylamine, or N-ethyldiisopropylamine, an inorganic base such as sodium hydroxide, and/or a ligand such as dimethyl glyoxime, 2,2'-bipyridyl, or 1,10-phenanthrolin.

The reduction may also be carried out by catalytic hydrogenation in the presence of a transition metal catalyst such as palladium or platinum.

The reaction can be performed usually at about −80 to 100° C., preferably at about −80 to 70° C., and in general, the reaction is completed in about 30 minutes to 60 hours.

A compound represented by the general formula (IIA) where $Y^1$ represents the formula ($d^1$) or ($e^1$) and $R^{1'}$ represents —$NZ_3Z_4$ or a compound represented by the general formula (IIB) where $R^{1'}$ represents —$NZ_3Z_4$ can be produced by a reductive amination reaction shown in below Reaction-3. The starting compounds and target compounds may be the above-mentioned suitable salts.

[Reaction-3]

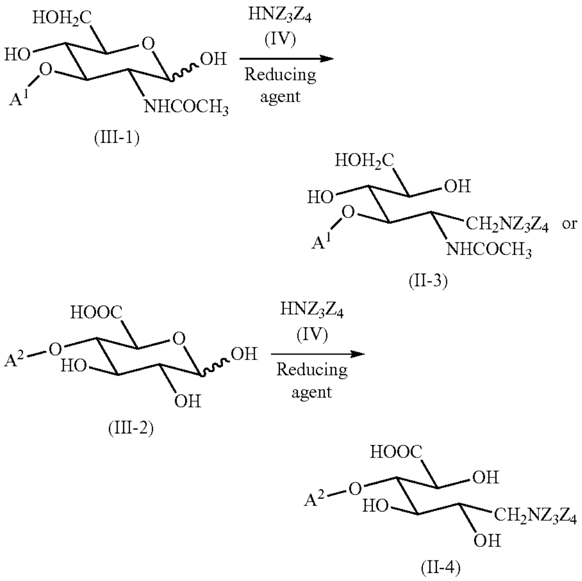

(III-1) (II-3) or (III-2) (II-4)

[In the formulae, $A^1$, $A^2$, $Z_3$, and $Z_4$ are each the same as described above.]

The reaction is, for example, what is called a reductive amination reaction in which a compound (III-1) or (III-2) is allowed to react with an amine (IV) in an appropriate solvent in the presence of a reducing agent to form a Schiff base, followed by reduction.

The amine (IV) is usually used in about 1- to 5-fold per mole of the compound (III-1) or (III-2).

Examples of the solvent to be used in the reaction include: water; lower alcohols such as methanol, ethanol, isopropanol, butanol, tert-butanol, and ethylene glycol; acetonitrile; fatty acids such as formic acid and acetic acid; ethers such as diethyl ether, tetrahydrofuran, dioxane, monoglyme, and diglyme; aromatic hydrocarbons such as benzene, toluene, and xylene; halogenated hydrocarbons such as dichloromethane, dichloroethane, chloroform, and carbon tetrachloride; N,N-dimethylformamide; and mixed solvents thereof.

Examples of the reducing agent to be used in the reaction include sodium borohydride, lithium borohydride, potassium borohydride, tetrabutylammonium borohydride, sodium cyanotrihydridoborate, and sodium triacetoxyhydroborate. The reducing agent is usually used in about 0.1- to 60-fold per mole of the compound (III).

The reaction may be performed usually at about −80 to 100° C., preferably at about −80 to 70° C., and in general, the reaction is completed in about 30 minutes to 60 hours.

The reaction may be performed in the presence of organic acids or salts thereof in 1- to 50-fold per mole as required. Examples of the organic acids or the salts thereof include acetic acid, trifluoroacetic acid, and alkali metal salts of these acids (such as sodium acetate).

Zinc chloride, cobalt(II) chloride, samarium(III) chloride, cerium(III) chloride, titanium(III) chloride, iron(II) chloride, iron (III) chloride, or nickel (II) chloride may be added to the system in the presence of an amine such as pyridine, trimethylamine, triethylamine, or N-ethyldiisopropylamine, an inorganic base such as sodium hydroxide, and/or a ligand such as dimethyl glyoxime, 2,2'-bipyridyl, or 1,10-phenanthrolin.

[Reaction-5]

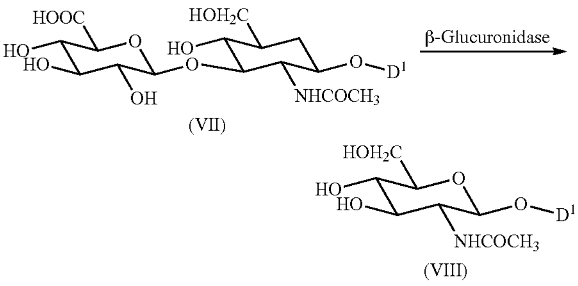

(VII)

(VIII)

[In the formulae, $D^1$ represents the following (r) or (s), and

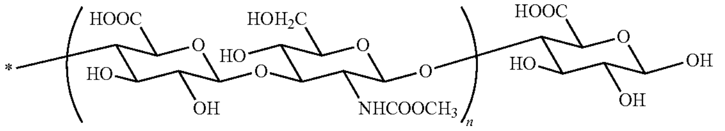

(r)

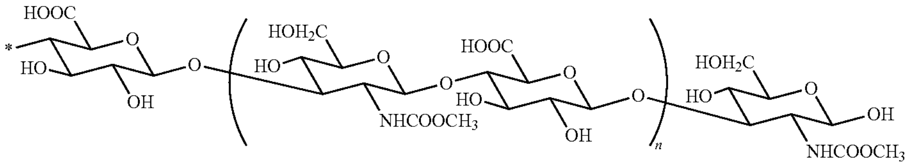

(s)

n and * are each the same as described above.]

The reaction is an elimination reaction of glucuronic acid using β-glucuronidase.

The compound (VIII) can be prepared by stirring the compound (VII) under presence of β-glucuronidase in an appropriate buffer.

The reaction can be performed usually at room temperature to 60° C., preferably at about 30 to 40° C., and in general, the reaction is completed in about 30 minutes to 60 hours.

Each of the target compounds obtained in the above-mentioned reaction formulae can be purified by purification methods commonly used for various modified saccharides. Specific purification methods include desalting using gel filtration, neutralization, and dialysis, a collecting operation using a precipitating operation by addition of an organic solvent, and a collecting operation by freeze-drying.

The compound of the present invention, as shown in the examples described below, shows an anti-allergy action and an anti-inflammatory action, and does not show any vascular permeability increasing activity, and hence is useful in pharmaceuticals for prevention and/or treatment of allergic diseases such as pollinosis, allergic rhinitis, allergic conjunctivitis, atopic dermatitis, and asthma.

Those pharmaceuticals are formed as a general form of medical formulation using the compound of the present invention into, and are prepared by using a diluting agent such as a filler, an expander, a binder, a humectant, a disintegrant, a surfactant, or a lubricant, or an excipient.

Those pharmaceuticals can be selected from various forms depending on the therapeutic purposes, and typical examples of the pharmaceuticals include a tablet, a pill, a powder, a liquid, a suspension, an emulsion, a granule, a capsule, a suppository, an injection (liquid, suspension, and the like), an eye-drop, an ointment, and an inhalant.

Further, an appropriate amount of boric acid may be added to the reaction system.

Transformation between compounds having even numbered sugars and compounds having odd numbered sugars can be performed through the following Reaction-4 or Reaction-5 in order to prepare a compound in which one constitutional sugars is subtracted from a starting compound.

[Reaction-4]

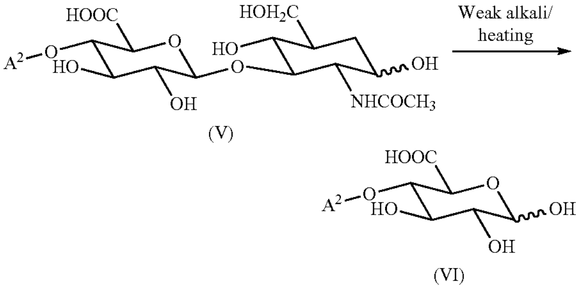

(V)

(VI)

[In the formulae, $A^2$ is the same as described above.]

The reaction is an elimination reaction from N-acetylglucosamine with a weak alkali treatment under heating.

The compound (VI) can be prepared by stirring the compound (V) under heating in a borate buffer having a pH of 9.18, following the method of Reissig et al. (Reissig. J. L., et al., J. Biol. Chem., 217, 959 (1955)).

The reaction can be performed usually at about 50 to 120° C., preferably at about 70 to 90° C., and in general, the reaction is completed in about 30 minutes to 60 hours.

Any known carrier may be used when forming a tablet. Examples thereof include: excipients such as lactose, sucrose, sodium chloride, glucose, urea, starch, calcium carbonate, kaolin, and crystalline cellulose; binders such as water, ethanol, propanol, single syrup, a glucose liquid, a starch liquid, a gelatin solution, carboxymethylcellulose, shellac, methylcellulose, potassium phosphate, and polyvinyl pyrrolidone; disintegrants such as dry starch, a polyoxyethylene sorbitan fatty acid ester, sodium lauryl sulfate, stearic acid monoglyceride, starch, and lactose; disintegration suppressants such as sucrose, stearin, cacao butter, and a hydrogenated oil; absorbefacients such as a quaternary ammonium base and sodium lauryl sulfate; humectants such as glycerin and starch; adsorbents such as starch, lactose, kaolin, bentonite, and colloidal silicic acid; and lubricants such as purified talc, a stearate, powdered boric acid, and polyethylene glycol.

Further, the tablet can be, as required, prepared as a coated tablet. Examples thereof include sugar coated agents, gelatin encapsulated tablets, enteric-coated tablets, and film coated tablets, or double layered tablets and multi-layered tablets.

Any known carrier may be used when forming a pill. Examples thereof include: excipients such as glucose, lactose, starch, a cacao oil, a hardened vegetable oil, kaolin, and talc; binders such as powdered acacia, powdered tragacanth, gelatin, and ethanol; and disintegrants such as laminaran and agar.

Any known carrier may be used when forming a suppository. Examples thereof include polyethylene glycol, a cacao oil, higher alcohols, esters of higher alcohols, gelatin, and semi-synthetic glyceride.

When the pharmaceutical is prepared as an injection agent, a liquid, an emulsion, and a suspension are preferable to be sterilized and be isotonic to blood. A widely used and known diluent may be used for preparing liquid, emulsion, and suspension. Examples of the diluting agent include water, ethanol, propylene glycol, ethoxylated isostearyl alcohol, polyoxylated isostearyl alcohol, and a polyoxyethylene sorbitan fatty acid ester. In this case, the medical formulation may contain sodium chloride, glucose, or glycerol in an amount enough for adjusting an isotonic liquid, and alternatively, the medical formulation may contain, for example, a general solubilizing agent, buffer, or soothing agent, and may contain a colorant, a preservative, a flavor, a savoring agent, a sweetener, or another pharmaceutical as required.

The amount of the compound of the present invention contained in the pharmaceutical is not particularly limited and can be appropriately selected from a wide range. In general, it is preferred that the compound of the present invention be contained in an amount of 1 to 70 wt % of the pharmaceutical.

The method of administering the pharmaceutical according to the present invention is not particularly limited, and the pharmaceutical is administered by any kinds of method depending on the form of various preparations, the age, sex, and condition of the disease of a patient, and other conditions. For example, a tablet, a pill, a liquid, a suspension, an emulsion, a granule, and a capsule are orally administered. Alternatively, an injection may be administered alone or in combination with a general fluid replacement such as a liquid of glucose or a liquid of an amino acid in the vein, and moreover, can be administered alone intramuscularly, intradermally, subcutaneously, or intraperitoneally as required. A suppository is administered intrarectally.

The dosage of the above pharmaceutical may be appropriately selected depending on the usage, the age, sex, and degree of the disease of a patient, and other conditions, and the pharmaceutical is administered in a daily dosage of 0.001 to 100 mg, preferably 0.001 to 50 mg per kg body weight once or in several portions a day. The above dosage varies depending on various conditions, a fewer dosage than the above ranges is sufficient in some cases, and a more dosage than the above ranges is necessary in other cases.

EXAMPLE

Hereinafter, the present invention is explained in more detail by exemplifying examples.

$^1$H-NMR measursement was performed by using deuterated water ($D_2O$) as a solvent with AVANCE III 400 (manufactured by Burker) or AVANCE 500 (manufactured by Burker).

Production Examples 1 to 54

Production of Material Compound

Methods in Production Examples 1 to 54 mentioned below were used to produce material compounds shown in Tables 1 to 7.

Mass spectrometry was conducted by using a Voyager DE-PRO (Applied Biosystems Japan Ltd.).

Production Example 1

Sodium hyaluronate (BIO Sodium Hyaluronate HA9, manufactured by Shiseido Co., Ltd.) and bovine testis-derived hyaluronidase (Hyaluronidase Bovine T 100KU, manufactured by Calbiochem Behring Corporation) were subjected to separation in accordance with the method described in Glycobiology, vol. 12, No. 7, pp. 421 to 426, 2002, to yield a hyaluronan oligosaccharide 4-mer. The hyaluronan oligosaccharide 4-mer (20 mg) was dissolved in methanol (1 ml) and water (0.5 ml), and sodium borohydride (10 mg) was added to the mixture while cooling with ice, followed by stirring. The temperature of the resultant was warmed to room temperature and the mixture was stirred overnight. The completion of the reaction was confirmed by mass spectrometry.

A 10% acetic acid solution in methanol (0.5 ml) and water (1 ml) were added to the resultant while cooling with ice, and the mixture was then subjected to concentration under reduced pressure. Another 10% acetic acid solution in methanol (0.5 ml) was added and the resultant was subjected to azeotropy. After that, methanol (2 ml) was added and the resultant was subjected to azeotropy twice.

The residue was dissolved in water (2 ml) and the resultant was filtrated through a disk filter (manufactured by Nihon Pall Ltd., 0.45 μm). The filtrate was passed through a short column (Dowex (registered trademark) 50 W×8 hydrogen form, manufactured by Sigma-Aldrich Corporation) to yield a protonated compound, followed by concentration under reduced pressure. The AKTA system (manufactured by GE Healthcare Bioscience Bioprocess Corp.) was used to apply the concentrate to gel filtration chromatography (G-10, 16 mm×600 mm, water) for desalting, and then, target fractions were freeze-dried to yield a target product (12 mg, white powder).

MS [M+Na]$^+$: 846.21

$^1$H-NMR: FIG. 1 illustrates the chart.

Production Example 2

The same reaction process as that in Production Example 1 was performed except that a hyaluronan oligosaccharide 6-mer (60 mg) was used instead as a material to yield a target product (50 mg, white powder).

MS $[M-H]^-$: 1157.81

Figure 2:
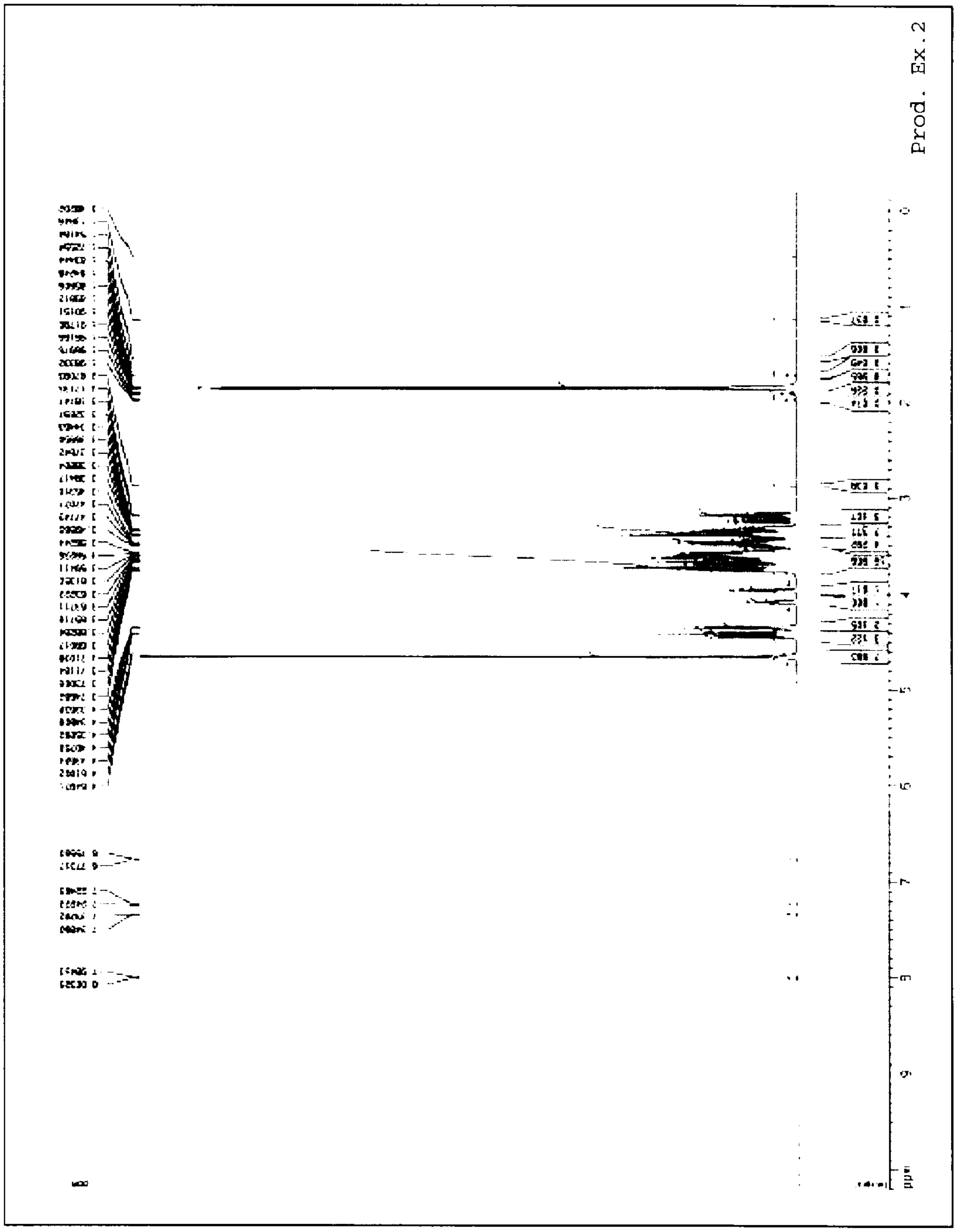
FIG. 2 is a $^1$H-NMR chart of a compound obtained in Production Example 2.

$^1$H-NMR: FIG. 2 illustrates the chart.

Production Example 3

A hyaluronan oligosaccharide 8-mer (60 mg) was subjected to a reaction by the same process as that in Production Example 1 to yield a target product (51 mg, white powder).

MS $[M-H]^-$: 1535.57

Figure 3:
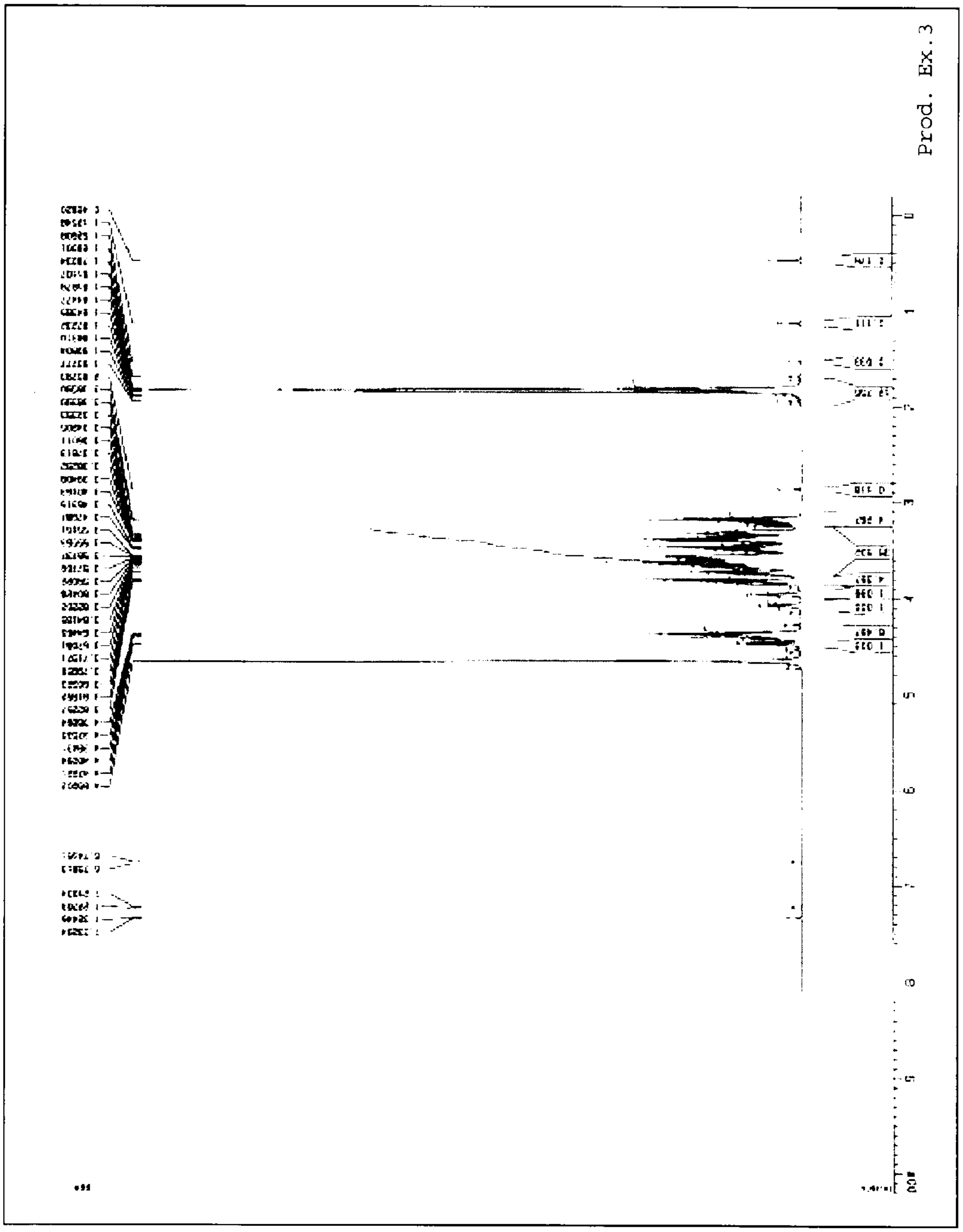
FIG. 3 is a $^1$H-NMR chart of a compound obtained in Production Example 3.

$^1$H-NMR: FIG. 3 illustrates the chart.

Production Example 4

A hyaluronan oligosaccharide 10-mer (60 mg) was subjected to a reaction by the same process as that in Production Example 1 to yield a target product (48 mg, white powder).

MS [M-H]: 1915.72

Figure 4:
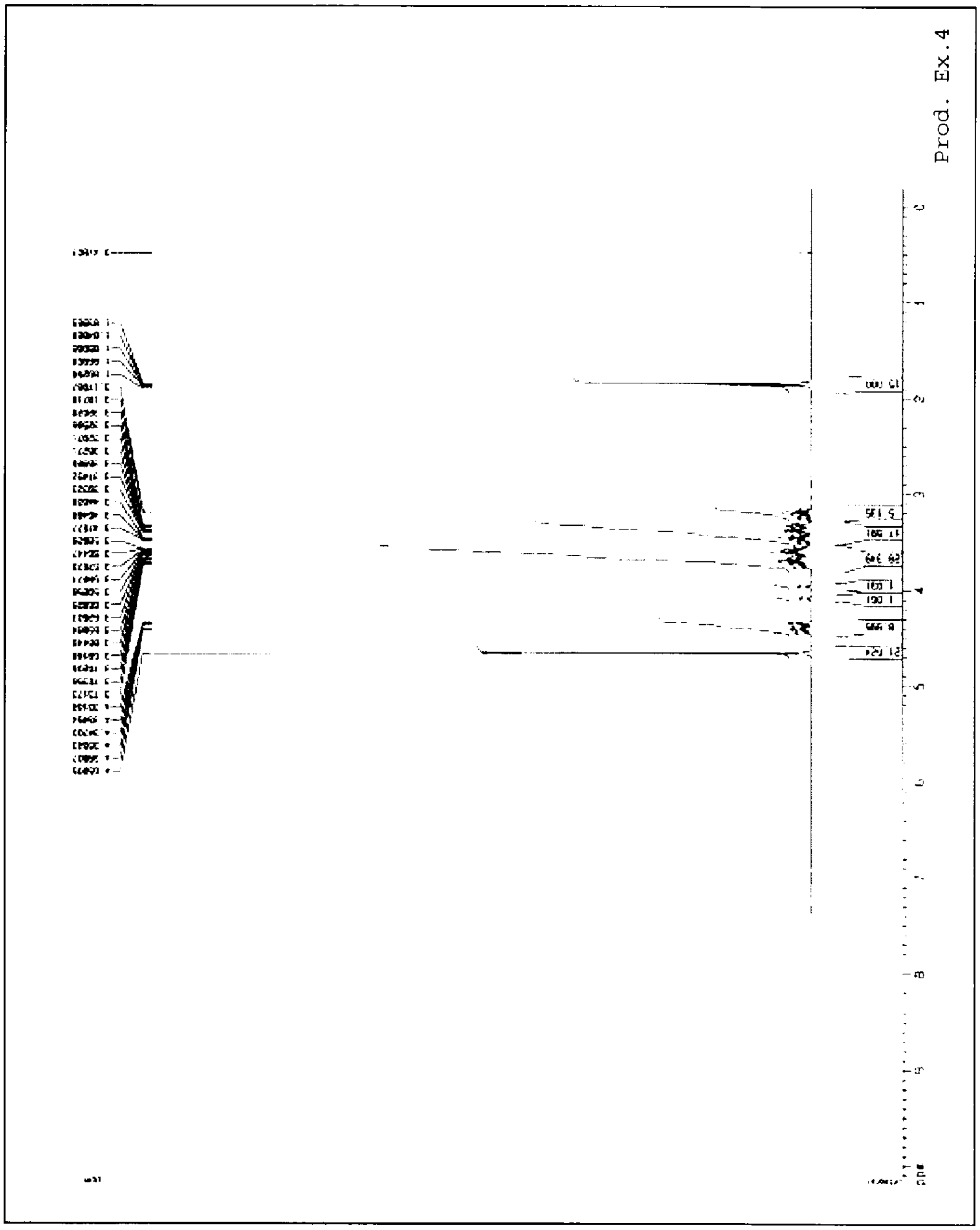
FIG. 4 is a $^1$H-NMR chart of a compound obtained in Production Example 4.

$^1$H-NMR: FIG. 4 illustrates the chart.

Production Example 5

A hyaluronan oligosaccharide 12-mer (60 mg) was subjected to a reaction by the same process as that in Production Example 1 to yield a target product (60 mg, white powder).

MS $[M-H]^-$: 2294.98

Figure 5:
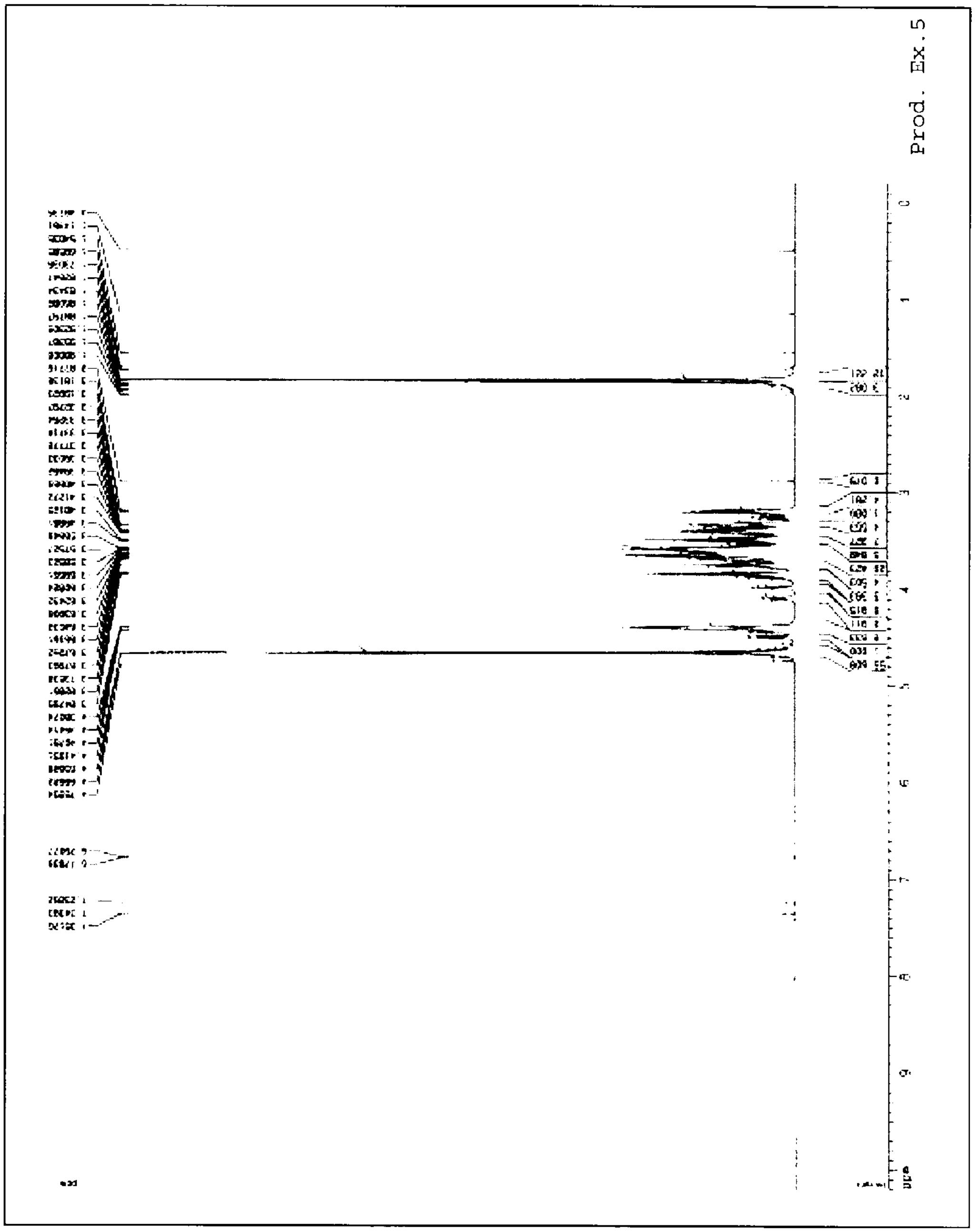
FIG. 5 is a $^1$H-NMR chart of a compound obtained in Production Example 5.

$^1$H-NMR: FIG. 5 illustrates the chart.

Production Example 6

The same process as that in Production Example 1 was performed except that a hyaluronan oligosaccharide 14-mer (20 mg) was used instead as a material to yield a target product (20 mg, white powder).

Figure 6:
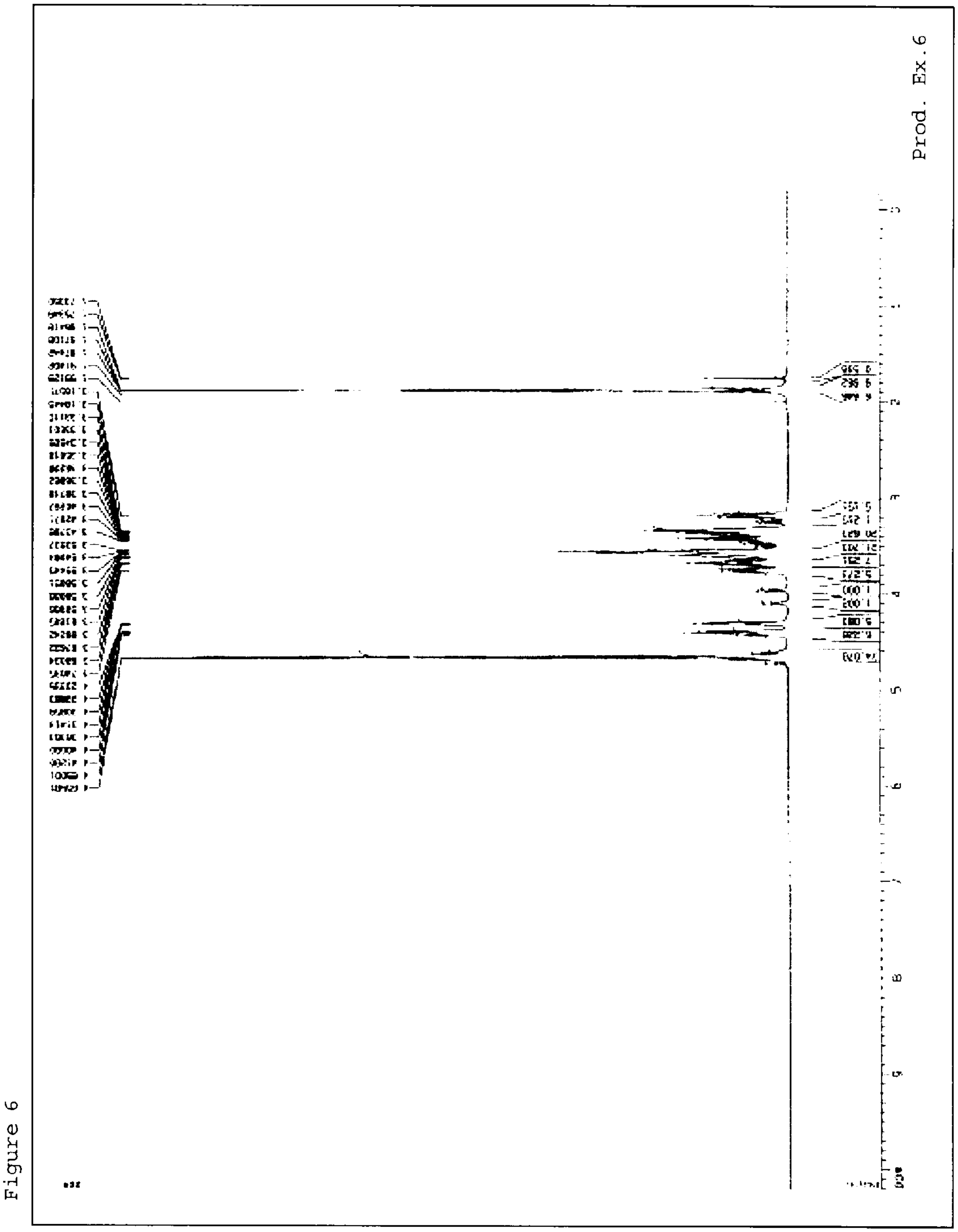
FIG. 6 is a $^1$H-NMR chart of a compound obtained in Production Example 6.

$^1$H-NMR: FIG. 6 illustrates the chart.

Production Example 7

The hyaluronan oligosaccharide 16-mer (10 mg) was dissolved in methanol (0.6 ml) and water (0.3 ml), and sodium borohydride (5 mg) was added to the mixture while cooling with ice, followed by stirring. The temperature of the resultant was warmed to room temperature and the mixture was stirred overnight. The completion of the reaction was confirmed by mass spectrometry.

A 10% acetic acid solution in methanol (0.1 ml) and water (0.2 ml) were added to the resultant while cooling with ice, and the mixture was then subjected to concentration under reduced pressure.

The residue was dissolved in water (1 ml) and the resultant was filtrated through a disk filter (manufactured by Nihon Pall Ltd., 0.45 μm). The AKTA system (manufactured by GE Healthcare Bioscience Bioprocess Corp.) was used to apply the concentrate to gel filtration chromatography (G-10, 16 mm×600 mm, water) to perform desalting, and then, target fractions were freeze-dried to yield a target product (10 mg, white powder).

Figure 7:
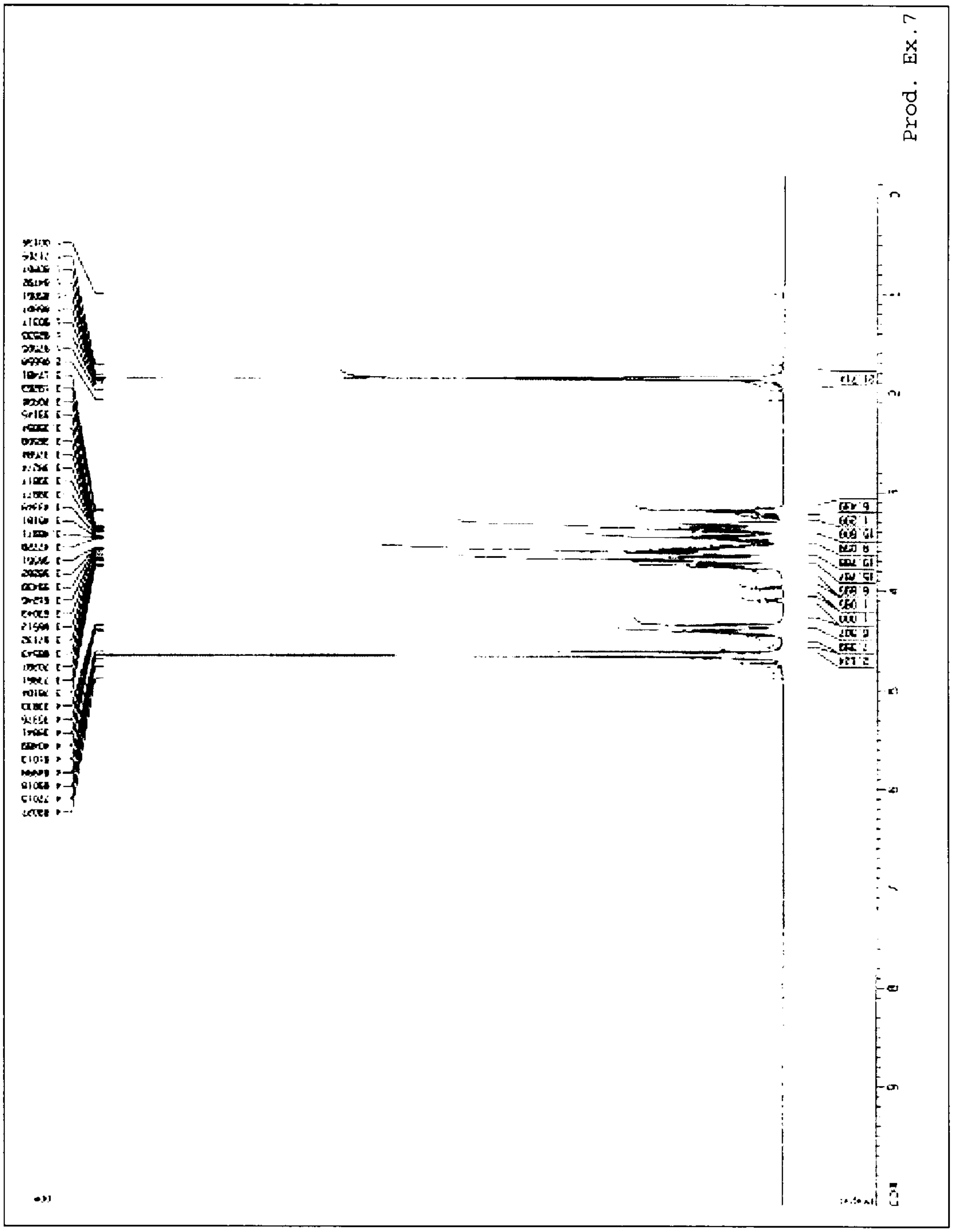
FIG. 7 is a $^1$H-NMR chart of a compound obtained in Production Example 7.

$^1$H-NMR: FIG. 7 illustrates the chart.

Production Example 8

The same process as that in Production Example 1 was performed except that a hyaluronan oligosaccharide 18-mer (20 mg) was used instead as a material to yield a target product (20 mg, white powder).

Figure 8:
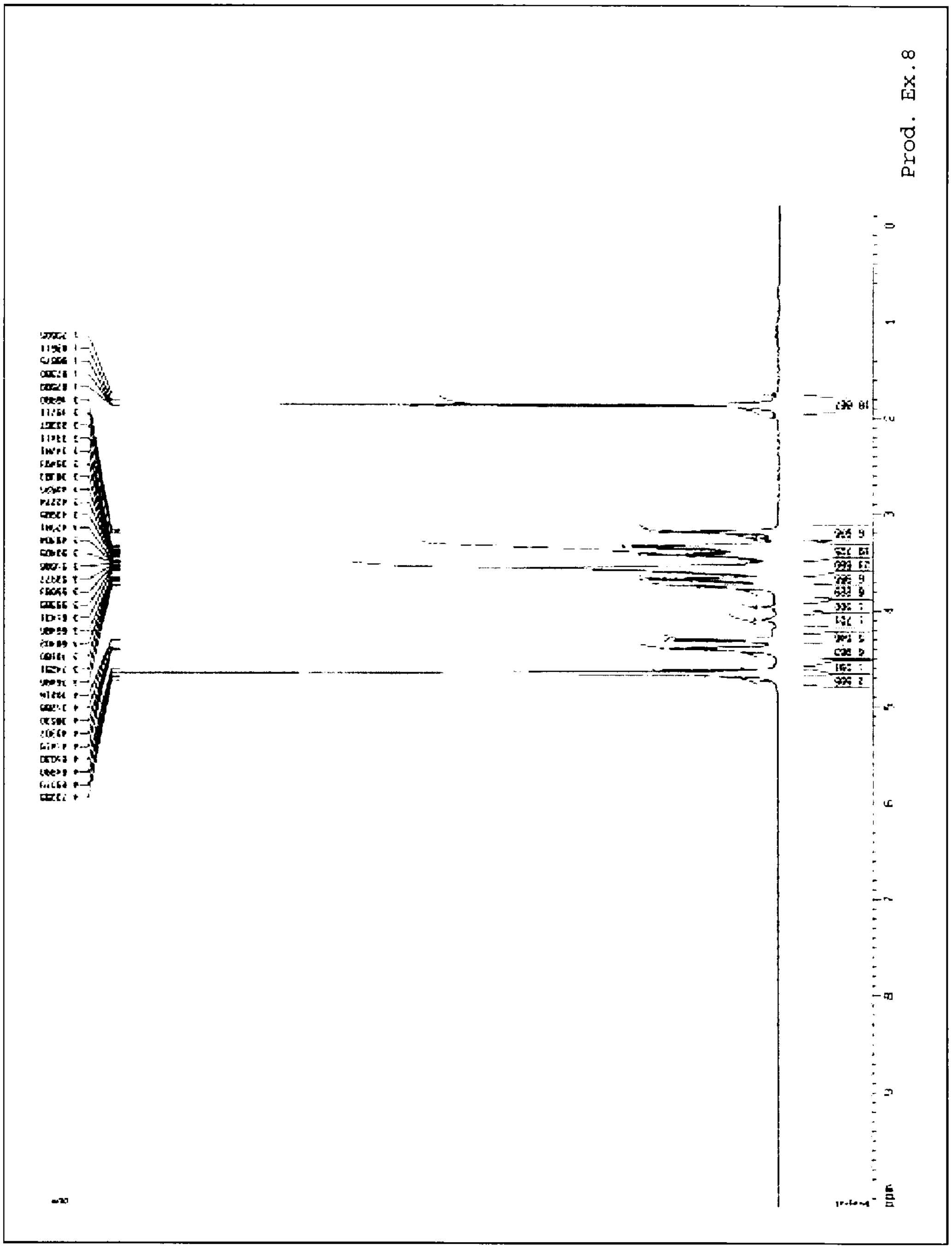
FIG. 8 is a $^1$H-NMR chart of a compound obtained in Production Example 8.

$^1$H-NMR: FIG. 8 illustrates the chart.

Production Example 9

The same process as that in Production Example 1 was performed except that a hyaluronan oligosaccharide 20-mer (42 mg) was used instead as a material to yield a target product (40 mg, white powder).

Figure 9:
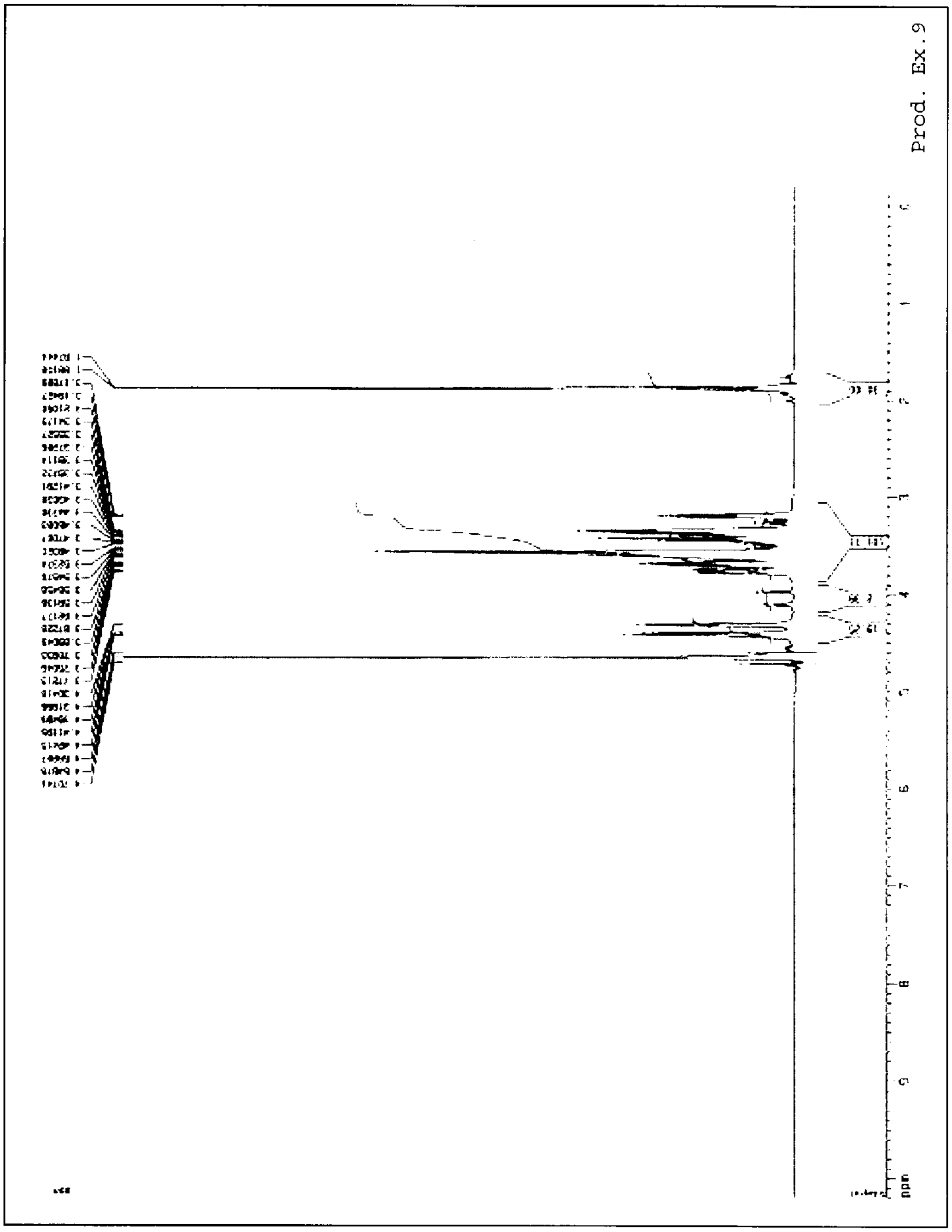
FIG. 9 is a $^1$H-NMR chart of a compound obtained in Production Example 9.

$^1$H-NMR: FIG. 9 illustrates the chart.

Production Example 10

A hyaluronan oligosaccharide 10-mer (20 mg) was dissolved in water (0.8 ml), followed by cooling with ice. Anthranilic acid (30 mg), boronic acid (40 mg), sodium acetate (80 mg), and sodium cyanotrihydridoborate (5 mg) were dissolved in methanol (1 ml) and water (0.2 ml). The resultant solution was added to the solution of the hyaluronan oligosaccharide 10-mer, followed by stirring at 80° C. for 5 hours. The completion of the reaction was confirmed by mass spectrometry.

The resultant was concentrated under reduced pressure, and the residue was dissolved in methanol (1 ml) and water (1 ml). Then, the mixture was filtrated through a disk filter (manufactured by Nihon Pall Ltd., 0.45 μm). The filtrate was applied to gel filtration chromatography (LH-20, 18 mm×500 mm, water:methanol=1:1) to perform purification, and then, target fractions were freeze-dried to yield a target product (24 mg, white powder).

Figure 10:
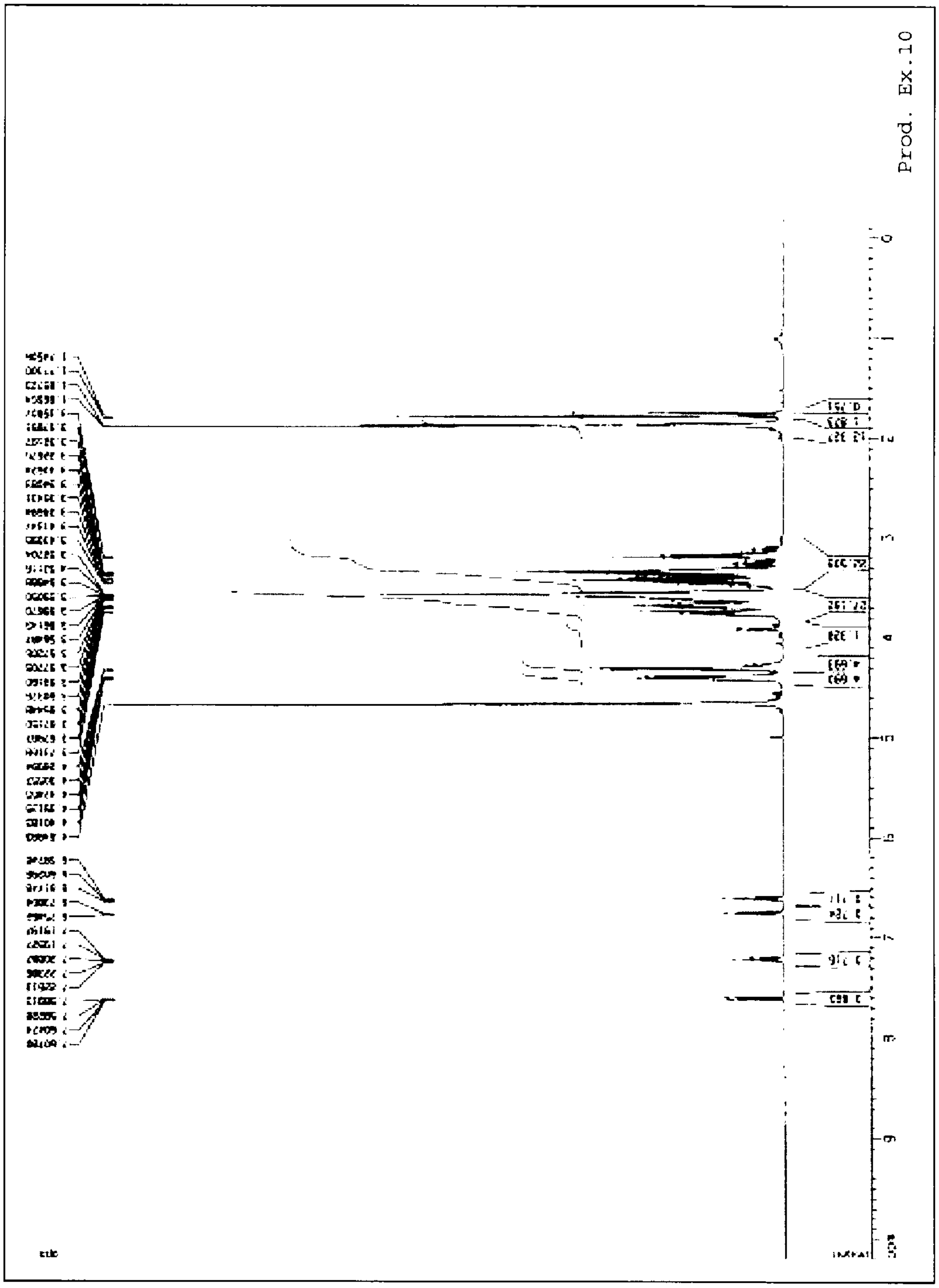
FIG. 10 is a $^1$H-NMR chart of a compound obtained in Production Example 10.

$^1$H-NMR: FIG. 10 illustrates the chart.

Production Example 11

A hyaluronan oligosaccharide 10-mer (20 mg) was dissolved in water (0.8 ml), followed by cooling with ice. Aniline (30 mg), boronic acid (40 mg), sodium acetate (80 mg), and sodium cyanotrihydridoborate (5 mg) were dissolved in methanol (1 ml) and water (0.2 ml). The resultant solution was added to the solution of the hyaluronan oligosaccharide 10-mer, followed by stirring at 80° C. for 5 hours. The completion of the reaction was confirmed by mass spectrometry.

The resultant was concentrated under reduced pressure, and the residue was dissolved in methanol (1 ml) and water (1 ml). Then, the mixture was filtrated through a disk filter (manufactured by Nihon Pall Ltd., 0.45 μm). The filtrate was applied to gel filtration chromatography (LH-20, 18 mm×500 mm, water:methanol=1:1) to perform purification, and then, target fractions were freeze-dried to yield a target product (17 mg, white powder).

Figure 11:
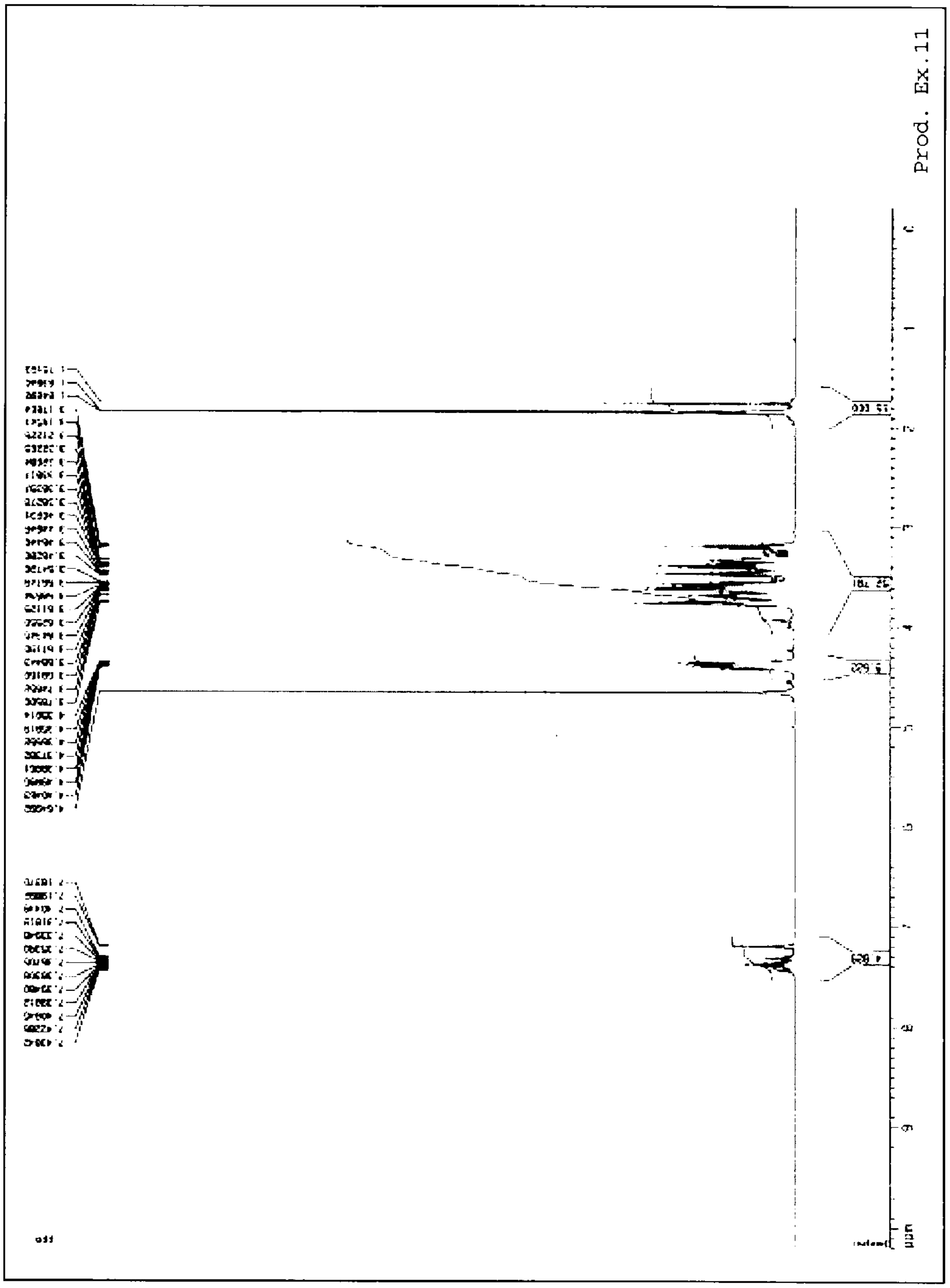
FIG. 11 is a $^1$H-NMR chart of a compound obtained in Production Example 11.

$^1$H-NMR: FIG. 11 illustrates the chart.

Production Example 12

The same process as that in Production Example 1 was performed except that a hyaluronan oligosaccharide 24-mer to 32-mer (10 mg) was used instead as a material to yield a target product (10 mg, white powder).

Production Example 13

The same process as that in Production Example 1 was performed except that a hyaluronan oligosaccharide 34-mer to 46-mer (10 mg) was used instead as a material to yield a target product (10 mg, white powder).

The structures of the target products in the Production Examples 1 to 13 are shown in Table 1 below.

TABLE 1

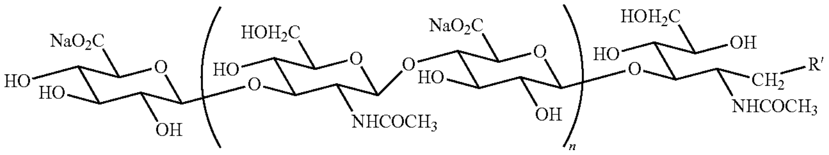

| Production Example No. | n | R' |
|---|---|---|
| 1 | 1 | OH |
| 2 | 2 | OH |
| 3 | 3 | OH |
| 4 | 4 | OH |
| 5 | 5 | OH |
| 6 | 6 | OH |
| 7 | 7 | OH |
| 8 | 8 | OH |
| 9 | 9 | OH |
| 10 | 4 | 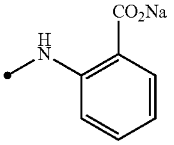 |
| 11 | 4 | 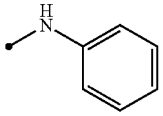 |
| 12 | 11-15 | OH |
| 13 | 16-22 | OH |

Production Example 14

Sodium hyaluronate (BIO Sodium Hyaluronate HA9, manufactured by Shiseido Co., Ltd.) and bovine testis-derived hyaluronidase (Hyaluronidase Bovine T 100KU, manufactured by Calbiochem Behring Corporation) were subjected to separation in accordance with the document, Glycobiology, vol. 12, No. 7, pp. 421 to 426, 2002 to yield a hyaluronan oligosaccharide 4-mer. The hyaluronan oligosaccharide 4-mer (40 mg) thus obtained was dissolved in a borate buffer (pH 9.18) (3 ml), and the mixture was stirred at 80° C. for 1 hour. The temperature of the resultant was warmed to room temperature, and methanol (3 ml) was added to the mixture, followed by concentration under reduced pressure. The residue was dissolved in water (2 ml) and the resultant was filtrated through a disk filter (manufactured by Nihon Pall Ltd., 0.45 μm). After that, the AKTA system (manufactured by GE Healthcare Bioscience Bioprocess Corp.) was used to apply the filtrate to gel filtration chromatography (G-10, 16 mm×600 mm, water) to perform desalting, and then, target fractions were concentrated to yield white powders.

Subsequently, the obtained white powders (25 mg) were dissolved in methanol (1 ml) and water (0.5 ml), and sodium borohydride (10 mg) was added to the mixture while cooling with ice, followed by stirring. The temperature of the resultant was warmed to room temperature and the mixture was stirred overnight. The completion of the reaction was confirmed by mass spectrometry. A 10% acetic acid solution in methanol (0.2 ml) was added to the resultant while cooling with ice, and the mixture was then subjected to concentration under reduced pressure. The residue was dissolved in water (2 ml) and the resultant was filtrated through a disk filter (manufactured by Nihon Pall Ltd., 0.45 μm). After that, the AKTA system (manufactured by GE Healthcare Bioscience Bioprocess Corp.) was used to apply the filtrate to gel filtration chromatography (G-10, 16 mm×600 mm, water) to perform desalting, and then, target fractions were freeze-dried to yield a target product (18 mg, white powder).

MS $[M-H]^-$: 573.45

Figure 12:
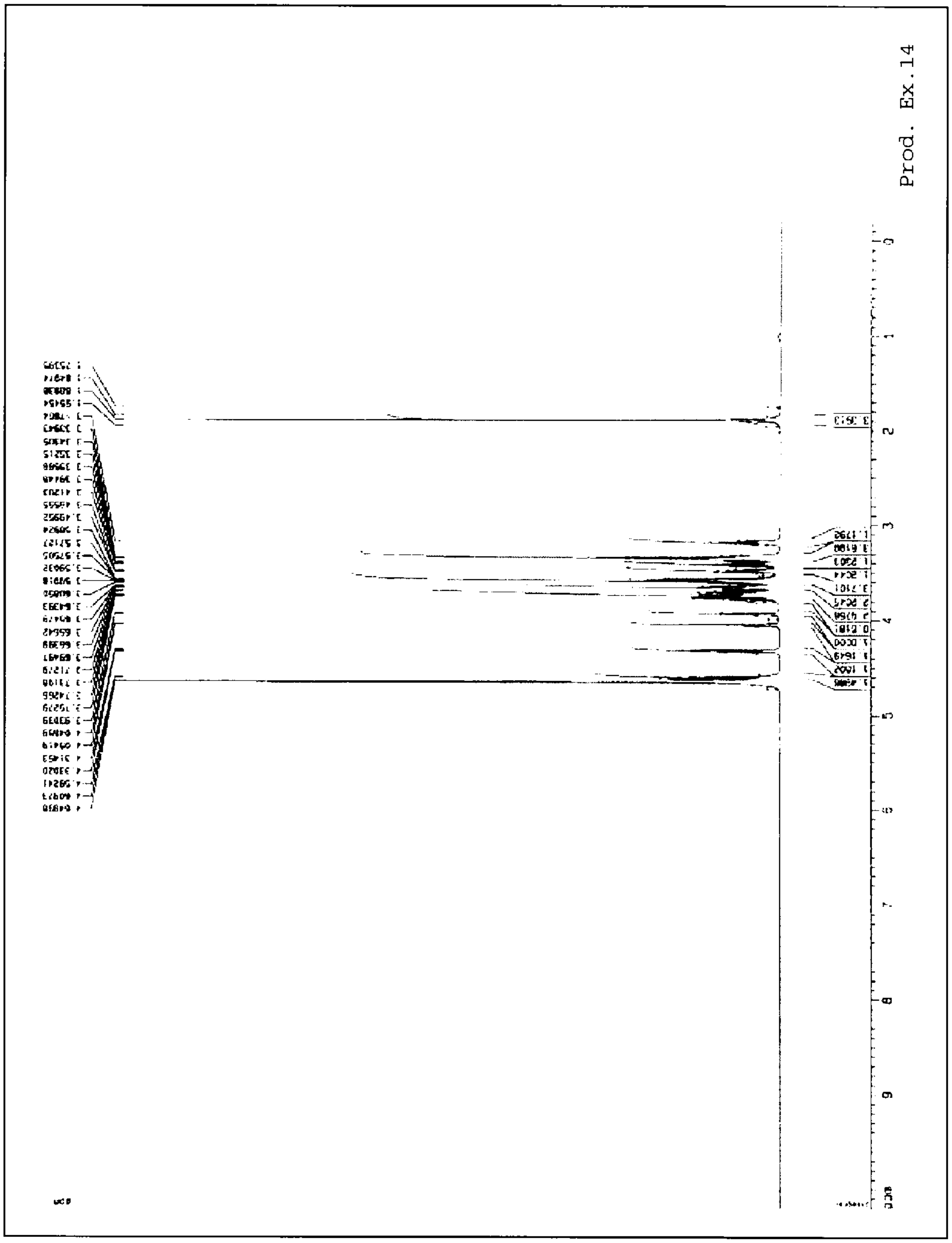
FIG. 12 is a $^1$H-NMR chart of a compound obtained in Production Example 14.

$^1$H-NMR: FIG. 12 illustrates the chart.

Production Example 15

The same reaction process as that in Production Example 14 was performed except that a hyaluronan oligosaccharide 6-mer (60 mg) was used instead as a material to yield a target product (34 mg, white powder).

MS $[M-H]^-$: 953.02

Figure 13:
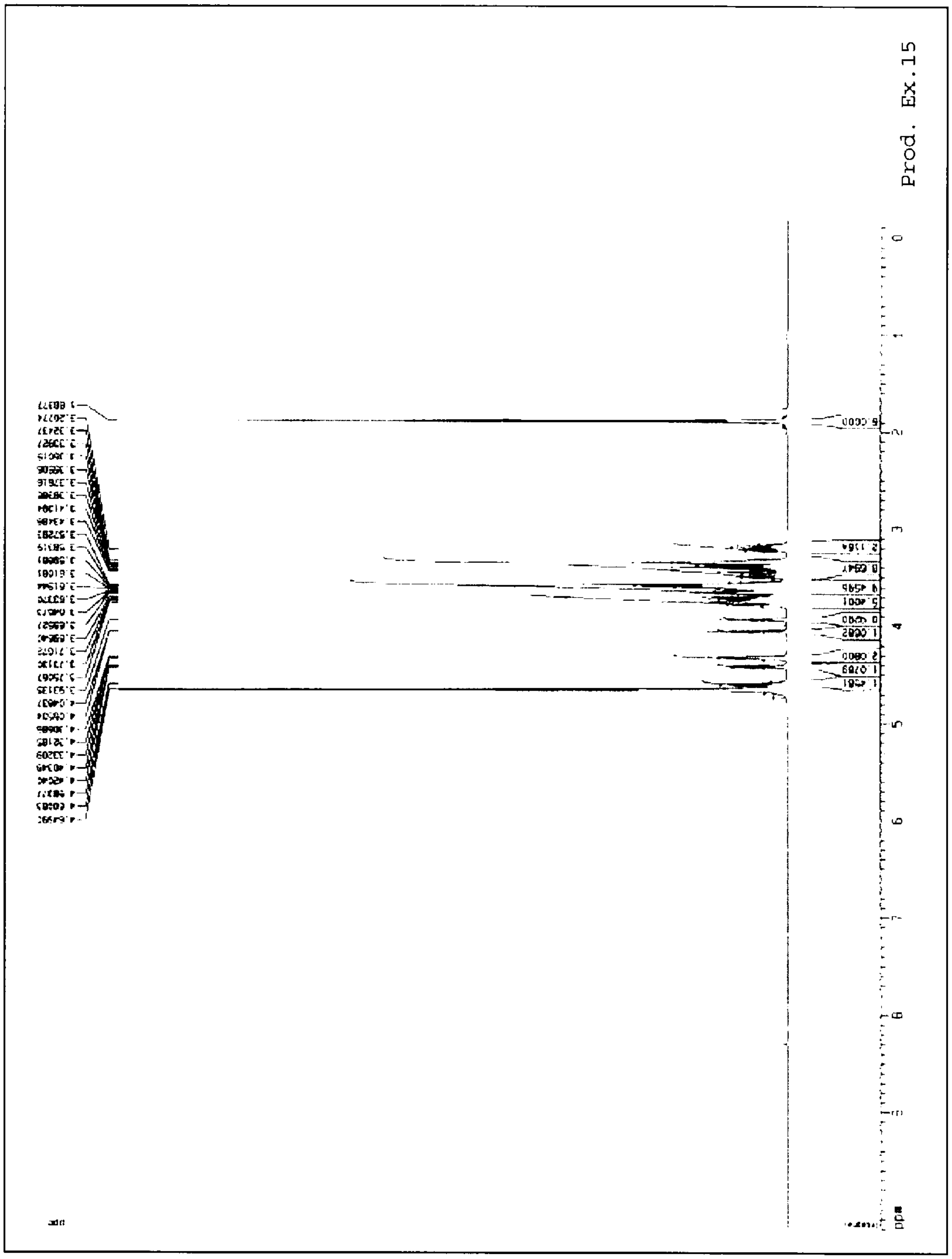
FIG. 13 is a $^1$H-NMR chart of a compound obtained in Production Example 15.

$^1$H-NMR: FIG. 13 illustrates the chart.

Production Example 16

The same reaction process as that in Production Example 14 was performed except that a hyaluronan oligosaccharide 8-mer (10 mg) was used instead as a material to yield a target product (8 mg, white powder).

MS $[M-H]^-$: 1331.54

Figure 14:
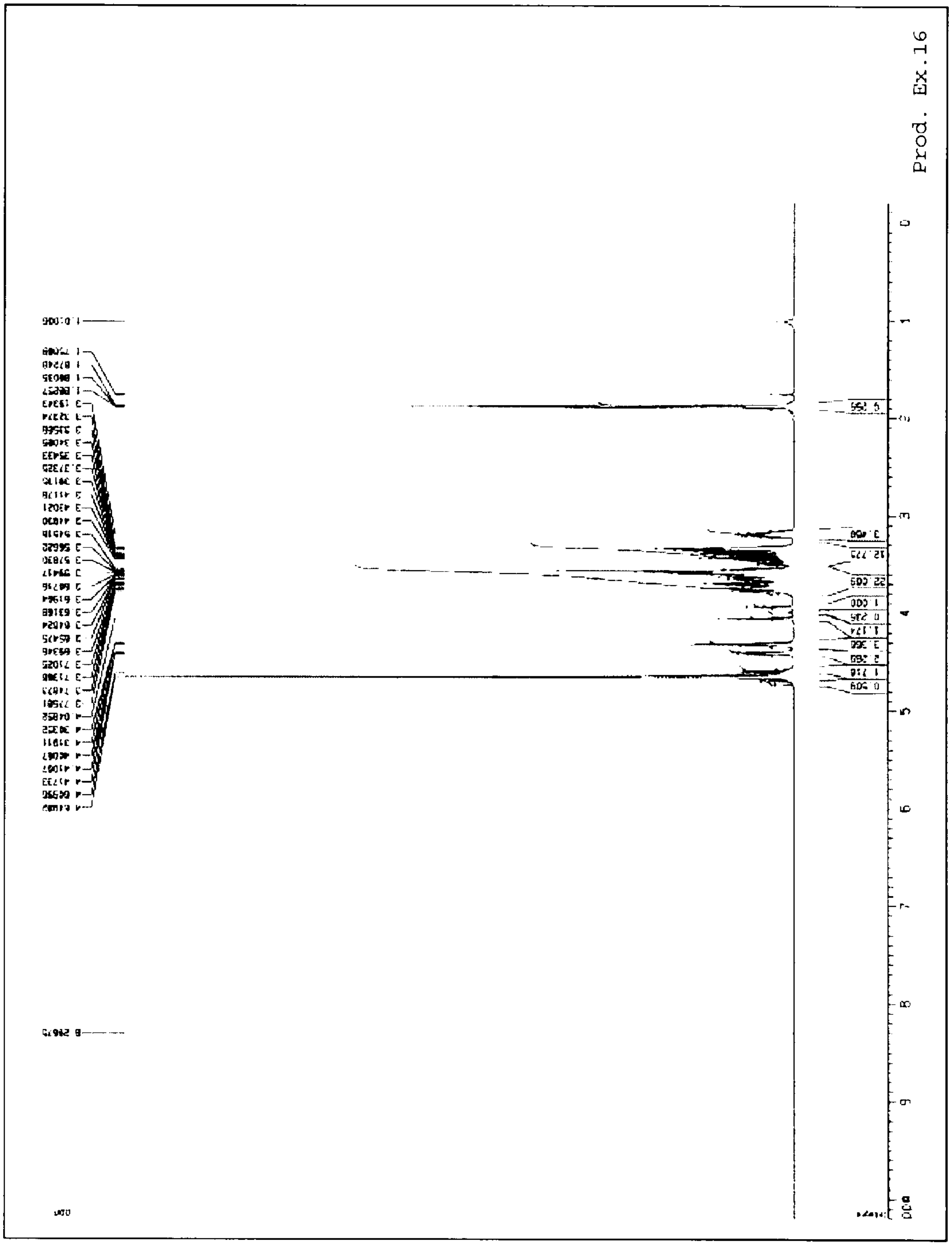
FIG. 14 is a $^1$H-NMR chart of a compound obtained in Production Example 16.

$^1$H-NMR: FIG. 14 illustrates the chart.

Production Example 17

The same reaction process as that in Production Example 14 was performed except that a hyaluronan oligosaccharide 10-mer (10 mg) was used instead as a material to yield a target product (8 mg, white powder).

MS $[M-H]^-$: 1710.28

Figure 15:
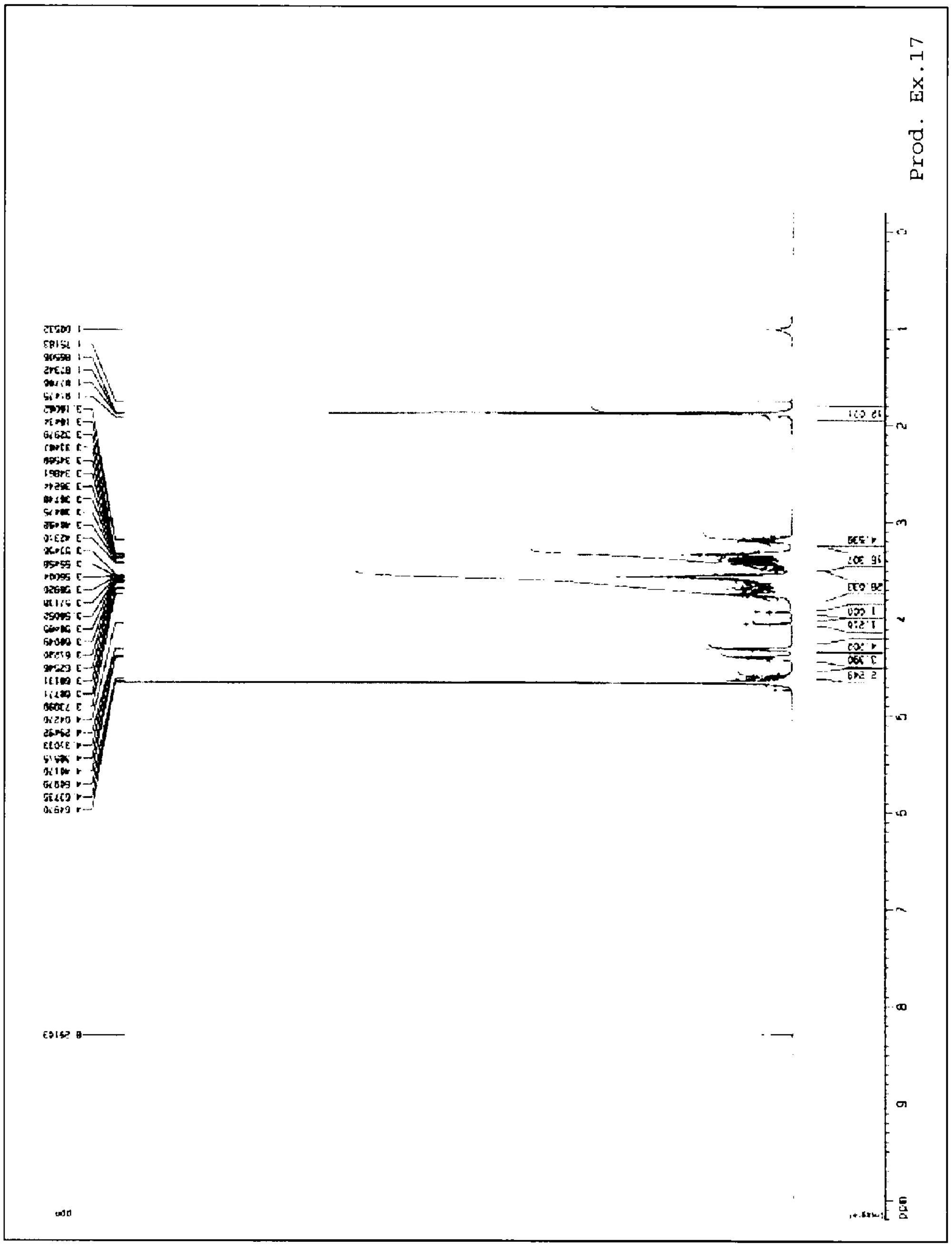
FIG. 15 is a $^1$H-NMR chart of a compound obtained in Production Example 17.

$^1$H-NMR: FIG. 15 illustrates the chart.

Production Example 18

The same reaction process as that in Production Example 14 was performed except that a hyaluronan oligosaccharide 12-mer (20 mg) was used instead as a material to yield a target product (16 mg, white powder).

MS $[M-H]^-$: 2090.01

Figure 16:
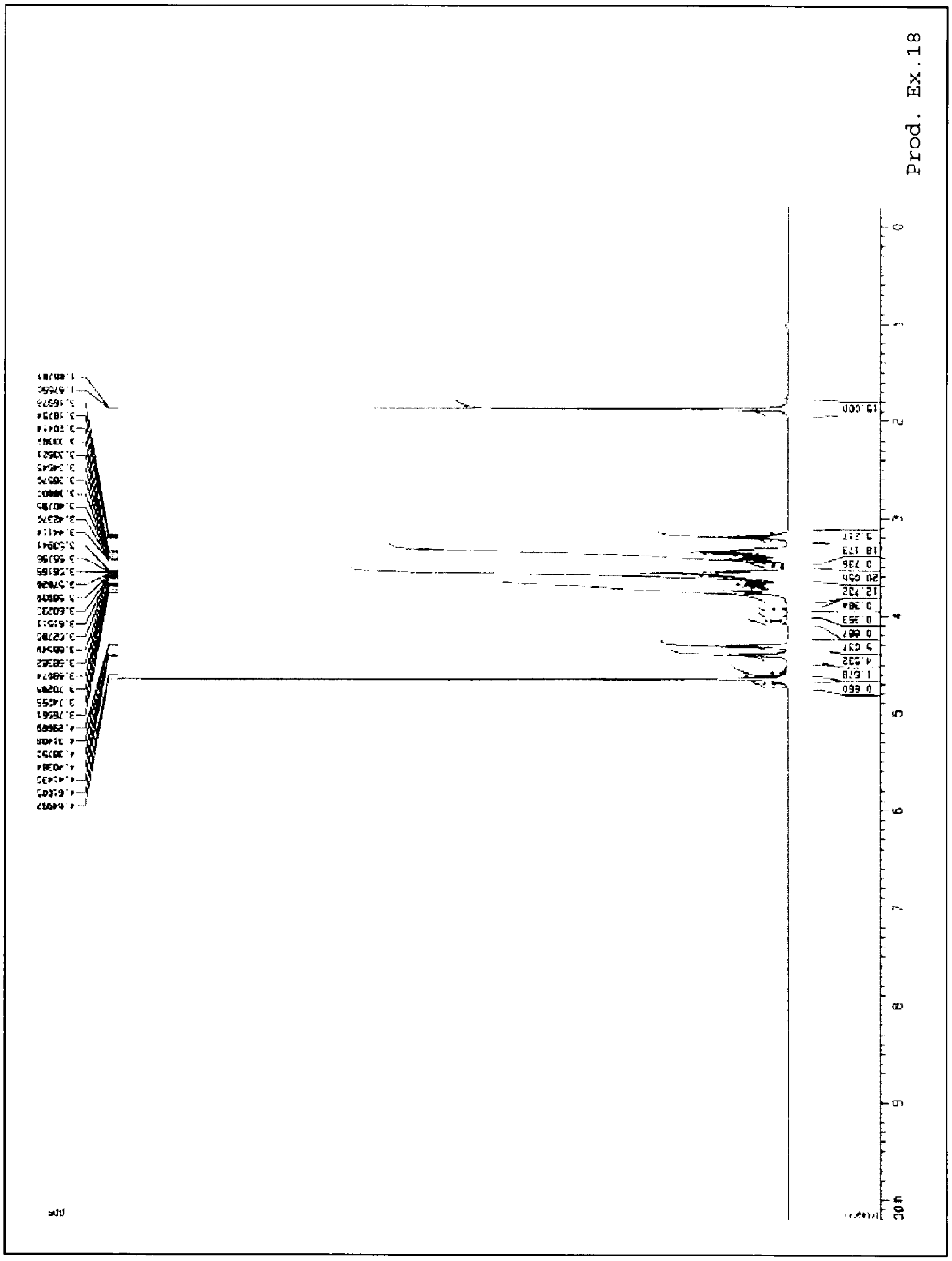
FIG. 16 is a $^1$H-NMR chart of a compound obtained in Production Example 18.

$^1$H-NMR: FIG. 16 illustrates the chart.

Production Example 19

The same reaction process as that in Production Example 14 was performed except that a hyaluronan oligosaccharide 14-mer (18 mg) was used instead as a material to yield a target product (11 mg, white powder).

MS [M-H]: 2469.52

Figure 17:
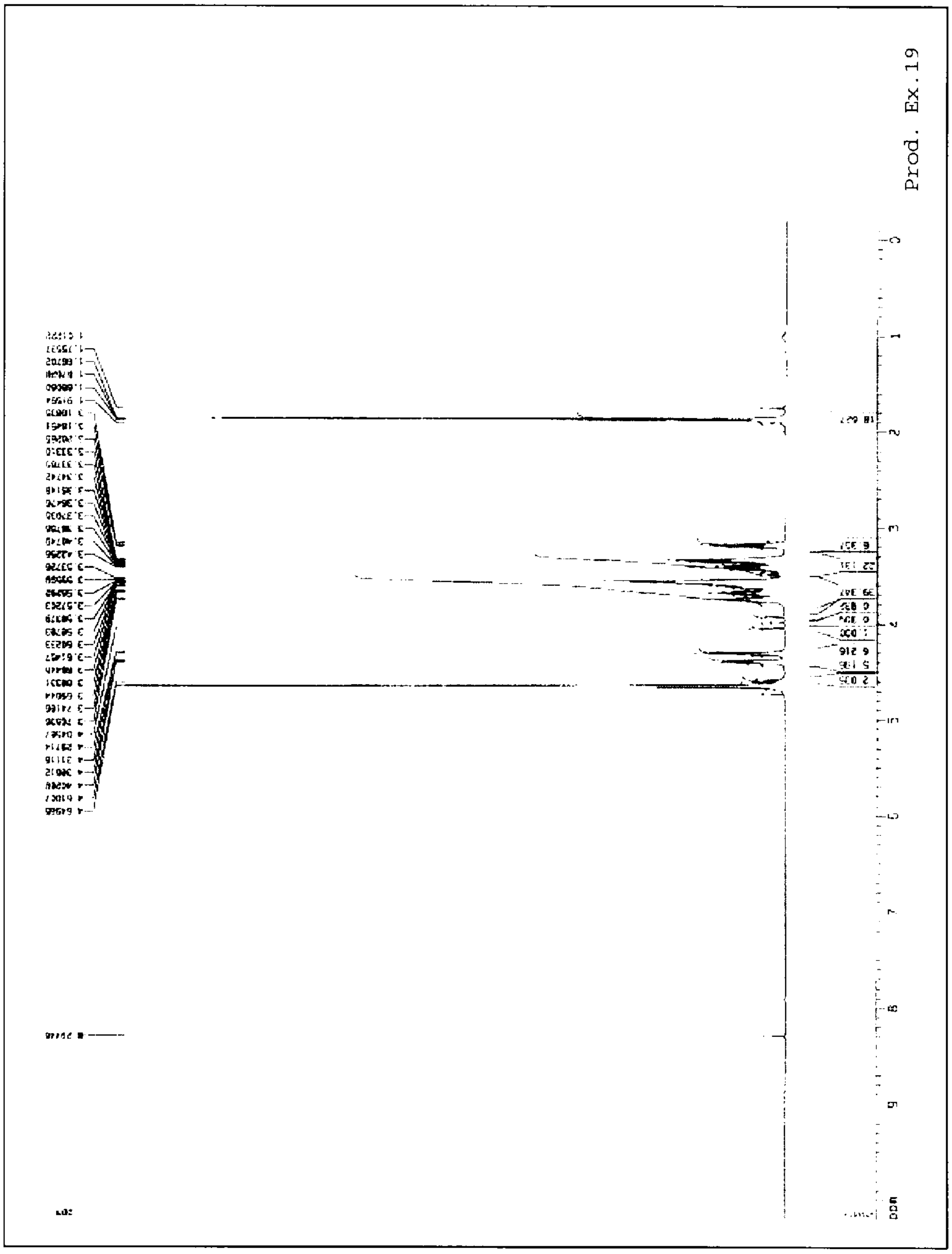
FIG. 17 is a $^1$H-NMR chart of a compound obtained in Production Example 19.

$^1$H-NMR: FIG. 17 illustrates the chart.

Production Example 20

The same reaction process as that in Production Example 14 was performed except that a hyaluronan oligosaccharide 16-mer (7 mg) was used instead as a material to yield a target product (5 mg, white powder).

MS $[M-H]^-$: 2848.59

Figure 18:
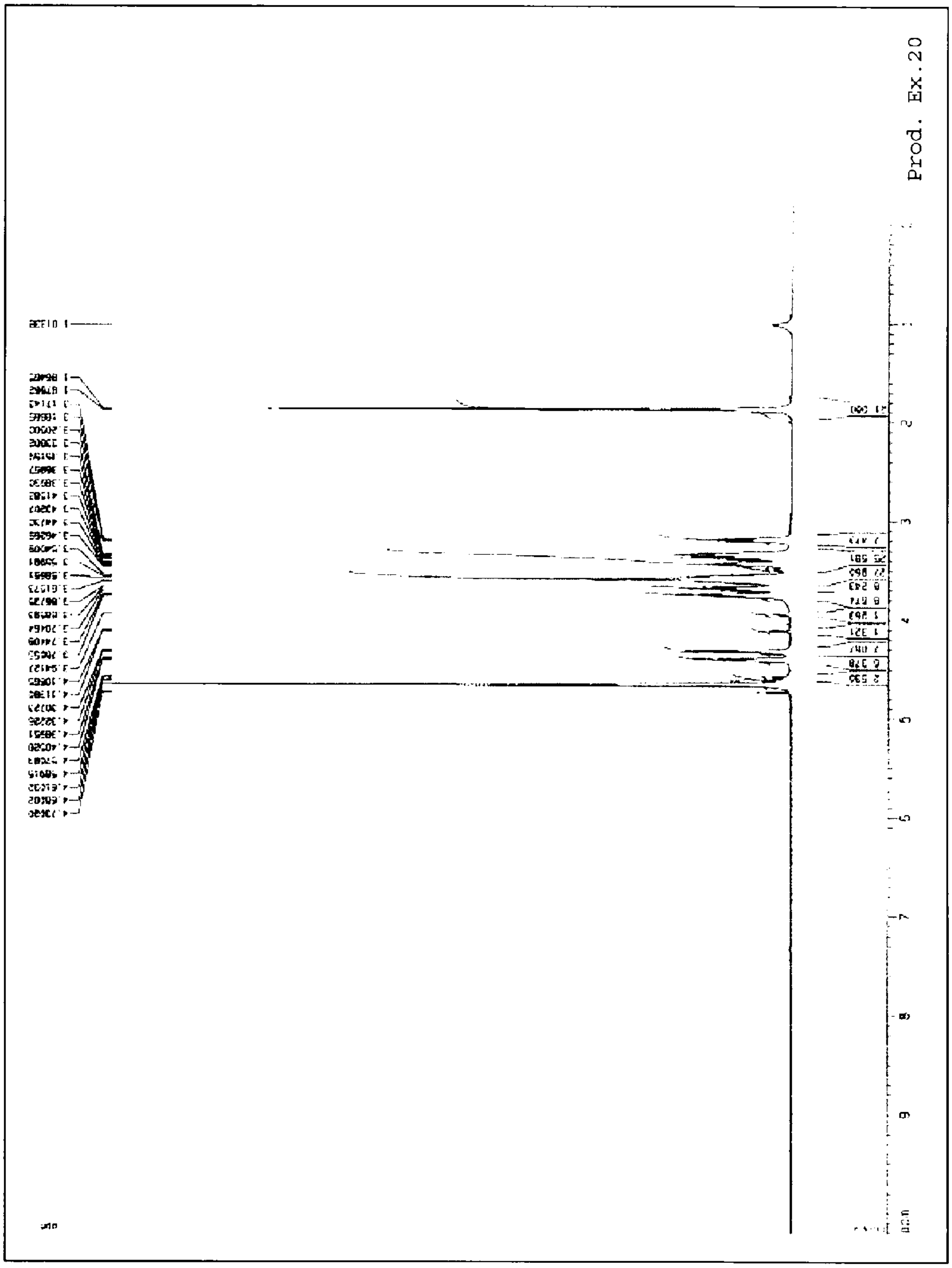
FIG. 18 is a $^1$H-NMR chart of a compound obtained in Production Example 20.

$^1$H-NMR: FIG. 18 illustrates the chart.

Production Example 21

The same reaction process as that in Production Example 14 was performed except that a hyaluronan oligosaccharide 18-mer (10 mg) was used instead as a material to yield a target product (9 mg, white powder).

MS $[M-H]^-$: 3225.70

Figure 19:
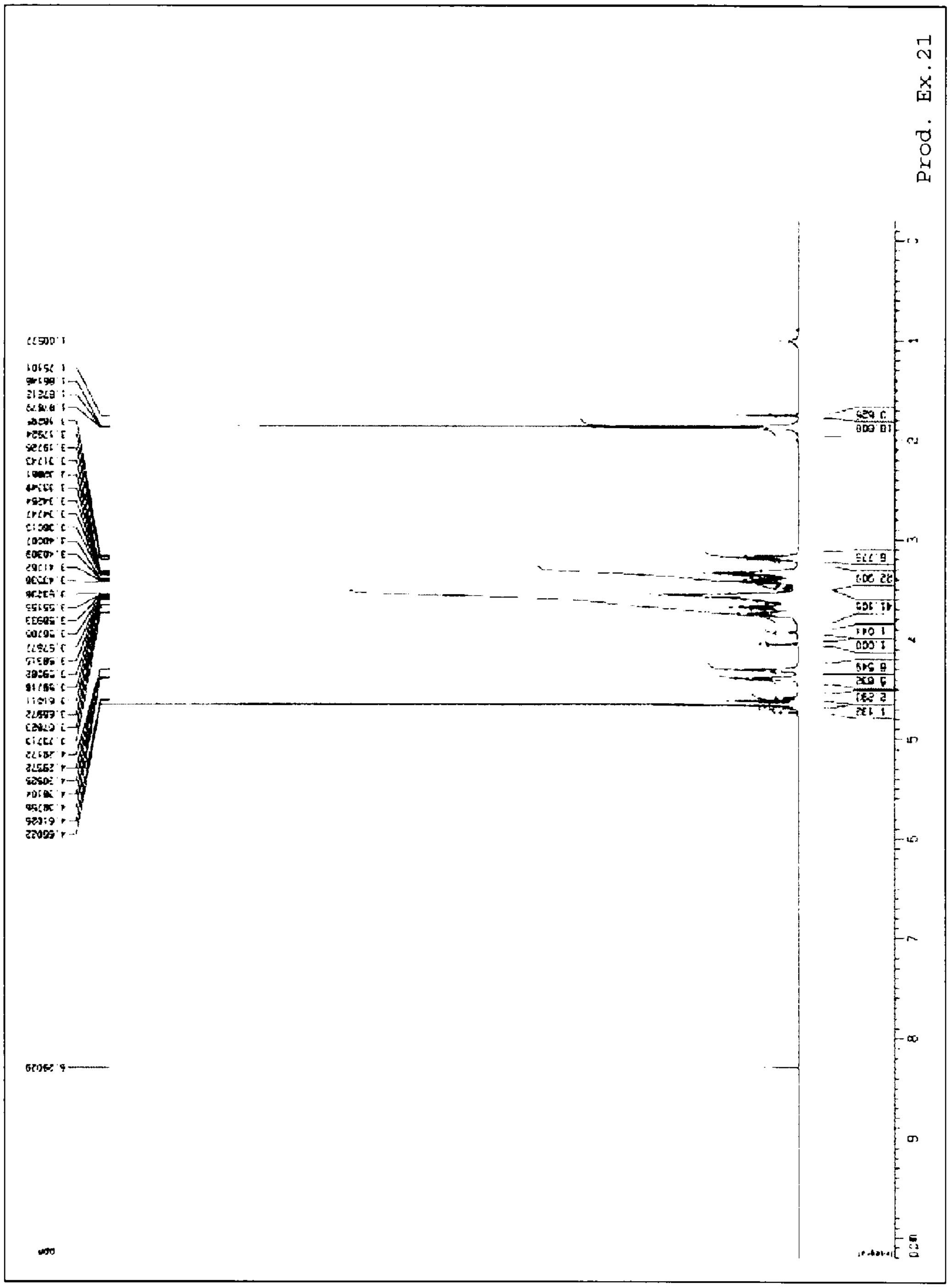
FIG. 19 is a $^1$H-NMR chart of a compound obtained in Production Example 21.

$^1$H-NMR: FIG. 19 illustrates the chart.

Production Example 22

The same reaction process as that in Production Example 14 was performed except that a hyaluronan oligosaccharide 20-mer (15 mg) was used instead as a material to yield a target product (13 mg, white powder).

MS $[M-H]^-$: 3604.16

Figure 20:
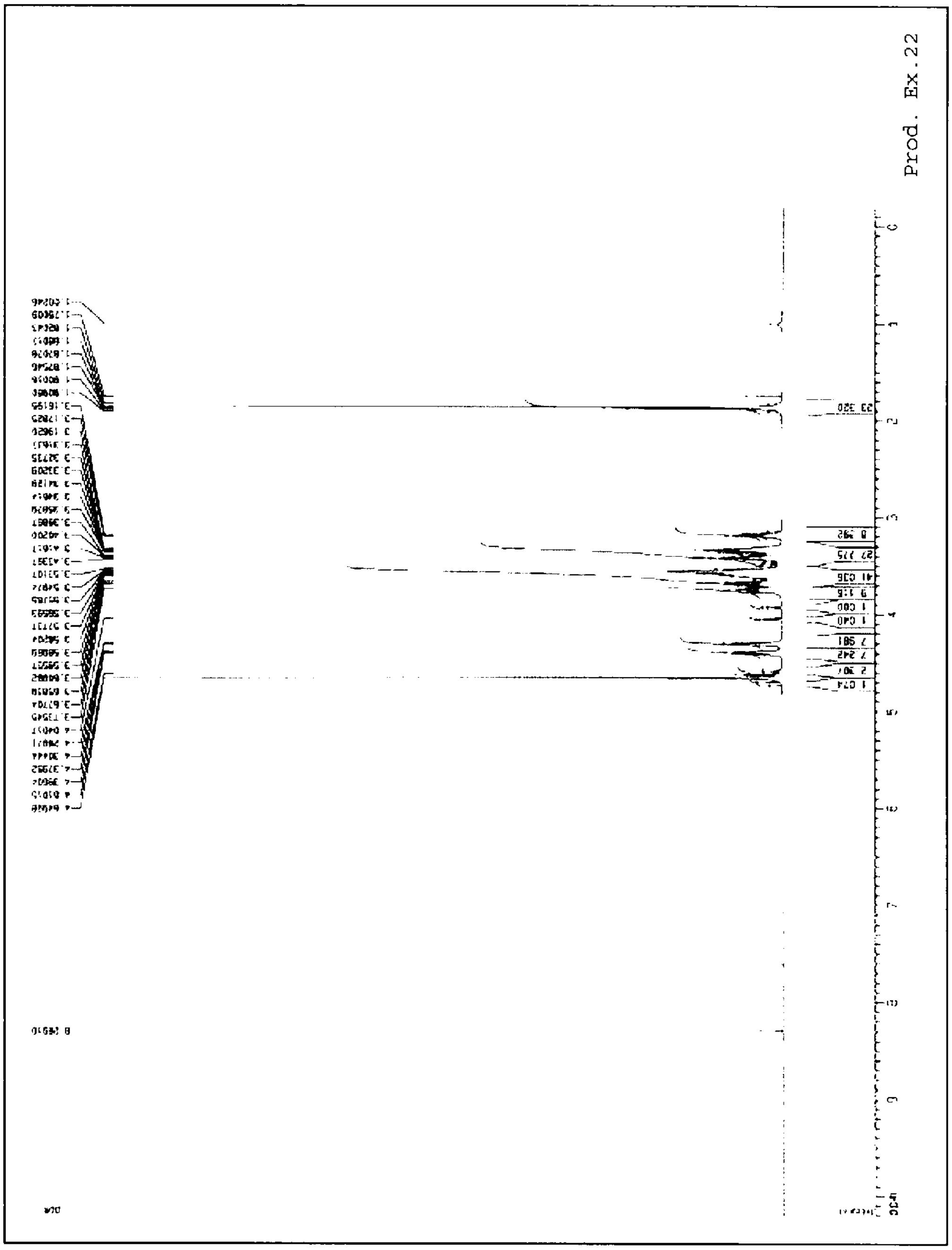
FIG. 20 is a $^1$H-NMR chart of a compound obtained in Production Example 22.

$^1$H-NMR: FIG. 20 illustrates the chart.

The structures of the target products in the Production Examples 14 to 22 are shown in Table 2 below.

Production Example 23

The compound obtained in Production Example 1 (17 mg) was dissolved in a buffer (prepared by mixing a sodium chloride aqueous solution (300 mM, 1 ml) and a sodium acetate aqueous solution (200 mM, 1 ml) and adjusting the pH to 5.2 with glacial acetic acid) (2 ml), and bovine liver β-glucuronidase Type B-1 (manufactured by Sigma-Aldrich Corporation) (8 mg) was added to the resultant, followed by incubation at 37° C. for 8 hours. The reaction solution was subjected to ultrafiltration (Amicon Ultra 4 ml 10K Nominal Molecular Weight Limit, manufactured by Millipore Corporation) to perform purification. After that, the AKTA system (manufactured by GE Healthcare Bioscience Bioprocess Corp.) was used to apply the filtrate to gel filtration chromatography (G-10, 16 mm×600 mm, water) to perform desalting, and then, target fractions were freeze-dried to yield a target product (8 mg, white powder).

MS [M-H]: 601.18

Figure 21:
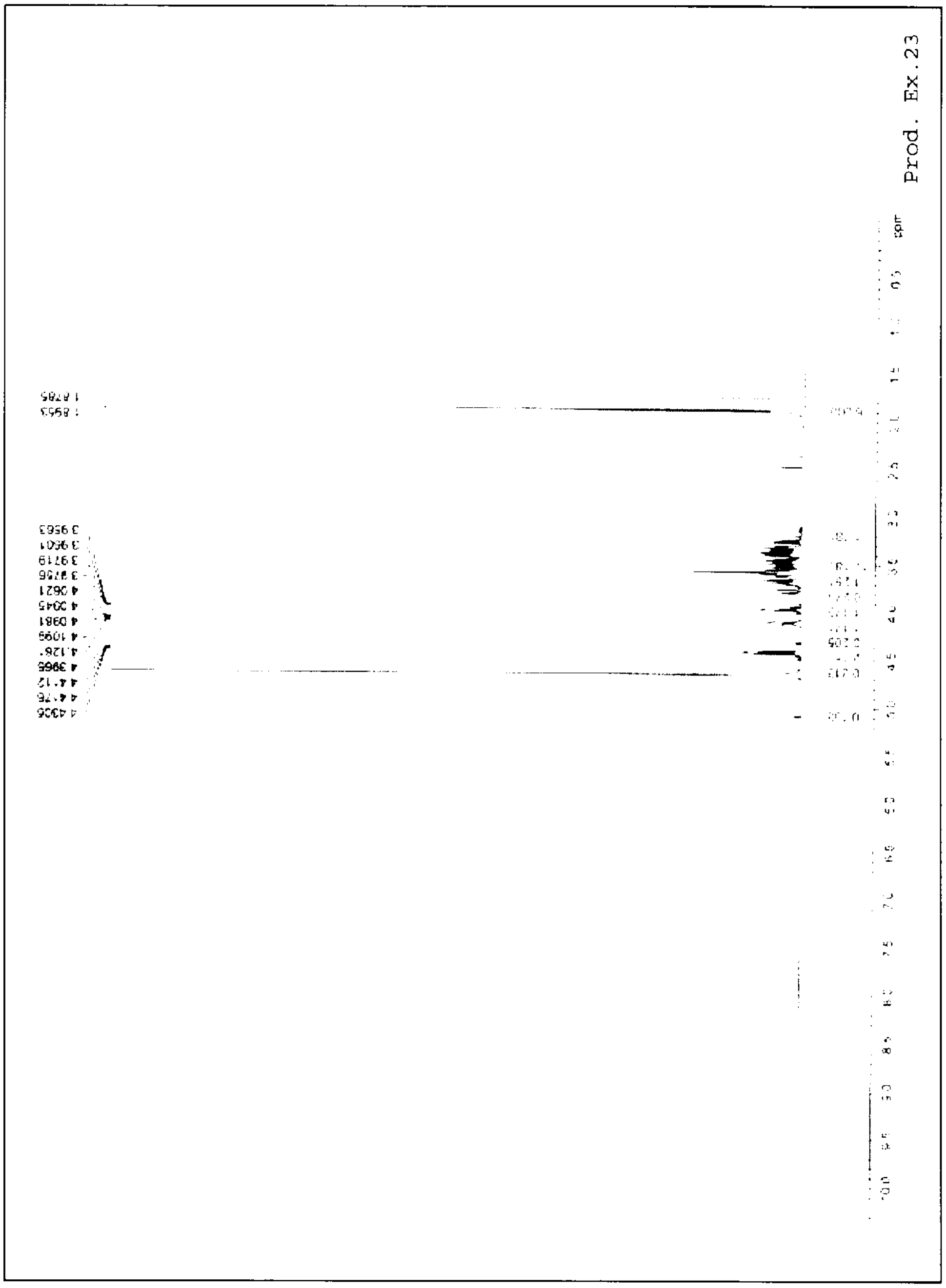
FIG. 21 is a $^1$H-NMR chart of a compound obtained in Production Example 23.

$^1$H-NMR: FIG. 21 illustrates the chart.

Production Example 24

The same reaction process as that in Production Example 23 was performed except that the compound obtained in Production Example 2 (11 mg) was used instead as a material to yield a target product (4 mg, white powder).

MS $[M-H]^-$: 980.29

Figure 22:
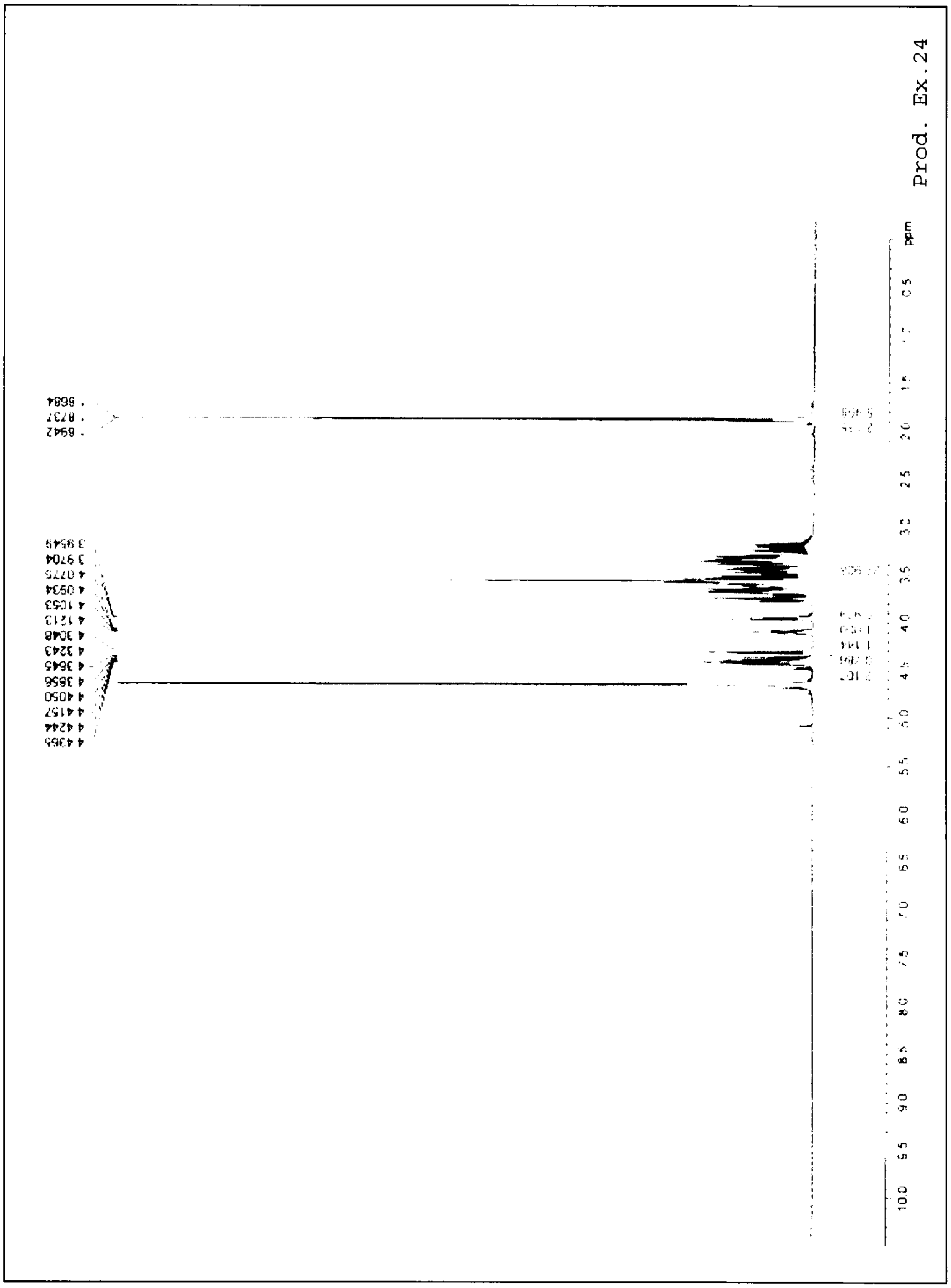
FIG. 22 is a $^1$H-NMR chart of a compound obtained in Production Example 24.

$^1$H-NMR: FIG. 22 illustrates the chart.

Production Example 25

The same reaction process as that in Production Example 23 was performed except that the compound obtained in Production Example 3 (10 mg) was used instead as a material to yield a target product (8 mg, white powder).

MS $[M-H]^-$: 1359.37

Figure 23:
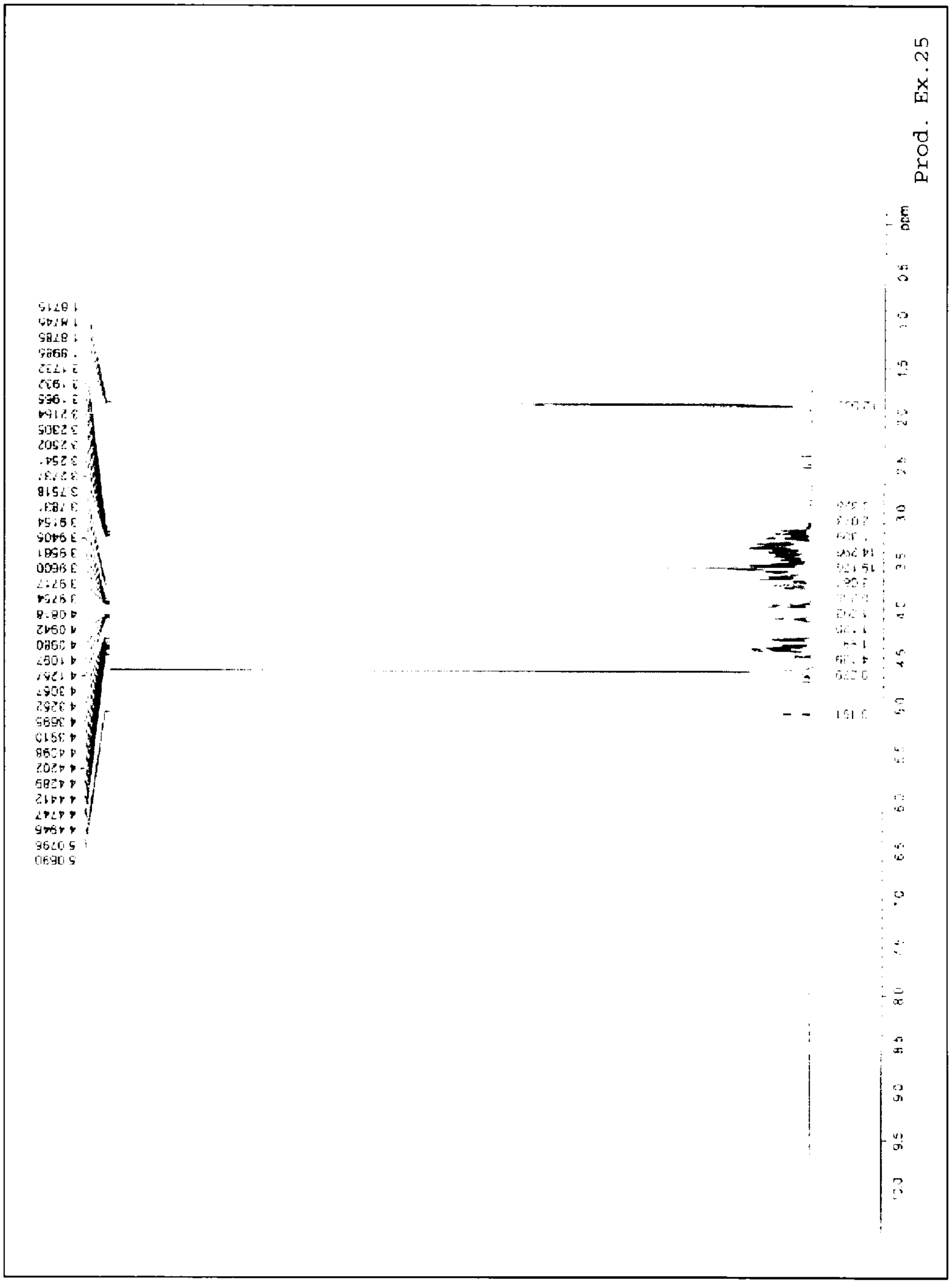
FIG. 23 is a $^1$H-NMR chart of a compound obtained in Production Example 25.

$^1$H-NMR: FIG. 23 illustrates the chart.

Production Example 26

The same reaction process as that in Production Example 23 was performed except that the compound obtained in Production Example 4 (30 mg) was used instead as a material to yield a target product (15 mg, white powder).

MS $[M-H]^-$: 1738.15

Figure 24:
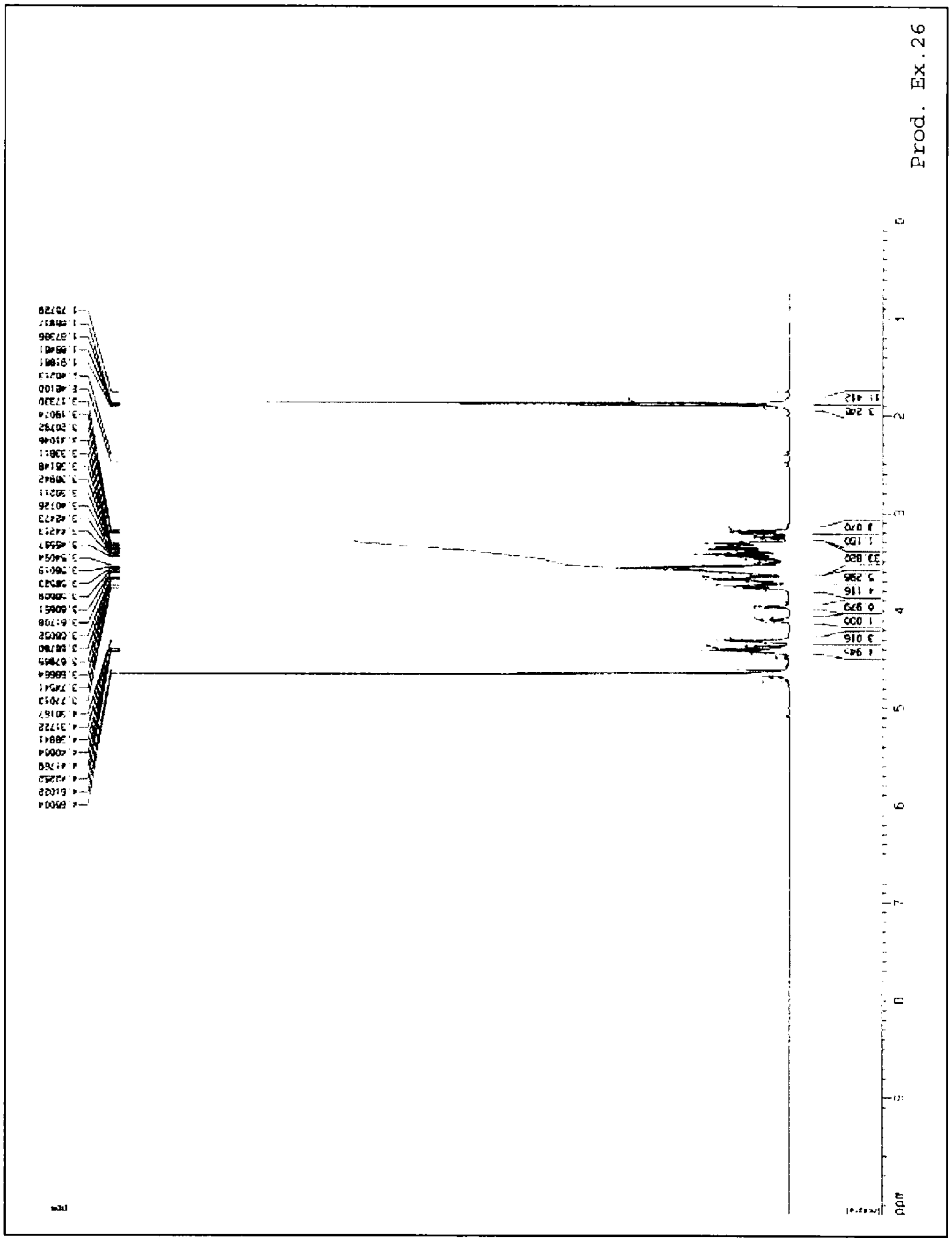
FIG. 24 is a $^1$H-NMR chart of a compound obtained in Production Example 26.

$^1$H-NMR: FIG. 24 illustrates the chart.

TABLE 2

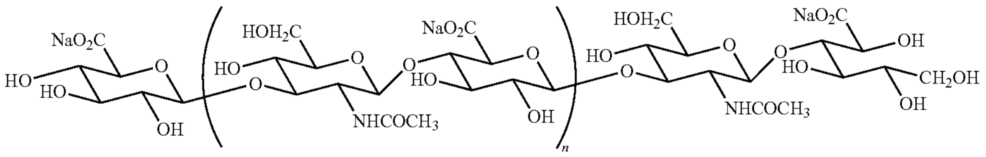

| Production Example No. | n |
|---|---|
| 14 | 0 |
| 15 | 1 |
| 16 | 2 |
| 17 | 3 |
| 18 | 4 |
| 19 | 5 |
| 20 | 6 |
| 21 | 7 |
| 22 | 8 |

Production Example 27

The same reaction process as that in Production Example 23 was performed except that the compound obtained in Production Example 5 (14 mg) was used instead as a material to yield a target product (7 mg, white powder).

MS [M-H]$^-$: 2117.50

Figure 25:
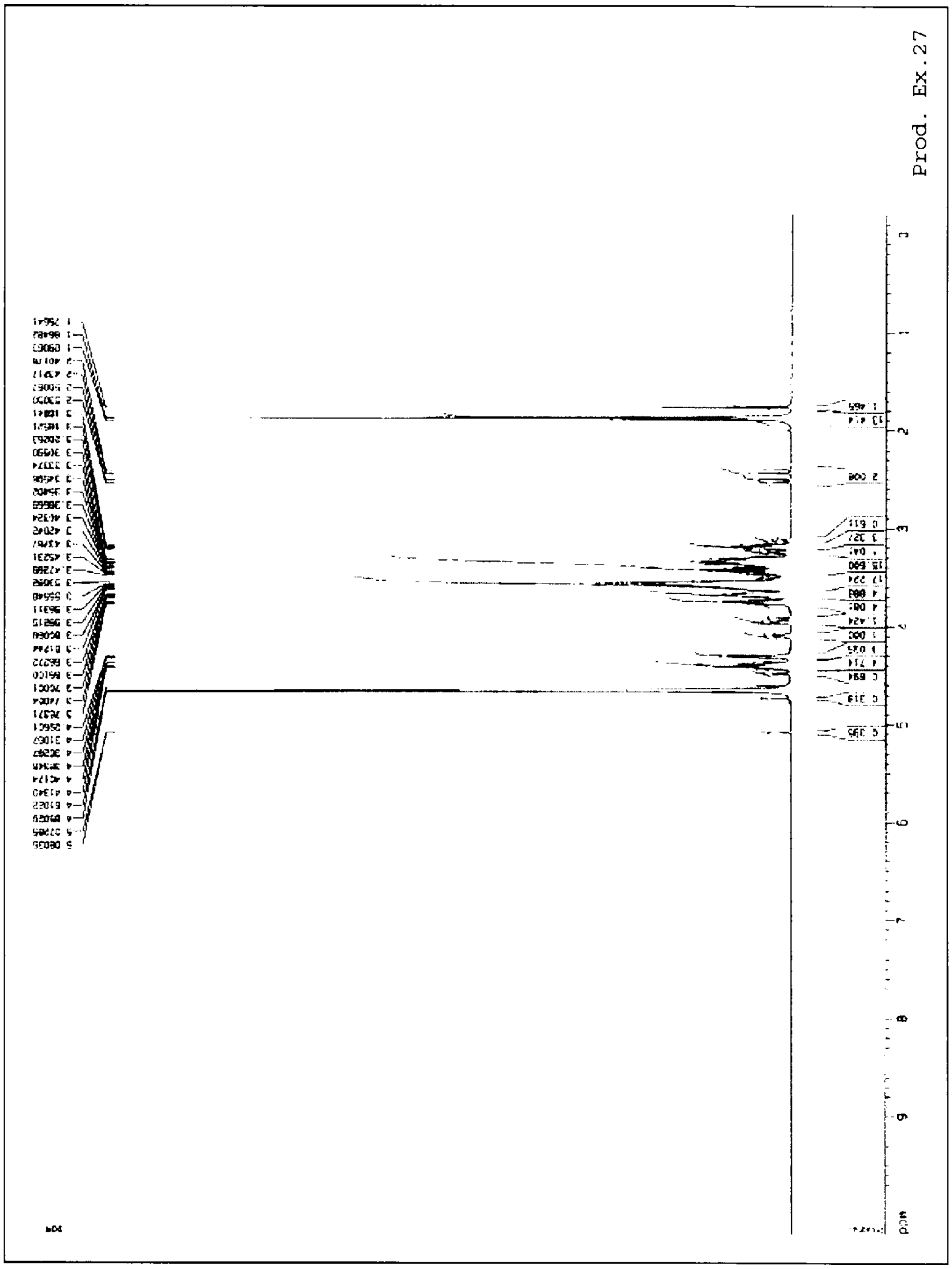
FIG. 25 is a $^1$H-NMR chart of a compound obtained in Production Example 27.

$^1$H-NMR: FIG. 25 illustrates the chart.

Production Example 28

The same reaction process as that in Production Example 23 was performed except that the compound obtained in Production Example 9 (10 mg) was used instead as a material to yield a target product (5 mg, white powder).

MS [M-H]$^-$: 3633.84

Figure 26:
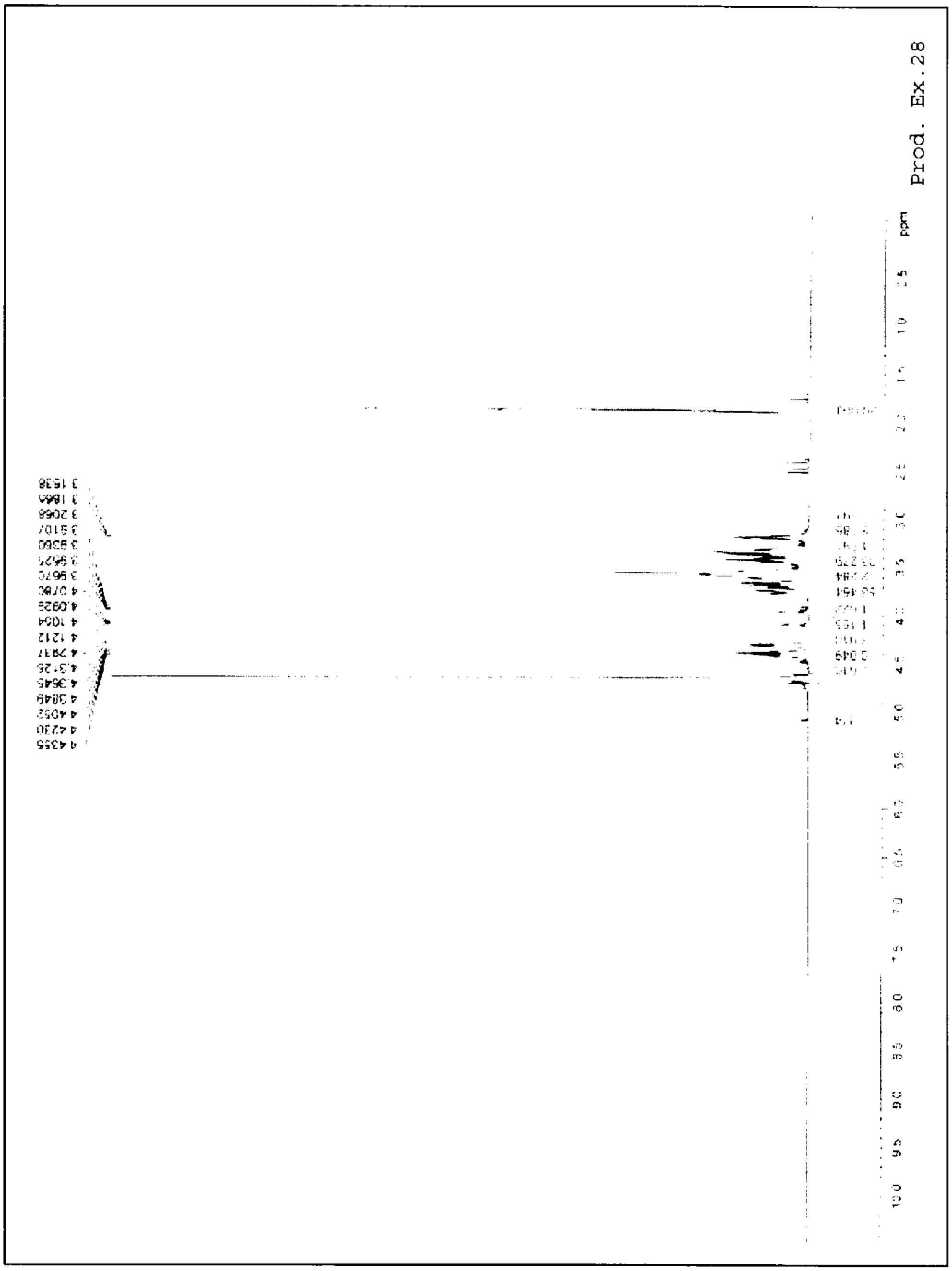
FIG. 26 is a $^1$H-NMR chart of a compound obtained in Production Example 28.

$^1$H-NMR: FIG. 26 illustrates the chart.

The structures of the target products in the Production Examples 23 to 28 are shown in Table 3 below.

TABLE 3

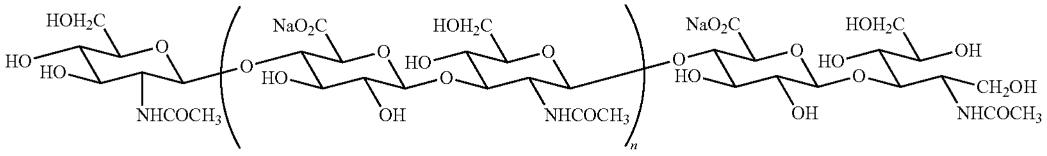

| Production Example No. | n |
|---|---|
| 23 | 0 |
| 24 | 1 |
| 25 | 2 |
| 26 | 3 |
| 27 | 4 |
| 28 | 8 |

Production Example 29

The same reaction process as that in Production Example 23 was performed except that the compound obtained in Production Example 15 (15 mg) was used instead as a material to yield a target product (9 mg, white powder).

MS [M-H]$^-$: 777.28

Figure 27:
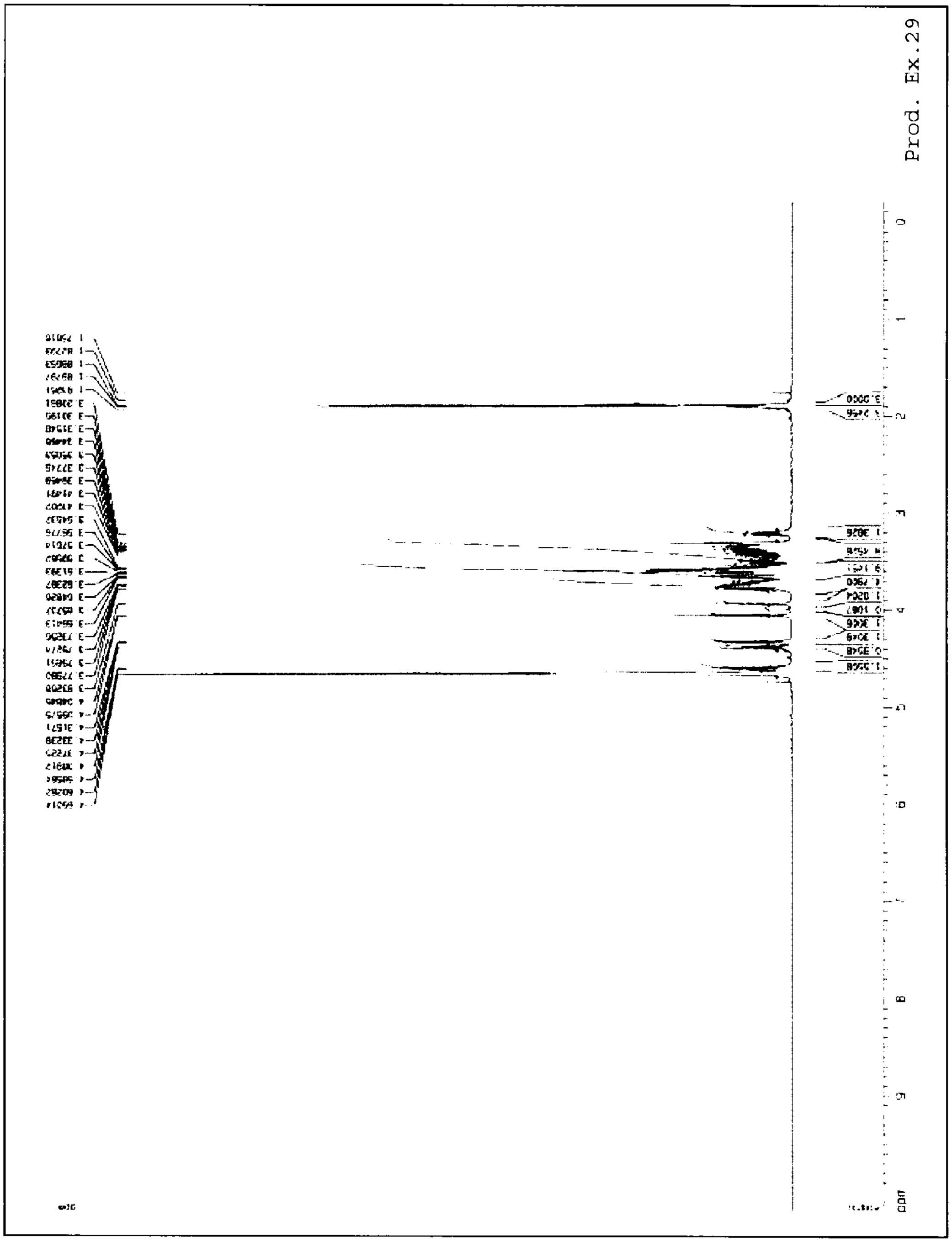
FIG. 27 is a $^1$H-NMR chart of a compound obtained in Production Example 29.

$^1$H-NMR: FIG. 27 illustrates the chart.

Production Example 30

The same reaction process as that in Production Example 23 was performed except that the compound obtained in Production Example 16 (11 mg) was used instead as a material to yield a target product (7 mg, white powder).

MS [M-H]: 1156.41

Figure 28:
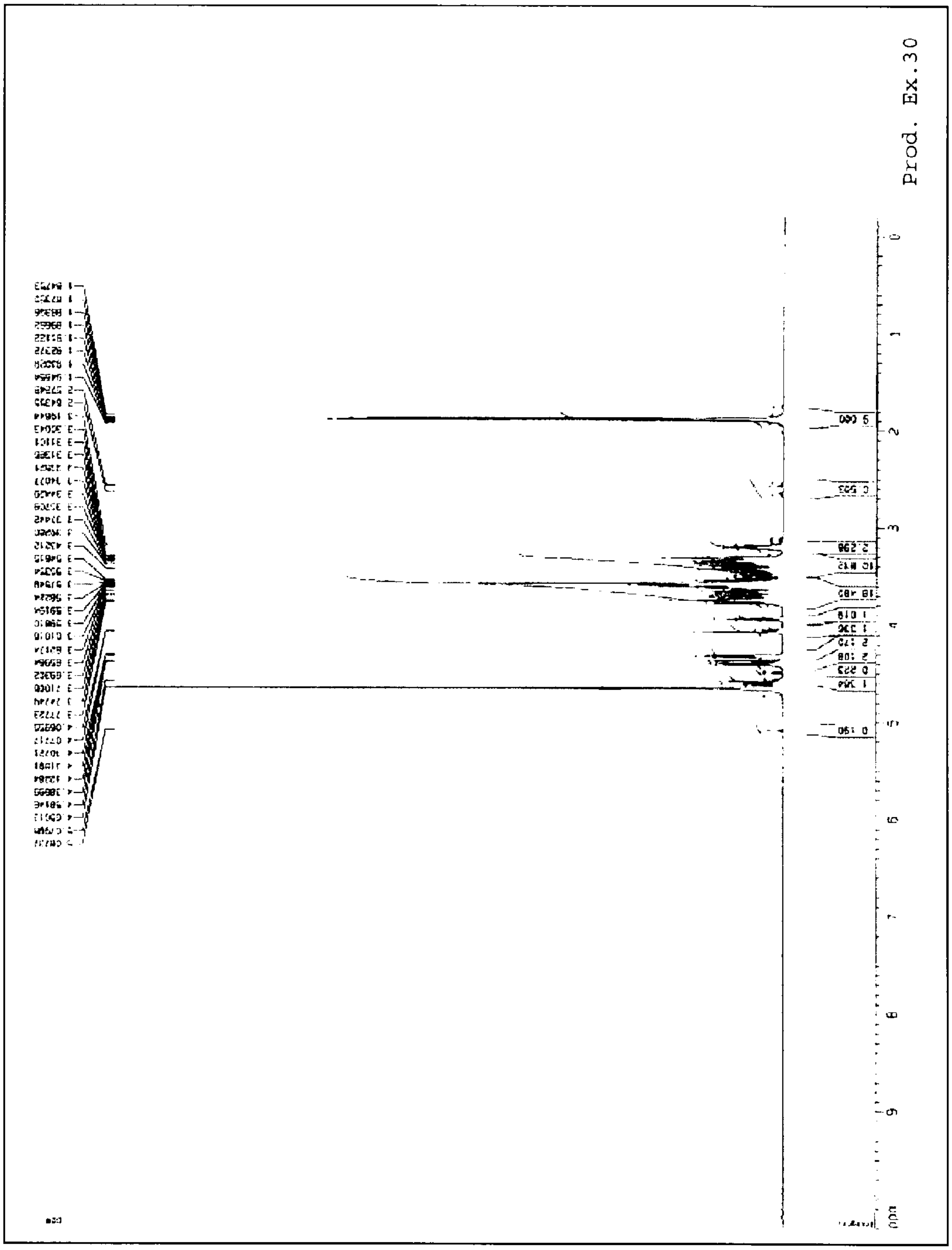
FIG. 28 is a $^1$H-NMR chart of a compound obtained in Production Example 30.

$^1$H-NMR: FIG. 28 illustrates the chart.

Production Example 31

The same reaction process as that in Production Example 23 was performed except that the compound obtained in Production Example 17 (23 mg) was used instead as a material to yield a target product (15 mg, white powder).

MS [M-H]$^-$: 1535.07

Figure 29:
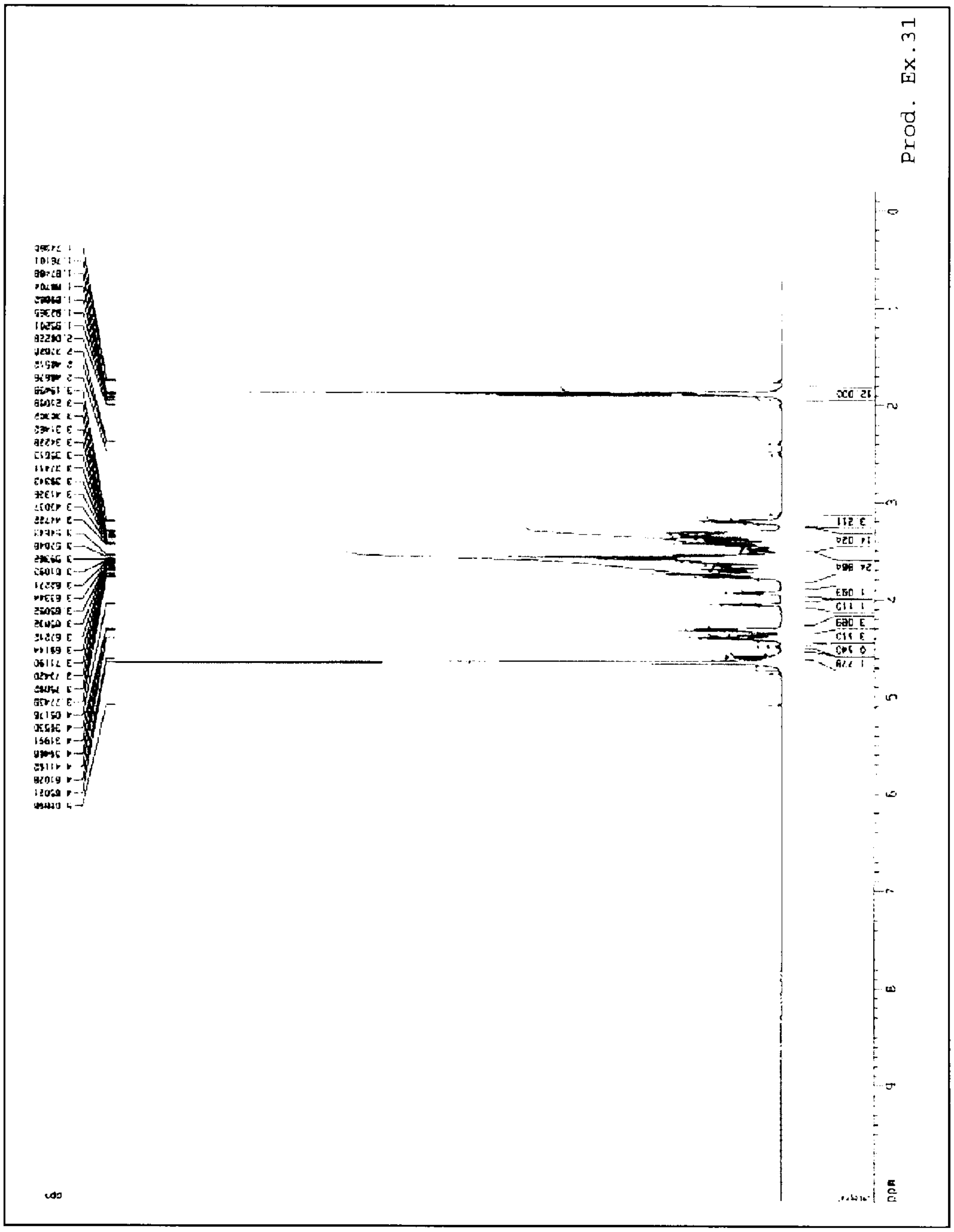
FIG. 29 is a $^1$H-NMR chart of a compound obtained in Production Example 31.

$^1$H-NMR: FIG. 29 illustrates the chart.

Production Example 32

The same reaction process as that in Production Example 23 was performed except that the compound obtained in Production Example 18 (14 mg) was used instead as a material to yield a target product (8 mg, white powder).

MS [M-H]$^-$: 1914.60

Figure 30:
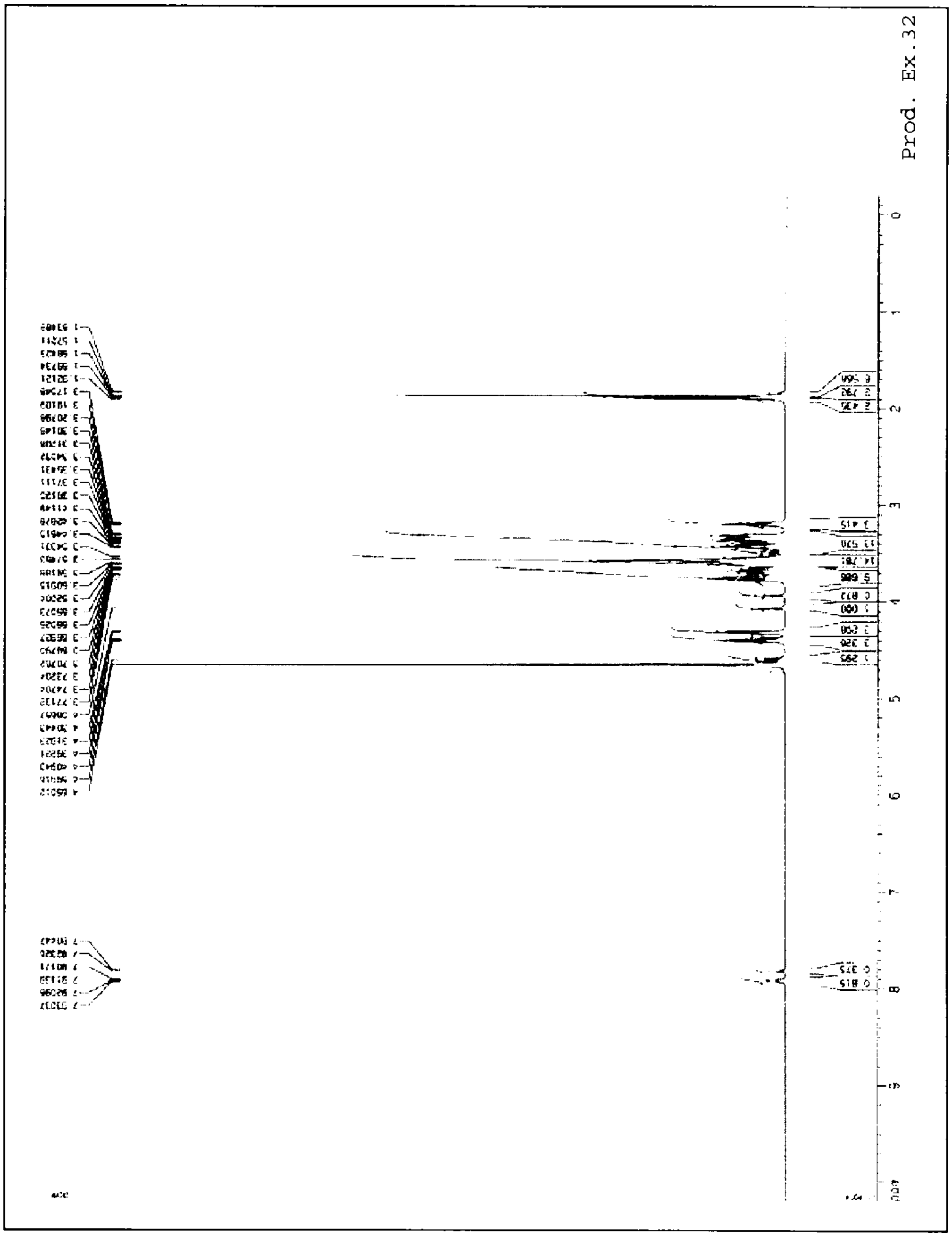
FIG. 30 is a $^1$H-NMR chart of a compound obtained in Production Example 32.

$^1$H-NMR: FIG. 30 illustrates the chart.

Production Example 33

The same reaction process as that in Production Example 23 was performed except that the compound obtained in Production Example 22 (8 mg) was used instead as a material to yield a target product (5 mg, white powder).

MS [M-H]$^-$: 3430.67

Figure 31:
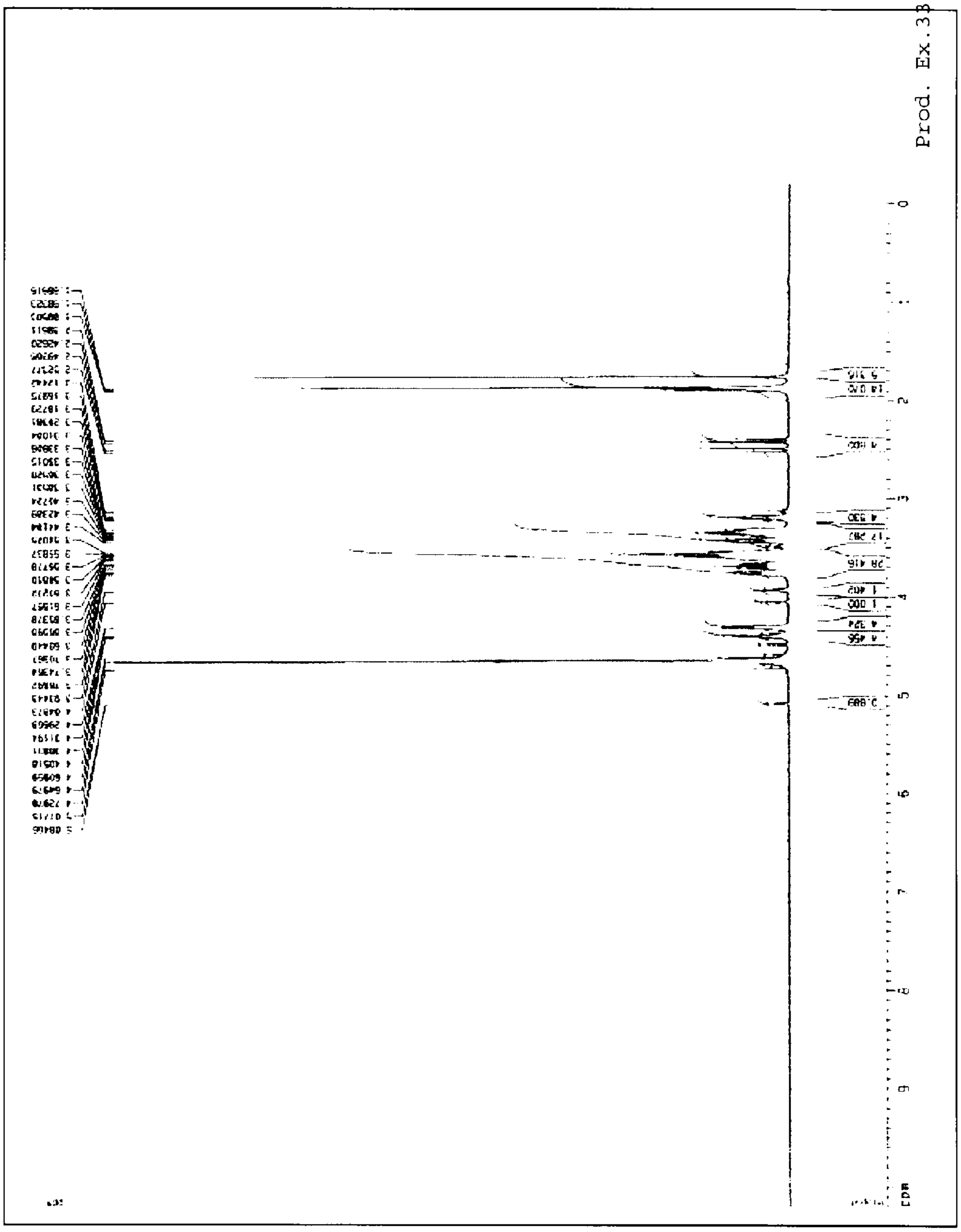
FIG. 31 is a $^1$H-NMR chart of a compound obtained in Production Example 33.

$^1$H-NMR: FIG. 31 illustrates the chart.

The structures of the target products in the Production Examples 29 to 33 are shown in Table 4 below.

TABLE 4

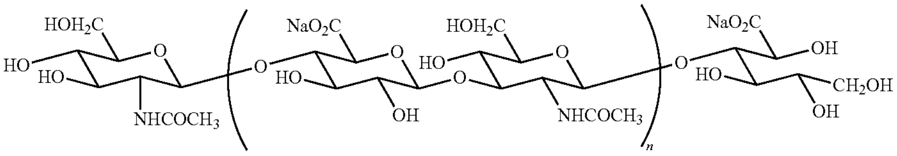

| Production Example No. | n |
|---|---|
| 29 | 1 |
| 30 | 2 |
| 31 | 3 |
| 32 | 4 |
| 33 | 8 |

Production Example 34

Sodium hyaluronate (Hyaluronic Acid FCH-SU, manufactured by FOOD CHEMIFA CO., LTD.) and *Streptomyces hyalurolyticus*-derived hyaluronidase (Hyaluronidase "Amano" 1, manufactured by Amano Enzyme Inc.) were subjected to separation in accordance with the document, Glycobiology, vol. 11, No. 1, pp. 57 to 64, 2001 to yield an unsaturated hyaluronan oligosaccharide 4-mer. The unsaturated hyaluronan oligosaccharide 4-mer (8 mg) was dissolved in methanol (2 ml) and water (1 ml), and sodium borohydride (4 mg) was added to the mixture while cooling with ice, followed by stirring. The temperature of the resultant was warmed to room temperature and the mixture was stirred overnight. The completion of the reaction was confirmed by mass spectrometry. A 10% acetic acid solution in methanol (0.2 ml) was added to the resultant while cooling with ice, and the mixture was then subjected to concentration under reduced pressure. After that, the AKTA system (manufactured by GE Healthcare Bioscience Bioprocess Corp.) was used to apply the concentrate to gel filtration chromatography (G-10, 16 mm×600 mm, water) to perform desalting, and then, target fractions were freeze-dried to yield a target product (3 mg, white powder).

MS $[M-H]^-$: 759.61

Figure 32:
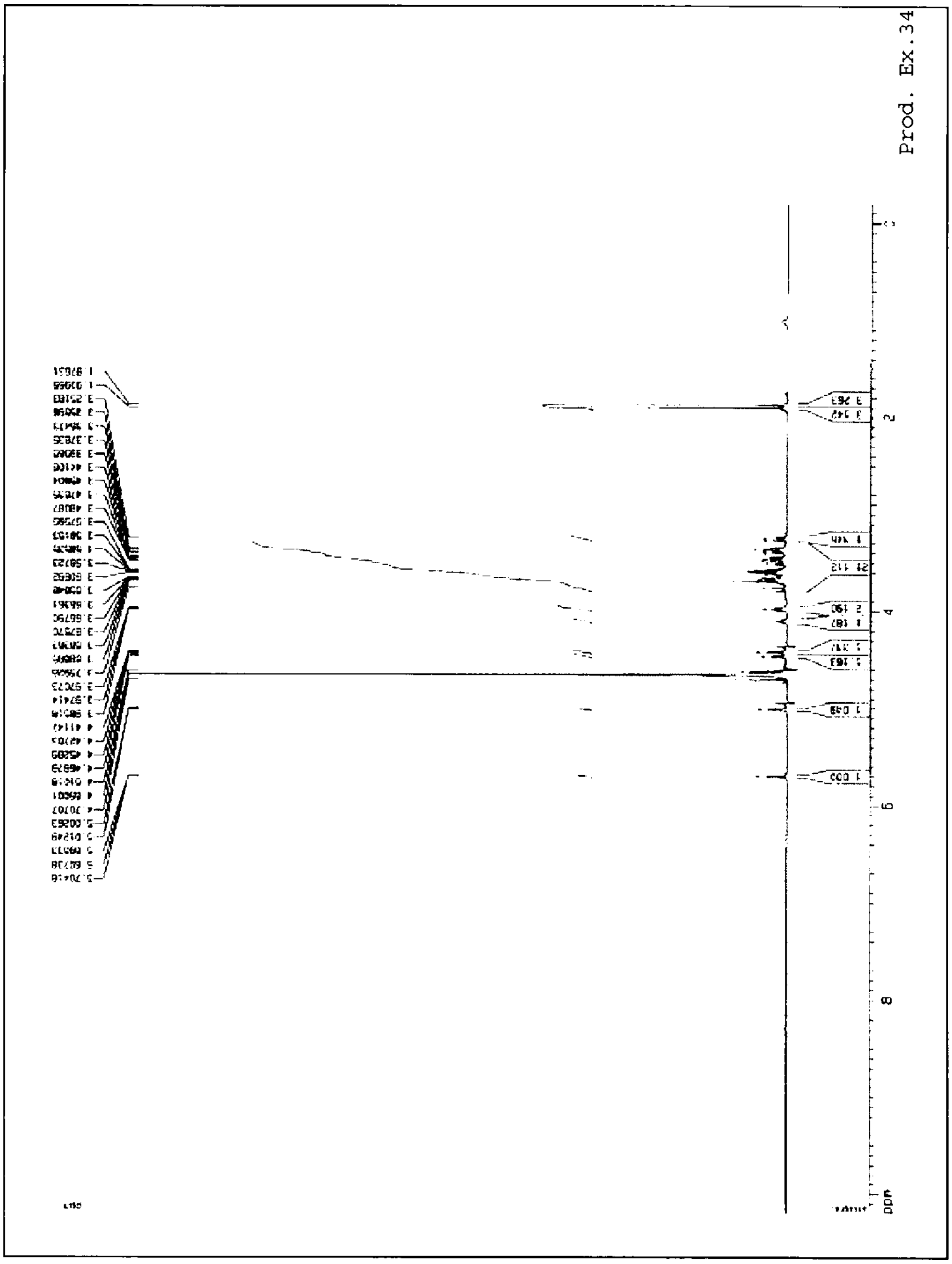
FIG. 32 is a $^1$H-NMR chart of a compound obtained in Production Example 34.

$^1$H-NMR: FIG. 32 illustrates the chart.

Production Example 35

The same reaction process as that in Production Example 34 was performed except that an unsaturated hyaluronan oligosaccharide 6-mer (10 mg) was used instead as a material to yield a target product (9 mg, white powder).

MS $[M-H]^-$: 1139.15

Figure 33:
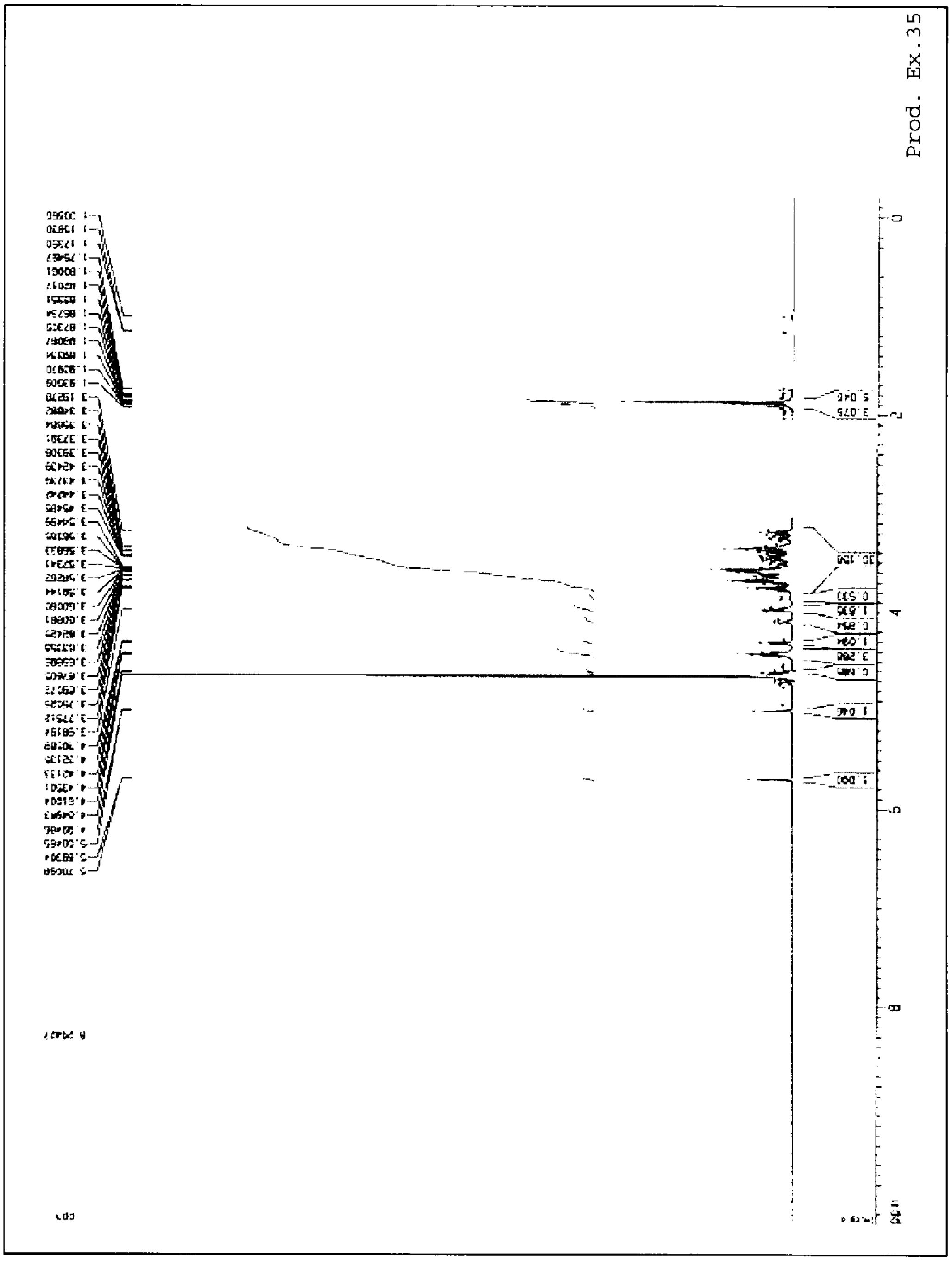
FIG. 33 is a $^1$H-NMR chart of a compound obtained in Production Example 35.

$^1$H-NMR: FIG. 33 illustrates the chart.

Production Example 36

The same reaction process as that in Production Example 34 was performed except that an unsaturated hyaluronan oligosaccharide 8-mer (10 mg) was used instead as a material to yield a target product (10 mg, white powder).

MS $[M-H]^-$: 1518.49

Figure 34:
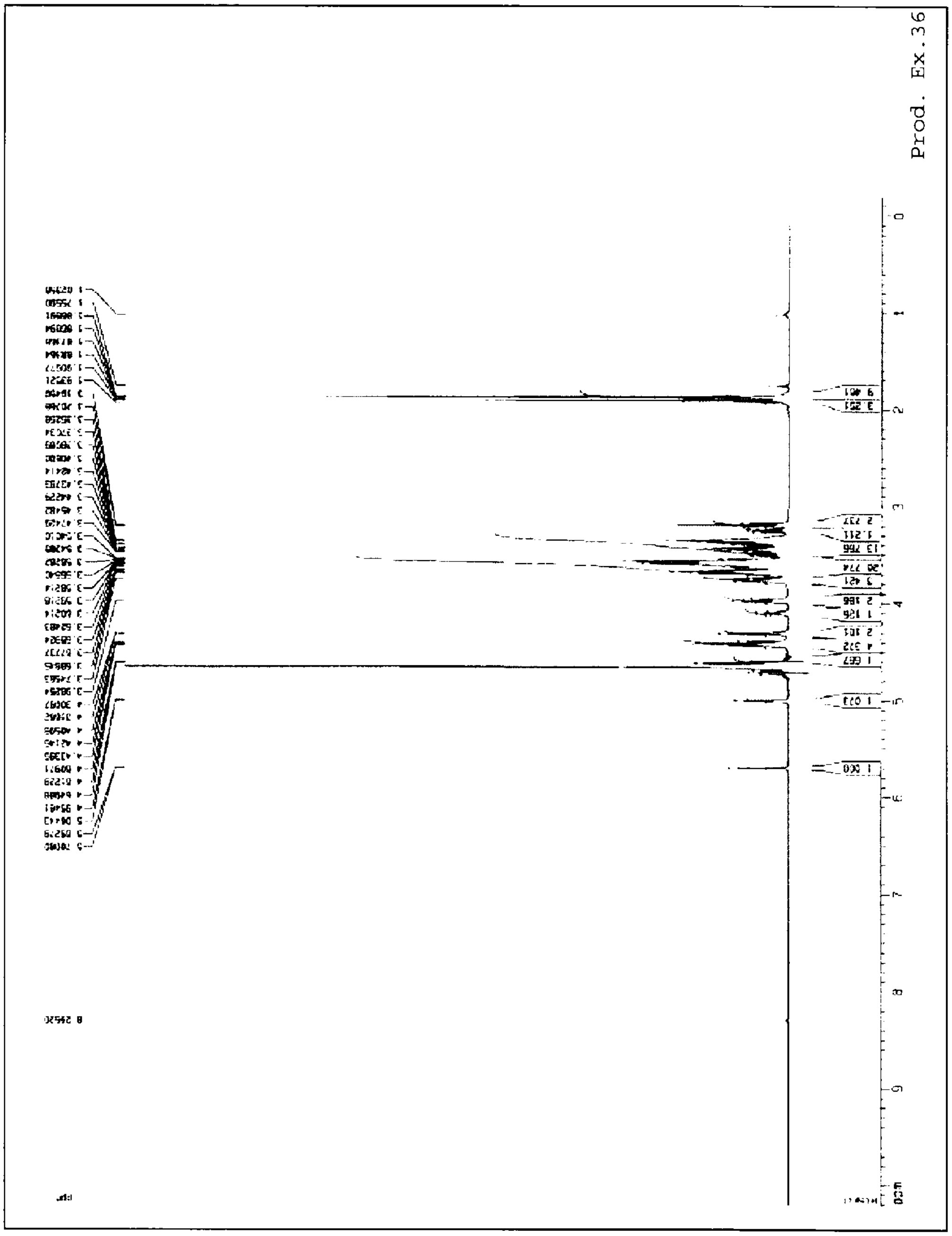
FIG. 34 is a $^1$H-NMR chart of a compound obtained in Production Example 36.

$^1$H-NMR: FIG. 34 illustrates the chart.

Production Example 37

The same reaction process as that in Production Example 34 was performed except that an unsaturated hyaluronan oligosaccharide 10-mer (10 mg) was used instead as a material to yield a target product (10 mg, white powder).

MS $[M-H]^-$: 1897.57

Figure 35:
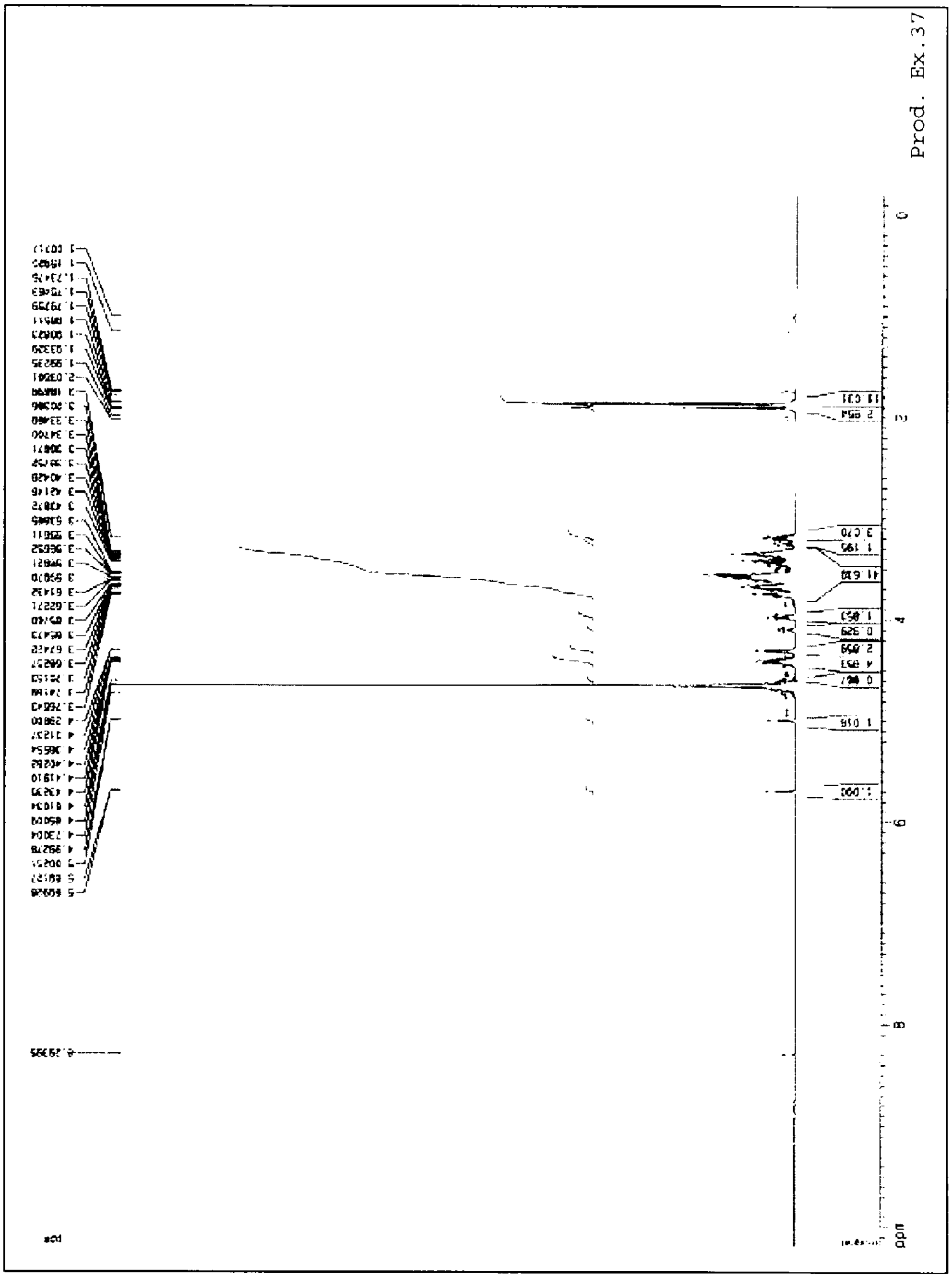
FIG. 35 is a $^1$H-NMR chart of a compound obtained in Production Example 37.

$^1$H-NMR: FIG. 35 illustrates the chart.

Production Example 38

The same reaction process as that in Production Example 34 was performed except that an unsaturated hyaluronan oligosaccharide 12-mer (10 mg) was used instead as a material to yield a target product (8 mg, white powder).

MS $[M-H]^-$: 2276.99

Figure 36:
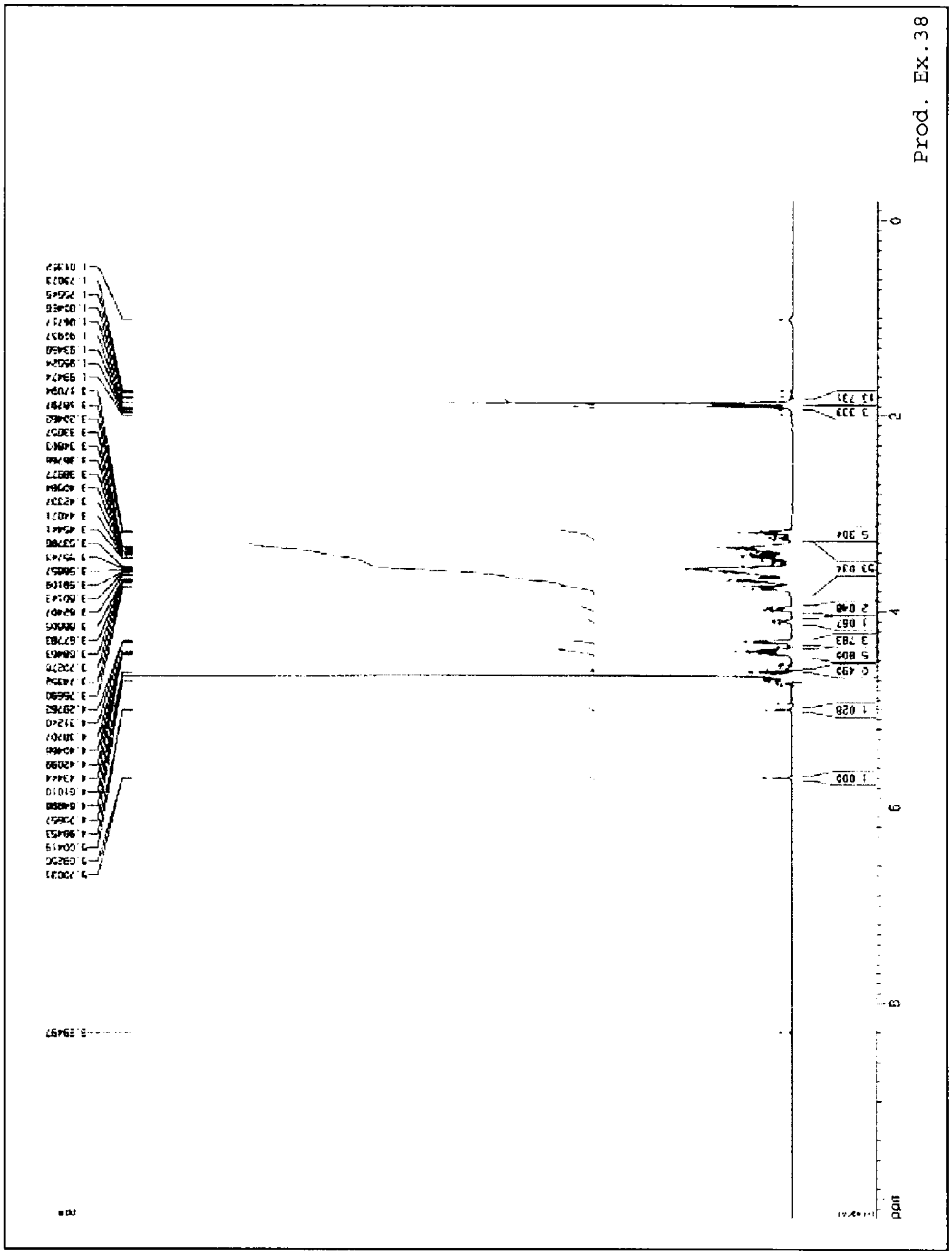
FIG. 36 is a $^1$H-NMR chart of a compound obtained in Production Example 38.

$^1$H-NMR: FIG. 36 illustrates the chart.

Production Example 39

The same reaction process as that in Production Example 34 was performed except that an unsaturated hyaluronan oligosaccharide 20-mer (12 mg) was used instead as a material to yield a target product (10 mg, white powder).

MS $[M-H]^-$: 3792.03

Figure 37:
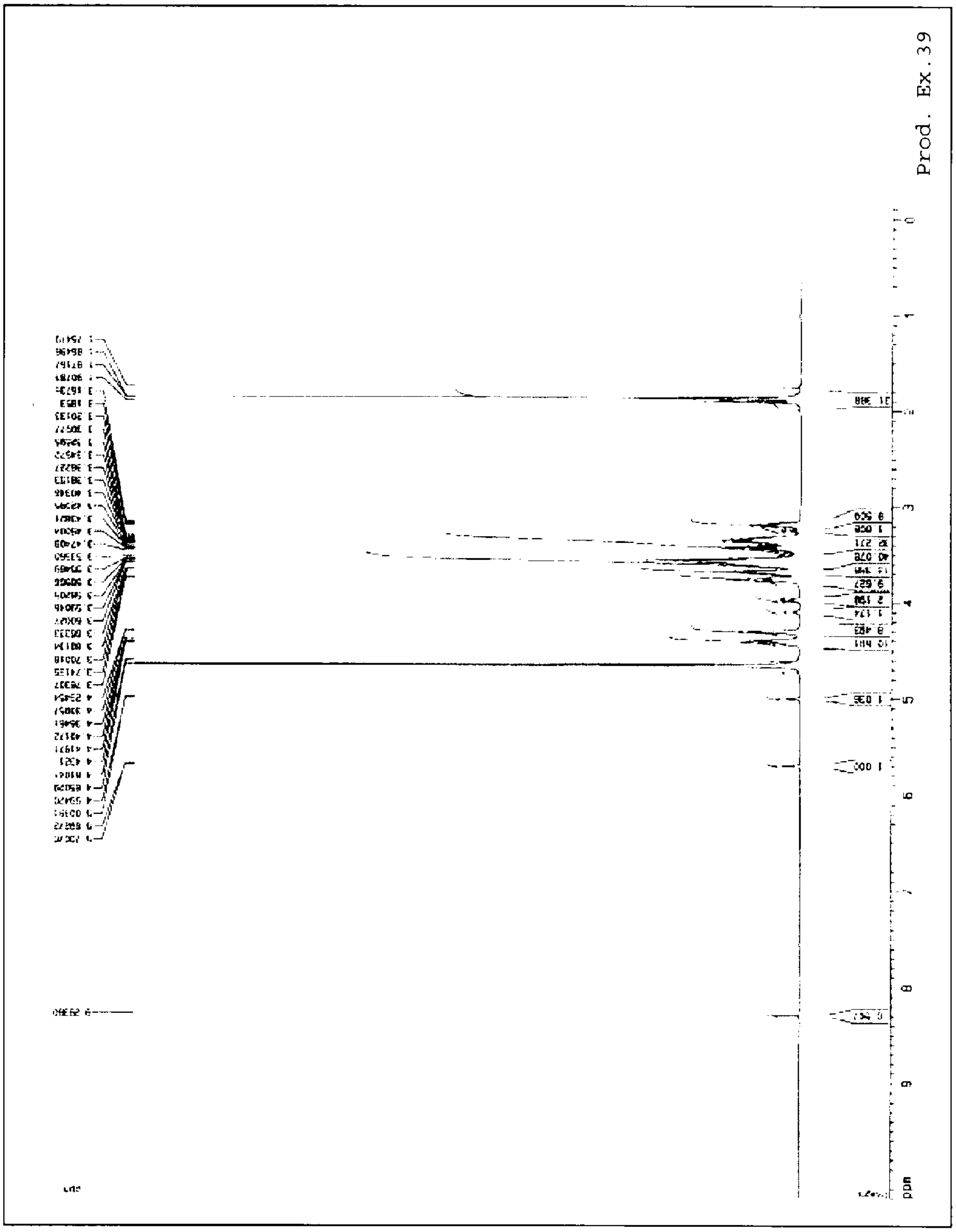
FIG. 37 is a $^1$H-NMR chart of a compound obtained in Production Example 39.

$^1$H-NMR: FIG. 37 illustrates the chart.

The structures of the target products in the Production Examples 34 to 39 are shown in Table 5 below.

TABLE 5

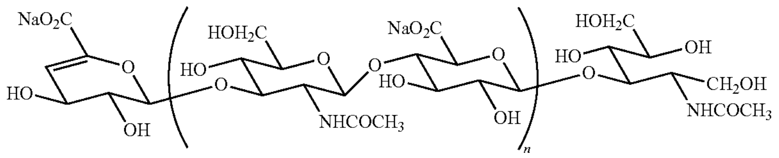

| Production Example No. | n |
|---|---|
| 34 | 1 |
| 35 | 2 |
| 36 | 3 |
| 37 | 4 |
| 38 | 5 |
| 39 | 9 |

Production Example 40

Sodium hyaluronate (Hyaluronic Acid FCH-SU, manufactured by FOOD CHEMIFA CO., LTD.) and *Streptomyces hyalurolyticus*-derived hyaluronidase (Hyaluronidase "Amano" 1, manufactured by Amano Enzyme Inc.) were subjected to separation in accordance with the document, Glycobiology, vol. 11, No. 1, pp. 57 to 64, 2001 to yield an unsaturated hyaluronan oligosaccharide 4-mer. The unsaturated hyaluronan oligosaccharide 4-mer (10 mg) was dissolved in a borate buffer (pH 9.18) (1 ml), and the mixture was stirred at 80° C. for 1 hour. The temperature of the resultant was warmed to room temperature, and methanol (3 ml) was added to the mixture, followed by concentration under reduced pressure. The residue was dissolved in water (2 ml) and the resultant was filtrated through a disk filter (manufactured by Nihon Pall Ltd., 0.45 μm). After that, the AKTA system (manufactured by GE Healthcare Bioscience Bioprocess Corp.) was used to apply the filtrate to gel filtration chromatography (G-10, 16 mm×600 mm, water) to perform desalting, and then, target fractions were concentrated to yield white powders.

Subsequently, the obtained white powders (6 mg) were dissolved in methanol (1 ml) and water (0.5 ml), and sodium borohydride (10 mg) was added to the mixture while cooling with ice, followed by stirring. The temperature of the resultant was warmed to room temperature and the mixture was stirred overnight. The completion of the reaction was confirmed by mass spectrometry. A 10% acetic acid solution in methanol (0.2 ml) was added to the resultant while cooling with ice, and the mixture was then subjected to concentration under reduced pressure. The residue was dissolved in water (2 ml) and the resultant was filtrated through a disk filter (manufactured by Nihon Pall Ltd., 0.45 μm). After that, the AKTA system (manufactured by GE Healthcare Bioscience Bioprocess Corp.) was used to apply the filtrate to gel filtration chromatography (G-10, 16 mm×600 mm, water) to perform desalting, and then, target fractions were freeze-dried to yield a target product (4 mg, white powder).

MS $[M-H]^-$: 556.77

Figure 38:
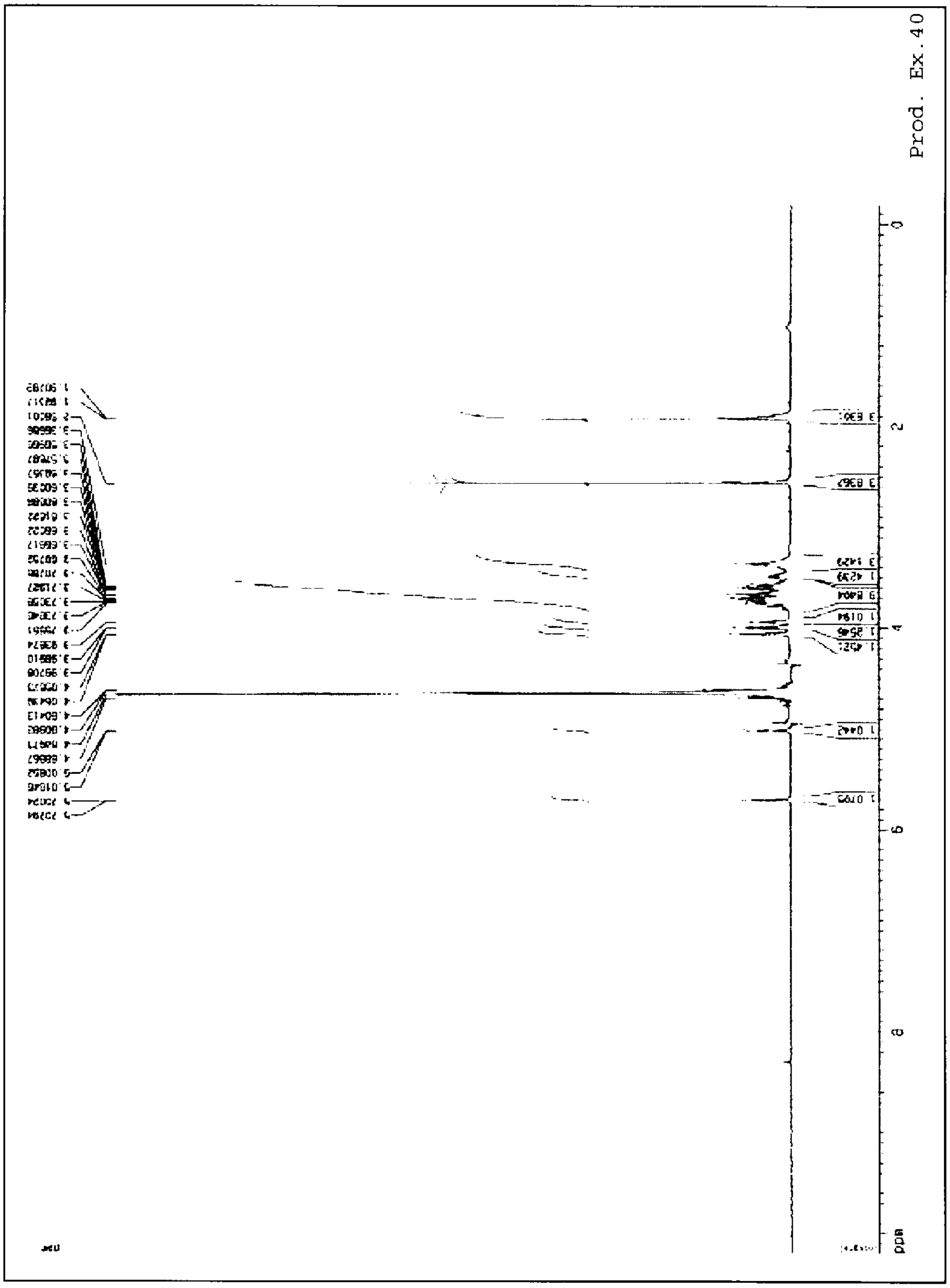
FIG. 38 is a $^1$H-NMR chart of a compound obtained in Production Example 40.

$^1$H-NMR: FIG. 38 illustrates the chart.

Production Example 41

The same reaction process as that in Production Example 40 was performed except that an unsaturated hyaluronan oligosaccharide 6-mer (10 mg) was used instead as a material to yield a target product (7 mg, white powder).

MS $[M-H]^-$: 935.49

Figure 39:
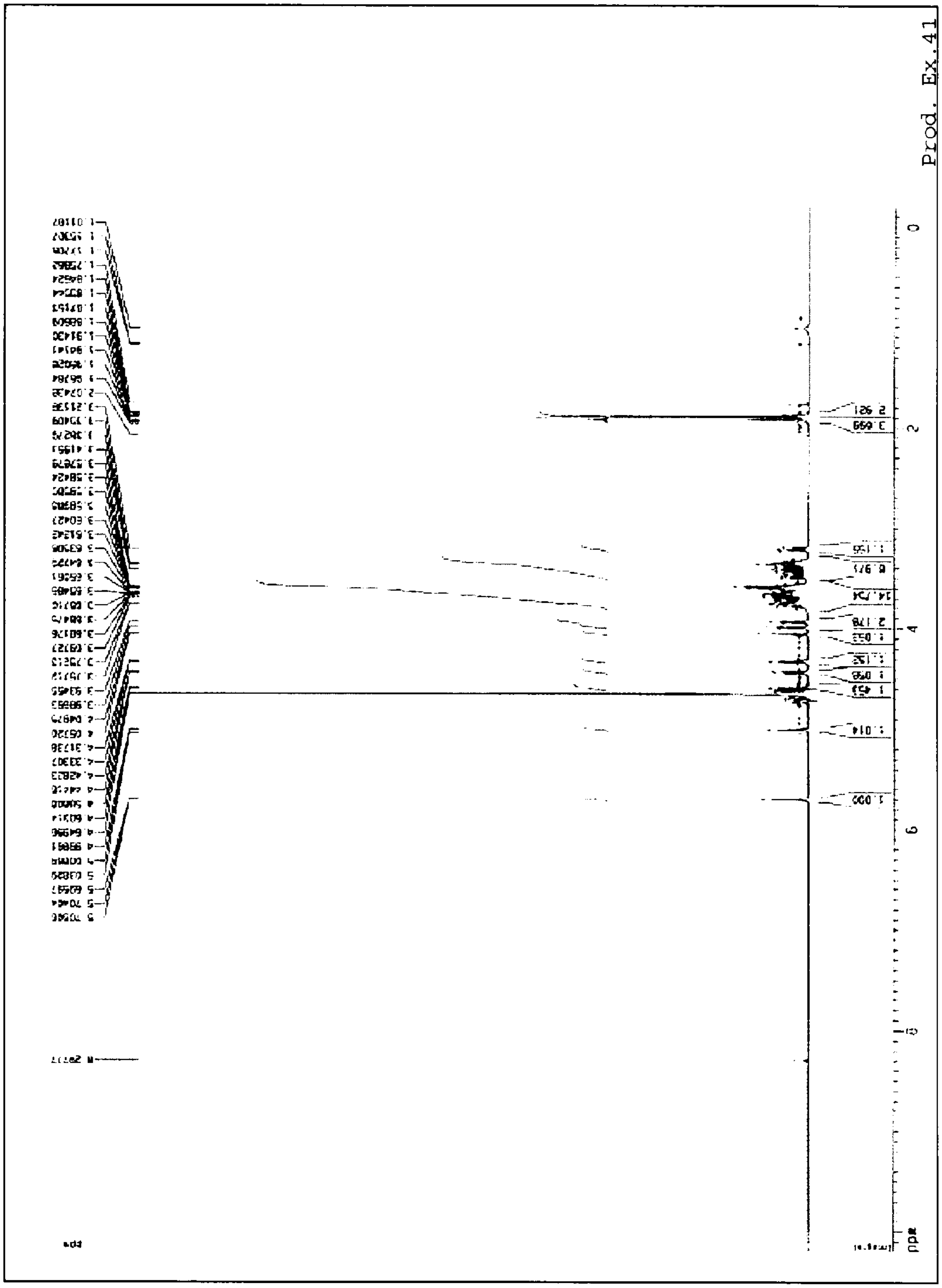
FIG. 39 is a $^1$H-NMR chart of a compound obtained in Production Example 41.

$^1$H-NMR: FIG. 39 illustrates the chart.

Production Example 42

The same reaction process as that in Production Example 40 was performed except that an unsaturated hyaluronan oligosaccharide 8-mer (10 mg) was used instead as a material to yield a target product (6 mg, white powder).

MS $[M-H]^-$: 1314.21

Figure 40:
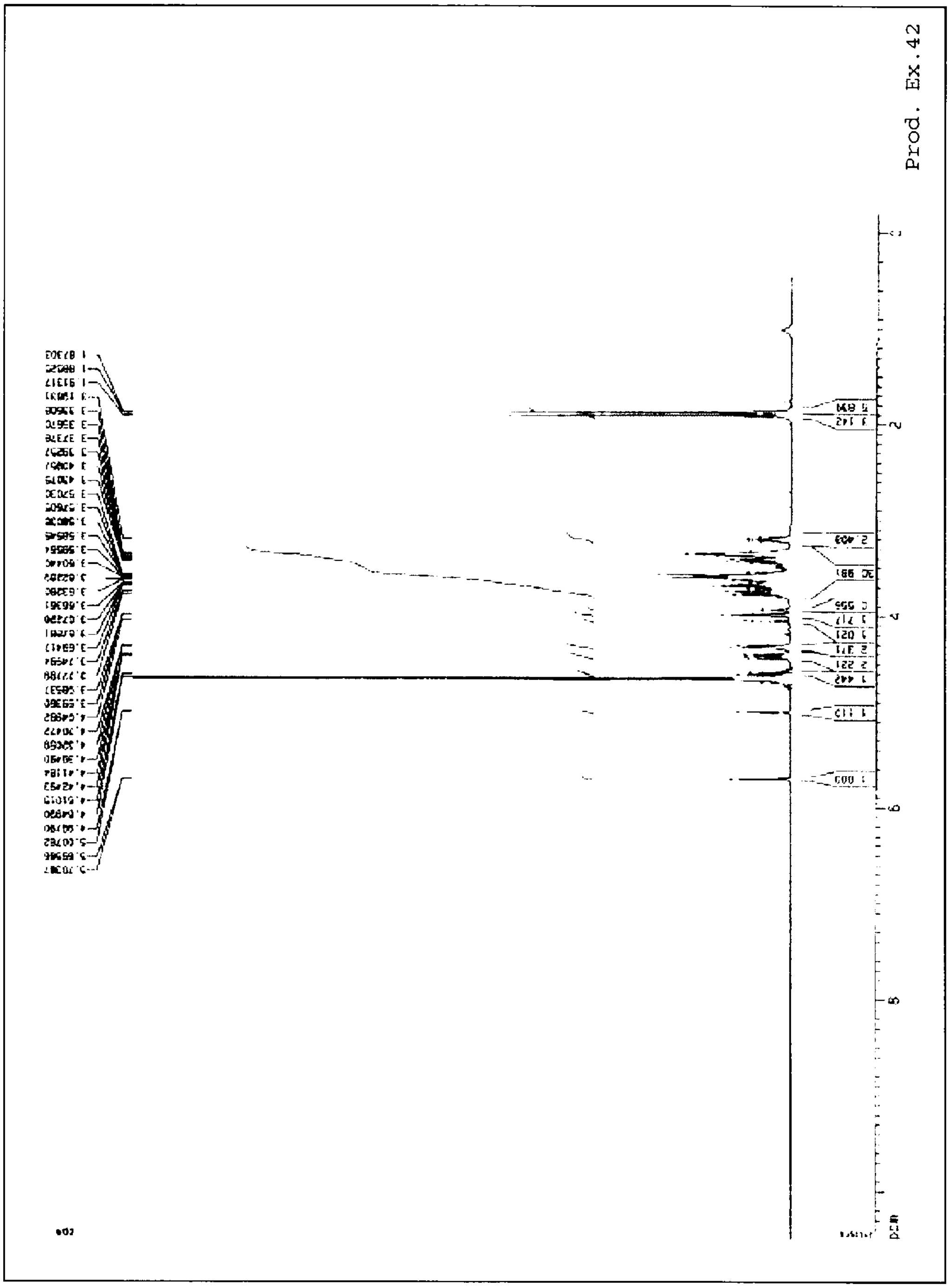
FIG. 40 is a $^1$H-NMR chart of a compound obtained in Production Example 42.

$^1$H-NMR: FIG. 40 illustrates the chart.

Production Example 43

The same reaction process as that in Production Example 40 was performed except that an unsaturated hyaluronan oligosaccharide 10-mer (10 mg) was used instead as a material to yield a target product (7 mg, white powder).

MS $[M-H]^-$: 1693.58

Figure 41:
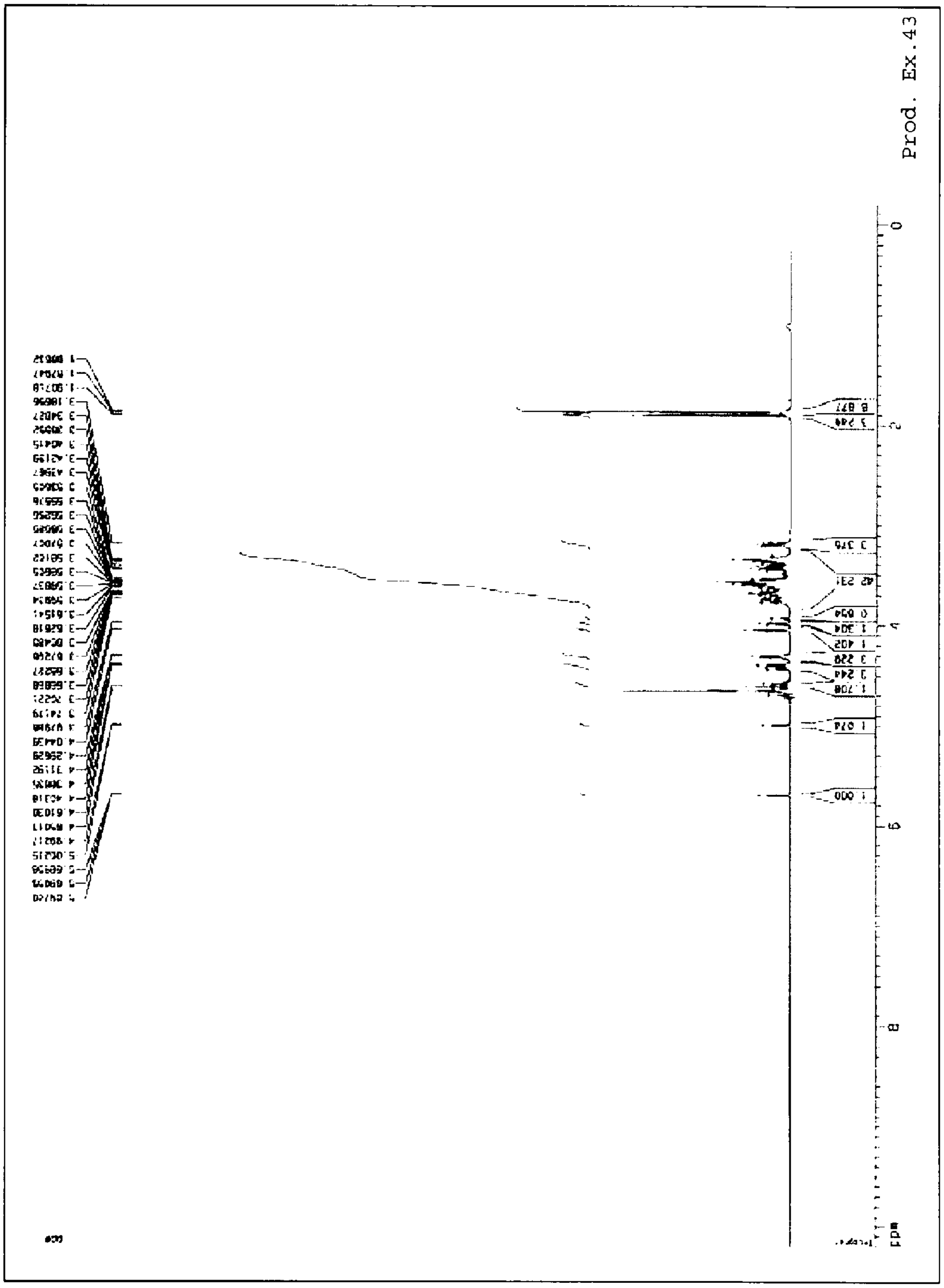
FIG. 41 is a $^1$H-NMR chart of a compound obtained in Production Example 43.

$^1$H-NMR: FIG. 41 illustrates the chart.

Production Example 44

The same reaction process as that in Production Example 40 was performed except that an unsaturated hyaluronan oligosaccharide 12-mer (10 mg) was used instead as a material to yield a target product (6 mg, white powder).

MS $[M-H]^-$: 2073.41

Figure 42:
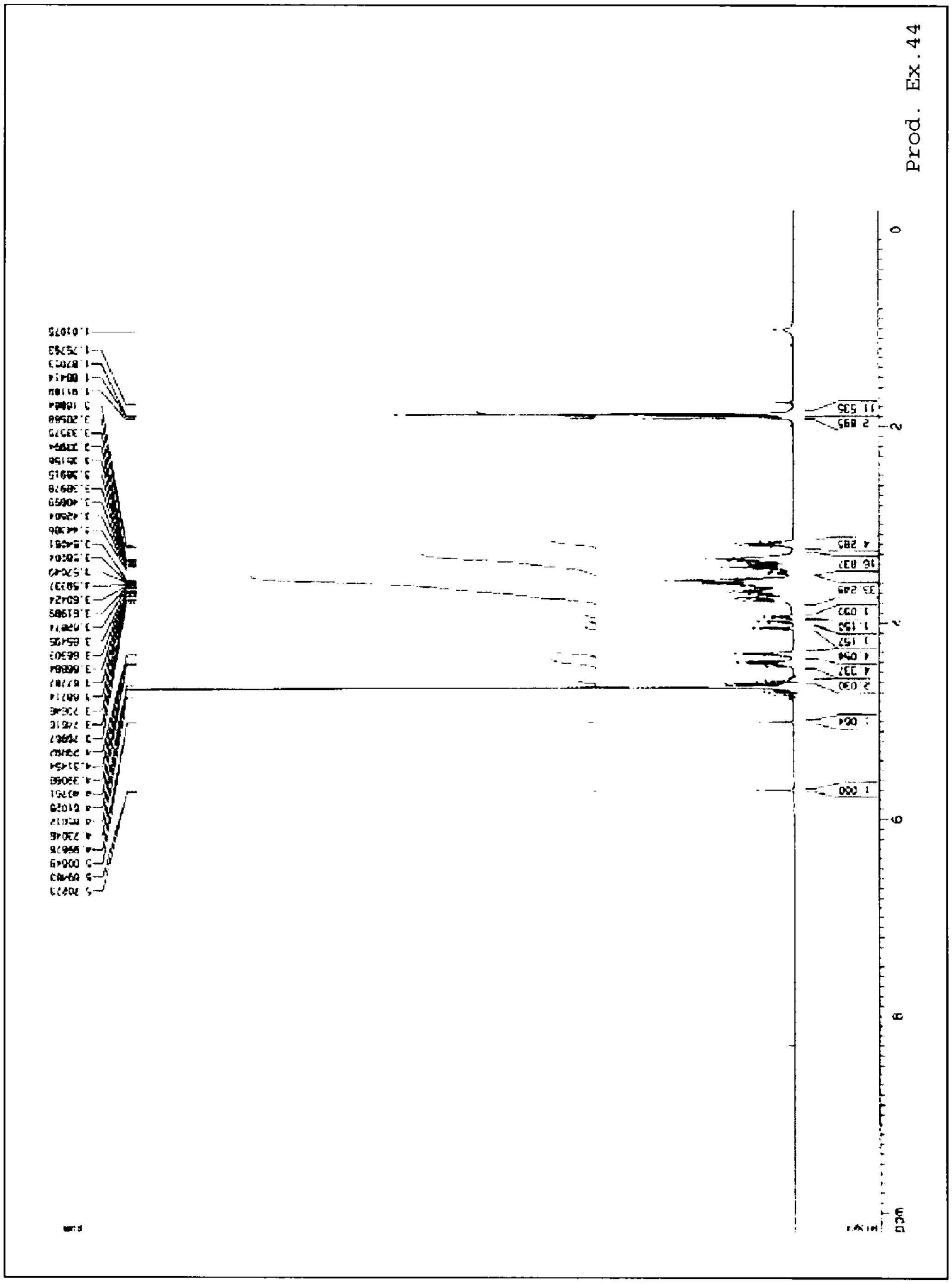
FIG. 42 is a $^1$H-NMR chart of a compound obtained in Production Example 44.

$^1$H-NMR: FIG. 42 illustrates the chart.

The structures of the target products in the Production Examples 40 to 44 are shown in Table 6 below.

TABLE 6

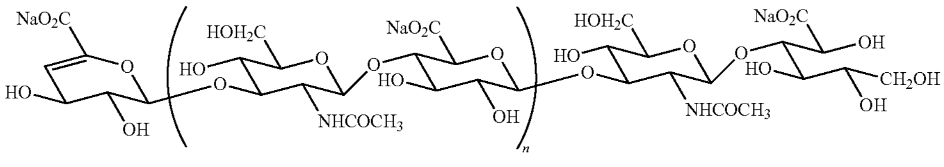

| Production Example No. | n |
|---|---|
| 40 | 0 |
| 41 | 1 |
| 42 | 2 |
| 43 | 3 |
| 44 | 4 |

Production Example 45

To a hyaluronan oligosaccharide 4-mer (10 mg), a solution in which benzylamine (24 mg), boronic acid (20 mg), sodium acetate (40 mg), and sodium cyanotrihydridoborate (15 mg) were dissolved in methanol (0.5 ml) and water (0.5 ml) was added, followed by stirring at 50° C. for 6 hours. The completion of the reaction was confirmed by mass spectrometry.

The resultant was concentrated under reduced pressure, and the residue was dissolved in water (2 ml). Then, the mixture was filtrated through a disk filter (manufactured by Nihon Pall Ltd., 0.45 μm). The filtrate was applied to gel filtration chromatography (G-10, 16 mm×600 mm, water) to perform purification, and then target fractions were freeze-dried to yield a target product (8 mg, white powder).

Figure 43:
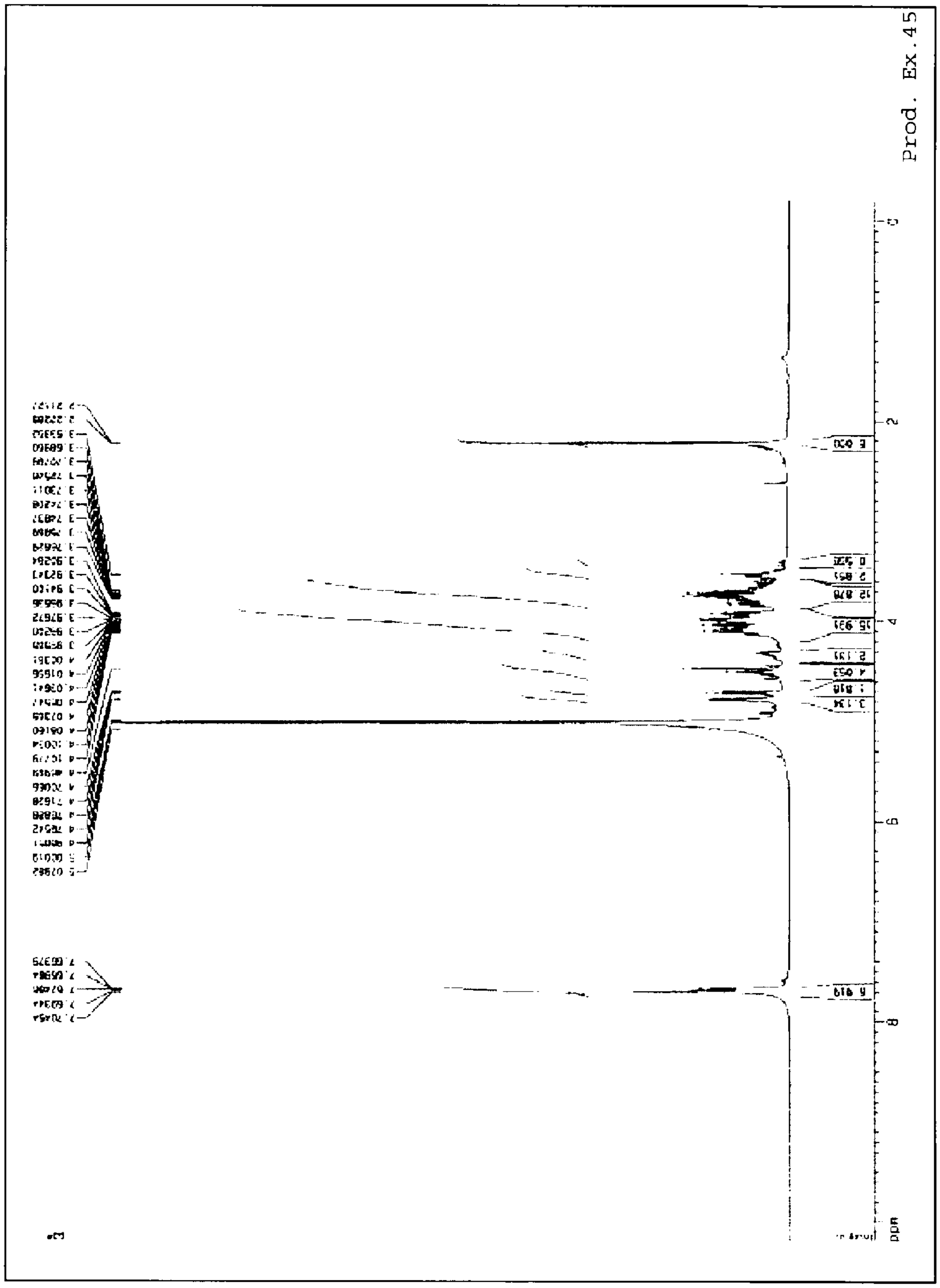
FIG. 43 is a $^1$H-NMR chart of a compound obtained in Production Example 45.

$^1$H-NMR: FIG. 43 illustrates the chart.

Production Example 46

To a hyaluronan oligosaccharide 4-mer (10 mg), a solution in which phenylalanine (5 mg), acetic acid (10 μl), sodium acetate (10 mg), and sodium cyanotrihydridoborate (10 mg) were dissolved in methanol (0.2 ml) and water (0.2 ml) was added, followed by stirring at 60° C. for 6 hours. The completion of the reaction was confirmed by mass spectrometry.

After the resultant was concentrated under reduced pressure, dichloromethane (5 ml) and water (5 ml) were added to the residue to be extracted. After the aqueous phase was concentrated under reduced pressure, and the resultant was dissolved in water (2 ml). Then, the mixture was filtrated through a disk filter (manufactured by Nihon Pall Ltd., 0.45 μm). The filtrate was applied to gel filtration chromatography (G-10, 16 mm×600 mm, water) to perform purification, and then target fractions were freeze-dried to yield a target product (11 mg, white powder).

Figure 44:
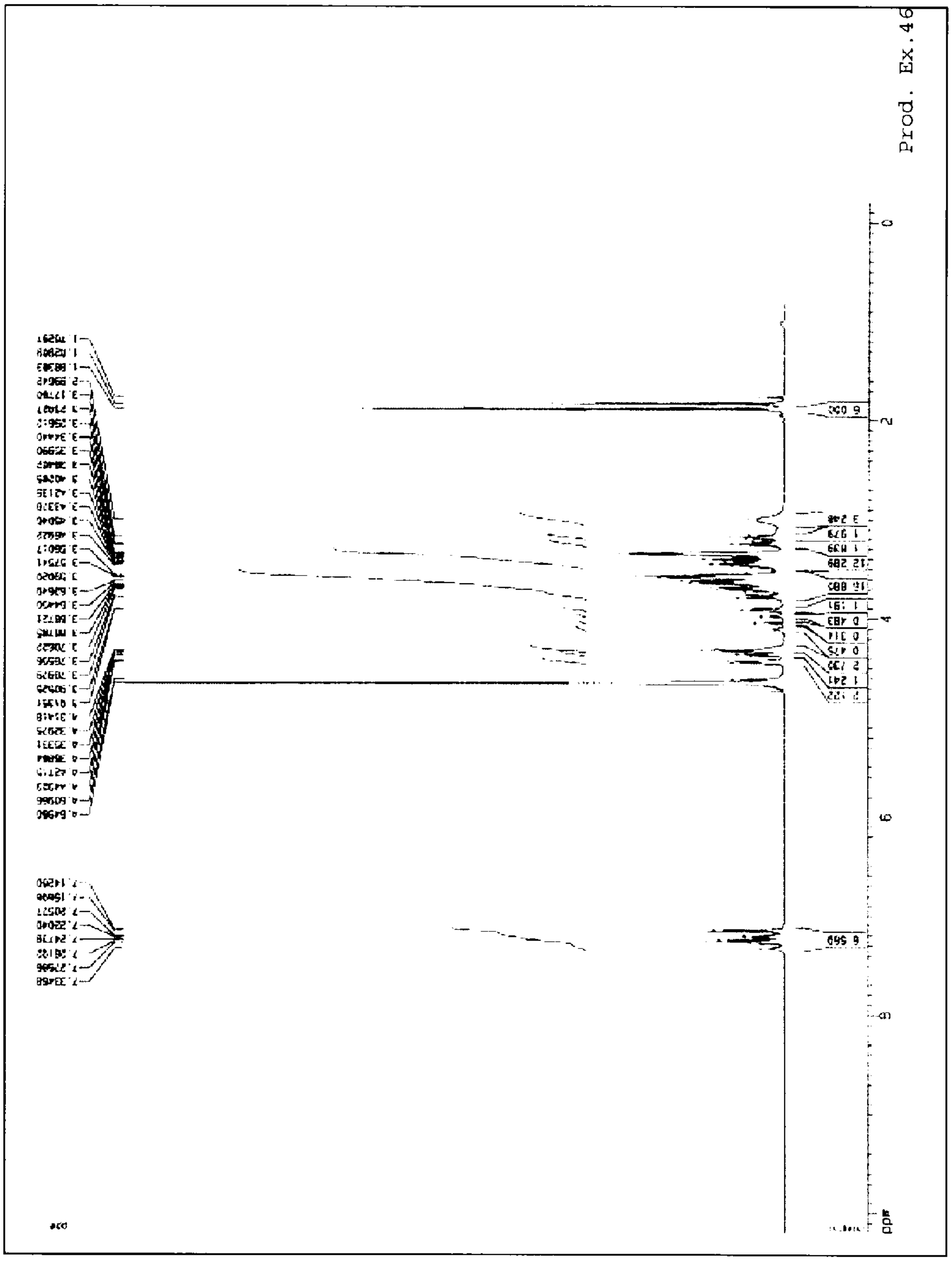
FIG. 44 is a $^1$H-NMR chart of a compound obtained in Production Example 46.

$^1$H-NMR: FIG. 44 illustrates the chart.

Production Example 47

The same reaction process as that in Production Example 46 was performed except that proline was used instead of phenylalanine to yield a target product (8 mg, white powder).

Figure 45:
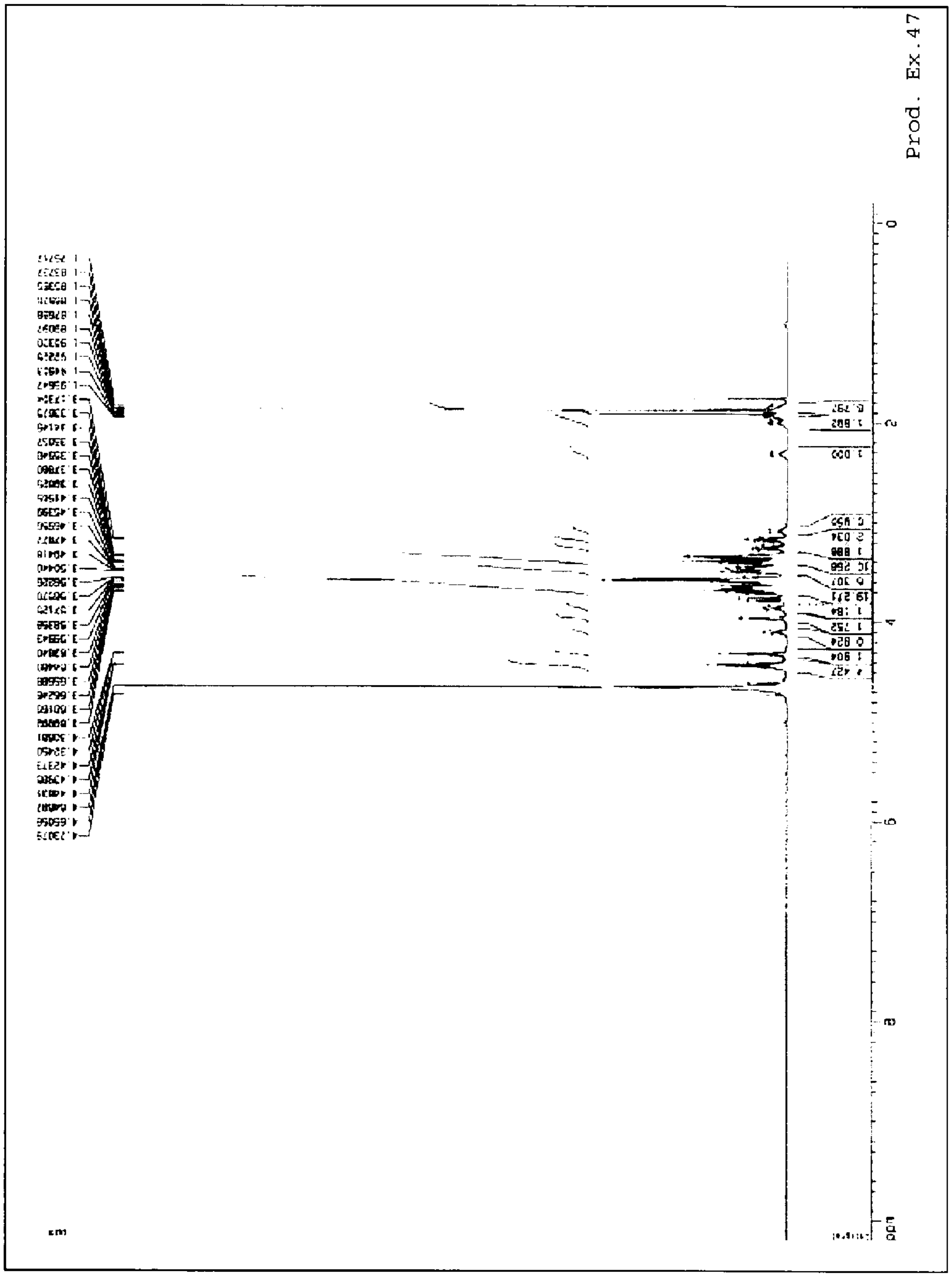
FIG. 45 is a $^1$H-NMR chart of a compound obtained in Production Example 47.

$^1$H-NMR: FIG. 45 illustrates the chart.

Production Example 48

The same reaction process as that in Production Example 46 was performed except that tryptophan was used instead of phenylalanine to yield a target product (7 mg, white powder).

Figure 46:
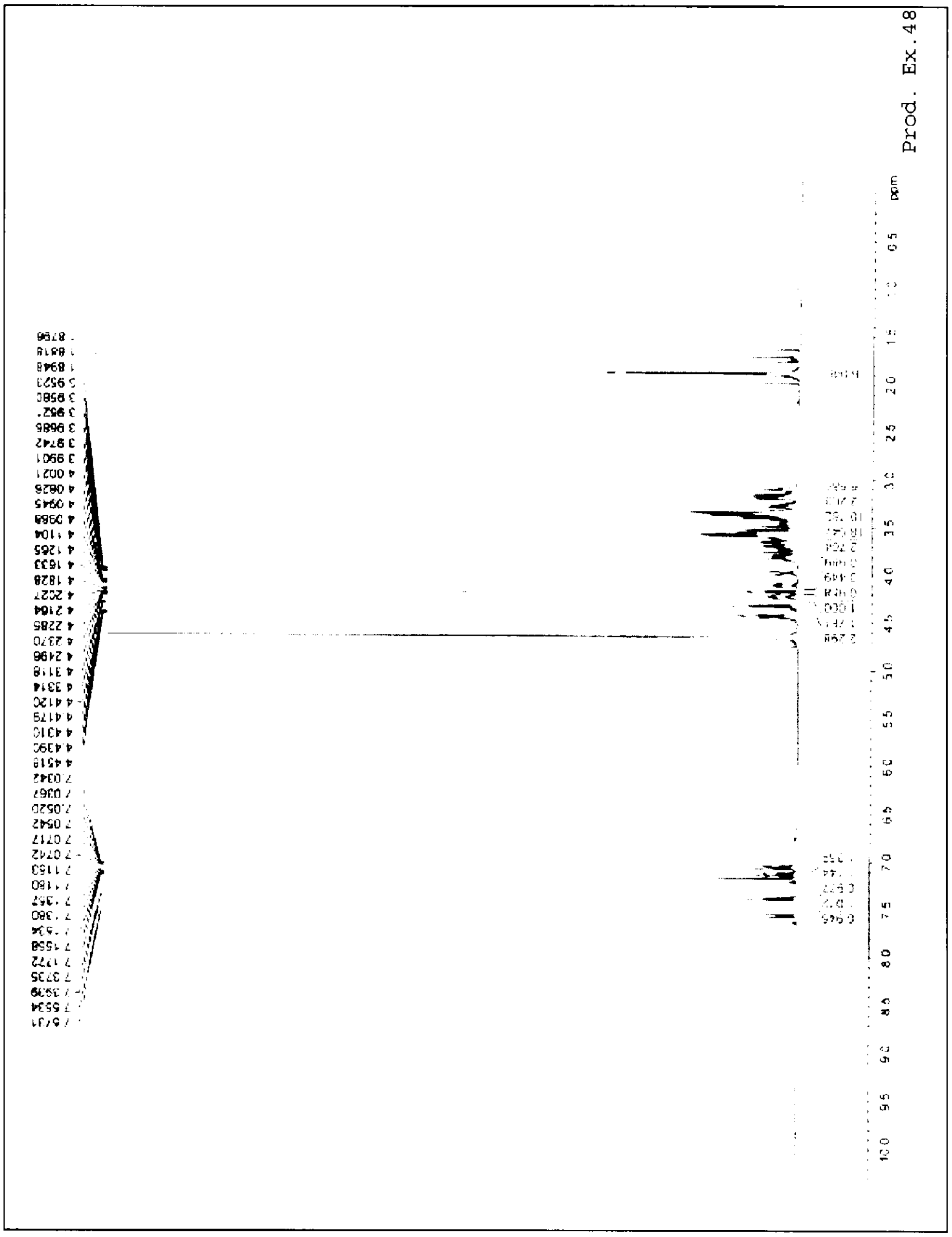
FIG. 46 is a $^1$H-NMR chart of a compound obtained in Production Example 48.

$^1$H-NMR: FIG. 46 illustrates the chart.

Production Example 49

The same reaction process as that in Production Example 46 was performed except that glycylphenylalanine amide was used instead of phenylalanine to yield a target product (4 mg, white powder).

Figure 47:
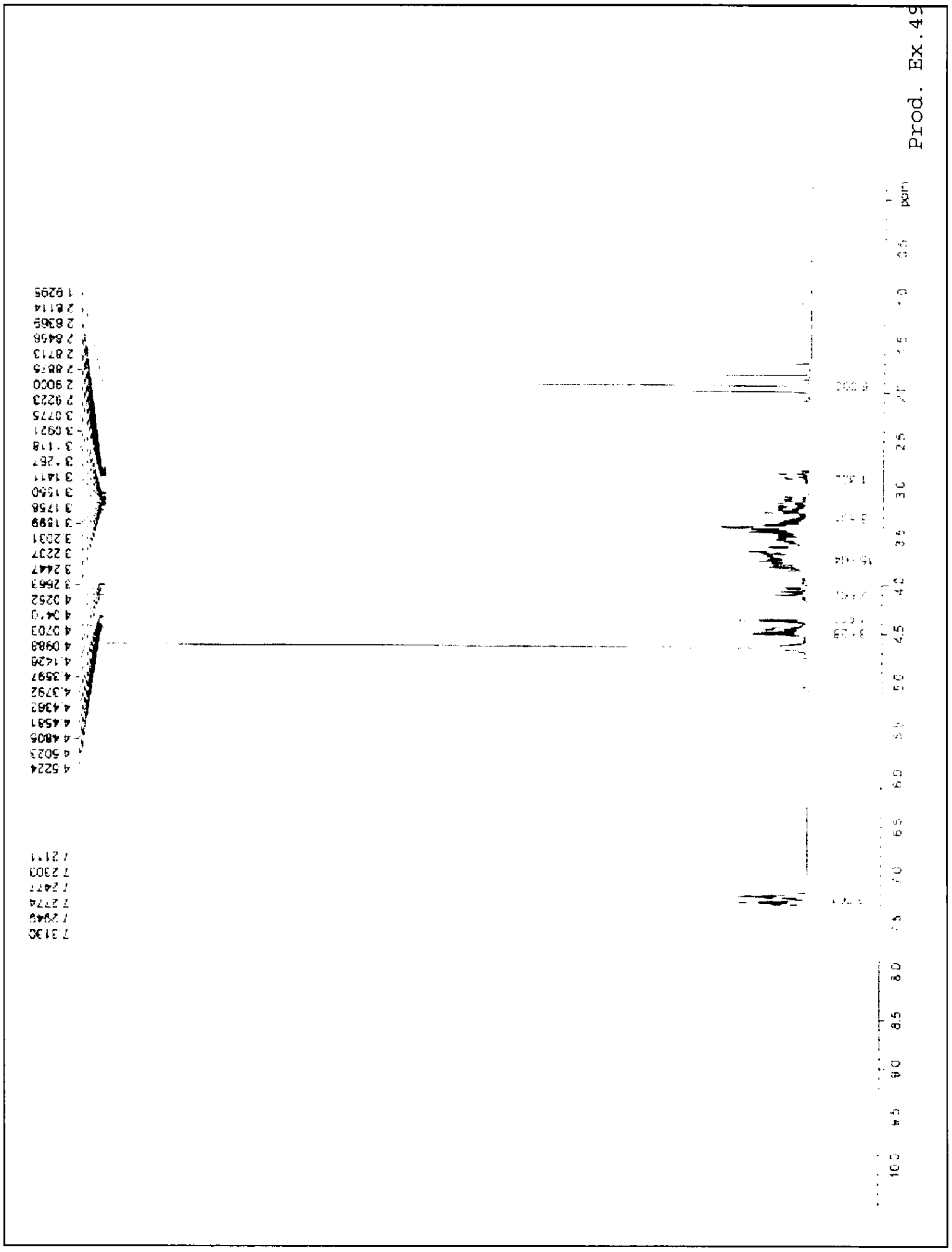
FIG. 47 is a $^1$H-NMR chart of a compound obtained in Production Example 49.

$^1$H-NMR: FIG. 47 illustrates the chart.

Production Example 50

The same reaction process as that in Production Example 46 was performed except that phenylalanylglycine was used instead of phenylalanine to yield a target product (14 mg, white powder).

Figure 48:
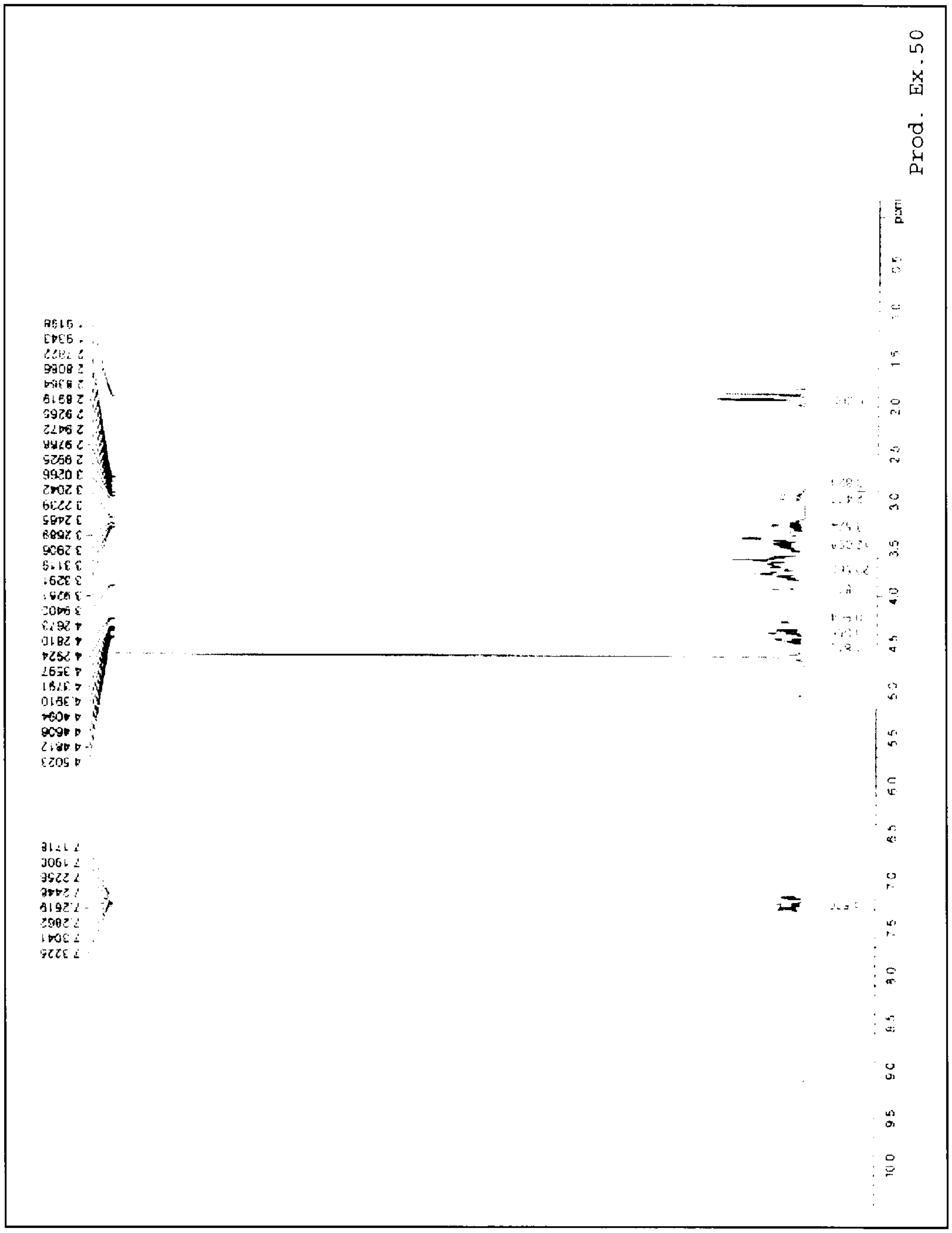
FIG. 48 is a $^1$H-NMR chart of a compound obtained in Production Example 50.

$^1$H-NMR: FIG. 48 illustrates the chart.

Production Example 51

The same reaction process as that in Production Example 45 was performed except that a hyaluronan oligosaccharide 10-mer (20 mg) was used as a starting material instead of a hyaluronan oligosaccharide 4-mer (10 mg), and except that 4-chloroaniline was used instead of benzylamine to yield a target product (10 mg, white powder).

Figure 49:
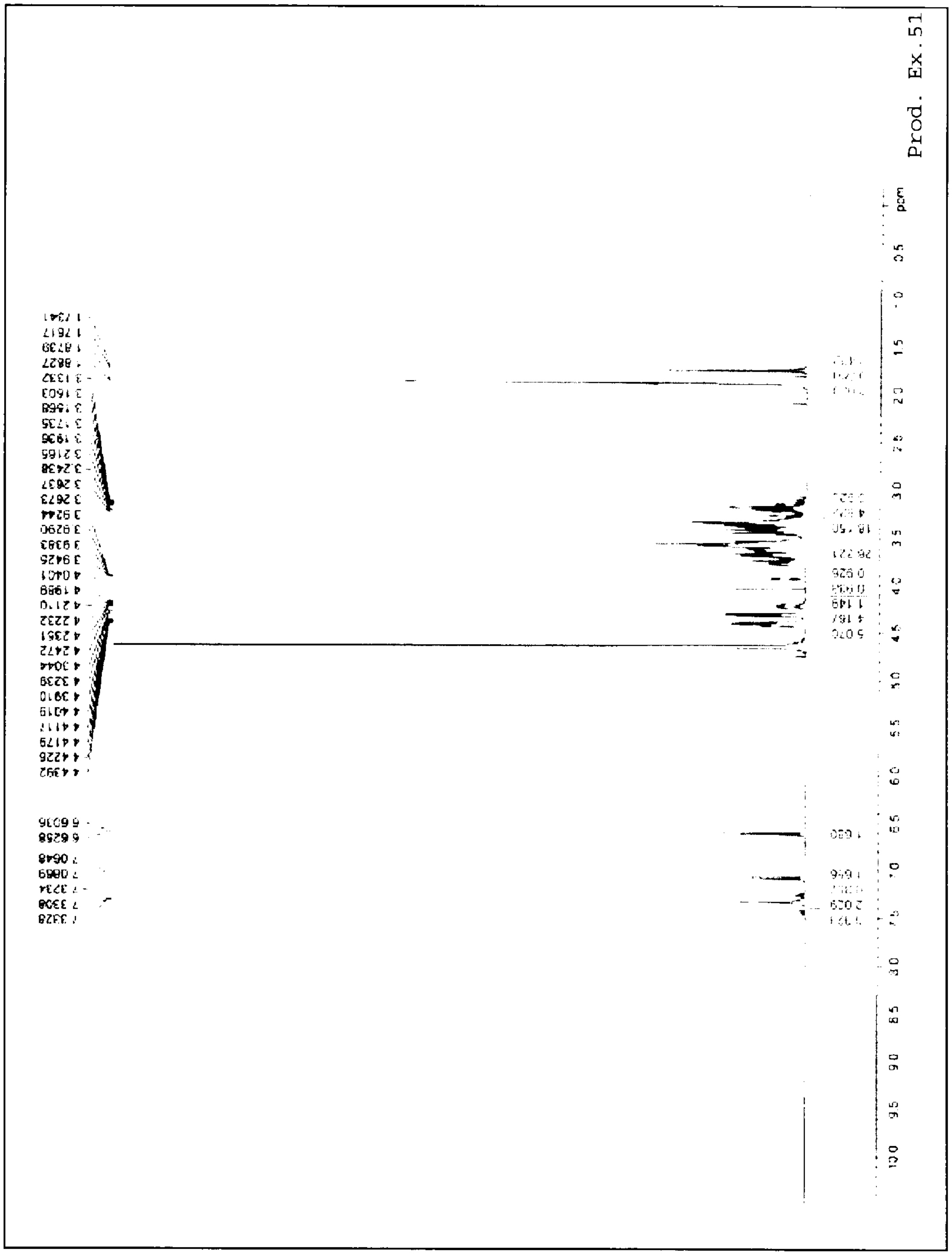
FIG. 49 is a $^1$H-NMR chart of a compound obtained in Production Example 51.

$^1$H-NMR: FIG. 49 illustrates the chart.

Production Example 52

The same reaction process as that in Production Example 45 was performed except that a hyaluronan oligosaccharide 10-mer was used instead of a hyaluronan oligosaccharide 4-mer, and except that 2-aminopyridine was used instead of benzylamine to yield a target product (12 mg, white powder).

Figure 50:
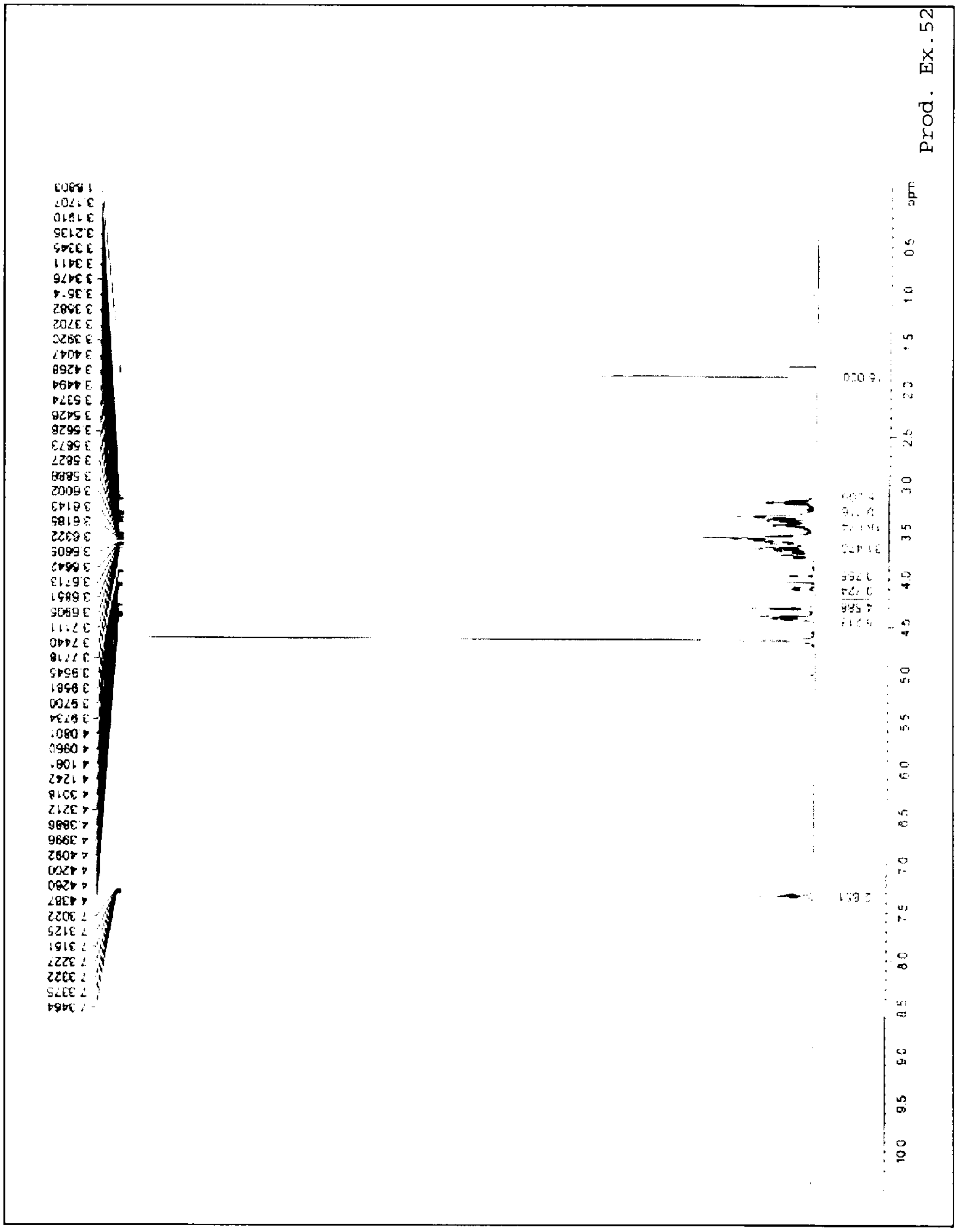
FIG. 50 is a $^1$H-NMR chart of a compound obtained in Production Example 52.

$^1$H-NMR: FIG. 50 illustrates the chart.

Production Example 53

The same reaction process as that in Production Example 46 was performed except that a hyaluronan oligosaccharide 10-mer was used instead of a hyaluronan oligosaccharide 4-mer, and except that phenylalanylglycylglycine was used instead of phenylalanine to yield a target product (5 mg, white powder).

Figure 51:
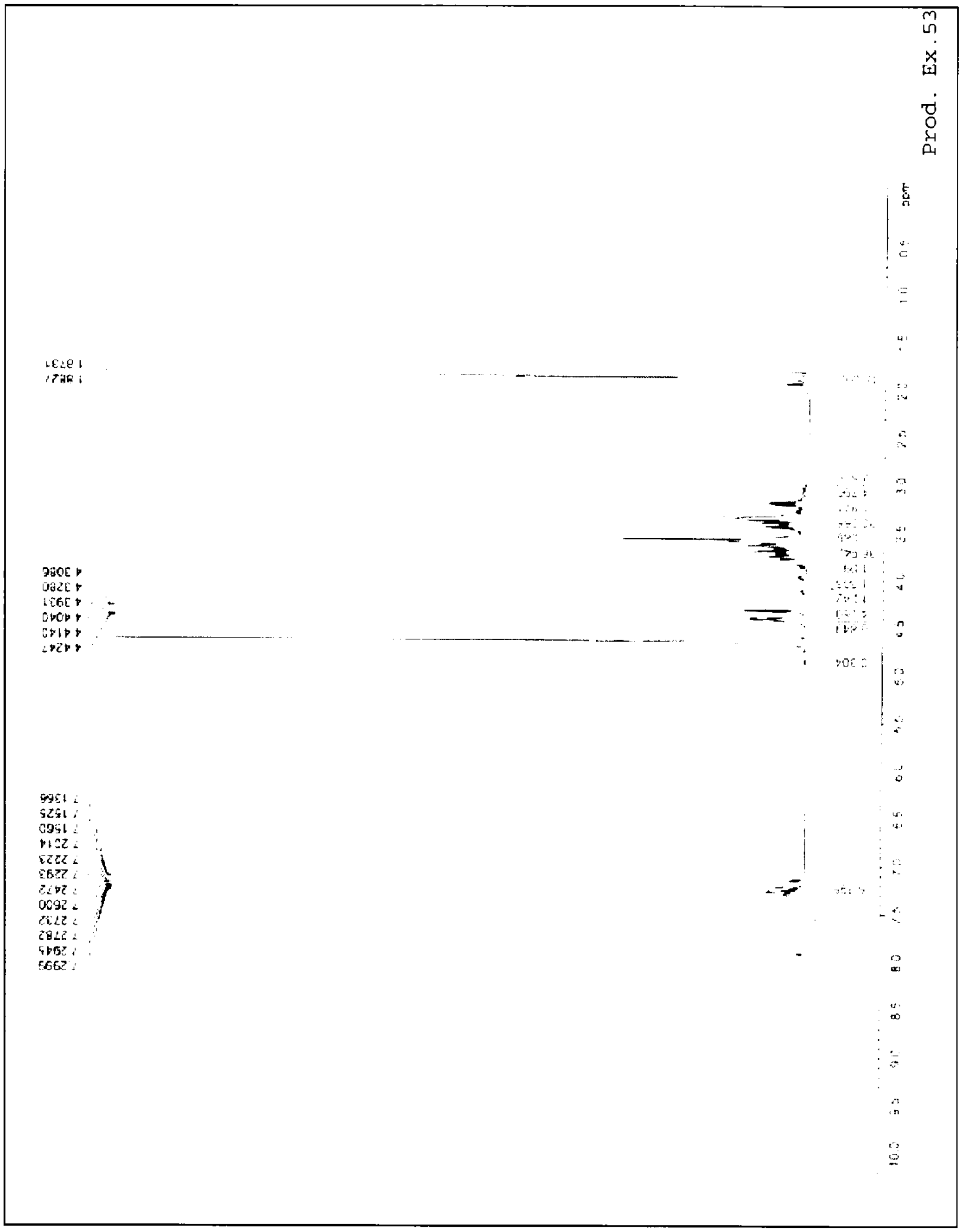
FIG. 51 is a $^1$H-NMR chart of a compound obtained in Production Example 53.

$^1$H-NMR: FIG. 51 illustrates the chart.

Production Example 54

The same reaction process as that in Production Example 46 was performed except that a hyaluronan oligosaccharide 10-mer was used instead of a hyaluronan oligosaccharide 4-mer to yield a target product (5 mg, white powder).

Figure 52:
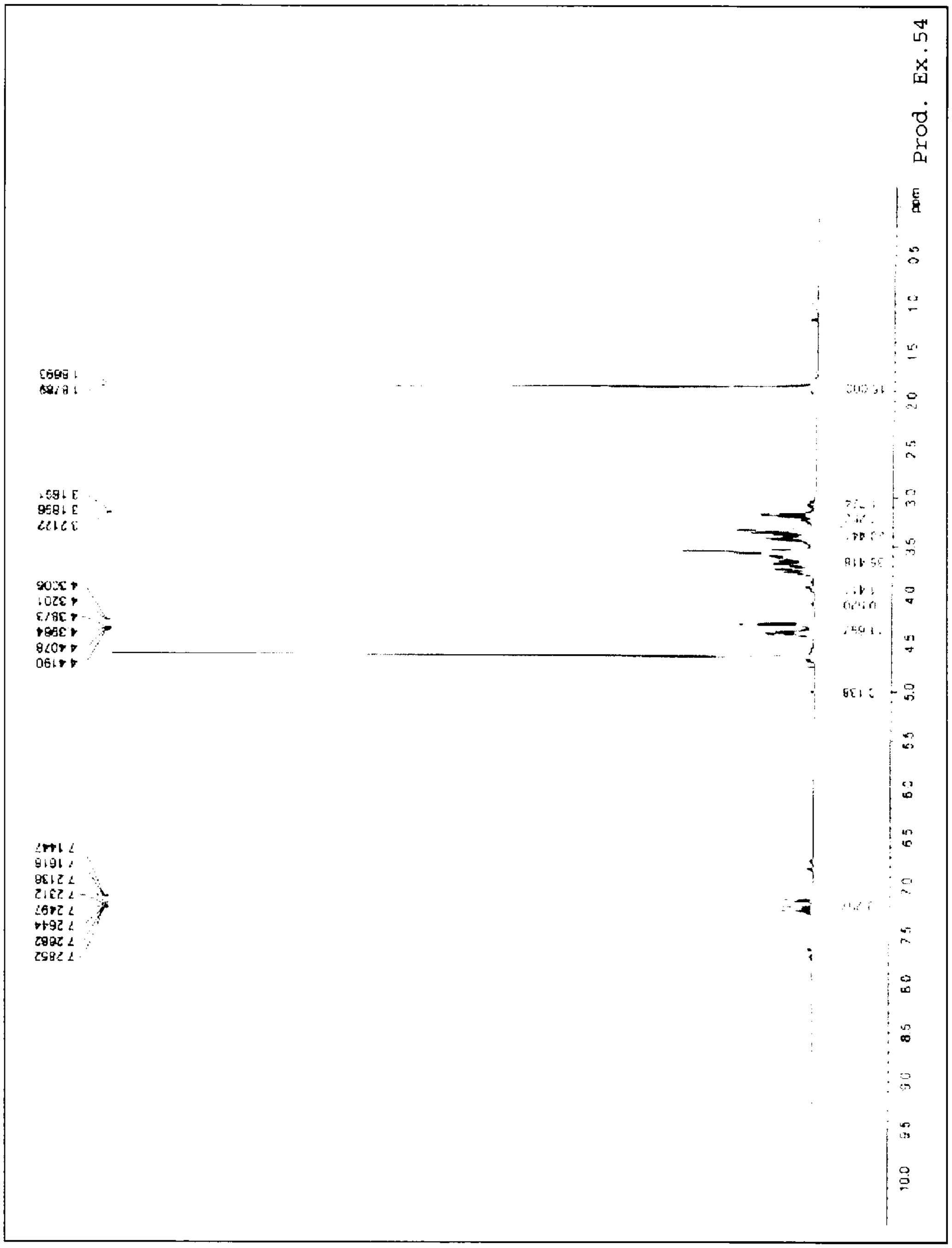
FIG. 52 is a $^1$H-NMR chart of a compound obtained in Production Example 54.

$^1$H-NMR: FIG. 52 illustrates the chart.

The structures of the target products in the Production Examples 45 to 54 are shown in Table 7 below.

TABLE 7

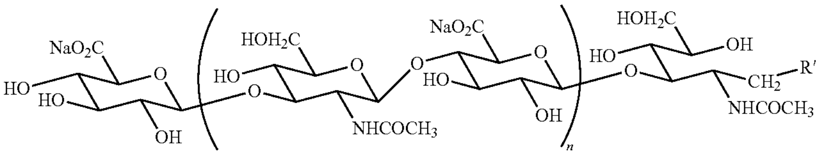

| Production Example No. | n | R' |
| --- | --- | --- |
| 45 | 1 | 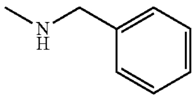 |
| 46 | 1 | 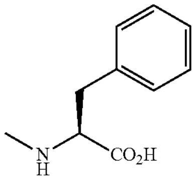 |
| 47 | 1 | 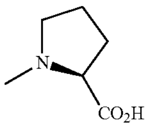 |

TABLE 7-continued
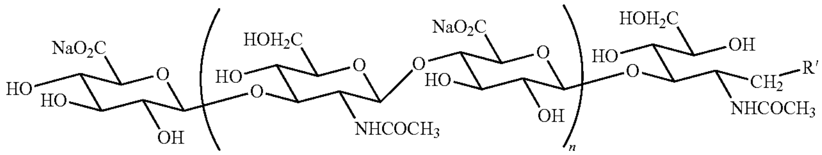
| Production Example No. | n | R' |
|---|---|---|
| 48 | 1 | 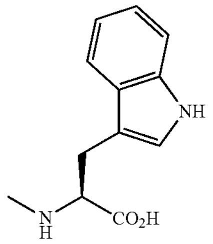 |
| 49 | 1 | 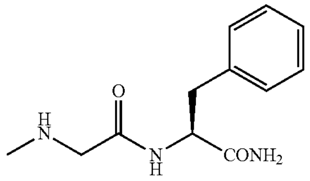 |
| 50 | 1 | 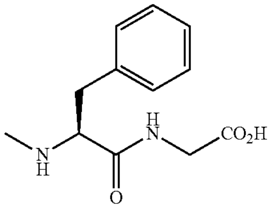 |
| 51 | 4 | 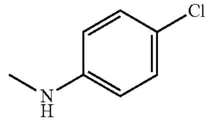 |
| 52 | 4 | 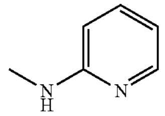 |
| 53 | 4 | 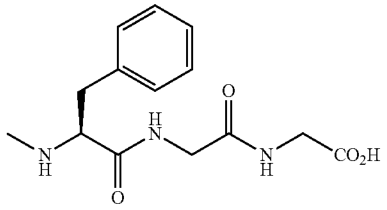 |
| 54 | 4 | 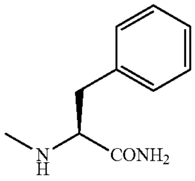 |

Examples 1 to 48

Production of Compound of the Present Invention

Methods in Examples 1 to 48 mentioned below were used to produce the compounds of the present invention shown in Tables 8 to 14. Mass spectrometry was conducted by using a QSTAR pulsar i (Applied Biosystems Japan Ltd.).

Example 1

The compound synthesized in Production Example 1 (12 mg) was dissolved in water (1 ml), and tributylamine (100 μl) was added to the mixture, followed by stirring. After that, the mixture was concentrated under reduced pressure. N,N-dimethylformamide (2 ml) was added to the concentrate, followed by azeotropy twice. The residue was dissolved in N,N-dimethylformamide (1 ml), and pyridine-sulfur trioxide (150 mg) was added to the resultant, followed by stirring at 42° C. for 3 hours under a nitrogen atmosphere.

After the resultant was cooled to 4° C., water (1 ml) was added to the resultant, and a saturated sodium acetate solution in ethanol (30 ml) was then added to cause precipitation. The solution was stirred with a Voltex mixer, and then, the resultant was subjected to centrifugation under cooling (at 4° C., at 3000 rpm, and for 15 minutes) to collect a precipitate. After the supernatant was discarded, water (1 ml) was added to dissolve the residue, and a saturated sodium acetate solution in ethanol (20 ml) was then added to cause precipitation. The solution was stirred with a Voltex mixer, and then, the resultant was subjected to centrifugation under cooling (at 4° C., at 3000 rpm, and for 15 minutes) to collect a precipitate. Again, after the supernatant was discarded, water (1 ml) was added to dissolve the residue, and a saturated sodium acetate solution in ethanol (20 ml) was then added to cause precipitation. The solution was stirred with a Voltex mixer, and then, the resultant was subjected to centrifugation under cooling (at 4° C., at 3000 rpm, and for 15 minutes) to collect a precipitate. Then, after the supernatant was discarded, the residue was dissolved in water (2 ml), followed by concentration under reduced pressure.

The residue was dissolved in water (2 ml), followed by filtration through a disk filter (manufactured by Nihon Pall Ltd., 0.45 μm). The AKTA system (manufactured by GE Healthcare Bioscience Bioprocess Corp.) was used to apply the filtrate to gel filtration chromatography (G-10, 16 mm×600 mm, water) to perform desalting, and then, target fractions were freeze-dried to yield Compound 1 (24 mg, white powder).

$[M+2Na]^{2+}$: 994.75

Figure 53:
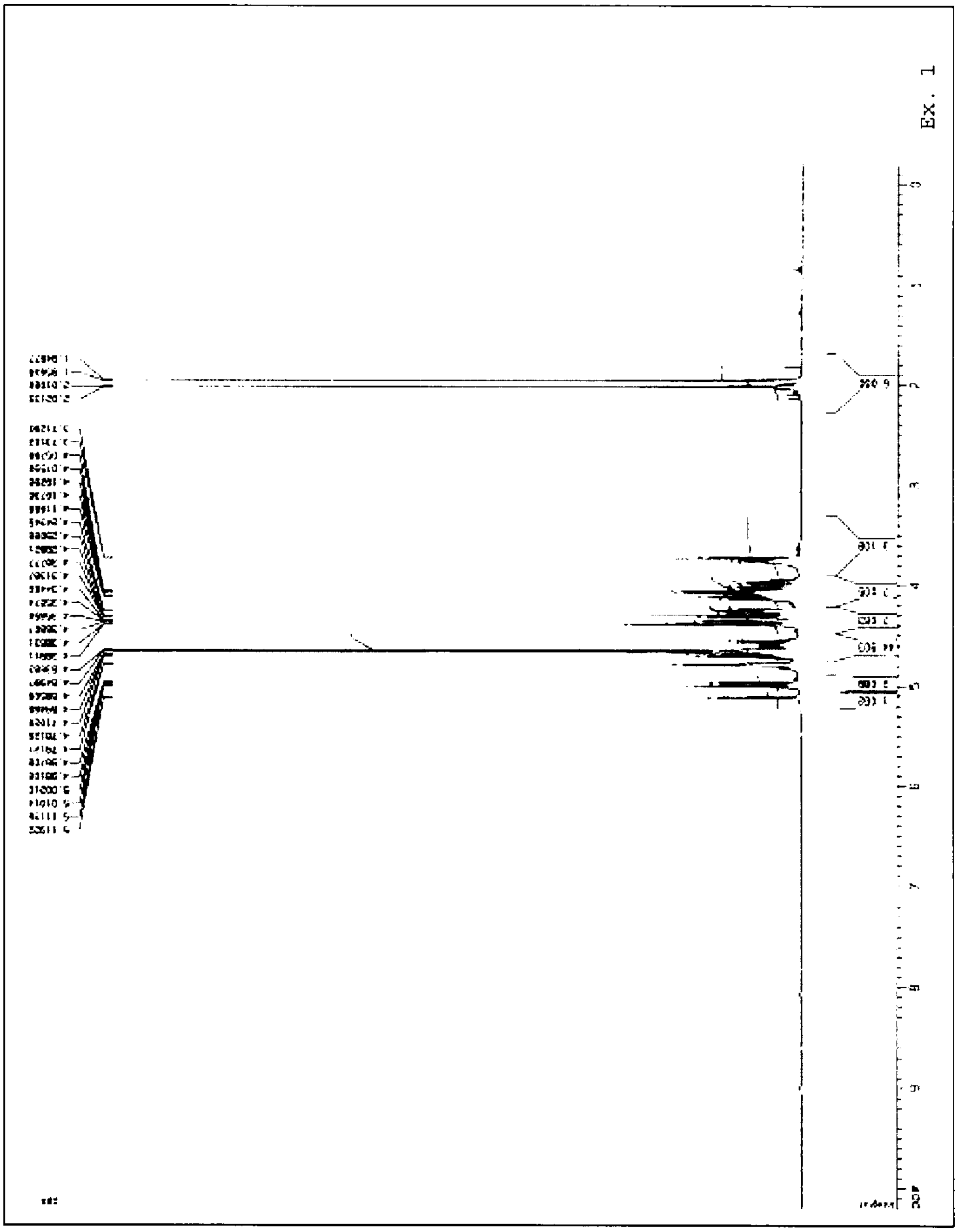
FIG. 53 is a $^1$H-NMR chart of Compound 1.

$^1$H-NMR: FIG. 53 illustrates the chart.

Example 2

The same process as that in Example 1 was performed except that the compound obtained in Production Example 2 (47 mg) was used instead as a material to yield Compound 2 (76 mg, white powder).

Figure 54:
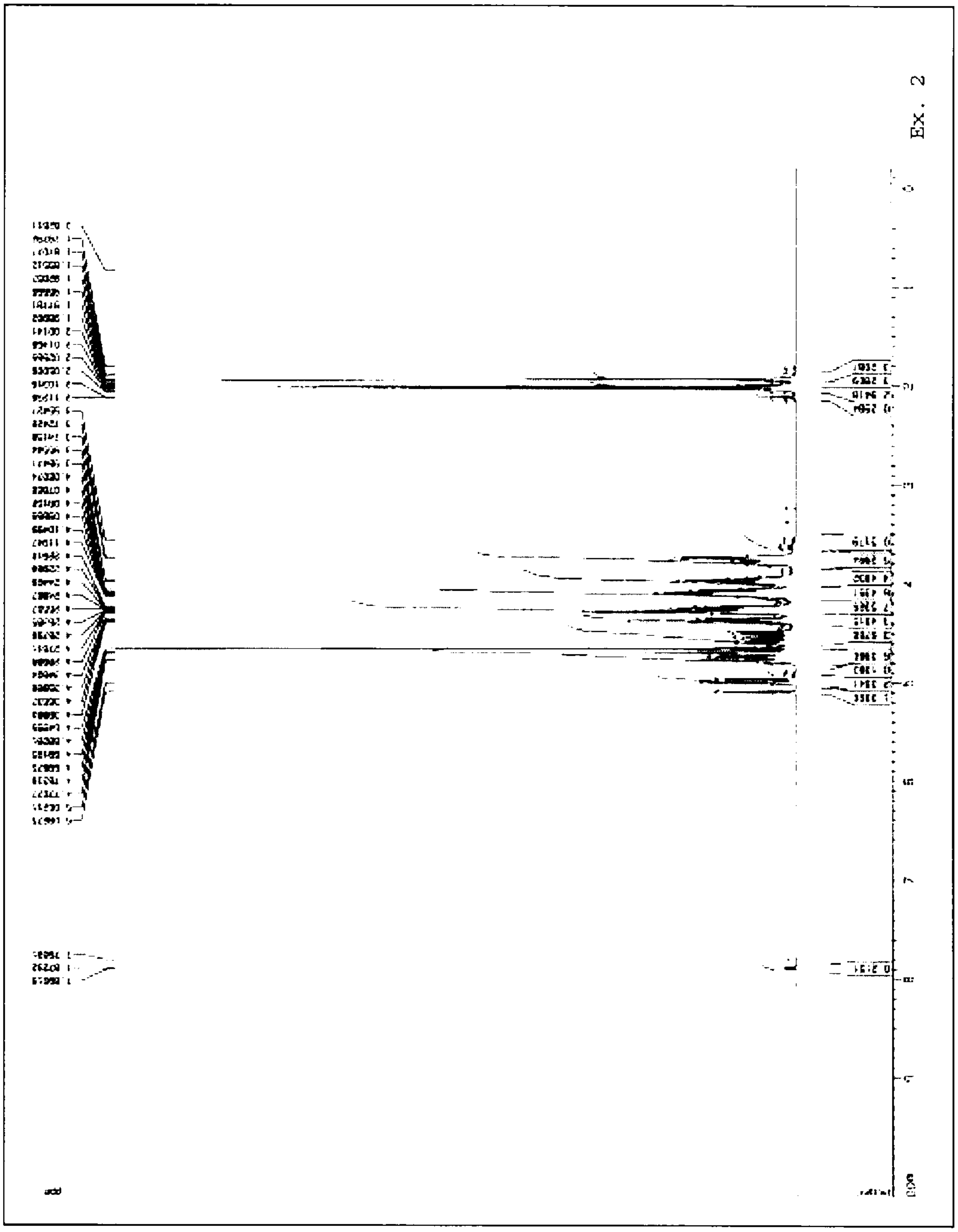
FIG. 54 is a $^1$H-NMR chart of Compound 2.

$^1$H-NMR: FIG. 54 illustrates the chart.

Example 3

The same process as that in Example 1 was performed except that the compound obtained in Production Example 3 (51 mg) was used instead as a material to yield Compound 3 (108 mg, white powder).

$[M+3Na]^{3+}$: 1210.10

Figure 55:
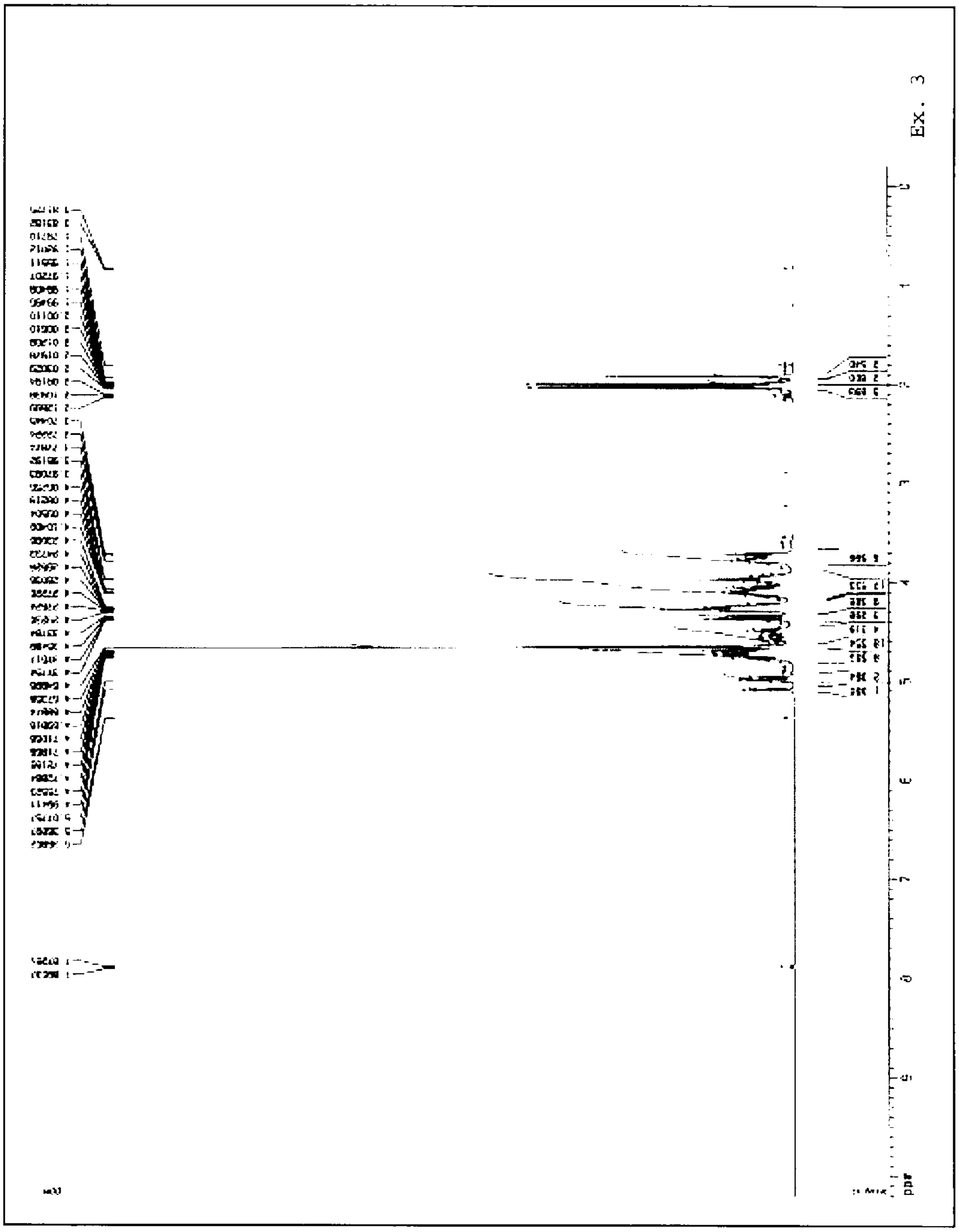
FIG. 55 is a $^1$H-NMR chart of Compound 3.

$^1$H-NMR: FIG. 55 illustrates the chart.

Example 4

The same process as that in Example 1 was performed except that the compound obtained in Production Example 4 (48 mg) was used instead as a material to yield Compound 4 (92 mg, white powder).

$[M+3Na]^{3+}$: 1479.73

Figure 56:
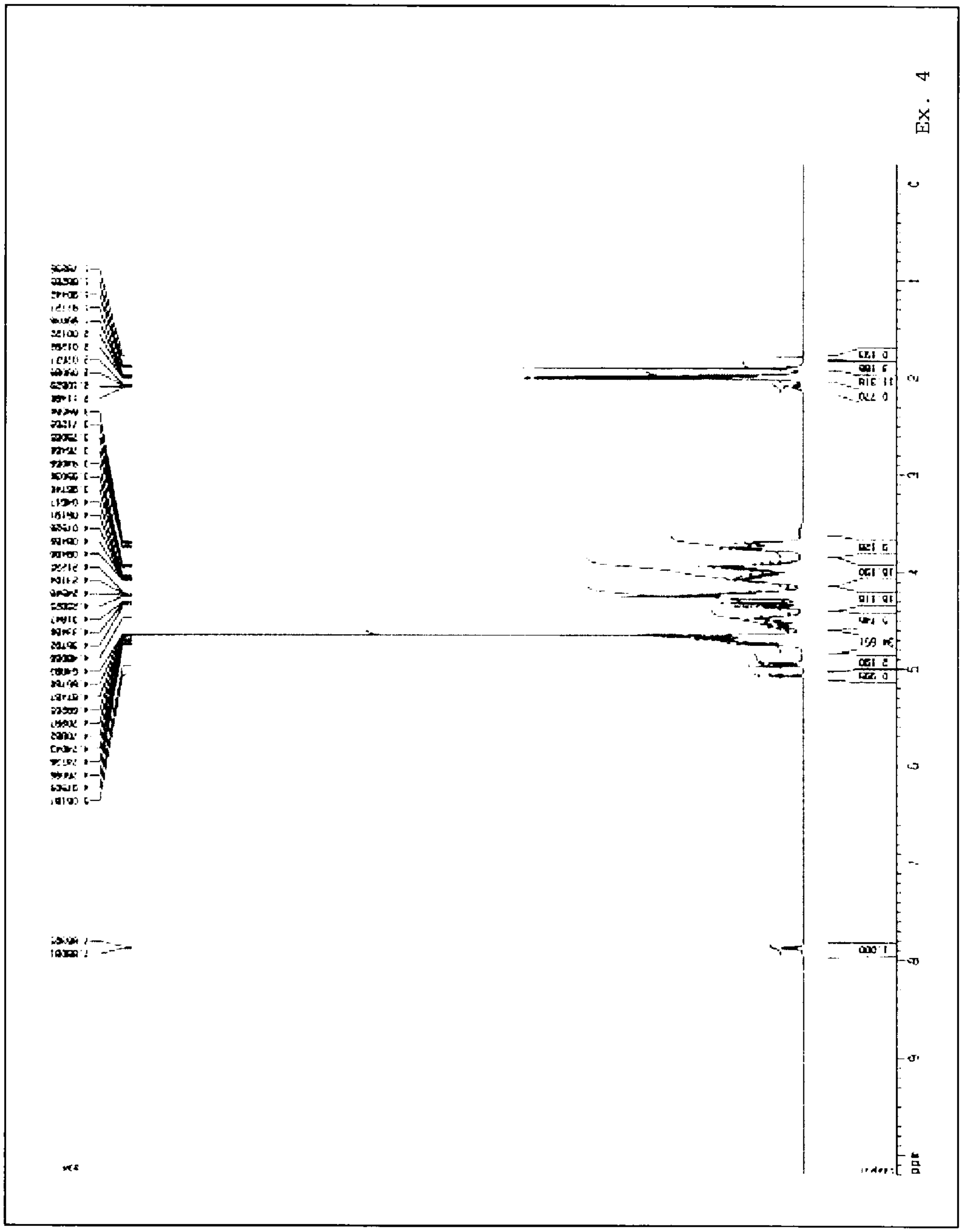
FIG. 56 is a $^1$H-NMR chart of Compound 4.

$^1$H-NMR: FIG. 56 illustrates the chart.

Example 5

The same process as that in Example 1 was performed except that the compound obtained in Production Example 5 (60 mg) was used instead as a material to yield Compound 5 (112 mg, white powder).

Figure 57:
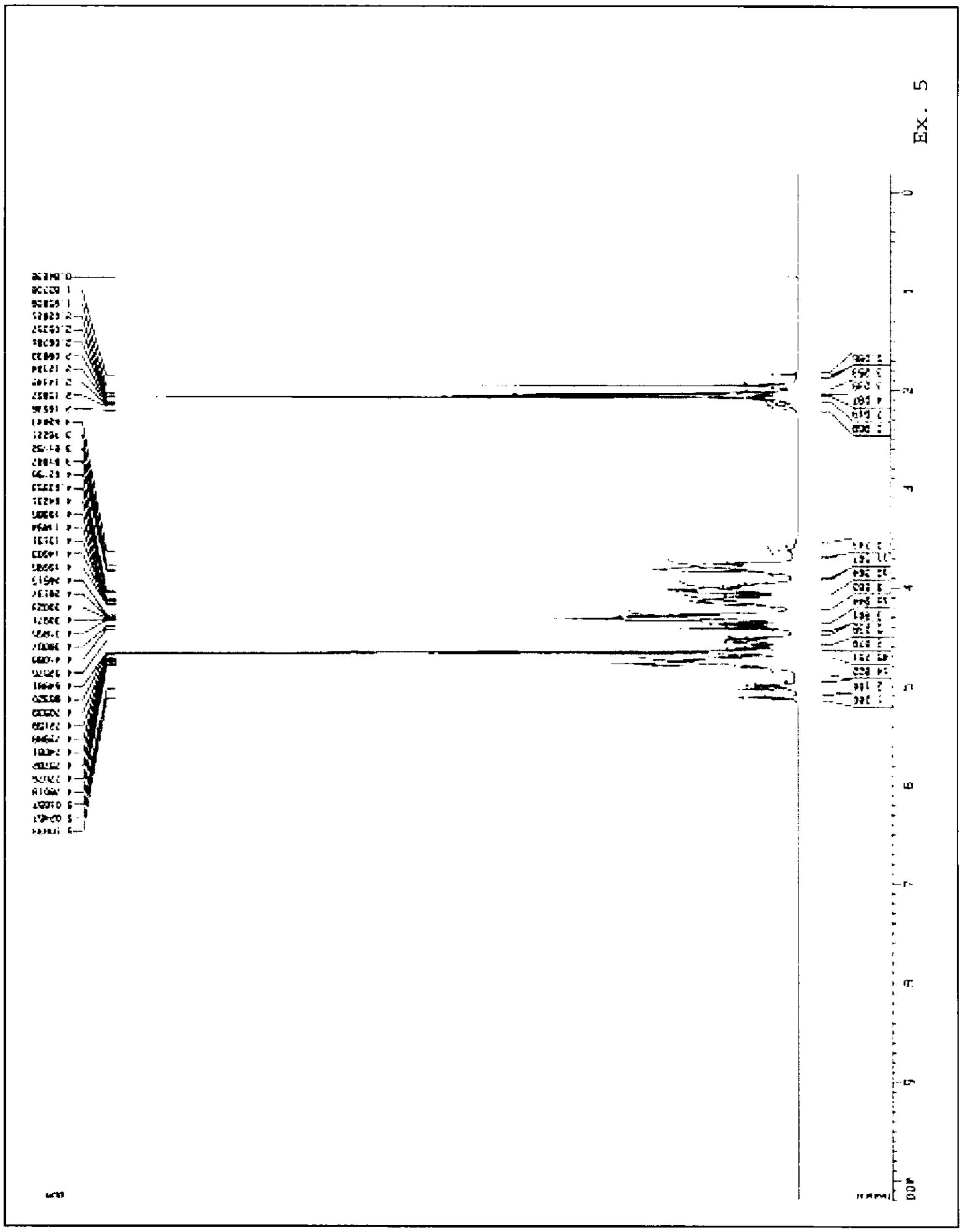
FIG. 57 is a $^1$H-NMR chart of Compound 5.

$[M+4Na]^{4+}$: 1317.74 $^1$H-NMR: FIG. 57 illustrates the chart.

Example 6

The same process as that in Example 1 was performed except that the compound obtained in Production Example 6 (20 mg) was used instead as a material to yield Compound 6 (22 mg, white powder).

Figure 58:
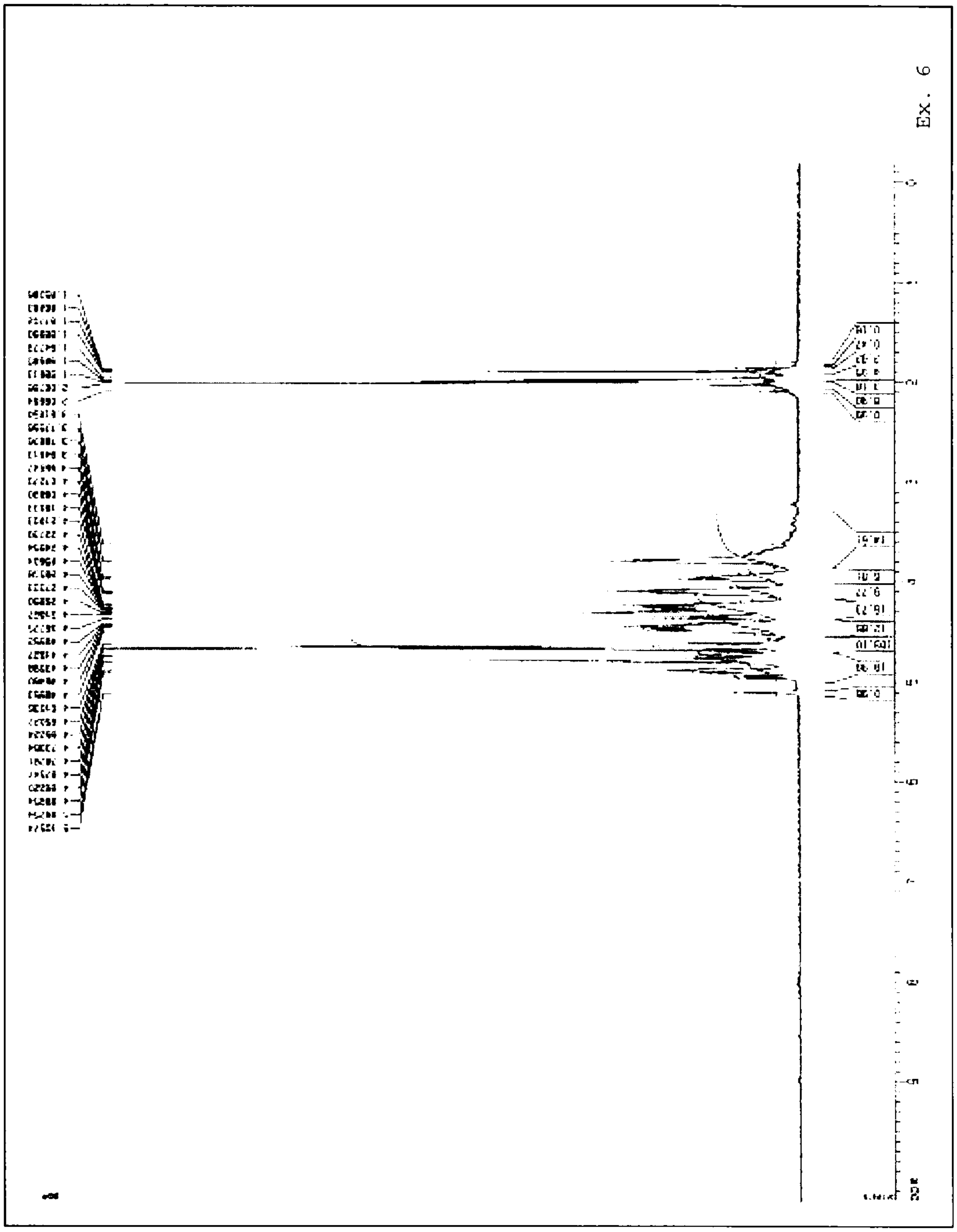
FIG. 58 is a $^1$H-NMR chart of Compound 6.

$^1$H-NMR: FIG. 58 illustrates the chart.

Example 7

The compound obtained in Production Example 7 (10 mg) was dissolved in N,N-dimethylformamide (1 ml), and pyridine-sulfur trioxide (150 mg) was added to the resultant, followed by stirring at 42° C. for 3 hours under a nitrogen atmosphere.

After the resultant was cooled to 4° C., water (1 ml) was added to the resultant, and a saturated sodium acetate solution in ethanol (25 ml) was then added to cause precipitation. The solution was stirred with a Voltex mixer, and then, the resultant was subjected to centrifugation under cooling (at 4° C., at 3000 rpm, and for 15 minutes) to collect a precipitate. After the supernatant was discarded, water (1 ml) was added to dissolve the residue, and a saturated sodium acetate solution in ethanol (20 ml) was then added to cause precipitation. The solution was stirred with a Voltex mixer, and then, the resultant was subjected to centrifugation under cooling (at 4° C., at 3000 rpm, and for 15 minutes) to collect a precipitate. Again, after the supernatant was discarded, water (1 ml) was added to dissolve the residue, and a saturated sodium acetate solution in ethanol (20 ml) was then added to cause precipitation. The solution was stirred with a Voltex mixer, and then, the resultant was subjected to centrifugation under cooling (at 4° C., at 3000 rpm, and for 15 minutes) to collect a precipitate. Then, after the supernatant was discarded, the residue was dissolved in water (2 ml), followed by concentration under reduced pressure.

The residue was dissolved in water (2 ml), followed by filtration through a disk filter (manufactured by Nihon Pall Ltd., 0.45 μm). The AKTA system (manufactured by GE Healthcare Bioscience Bioprocess Corp.) was used to apply the filtrate to gel filtration chromatography (G-10, 16 mm×600 mm, water) to perform desalting, and then, target fractions were freeze-dried to yield Compound 7 (16 mg, white powder).

Figure 59:
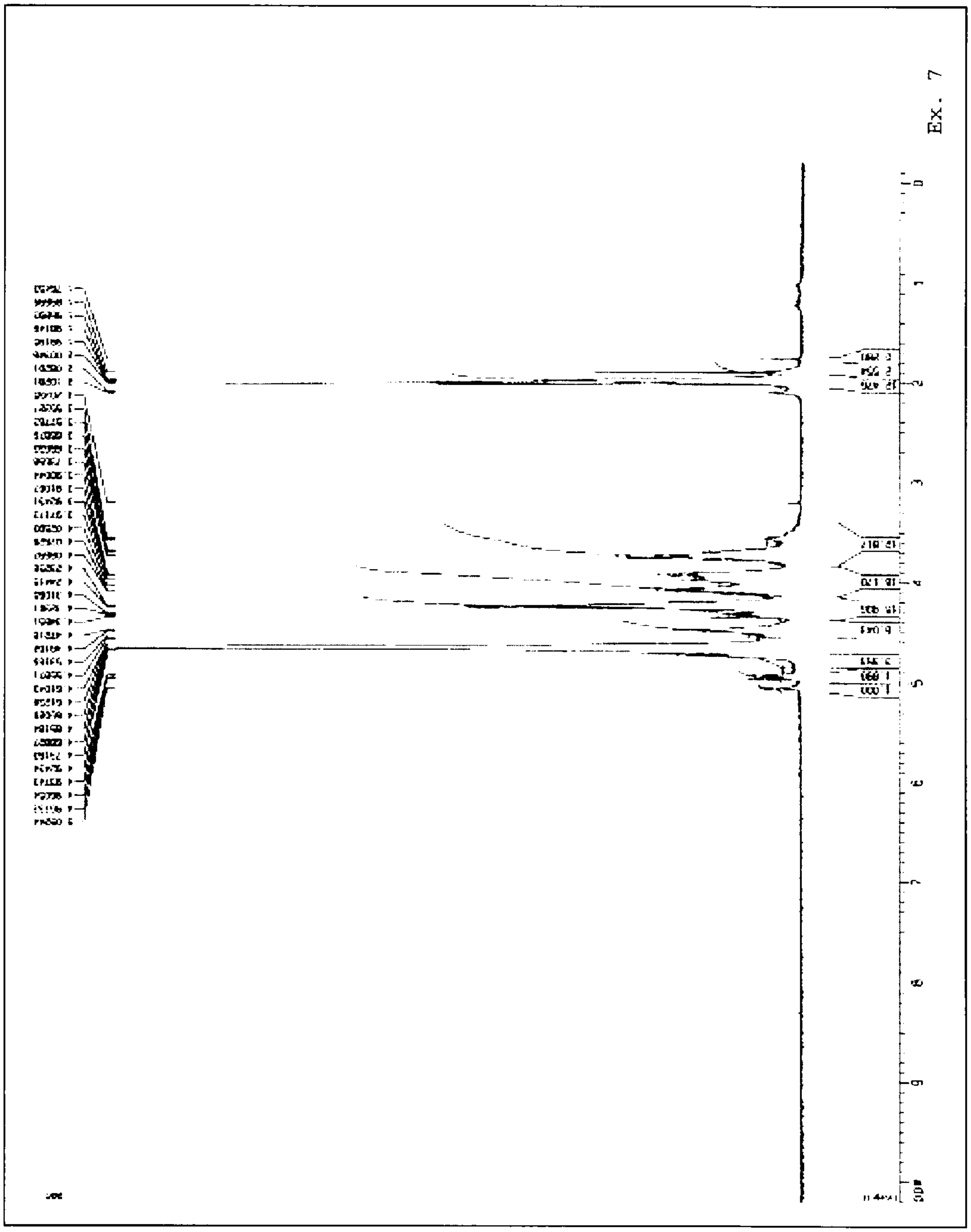
FIG. 59 is a $^1$H-NMR chart of Compound 7.

$^1$H-NMR: FIG. 59 illustrates the chart.

Example 8

The same process as that in Example 7 was performed except that the compound obtained in Production Example 8 (20 mg) was used instead as a material to yield Compound 8 (33 mg, white powder).

Figure 60:
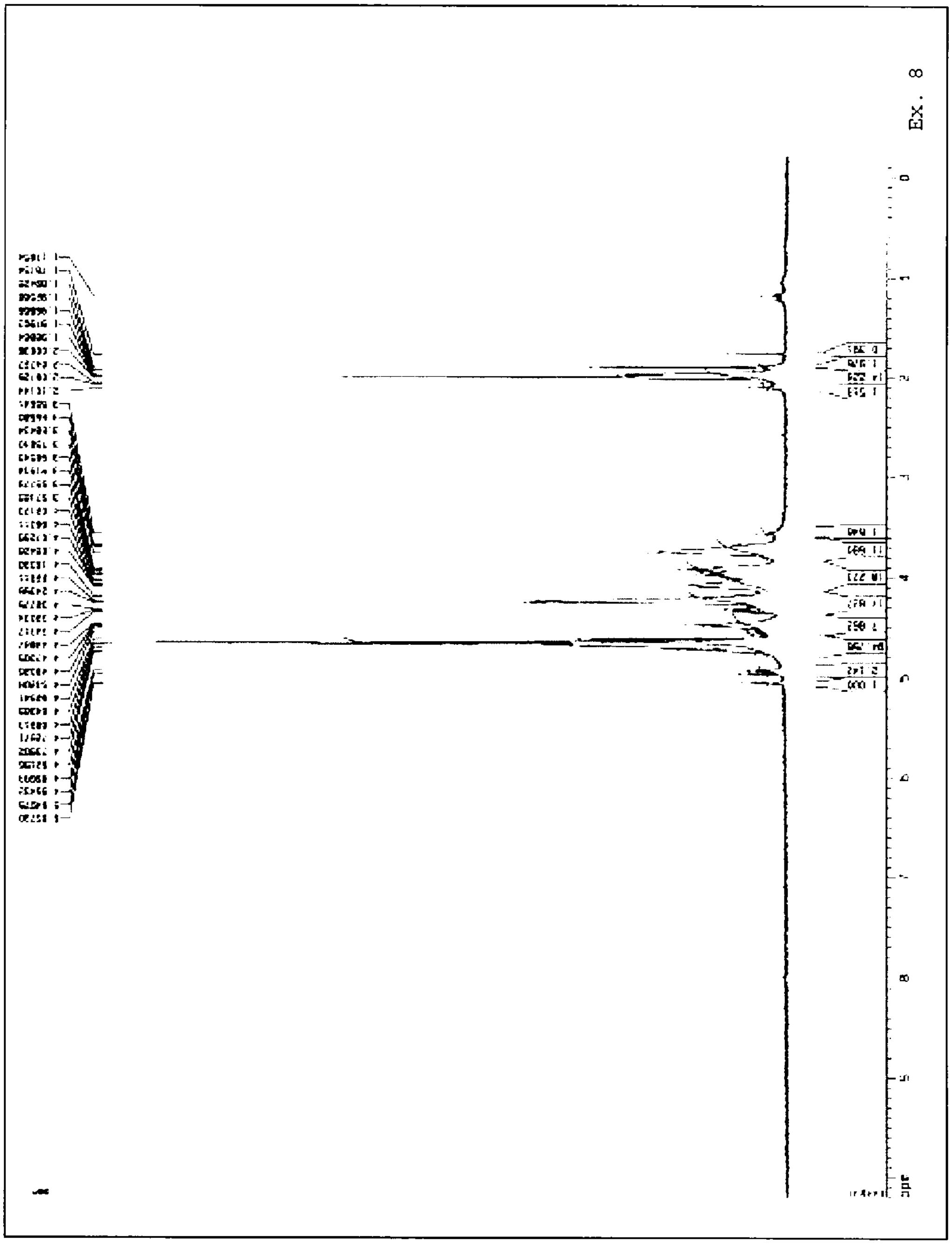
FIG. 60 is a $^1$H-NMR chart of Compound 8.

$^1$H-NMR: FIG. 60 illustrates the chart.

Example 9

The same process as that in Example 1 was performed except that the compound obtained in Production Example 9 (39 mg) was used instead as a material to yield Compound 9 (90 mg, white powder).

$[M+5Na]^{5+}$: 1707.07

Figure 61:
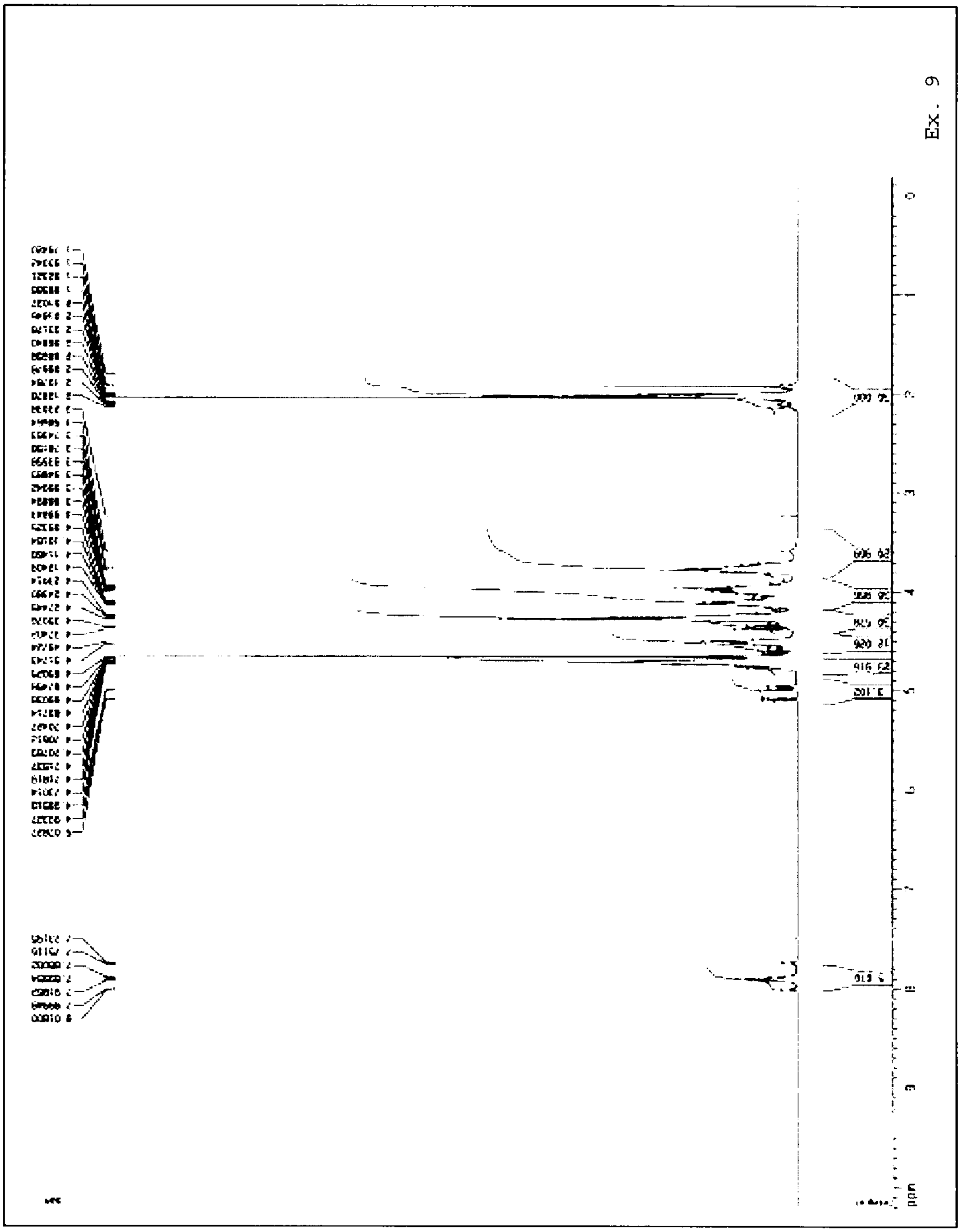
FIG. 61 is a $^1$H-NMR chart of Compound 9.

$^1$H-NMR: FIG. 61 illustrates the chart.

Example 10

The same process as that in Example 1 was performed except that the compound obtained in Production Example 10 (24 mg) was used instead as a material to yield Compound 10 (48 mg, white powder).

$[M+3Na]^{3+}$: 1493.42

Figure 62:
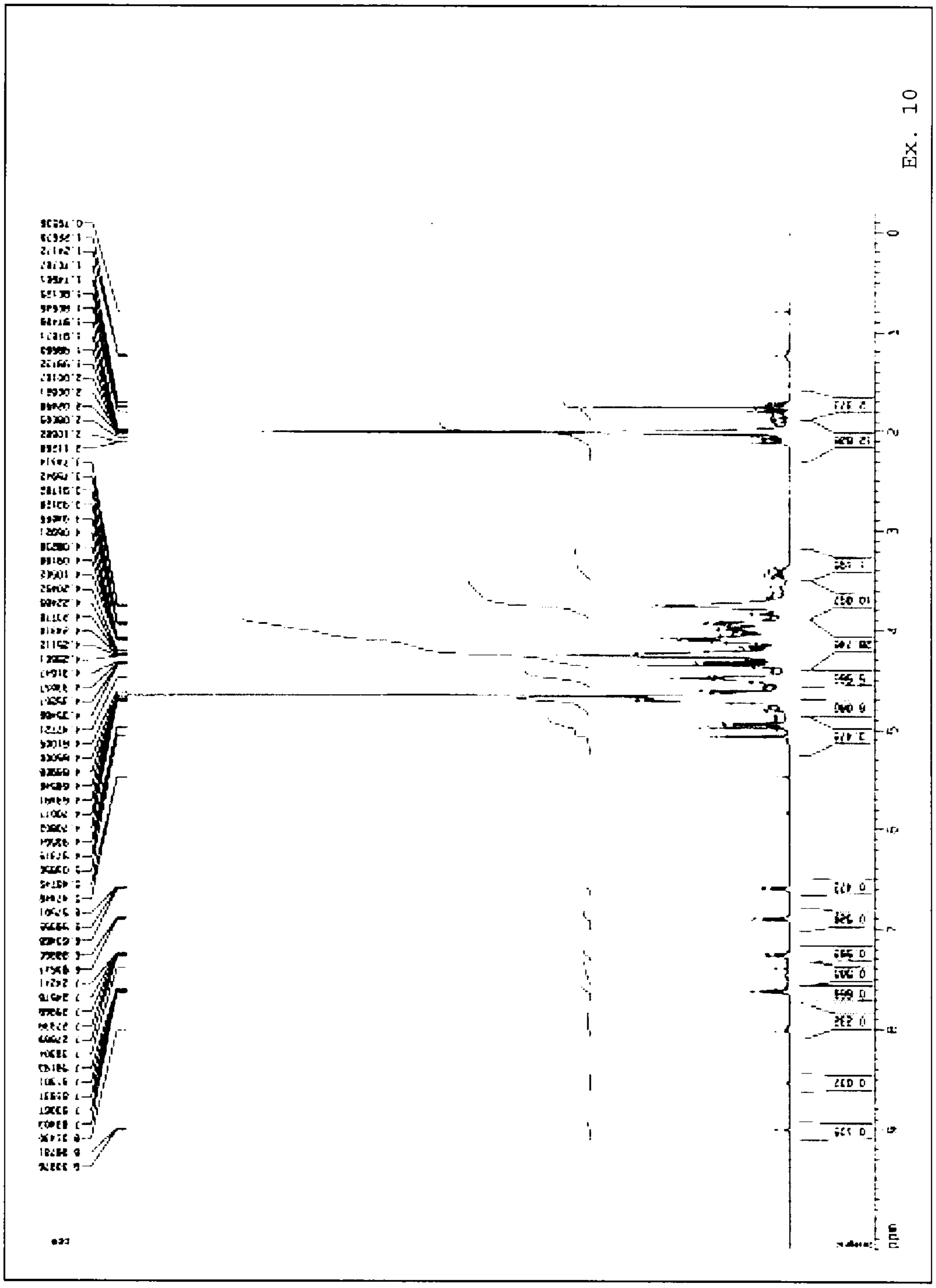
FIG. 62 is a $^1$H-NMR chart of Compound 10.

$^1$H-NMR: FIG. 62 illustrates the chart.

Example 11

The same process as that in Example 1 was performed except that the compound obtained in Production Example 11 (17 mg) was used instead as a material to yield Compound 11 (34 mg, white powder).

$[M+3Na]^{3+}$: 1505.11

Figure 63:
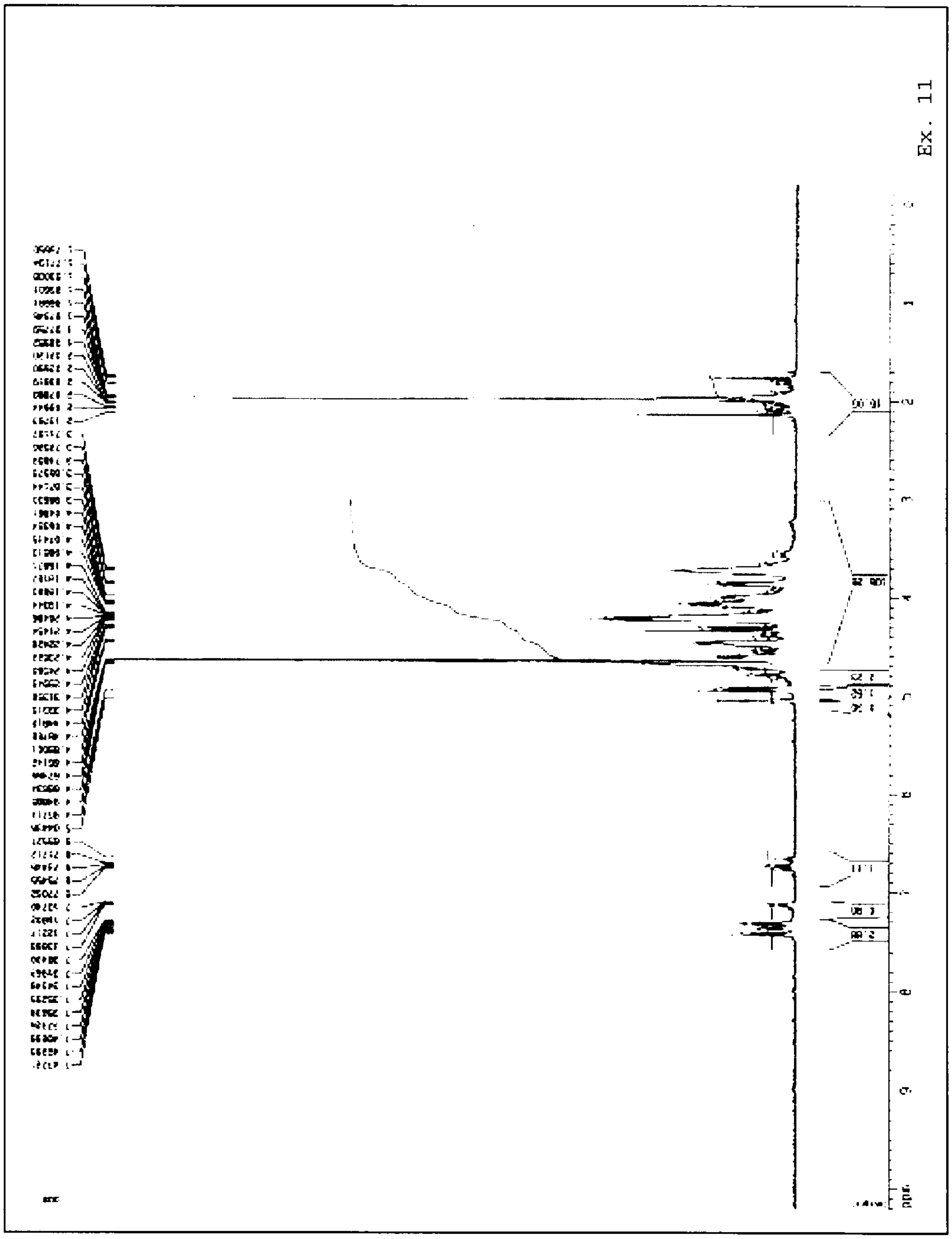
FIG. 63 is a $^1$H-NMR chart of Compound 11.

$^1$H-NMR: FIG. 63 illustrates the chart.

Example 12

The same process as that in Example 1 was performed except that the compound obtained in Production Example 12 (10 mg) was used instead as a material to yield Compound 12 (10 mg, white powder).

Example 13

The same process as that in Example 1 was performed except that the compound obtained in Production Example 13 (10 mg) was used instead as a material to yield Compound 13 (21 mg, white powder).

The structures of Compounds 1 to 13 are shown in Table 8 below.

TABLE 8

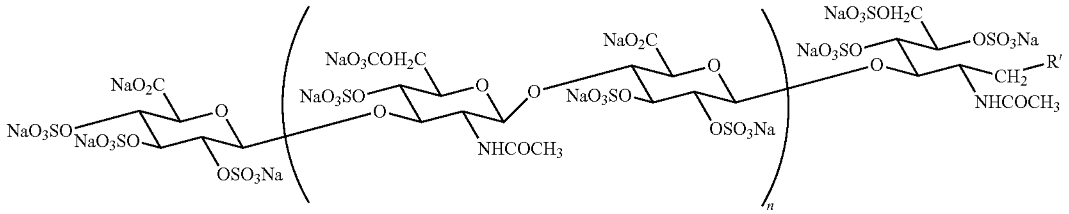

| Compound No. | n | R' |
|---|---|---|
| 1 | 1 | $OSO_3Na$ |
| 2 | 2 | $OSO_3Na$ |
| 3 | 3 | $OSO_3Na$ |
| 4 | 4 | $OSO_3Na$ |
| 5 | 5 | $OSO_3Na$ |
| 6 | 6 | $OSO_3Na$ |
| 7 | 7 | $OSO_3Na$ |
| 8 | 8 | $OSO_3Na$ |
| 9 | 9 | $OSO_3Na$ |
| 10 | 4 | 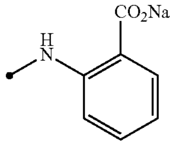 |
| 11 | 4 | 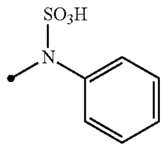 |
| 12 | 11-15 | $OSO_3Na$ |
| 13 | 16-22 | $OSO_3Na$ |

Example 14

The compound obtained in Production Example 14 (18 mg) was dissolved in N,N-dimethylformamide (2 ml), and pyridine sulfur trioxide (300 mg) was added thereto, followed by stirring at 42° C. for 3 hours under a nitrogen atmosphere.

After the resultant was cooled to 4° C., water (1 ml) was added to the resultant, and a saturated sodium acetate solution in ethanol (25 ml) was then added to cause precipitation. The solution was stirred with a Voltex mixer, and then, the resultant was subjected to centrifugation under cooling (at 4° C., at 3000 rpm, and for 15 minutes) to collect a precipitate. After the supernatant was discarded, water (1 ml) was added to dissolve the residue, and a saturated sodium acetate solution in ethanol (20 ml) was then added to cause precipitation. The solution was stirred with a Voltex mixer, and then, the resultant was subjected to centrifugation under cooling (at 4° C., at 3000 rpm, and for 15 minutes) to collect a precipitate. Again, after the supernatant was discarded, water (1 ml) was added to dissolve the residue, and a saturated sodium acetate solution in ethanol (25 ml) was then added to cause precipitation. The solution was stirred with a Voltex mixer, and then, the resultant was subjected to centrifugation under cooling (at 4° C., at 3000 rpm, and for 15 minutes) to collect a precipitate. Then, after the supernatant was discarded, the residue was dissolved in water (2 ml), followed by filtration through a disk filter (manufactured by Nihon Pall Ltd., 0.45 μm). The AKTA system (manufactured by GE Healthcare Bioscience Bioprocess Corp.) was used to apply the filtrate to gel filtration chromatography (G-10, 16 mm×600 mm, water) to perform desalting, and then, target fractions were freeze-dried to yield Compound 14 (30 mg, white powder).

$[M+2Na]^{2+}$: 791.30

Figure 64:
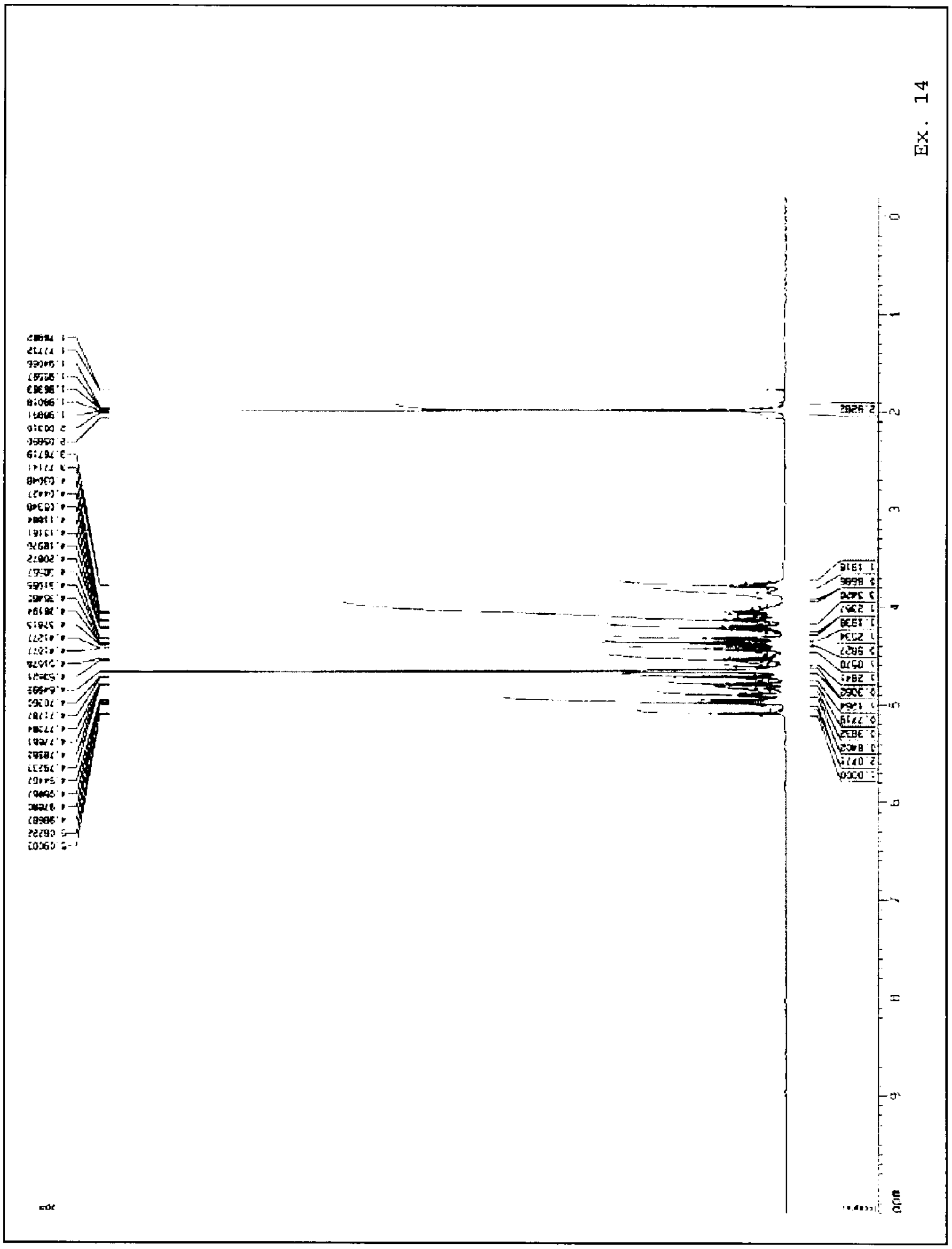
FIG. 64 is a $^1$H-NMR chart of Compound 14.

$^1$H-NMR: FIG. 64 illustrates the chart.

Example 15

The same process as that in Example 14 was performed except that the compound obtained in Production Example 15 (34 mg) was used instead as a material to yield Compound 15 (72 mg, white powder).

$[M+3Na]^{3+}$: 804.83

Figure 65:
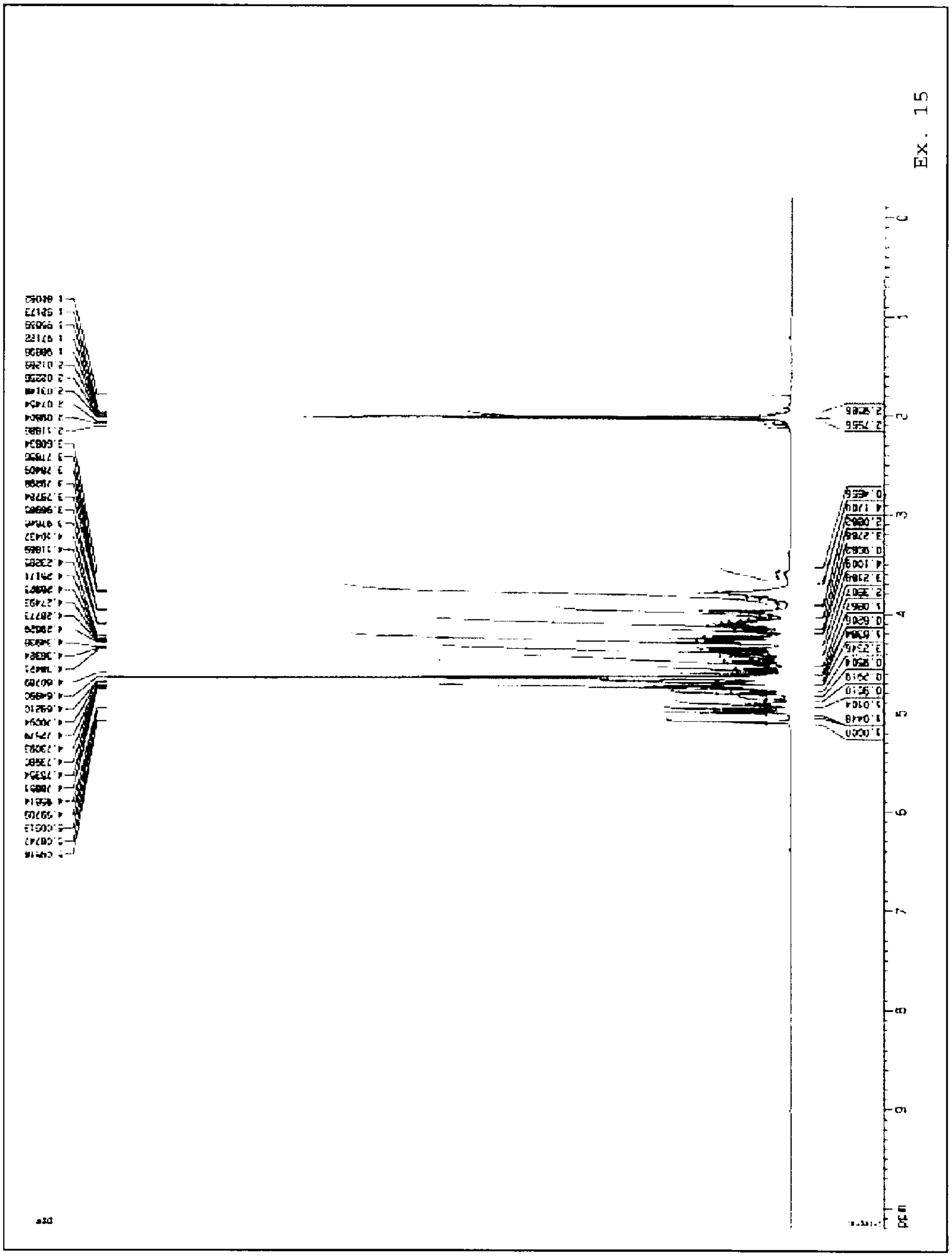
FIG. 65 is a $^1$H-NMR chart of Compound 15.

$^1$H-NMR: FIG. 65 illustrates the chart.

Example 16

The same process as that in Example 14 was performed except that the compound obtained in Production Example 16 (8 mg) was used instead as a material to yield Compound 16 (11 mg, white powder).

$[M+3Na]^{3+}$: 1074.42

Figure 66:
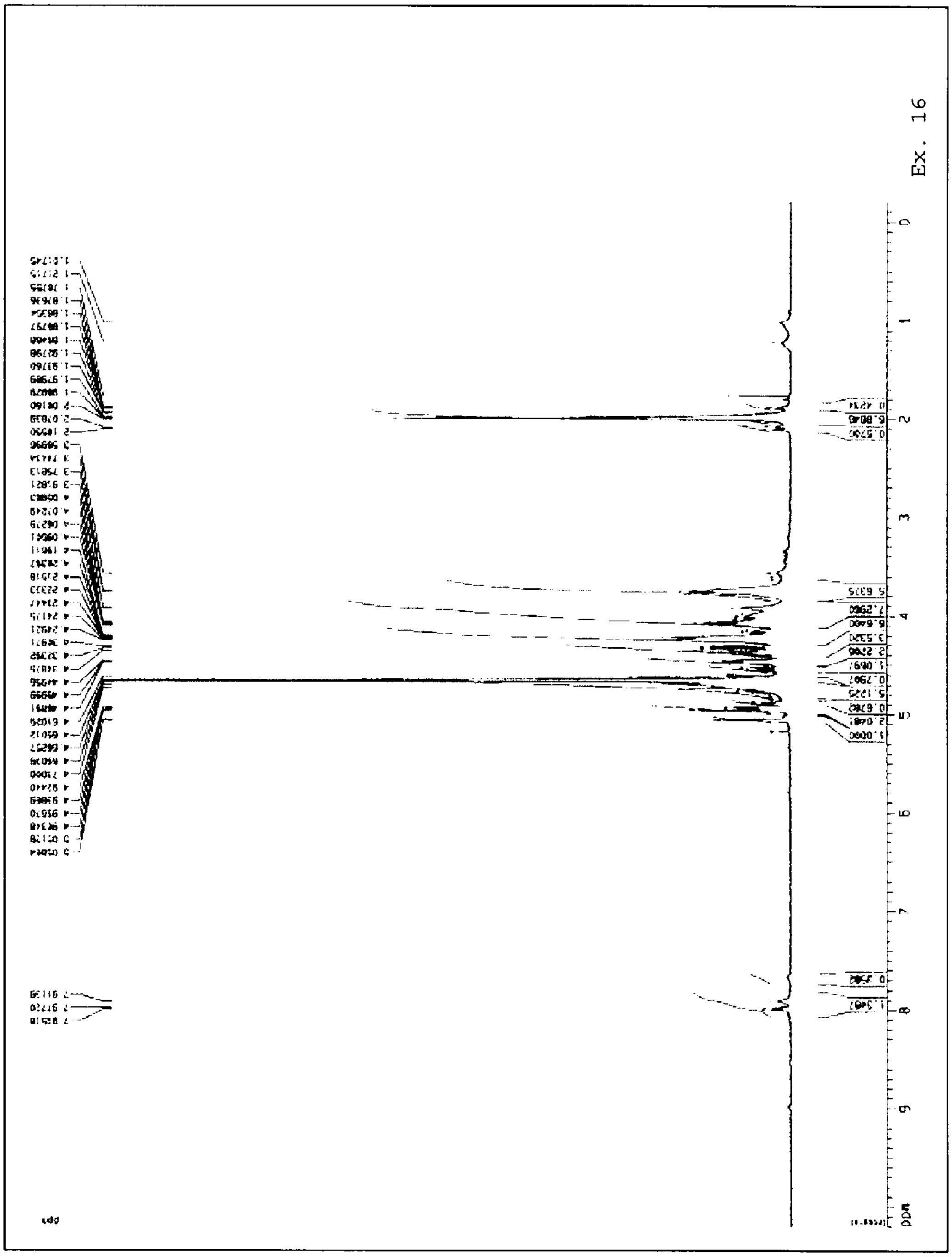
FIG. 66 is a $^1$H-NMR chart of Compound 16.

$^1$H-NMR: FIG. 66 illustrates the chart.

Example 17

The same process as that in Example 14 was performed except that the compound obtained in Production Example 17 (8 mg) was used instead as a material to yield Compound 17 (14 mg, white powder).

$[M+3Na]^{3+}$: 1344.06

Figure 67:
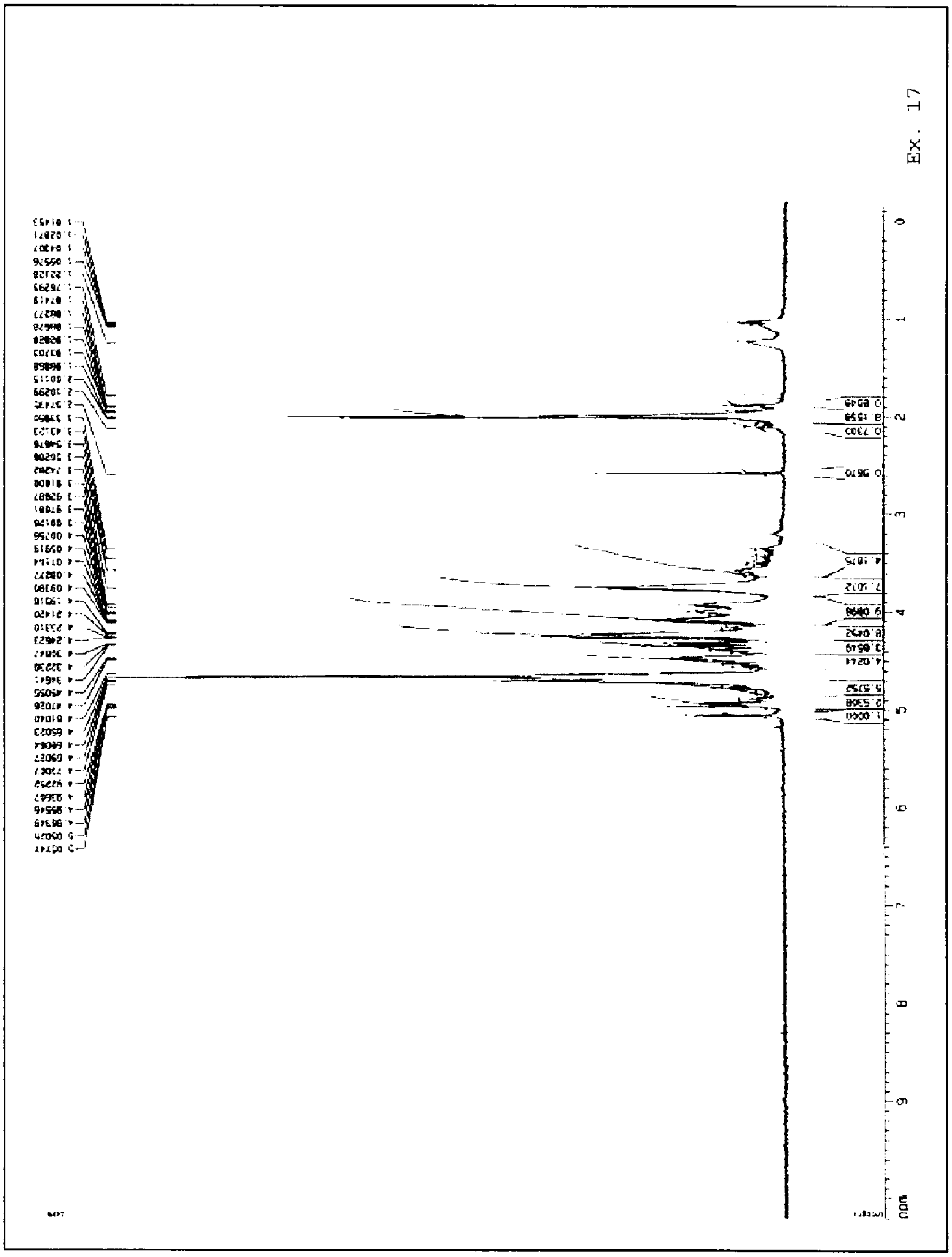
FIG. 67 is a $^1$H-NMR chart of Compound 17.

$^1$H-NMR: FIG. 67 illustrates the chart.

Example 18

The same process as that in Example 14 was performed except that the compound obtained in Production Example 18 (16 mg) was used instead as a material to yield Compound 18 (23 mg, white powder).

$[M+4Na]^{4+}$: 1217.00

Figure 68:
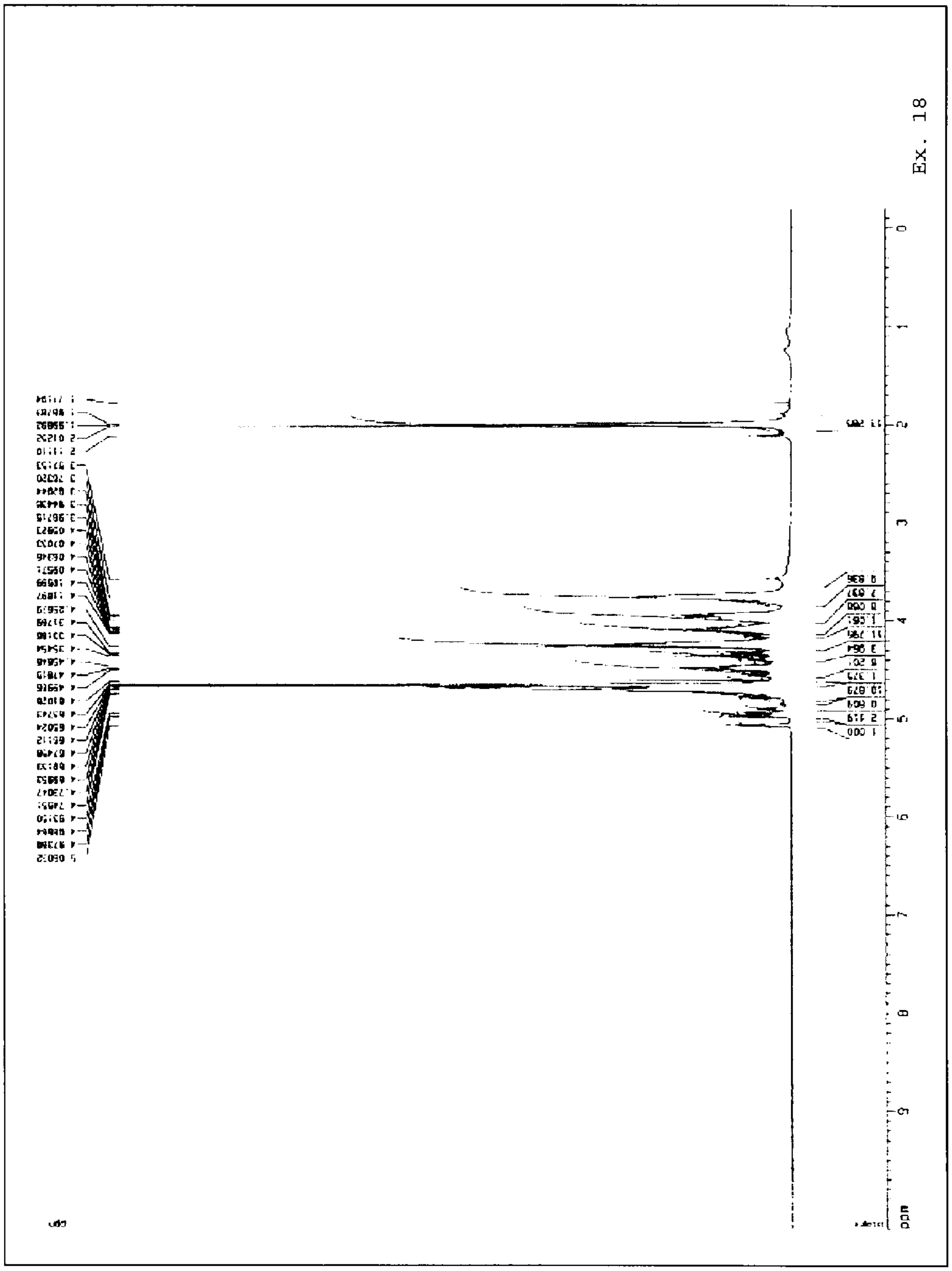
FIG. 68 is a $^1$H-NMR chart of Compound 18.

$^1$H-NMR: FIG. 68 illustrates the chart.

Example 19

The same process as that in Example 14 was performed except that the compound obtained in Production Example 19 (11 mg) was used instead as a material to yield Compound 19 (9 mg, white powder).

Figure 69:
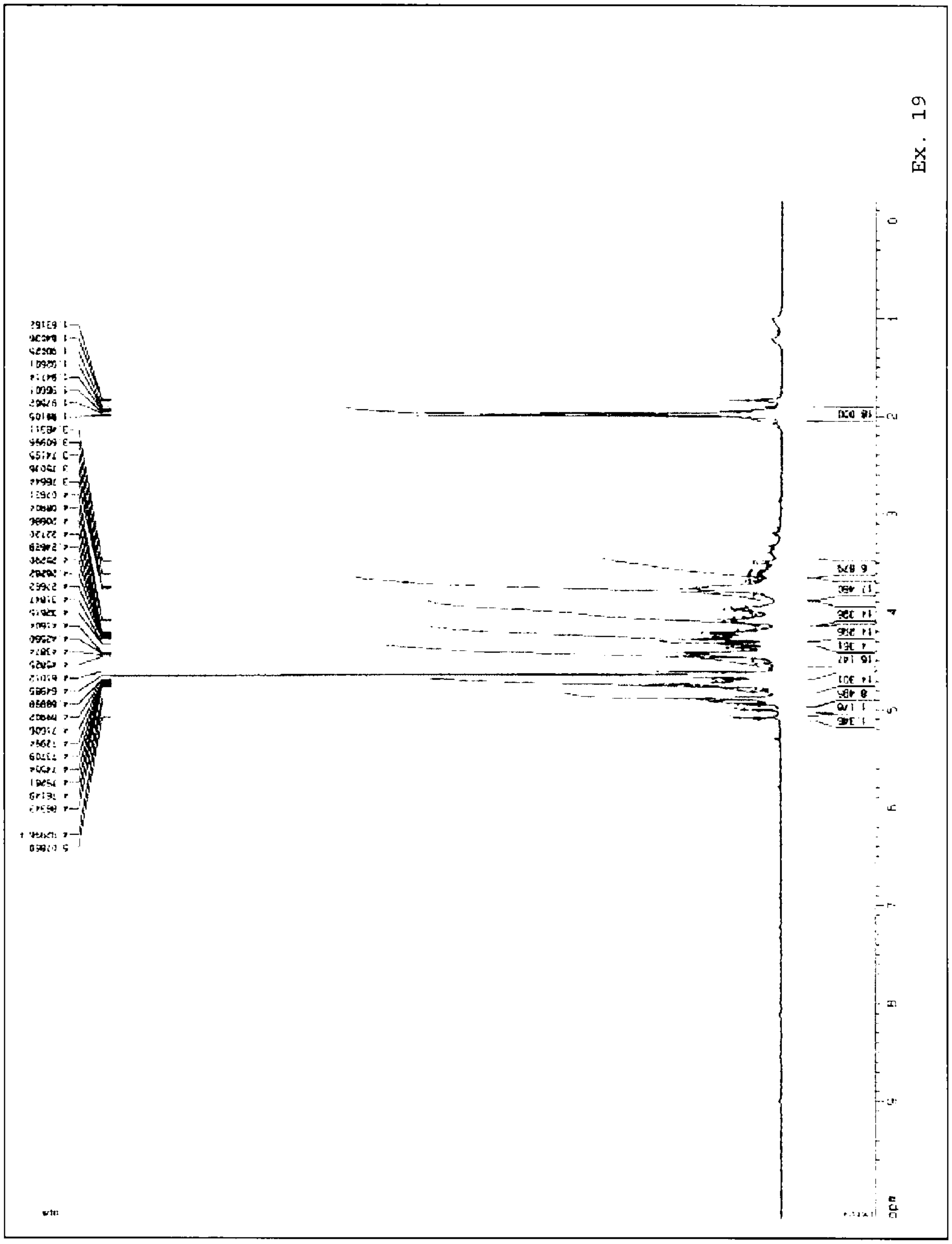
FIG. 69 is a $^1$H-NMR chart of Compound 19.

$^1$H-NMR: FIG. 69 illustrates the chart.

Example 20

The same process as that in Example 14 was performed except that the compound obtained in Production Example 20 (5 mg) was used instead as a material to yield Compound 20 (8 mg, white powder).

Figure 70:
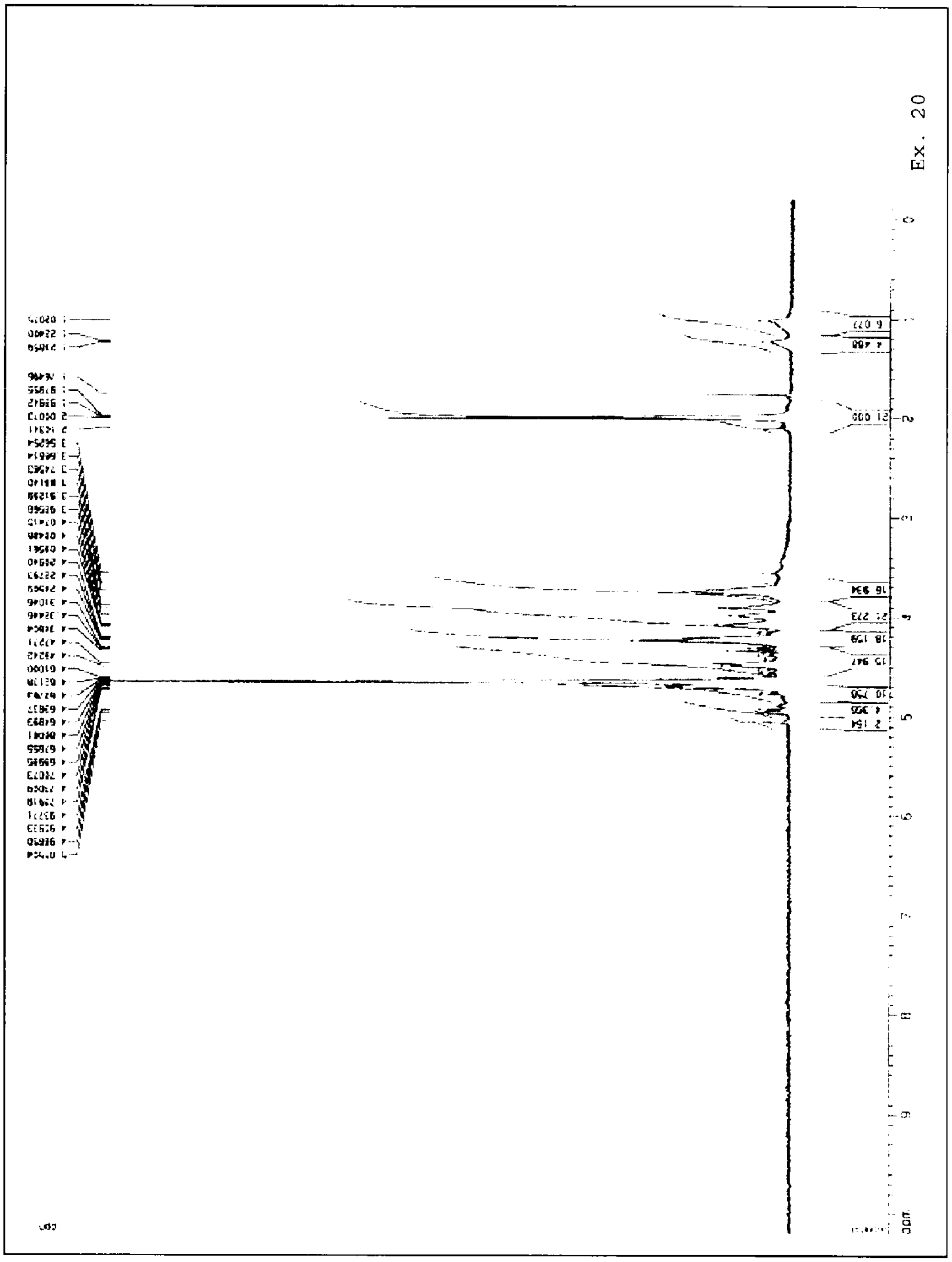
FIG. 70 is a $^1$H-NMR chart of Compound 20.

$^1$H-NMR: FIG. 70 illustrates the chart.

Example 21

The same process as that in Example 14 was performed except that the compound obtained in Production Example 21 (8 mg) was used instead as a material to yield Compound 21 (11 mg, white powder).

Figure 71:
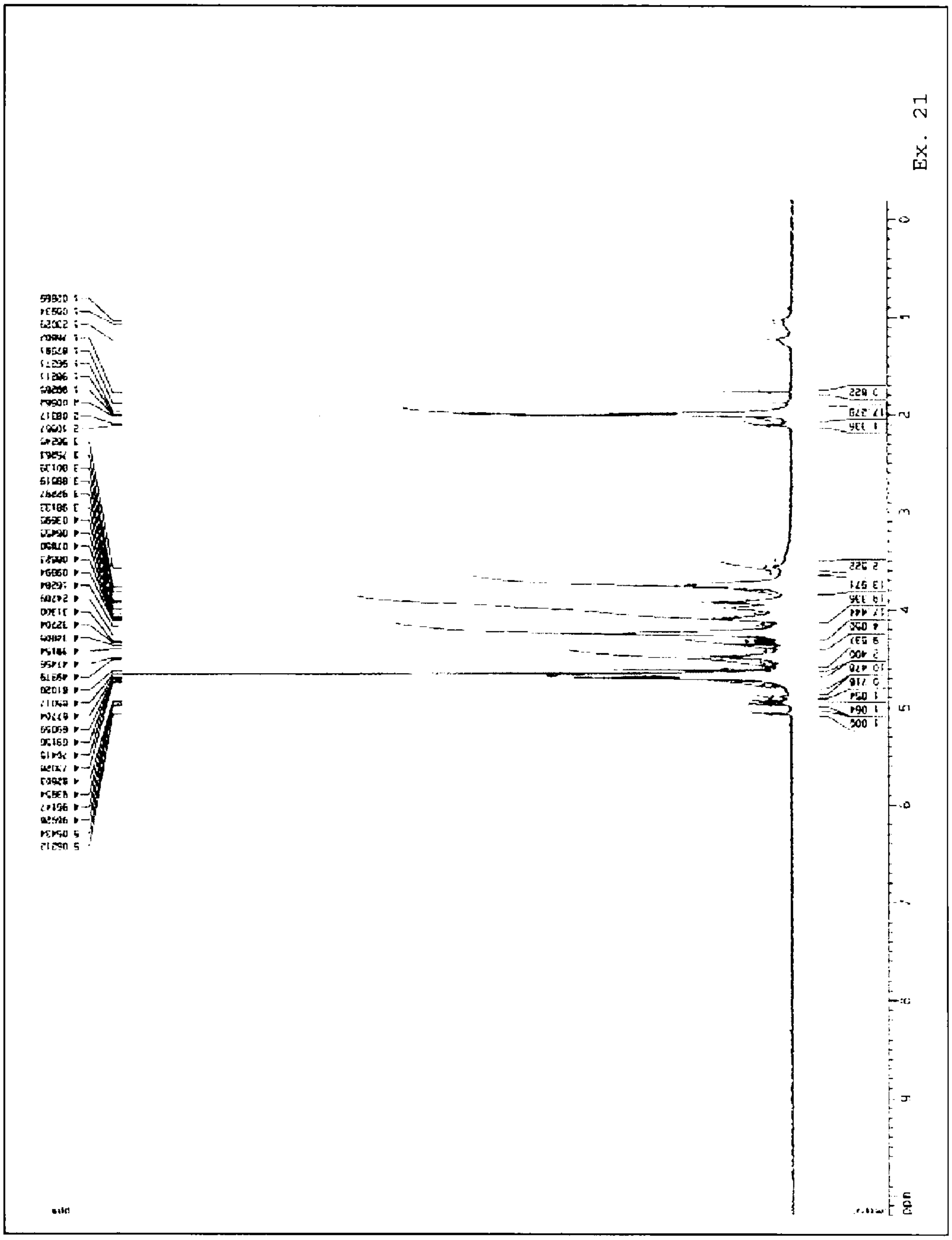
FIG. 71 is a $^1$H-NMR chart of Compound 21.

$^1$H-NMR: FIG. 71 illustrates the chart.

Example 22

The same process as that in Example 14 was performed except that the compound obtained in Production Example 22 (13 mg) was used instead as a material to yield Compound 22 (14 mg, white powder).

Figure 72:
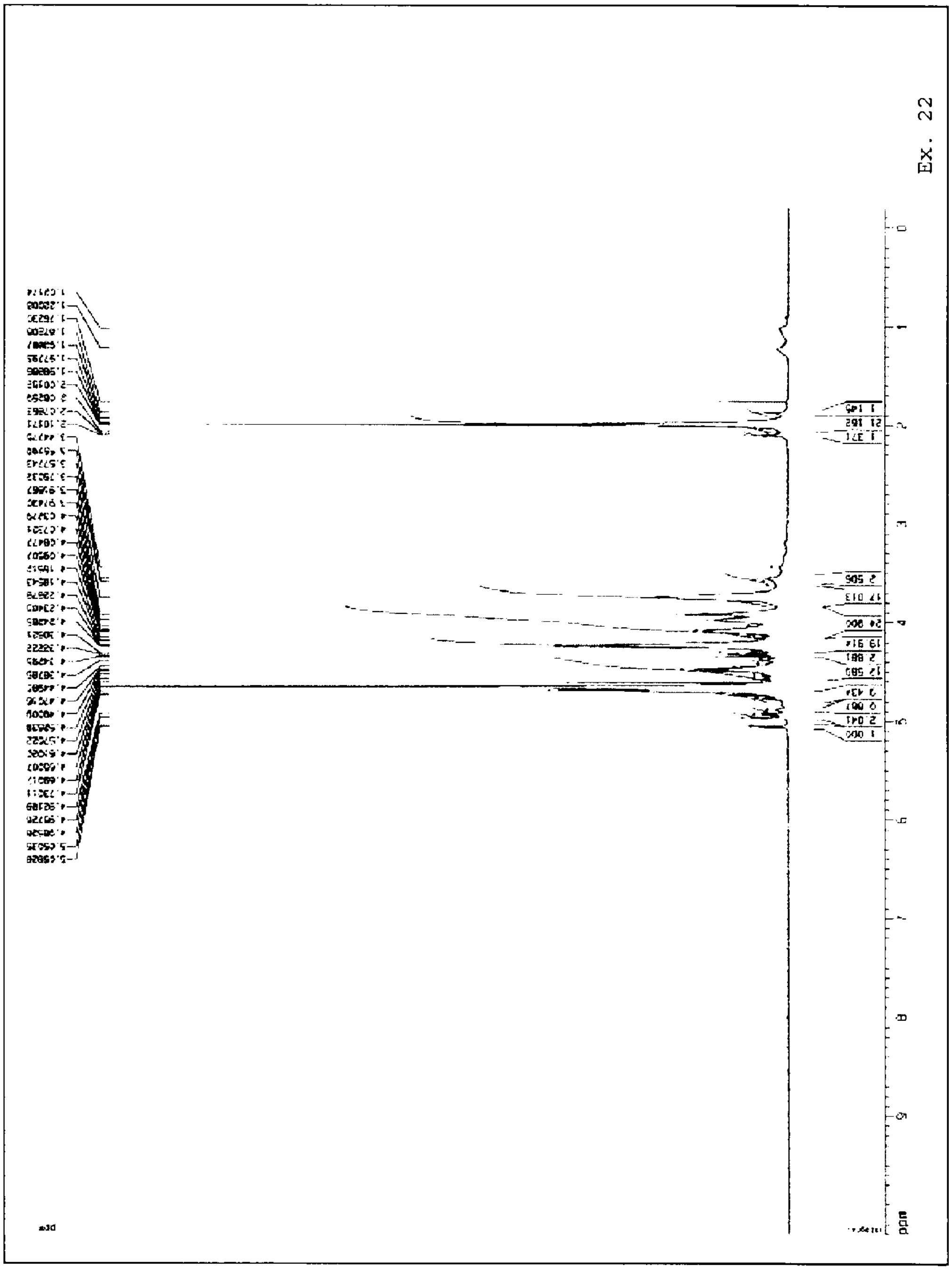
FIG. 72 is a $^1$H-NMR chart of Compound 22.

$^1$H-NMR: FIG. 72 illustrates the chart.

The structures of Compounds 14 to 22 are shown in Table 9 below.

TABLE 9

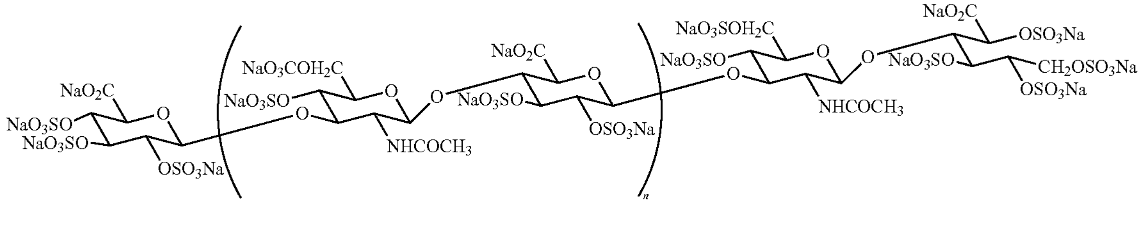

| Compound No. | n |
|---|---|
| 14 | 0 |
| 15 | 1 |

TABLE 9-continued

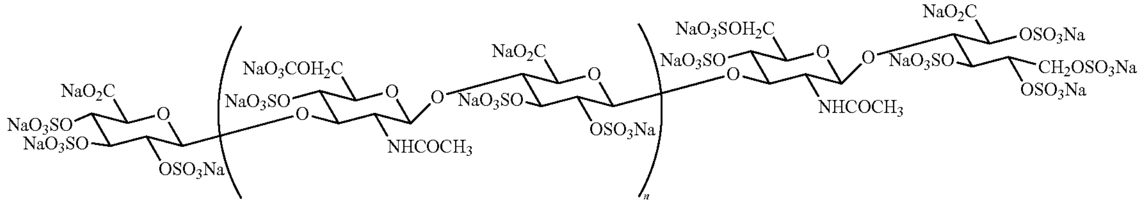

| Compound No. | n |
|---|---|
| 16 | 2 |
| 17 | 3 |
| 18 | 4 |
| 19 | 5 |
| 20 | 6 |
| 21 | 7 |
| 22 | 8 |

Example 23

The same process as that in Example 14 was performed except that the compound obtained in Production Example 23 (8 mg) was used instead as a material to yield Compound 23 (14 mg, white powder).

$[M+2Na]^{2+}$: 793.81

Figure 73:
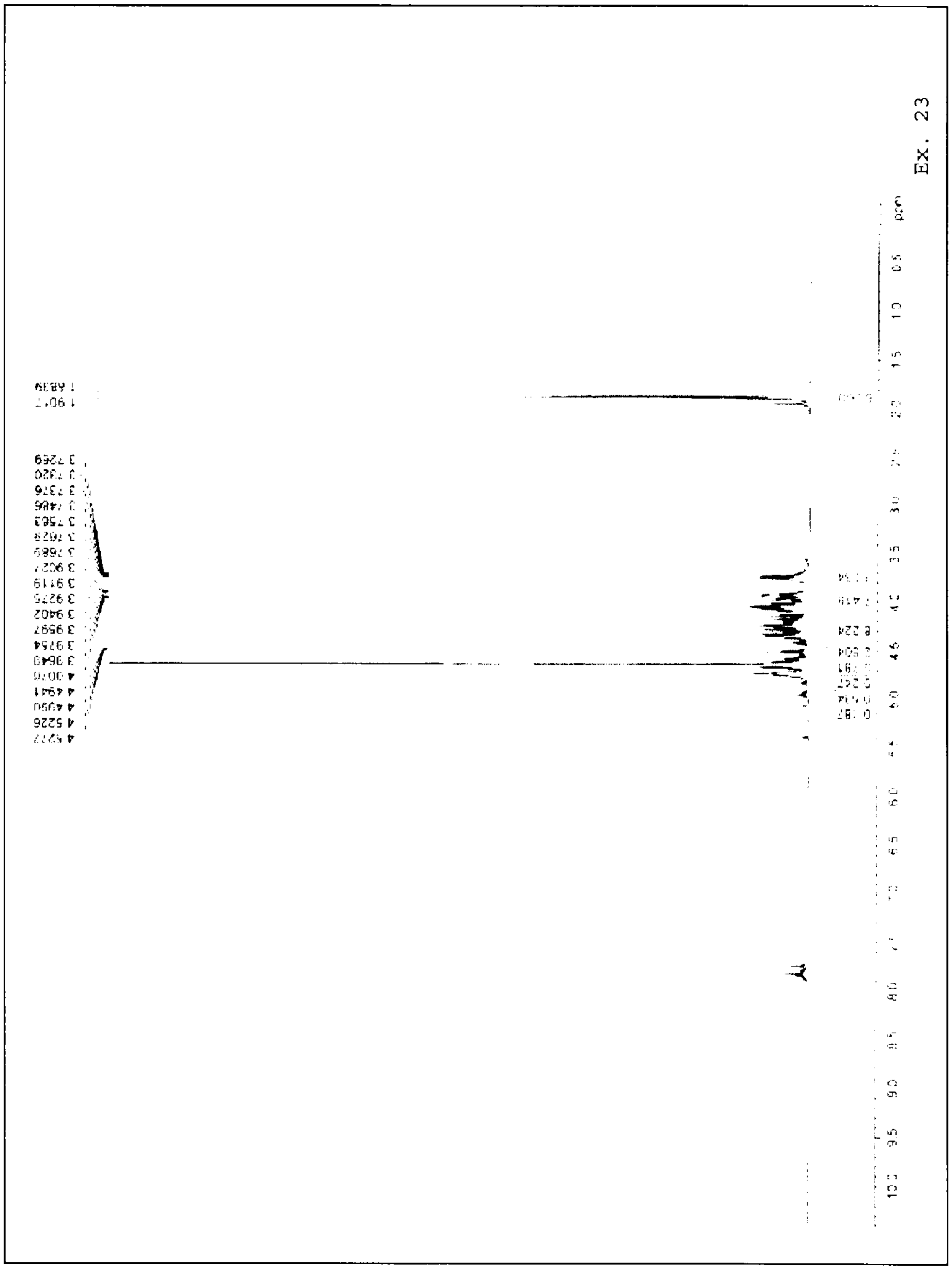
FIG. 73 is a $^1$H-NMR chart of Compound 23.

$^1$H-NMR: FIG. 73 illustrates the chart.

Example 24

The same process as that in Example 14 was performed except that the compound obtained in Production Example 24 (4 mg) was used instead as a material to yield Compound 24 (7 mg, white powder).

$[M+2H]^{2+}$: 1176.25

Figure 74:
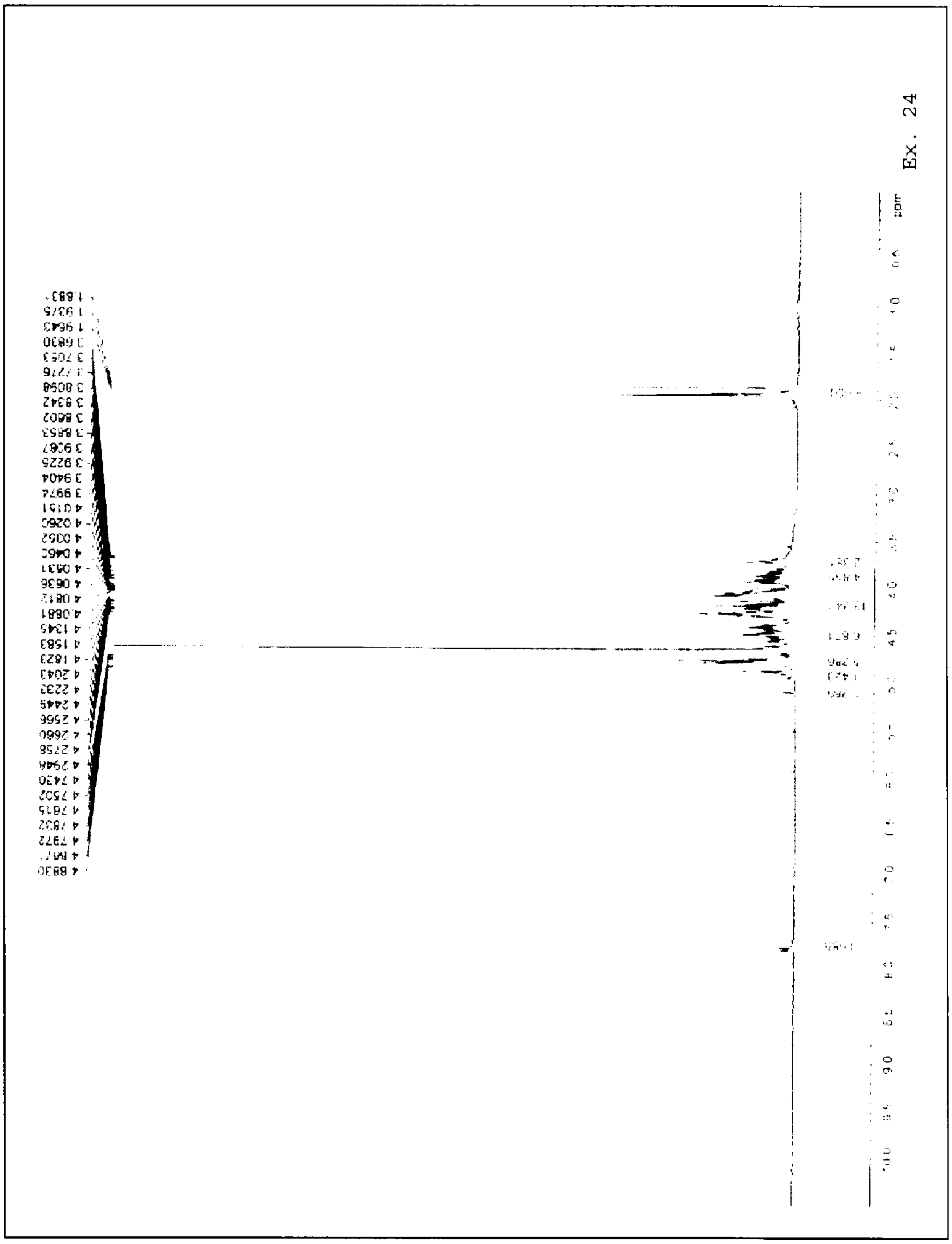
FIG. 74 is a $^1$H-NMR chart of Compound 24.

$^1$H-NMR: FIG. 74 illustrates the chart.

Example 25

The same process as that in Example 14 was performed except that the compound obtained in Production Example 25 (8 mg) was used instead as a material to yield Compound 25 (11 mg, white powder).

$[M+3Na]^{3+}$: 1076.10

Figure 75:
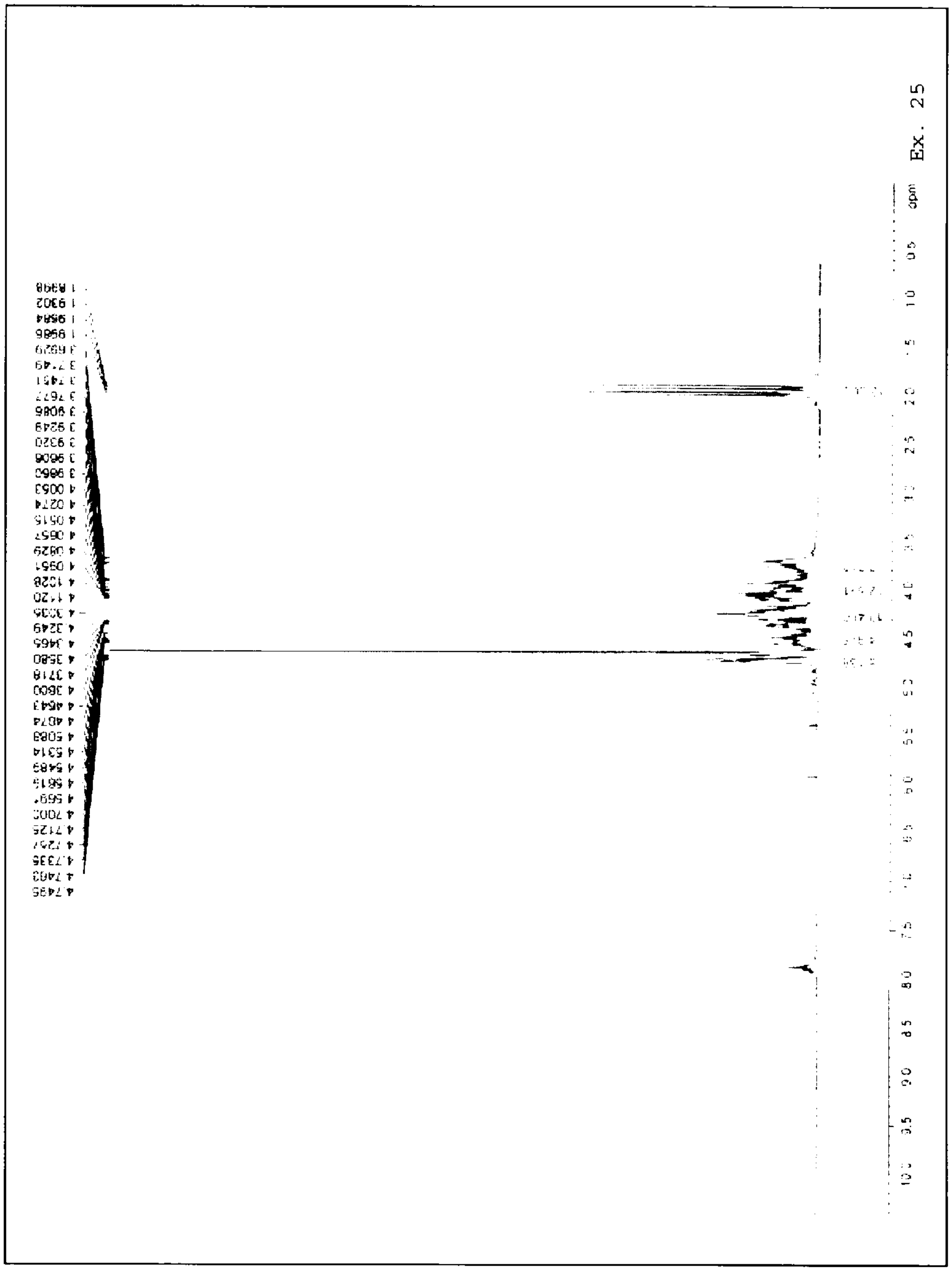
FIG. 75 is a $^1$H-NMR chart of Compound 25.

$^1$H-NMR: FIG. 75 illustrates the chart.

Example 26

The same process as that in Example 14 was performed except that the compound obtained in Production Example 26 (15 mg) was used instead as a material to yield Compound 26 (26 mg, white powder).

$[M+3Na]^{3+}$: 1345.72

Figure 76:
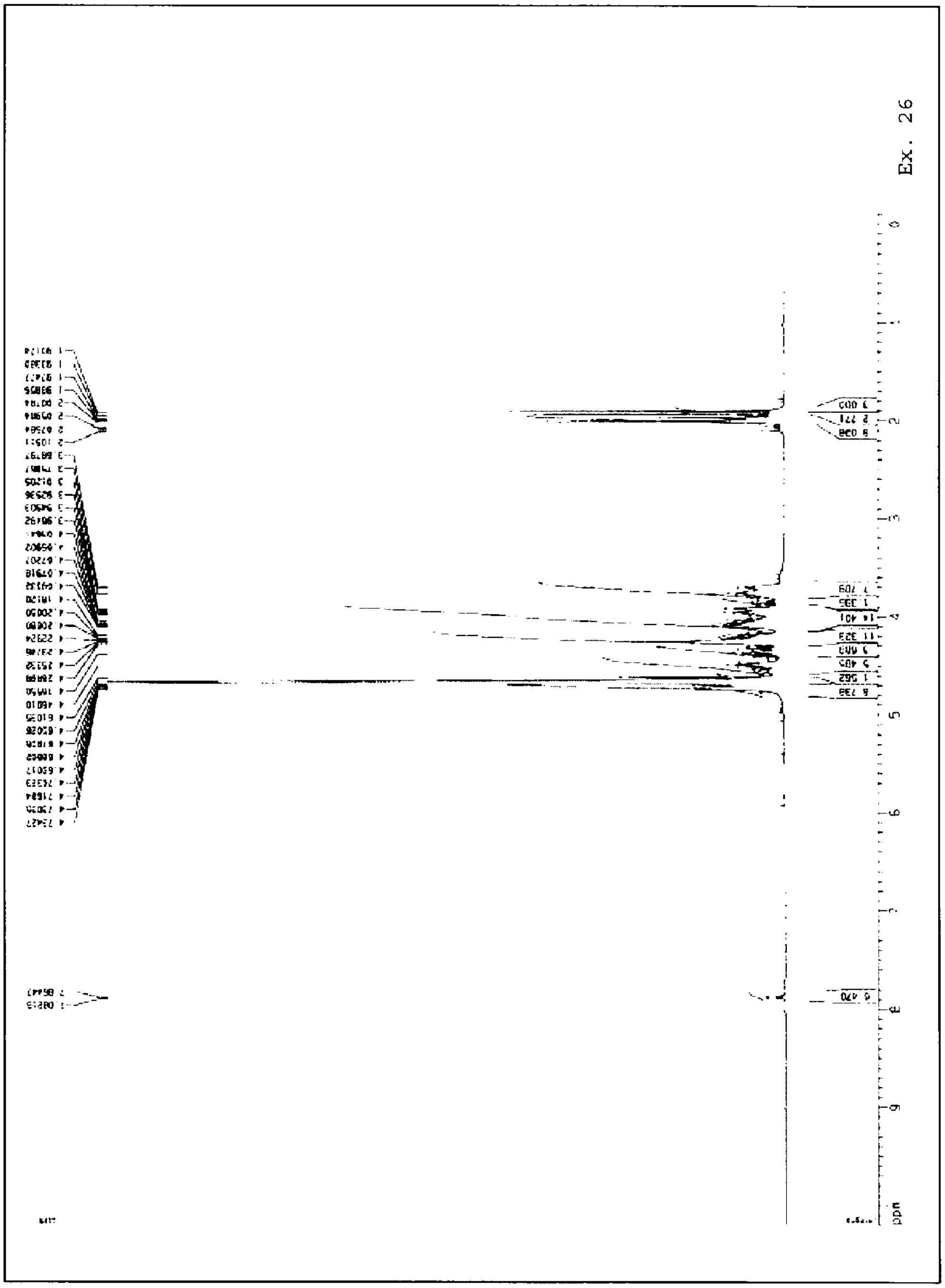
FIG. 76 is a $^1$H-NMR chart of Compound 26.

$^1$H-NMR: FIG. 76 illustrates the chart.

Example 27

The same process as that in Example 14 was performed except that the compound obtained in Production Example 27 (7 mg) was used instead as a material to yield Compound 27 (11 mg, white powder).

$[M+4Na]^{4+}$: 1616.67

Figure 77:
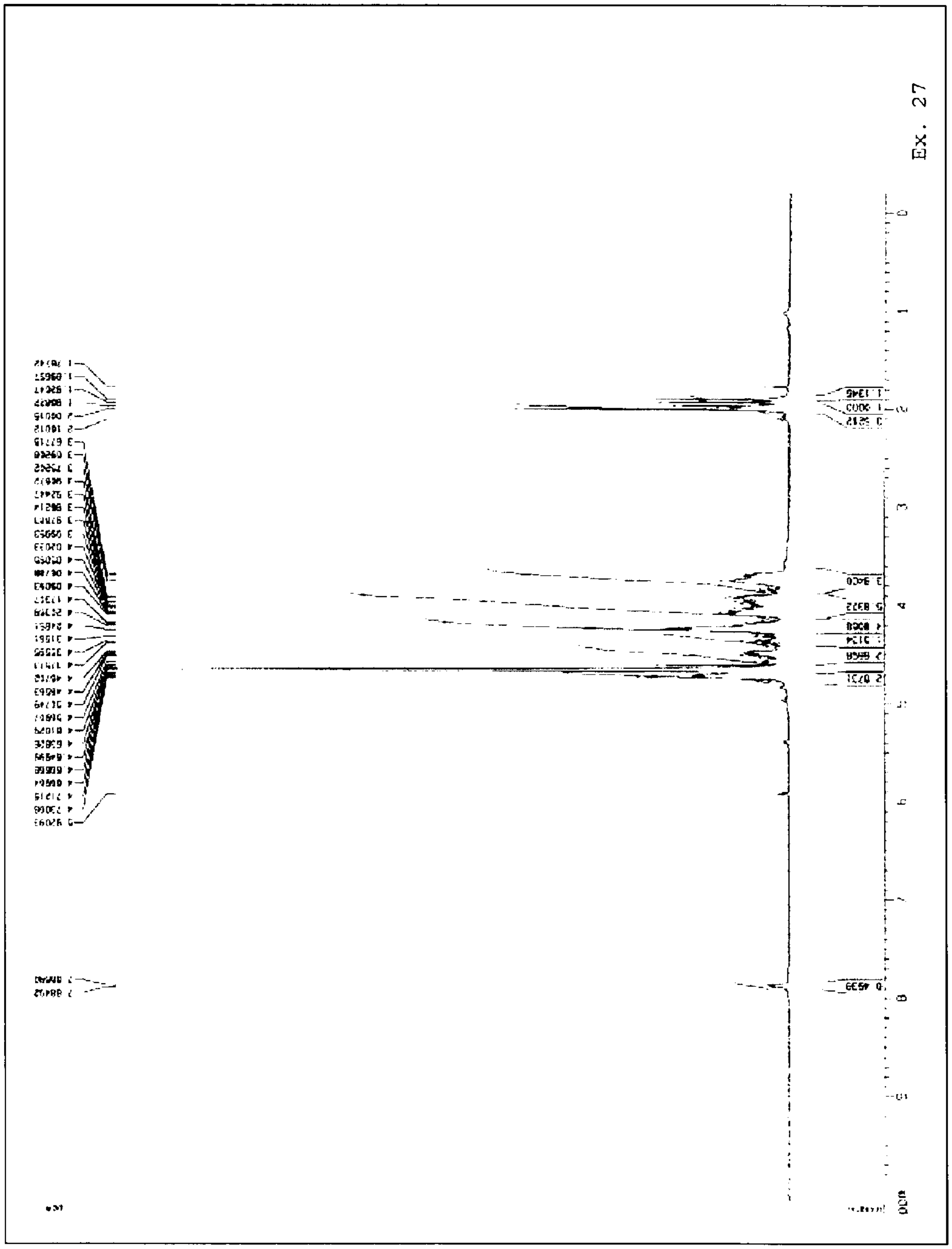
FIG. 77 is a $^1$H-NMR chart of Compound 27.

$^1$H-NMR: FIG. 77 illustrates the chart.

Example 28

The same process as that in Example 14 was performed except that the compound obtained in Production Example 28 (5 mg) was used instead as a material to yield Compound 28 (7 mg, white powder).

Figure 78:
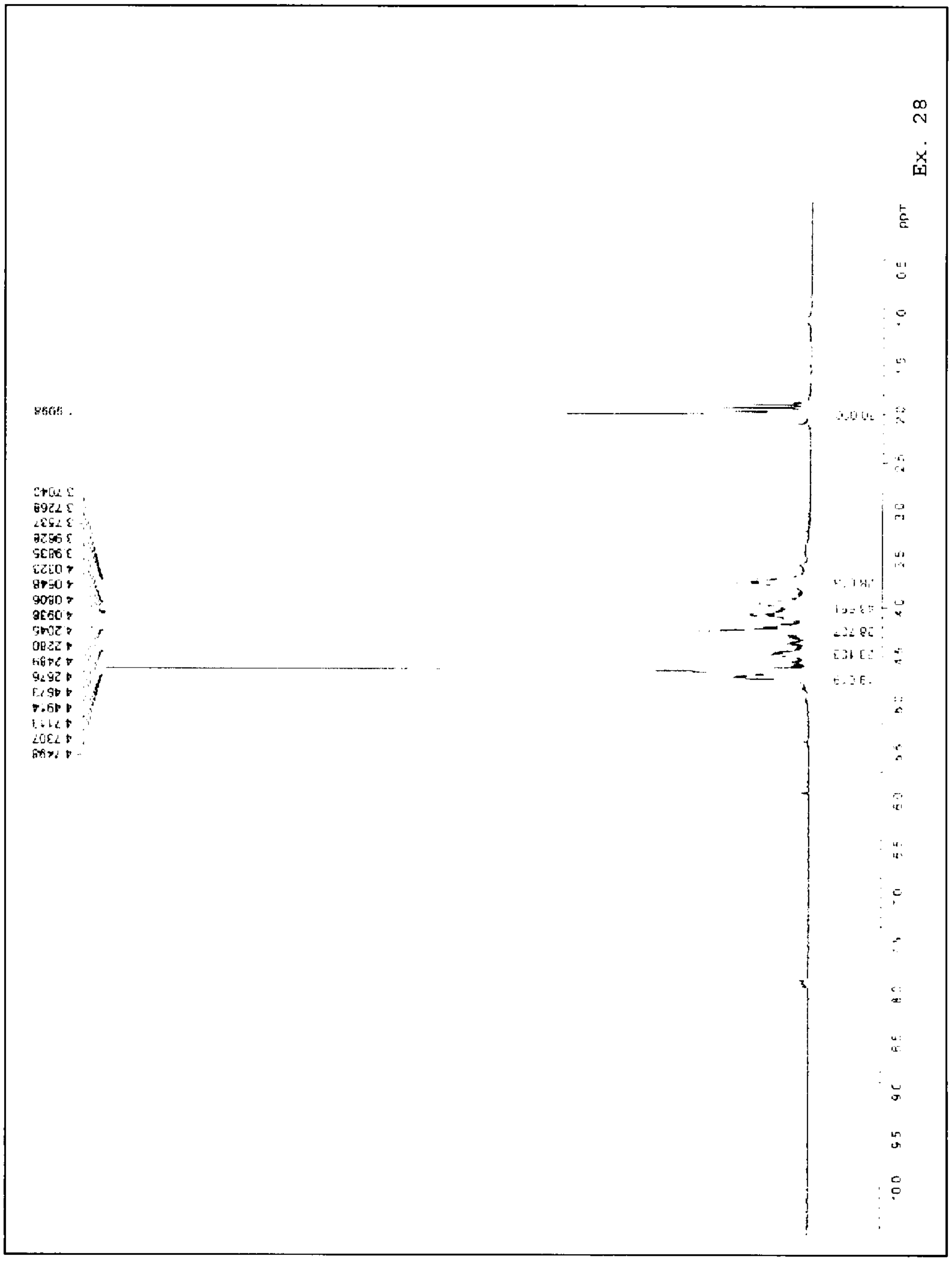
FIG. 78 is a $^1$H-NMR chart of Compound 28.

$^1$H-NMR: FIG. 78 illustrates the chart.

The structures of Compounds 23 to 28 are shown in Table 10 below.

TABLE 10

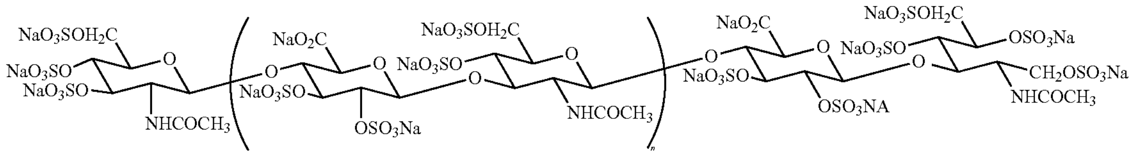

| Compound No. | n |
|---|---|
| 23 | 0 |
| 24 | 1 |
| 25 | 2 |
| 26 | 3 |
| 27 | 4 |
| 28 | 8 |

Example 29

The same process as that in Example 14 was performed except that the compound obtained in Production Example 29 (9 mg) was used instead as a material to yield Compound 29 (16 mg, white powder).

$[M+2H]^{2+}$: 972.77

Figure 79:
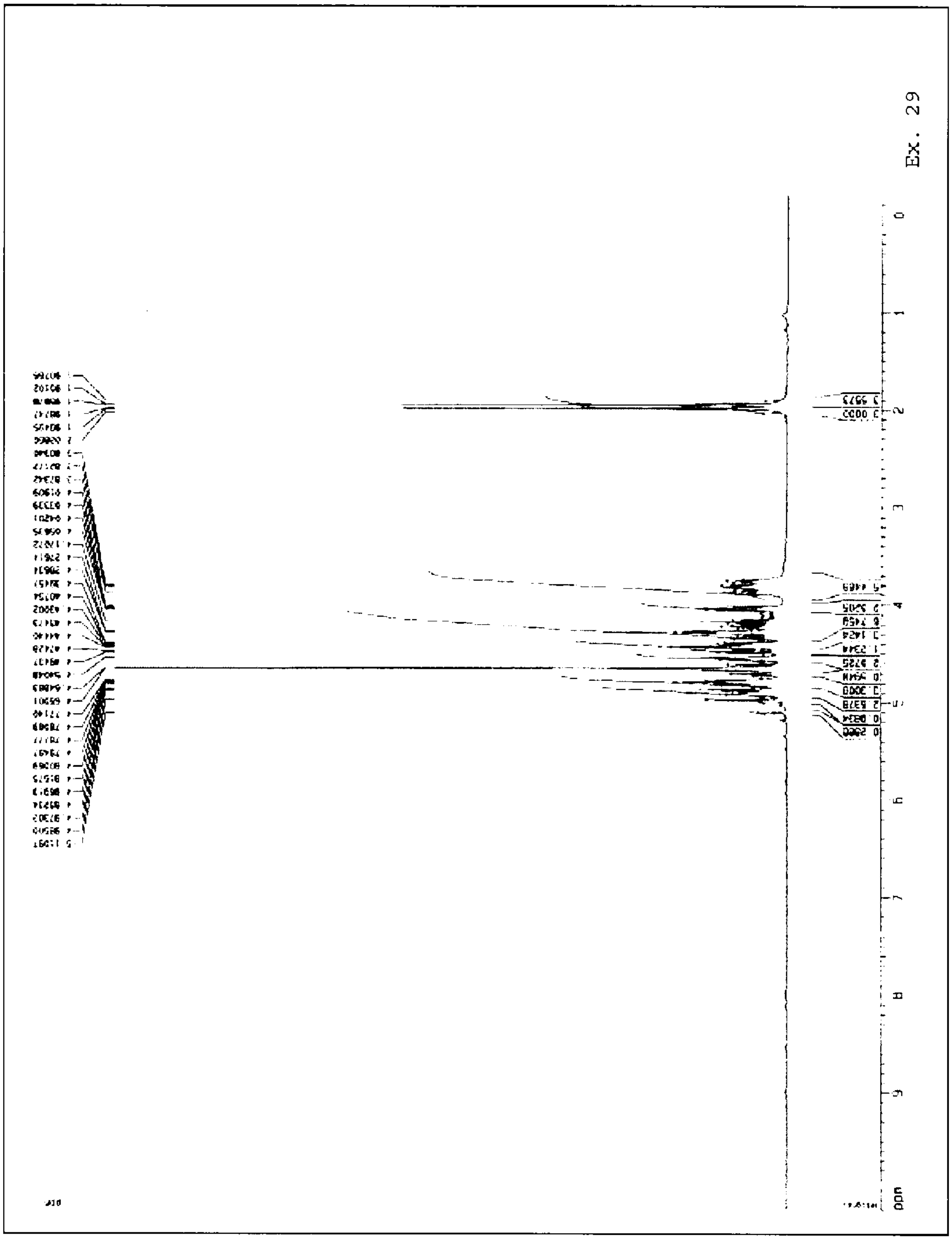
FIG. 79 is a $^1$H-NMR chart of Compound 29.

$^1$H-NMR: FIG. 79 illustrates the chart.

Example 30

The same process as that in Example 14 was performed except that the compound obtained in Production Example 30 (7 mg) was used instead as a material to yield Compound 30 (8 mg, white powder).

$[M+2H]^{2+}$: 1377.20

Figure 80:
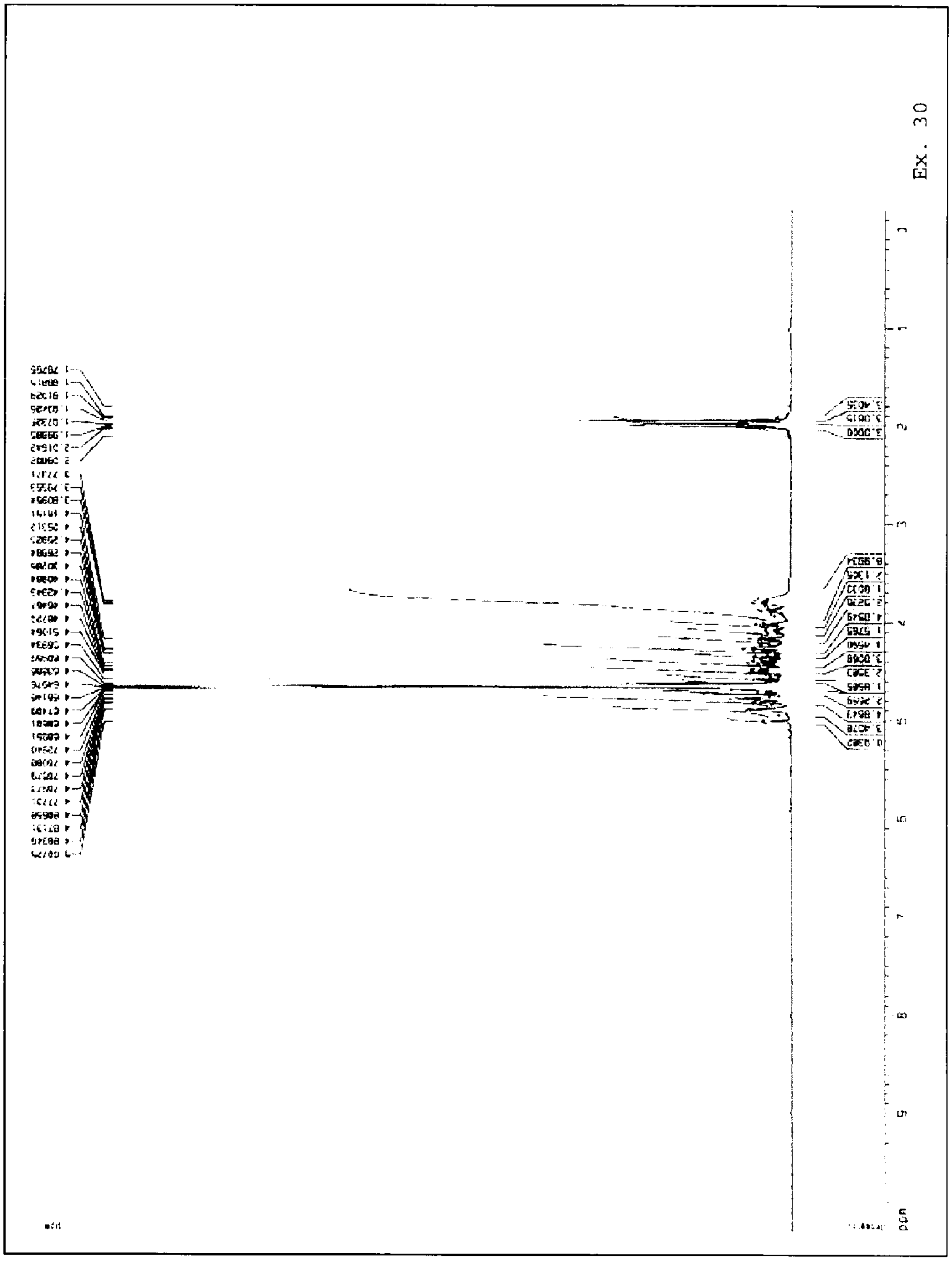
FIG. 80 is a $^1$H-NMR chart of Compound 30.

$^1$H-NMR: FIG. 80 illustrates the chart.

Example 31

The same process as that in Example 14 was performed except that the compound obtained in Production Example 31 (15 mg) was used instead as a material to yield Compound 31 (21 mg, white powder).

$[M+3Na]^{3+}$: 1210.07

Figure 81:
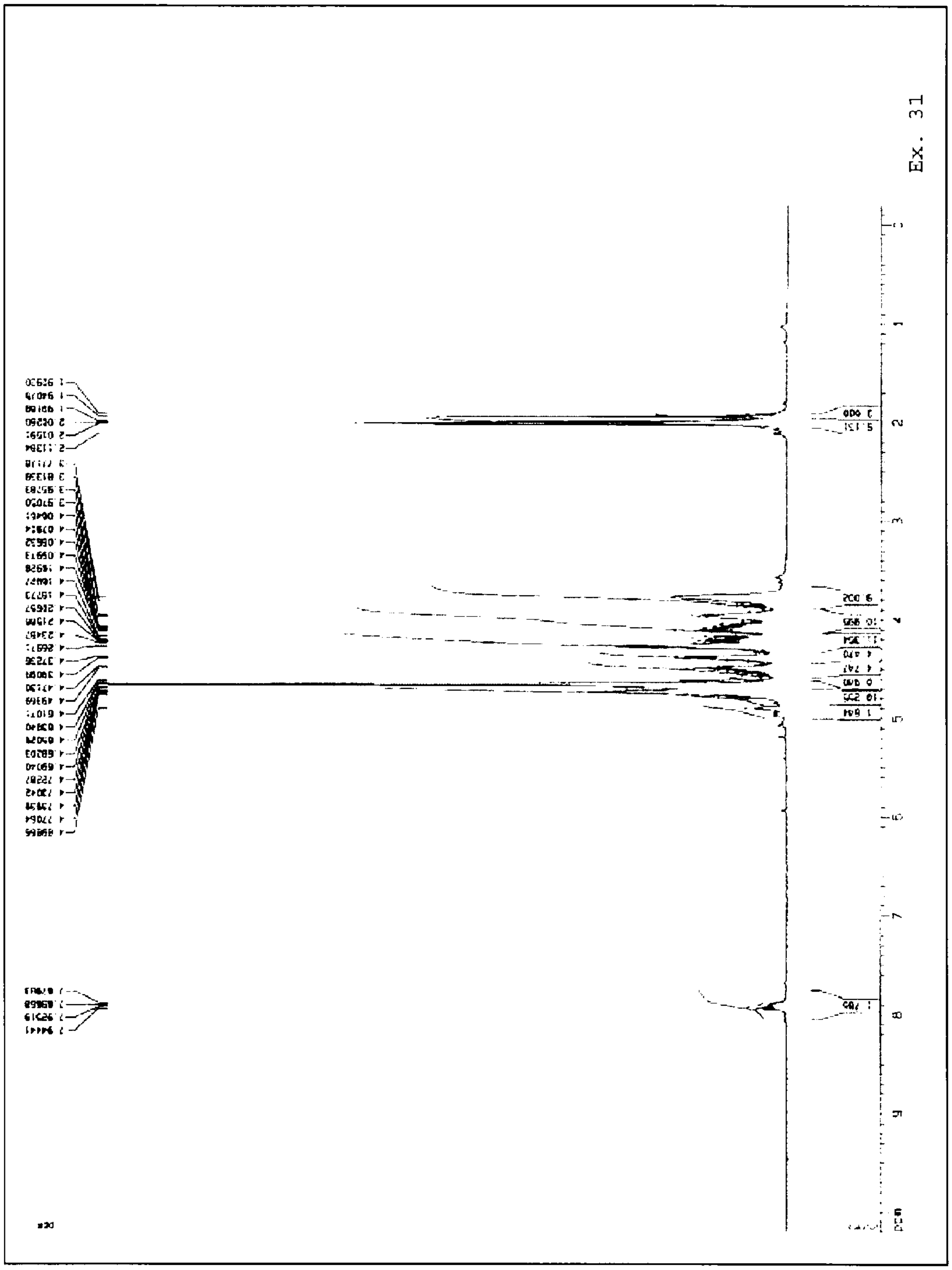
FIG. 81 is a $^1$H-NMR chart of Compound 31.

$^1$H-NMR: FIG. 81 illustrates the chart.

Example 32

The same process as that in Example 14 was performed except that the compound obtained in Production Example 32 (8 mg) was used instead as a material to yield Compound 32 (9 mg, white powder).

$[M+3H]^{3+}$: 1458.34

Figure 82:
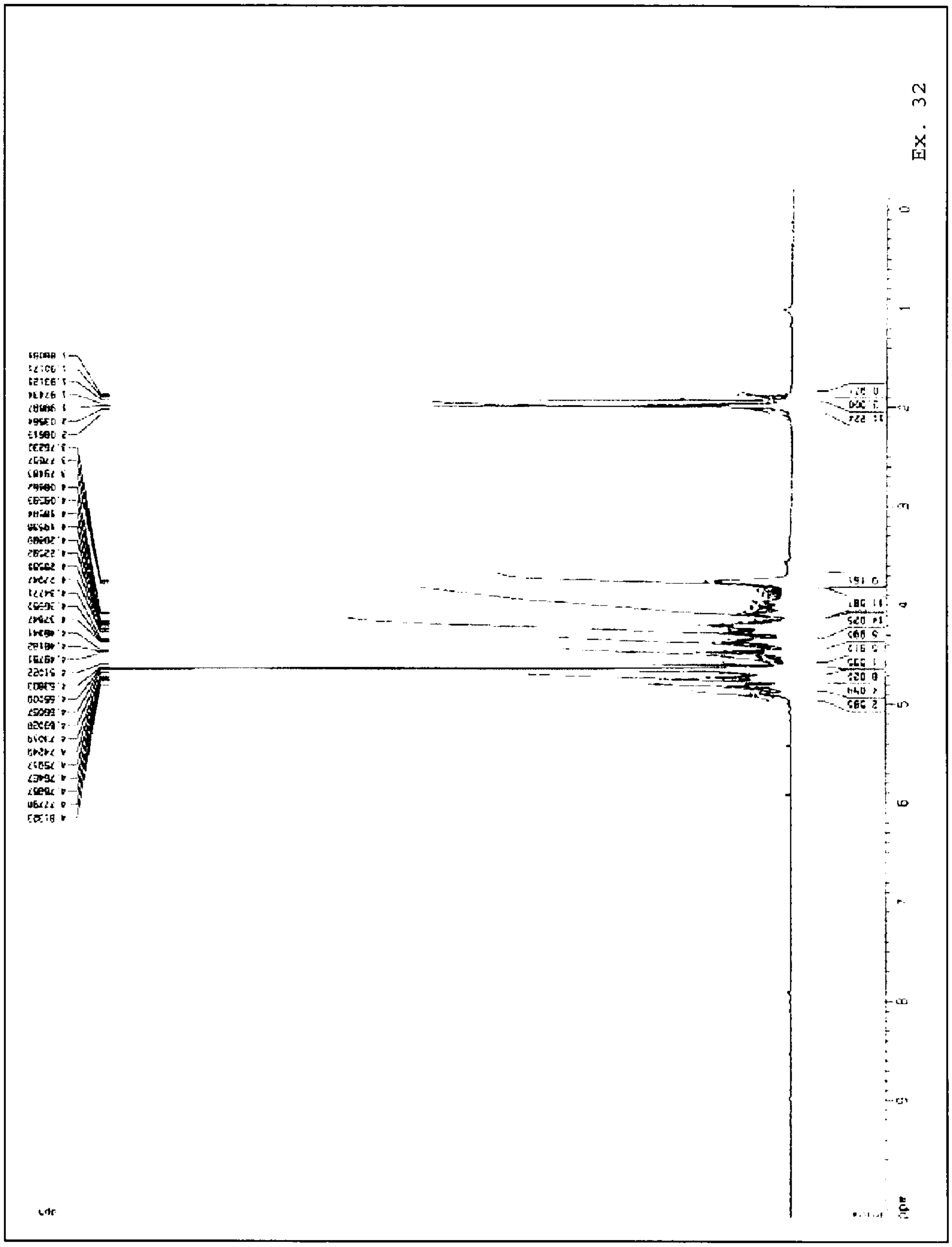
FIG. 82 is a $^1$H-NMR chart of Compound 32.

$^1$H-NMR: FIG. 82 illustrates the chart.

Example 33

The same process as that in Example 14 was performed except that the compound obtained in Production Example 33 (5 mg) was used instead as a material to yield Compound 33 (7 mg, white powder).

Figure 83:
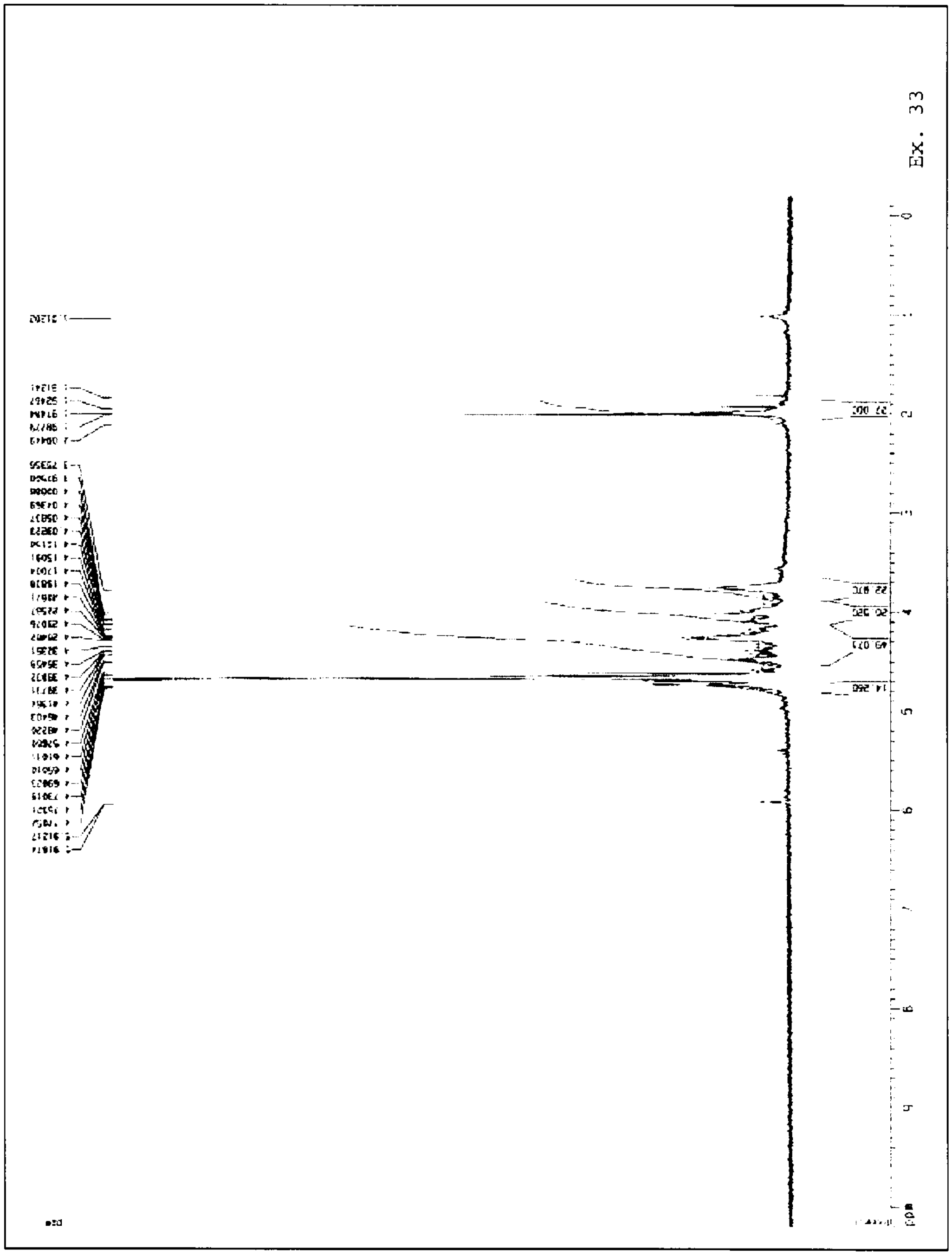
FIG. 83 is a $^1$H-NMR chart of Compound 33.

$^1$H-NMR: FIG. 83 illustrates the chart.

The structures of Compounds 29 to 33 are shown in Table 11 below.

Example 34

The compound synthesized in Production Example 36 (7 mg) was dissolved in N,N-dimethylformamide (0.7 ml), and triethylamine sulfur trioxide (75 mg) and trifluoromethanesulfonic acid (12 μl) are added thereto, followed by stirring at 0° C. for 48 hours under a nitrogen atmosphere.

After the resultant was cooled to 0° C., water (1 ml) was added to the resultant, and a saturated sodium acetate solution in ethanol (25 ml) was then added to cause precipitation. The solution was stirred with a Voltex mixer, and then, the resultant was subjected to centrifugation under cooling (at 4° C., at 3000 rpm, and for 15 minutes) to collect a precipitate. After the supernatant was discarded, water (1 ml) was added to dissolve the residue, and a saturated sodium acetate solution in ethanol (25 ml) was then added to cause precipitation. The solution was stirred with a Voltex mixer, and then, the resultant was subjected to centrifugation under cooling (at 4° C., at 3000 rpm, and for 15 minutes) to collect a precipitate. Again, after the supernatant was discarded, water (1 ml) was added to dissolve the residue, and a saturated sodium acetate solution in ethanol (25 ml) was then added to cause precipitation. The solution was stirred with a Voltex mixer, and then, the resultant was subjected to centrifugation under cooling (at 4° C., at 3000 rpm, and for 15 minutes) to collect a precipitate. Then, after the supernatant was discarded, the residue was dissolved in water (2 ml), followed by filtration through a disk filter (manufactured by Nihon Pall Ltd., 0.45 μm). The AKTA system (manufactured by GE Healthcare Bioscience Bioprocess Corp.) was used to apply the filtrate to gel filtration chromatography (G-10, 16 mm×600 mm, water) to perform desalting, and then, target fractions were freeze-dried to yield Compound 34 (9 mg, white powder).

Figure 84:
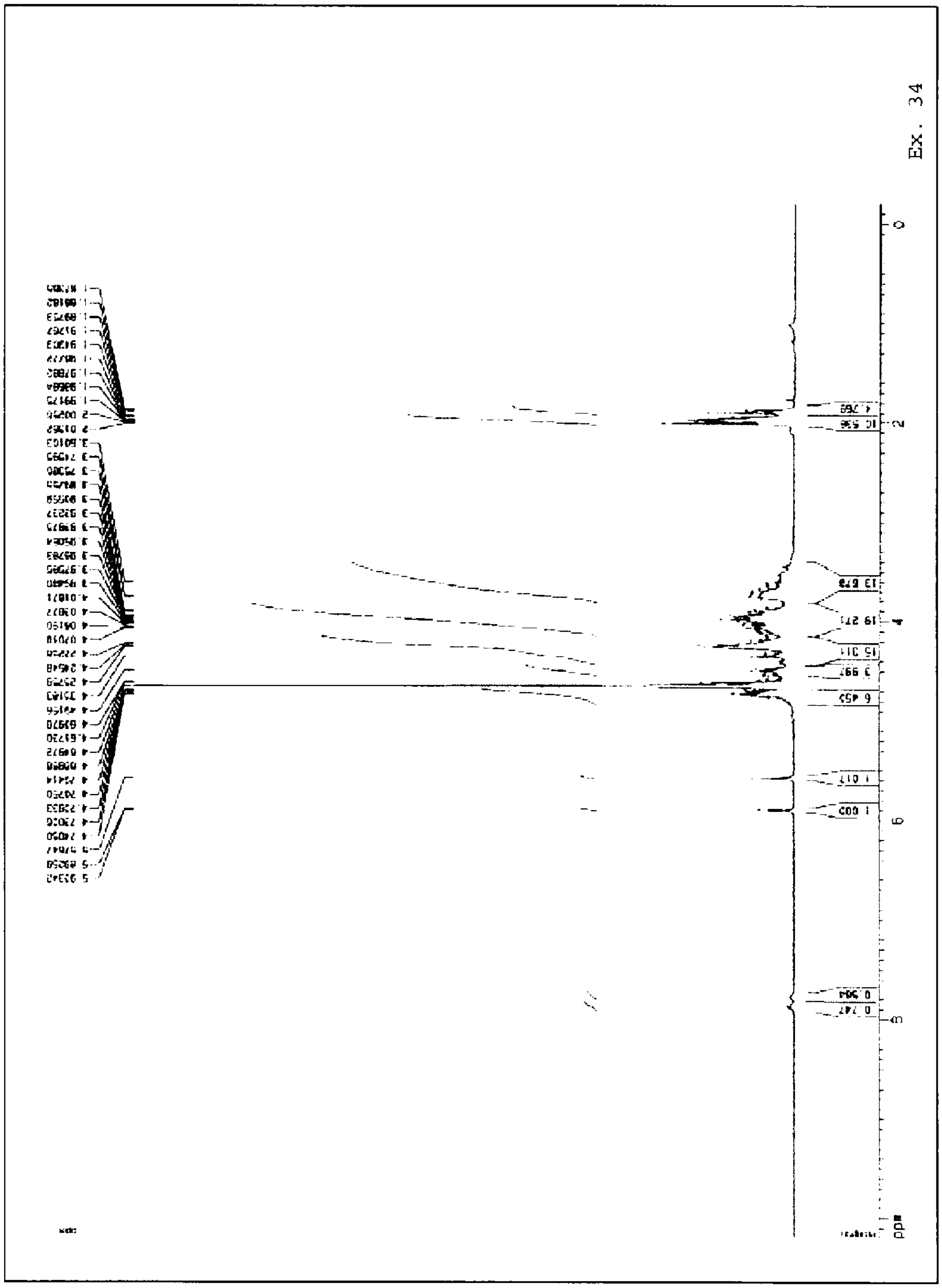
FIG. 84 is a $^1$H-NMR chart of Compound 34.

$^1$H-NMR: FIG. 84 illustrates the chart.

Example 35

The same process as that in Example 34 was performed except that the compound obtained in Production Example 37 (10 mg) was used instead as a material to yield Compound 35 (14 mg, white powder).

Figure 85:
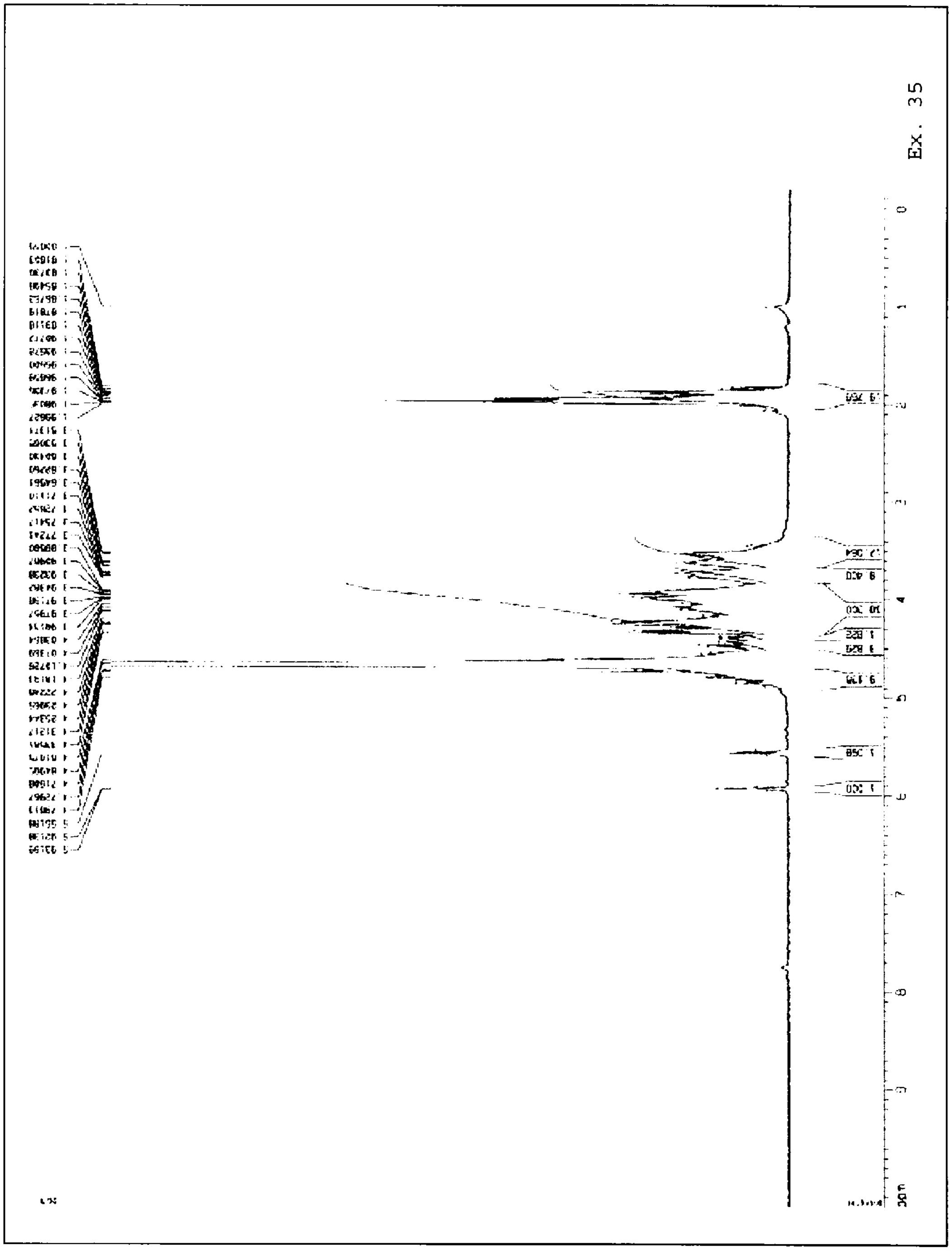
FIG. 85 is a $^1$H-NMR chart of Compound 35.

$^1$H-NMR: FIG. 85 illustrates the chart.

Example 36

The same process as that in Example 34 was performed except that the compound obtained in Production Example 38 (10 mg) was used instead as a material to yield Compound 36 (15 mg, white powder).

Figure 86:
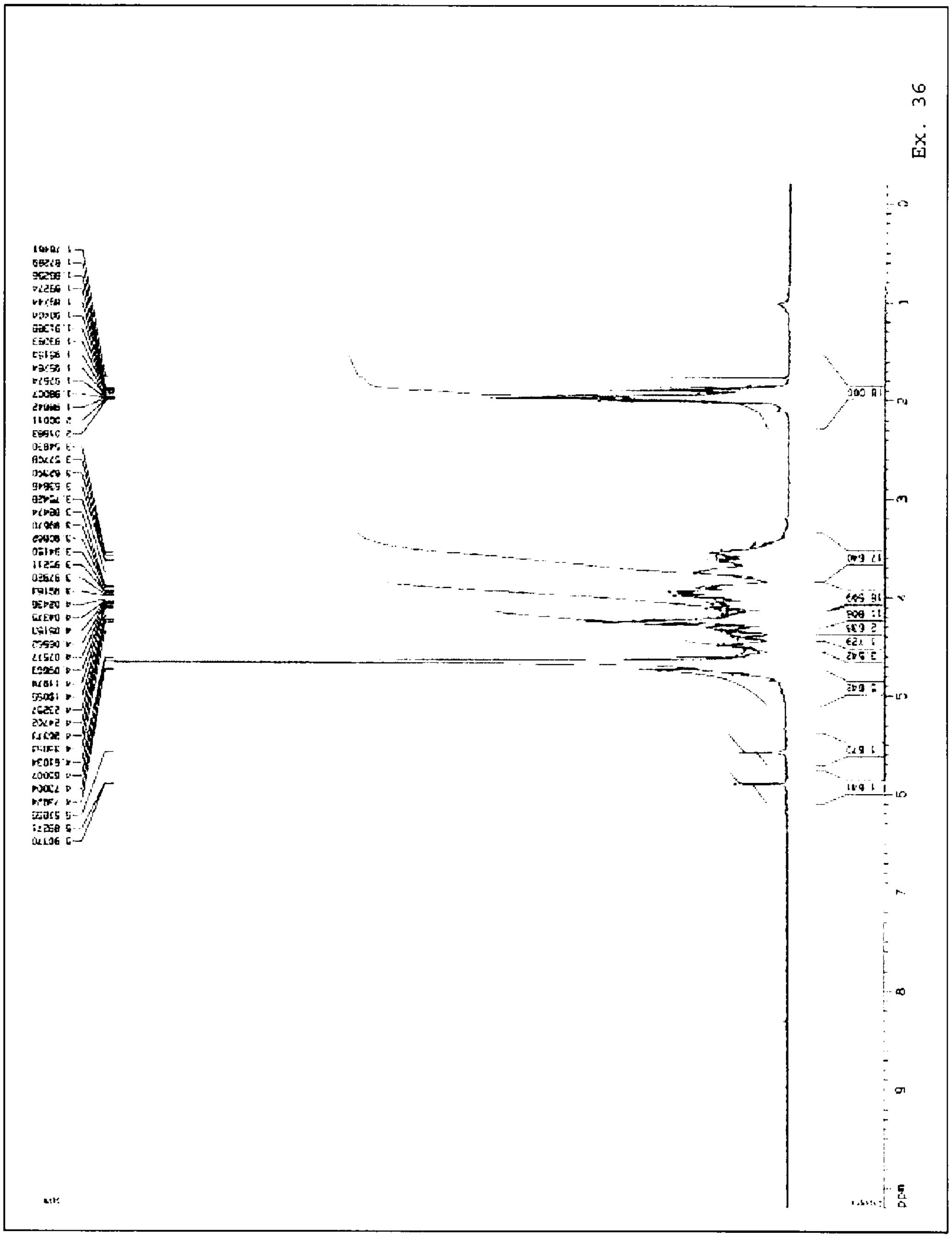
FIG. 86 is a $^1$H-NMR chart of Compound 36.

$^1$H-NMR: FIG. 86 illustrates the chart.

TABLE 11

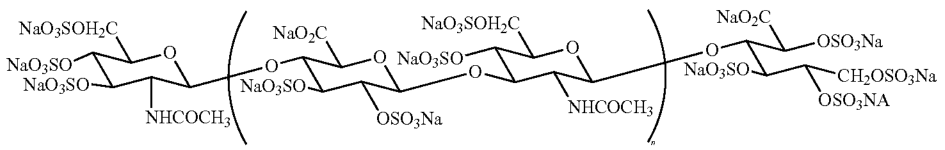

| Compound No. | n |
|---|---|
| 29 | 1 |
| 30 | 2 |
| 31 | 3 |
| 32 | 4 |
| 33 | 8 |

The structures of Compounds 34 to 36 are shown in Table 12 below.

TABLE 12

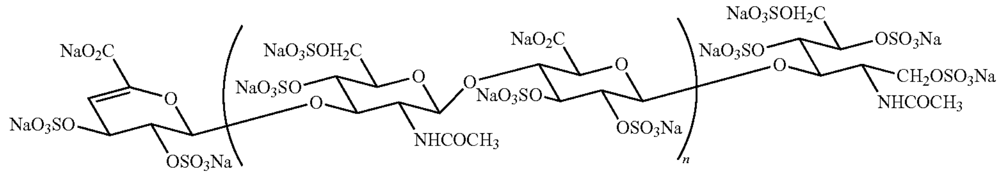

| Compound No. | n |
|---|---|
| 34 | 3 |
| 35 | 4 |
| 36 | 5 |

Example 37

The same process as that in Example 34 was performed except that the compound obtained in Production Example 41 (9 mg) was used instead as a material to yield Compound 37 (11 mg, white powder).

Figure 87:
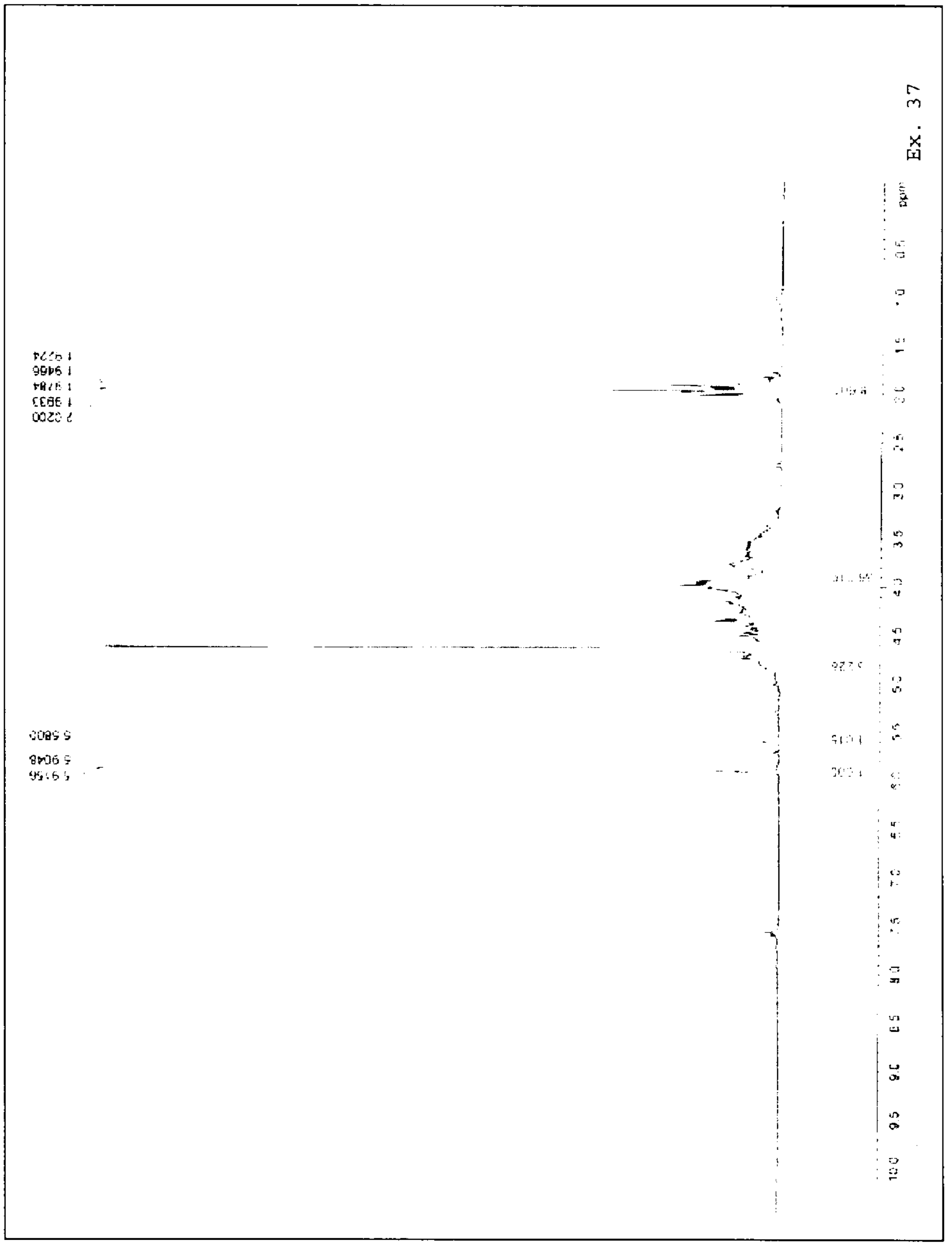
FIG. 87 is a $^1$H-NMR chart of Compound 37.

$^1$H-NMR: FIG. 87 illustrates the chart.

Example 38

The same process as that in Example 34 was performed except that the compound obtained in Production Example 44 (12 mg) was used instead as a material to yield Compound 38 (20 mg, yellow powder).

Figure 88:
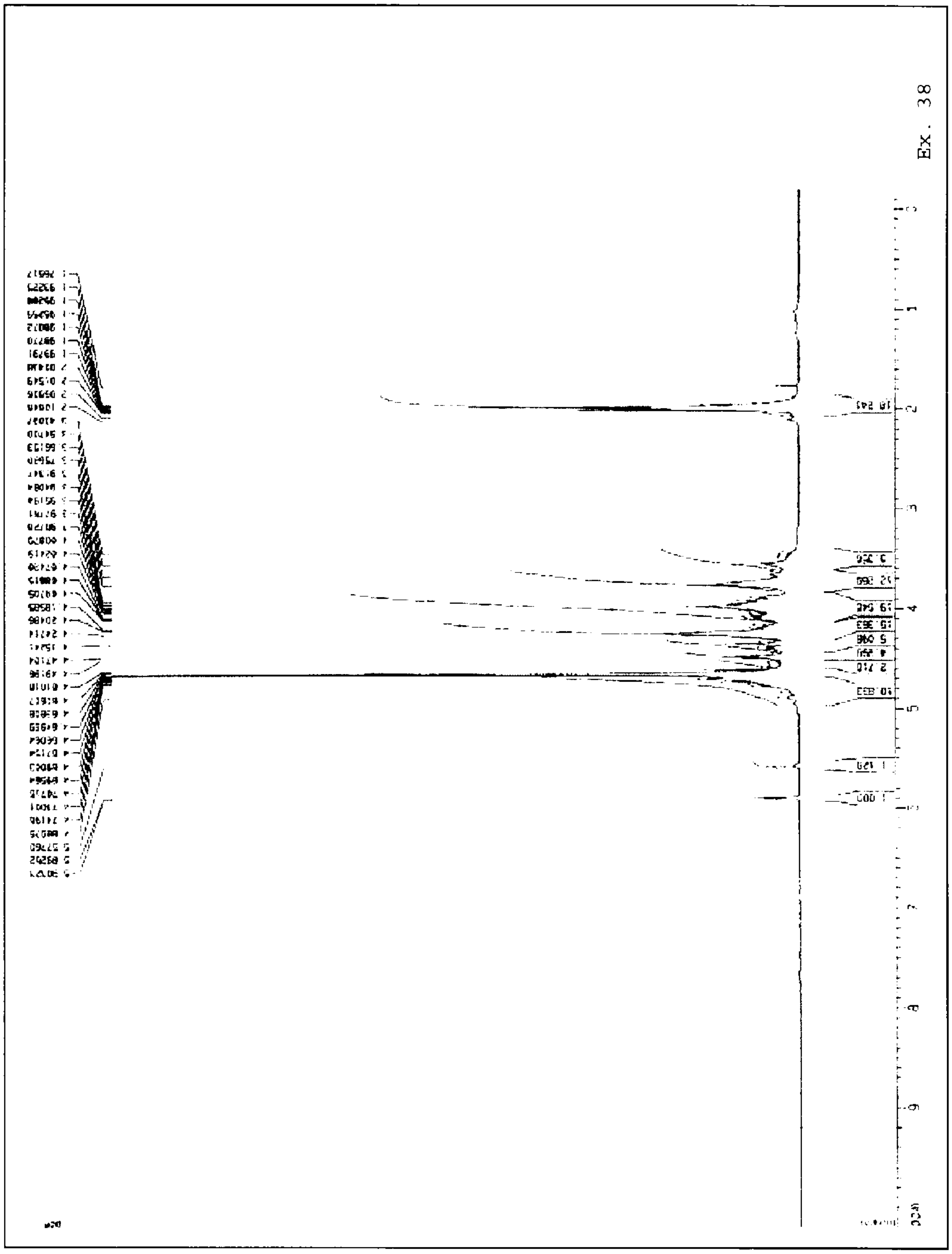
FIG. 88 is a $^1$H-NMR chart of Compound 38.

$^1$H-NMR: FIG. 88 illustrates the chart.

The structures of Compounds 37 and 38 are shown in Table 13 below

Example 41

The same process as that in Example 14 was performed except that the compound obtained in Production Example 47 (8 mg) was used instead as a material to yield Compound 41 (14 mg, white powder).

Figure 91:
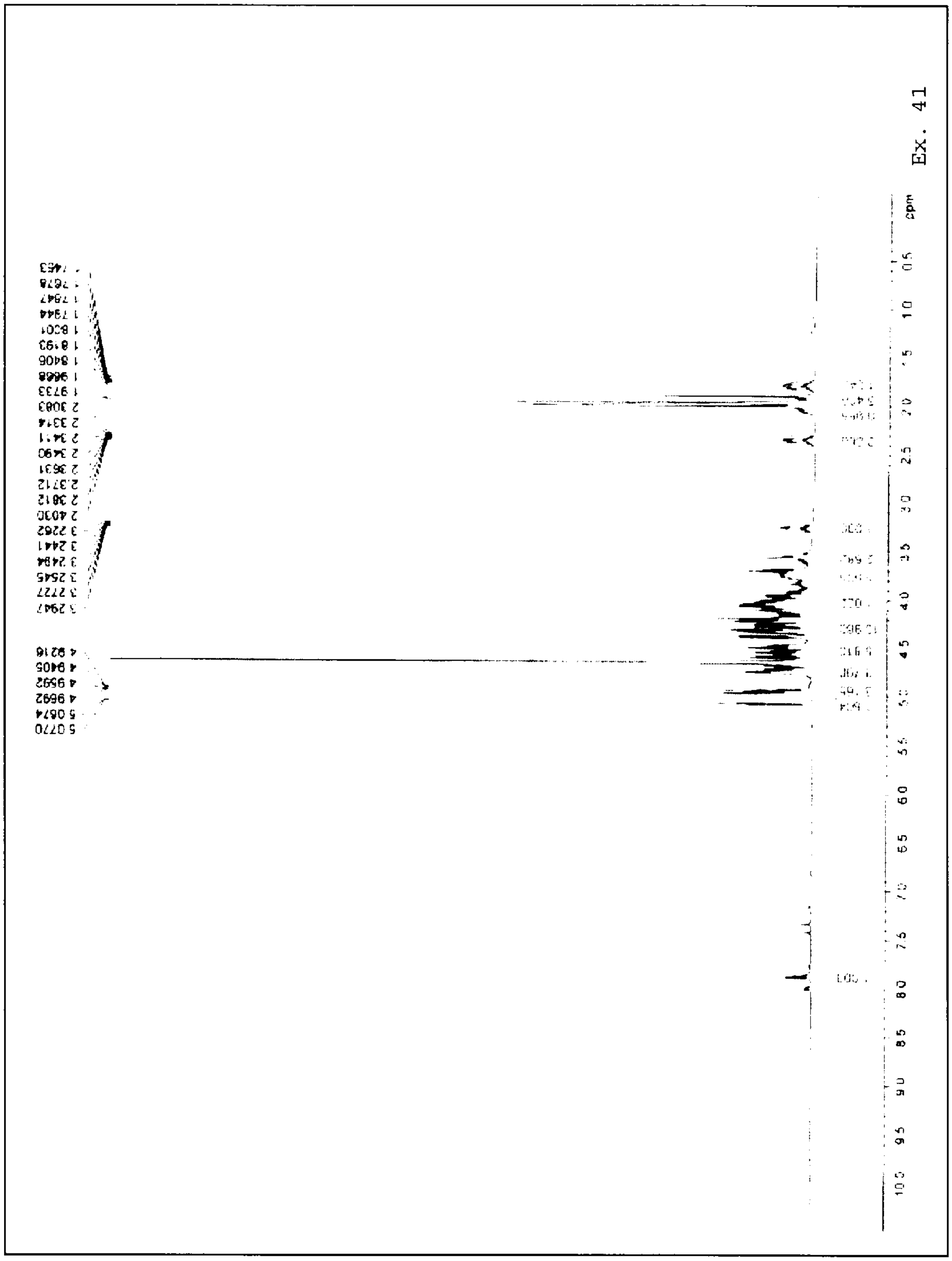
FIG. 91 is a $^1$H-NMR chart of Compound 41.

$^1$H-NMR: FIG. 91 illustrates the chart.

Example 42

The same process as that in Example 14 was performed except that the compound obtained in Production Example 48 (7 mg) was used instead as a material to yield Compound 42 (12 mg, white powder).

Figure 92:
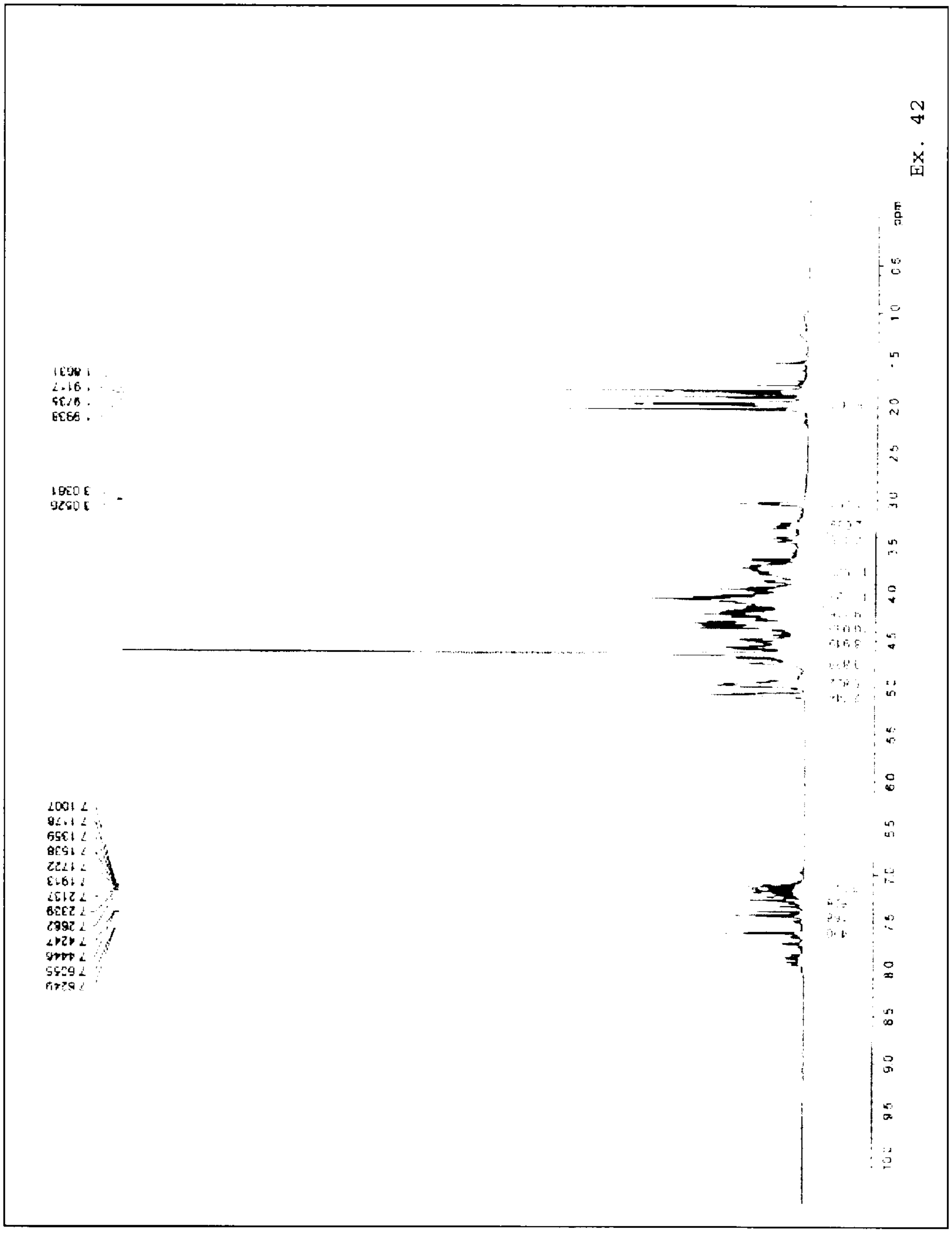
FIG. 92 is a $^1$H-NMR chart of Compound 42.

$^1$H-NMR: FIG. 92 illustrates the chart.

TABLE 13

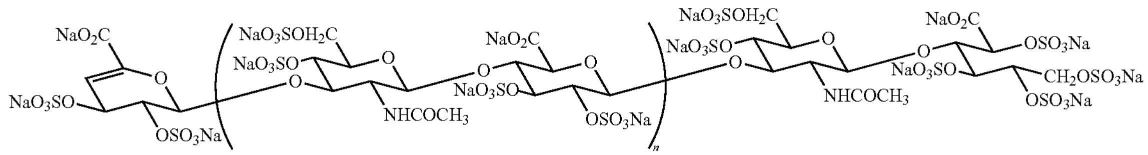

| Compound No. | n |
|---|---|
| 37 | 1 |
| 38 | 4 |

Example 39

The same process as that in Example 14 was performed except that the compound obtained in Production Example 45 (8 mg) was used instead as a material to yield Compound 39 (12 mg, white powder).

Figure 89:
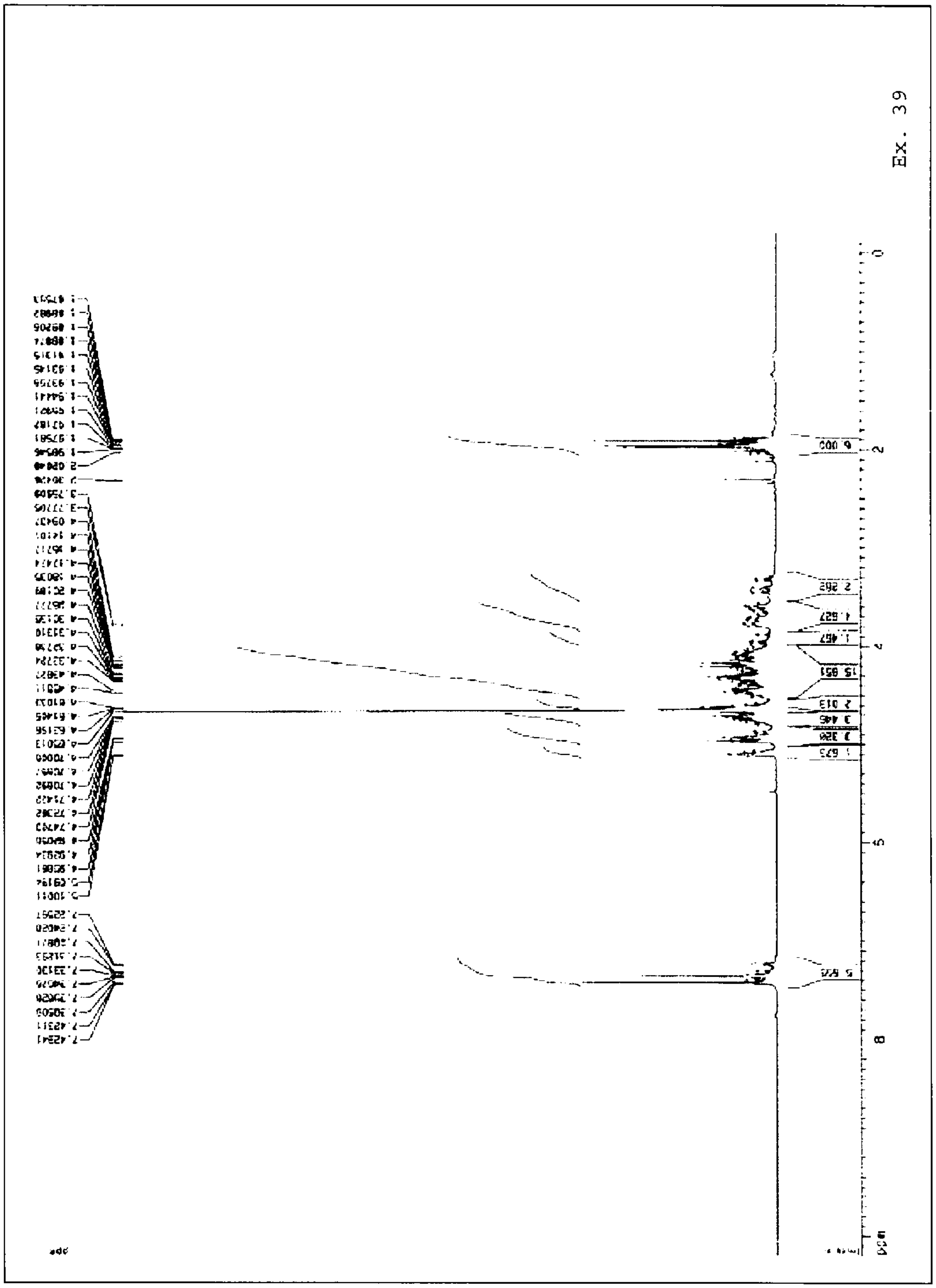
FIG. 89 is a $^1$H-NMR chart of Compound 39.

$^1$H-NMR: FIG. 89 illustrates the chart.

Example 40

The same process as that in Example 14 was performed except that the compound obtained in Production Example 46 (10 mg) was used instead as a material to yield Compound 40 (16 mg, white powder).

Figure 90:
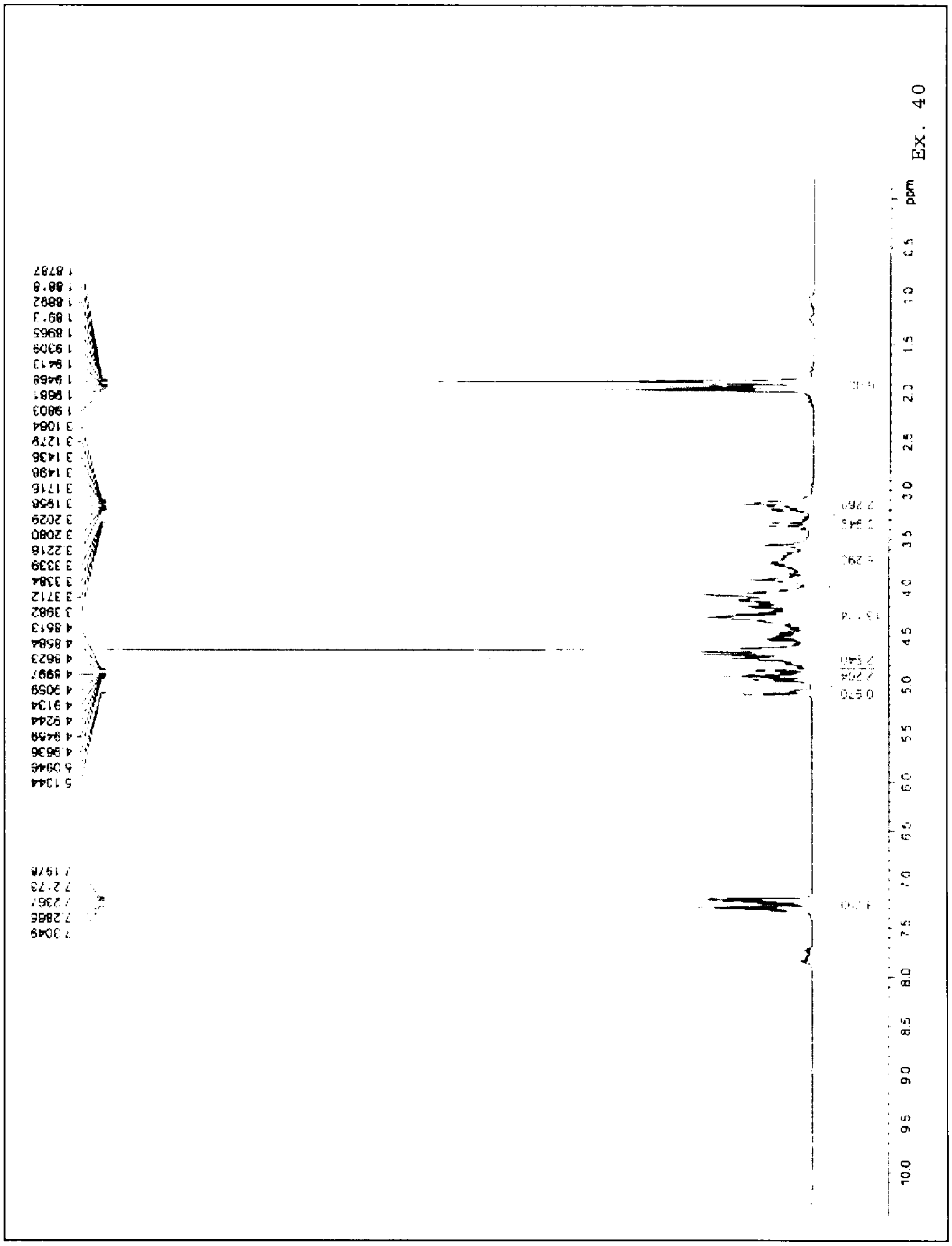
FIG. 90 is a $^1$H-NMR chart of Compound 40.

$^1$H-NMR: FIG. 90 illustrates the chart.

Example 43

The same process as that in Example 14 was performed except that the compound obtained in Production Example 49 (4 mg) was used instead as a material to yield Compound 43 (9 mg, white powder).

Figure 93:
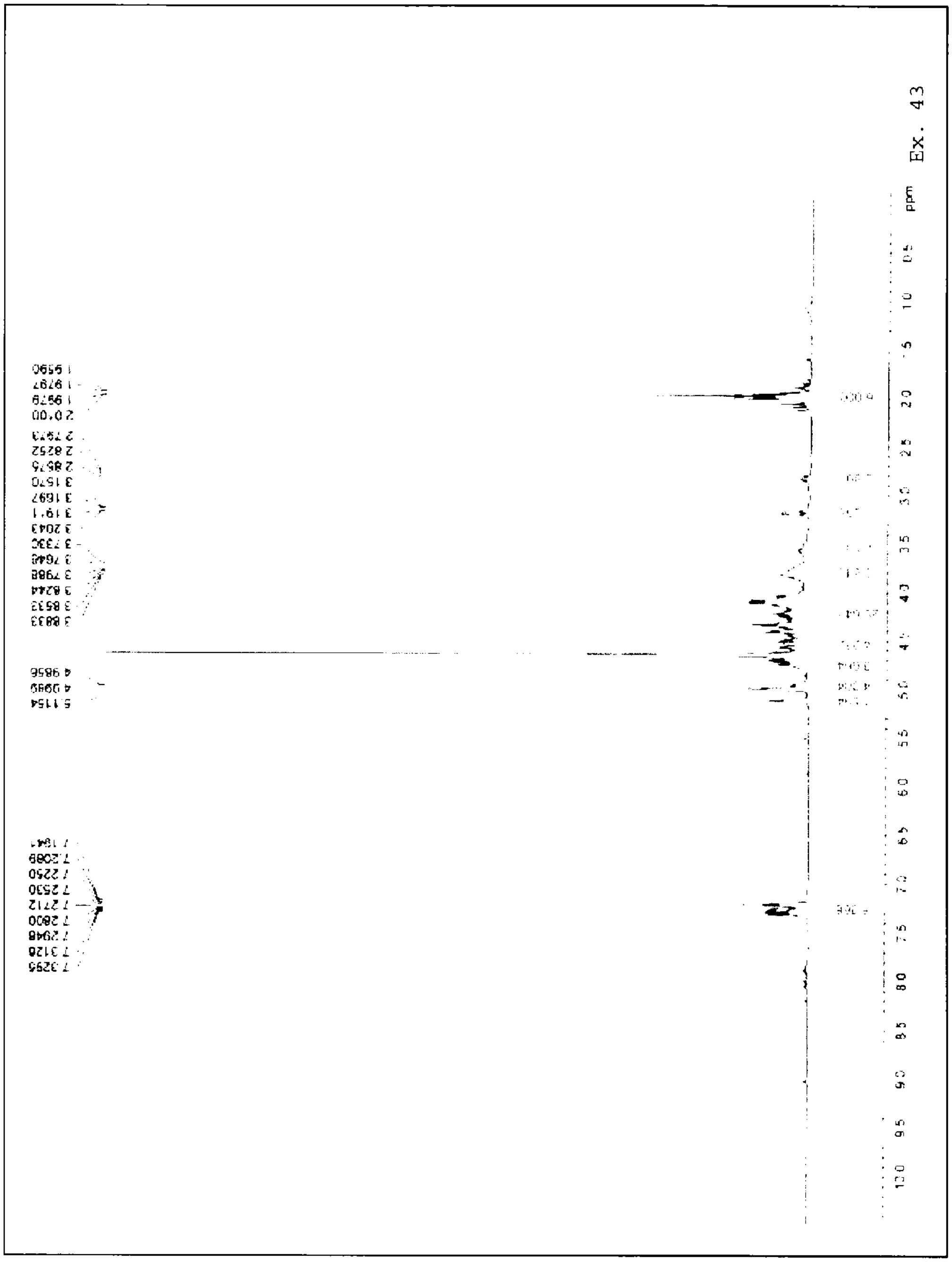
FIG. 93 is a $^1$H-NMR chart of Compound 43.

$^1$H-NMR: FIG. 93 illustrates the chart.

Example 44

The same process as that in Example 14 was performed except that the compound obtained in Production Example 50 (10 mg) was used instead as a material to yield Compound 44 (24 mg, white powder).

Figure 94:
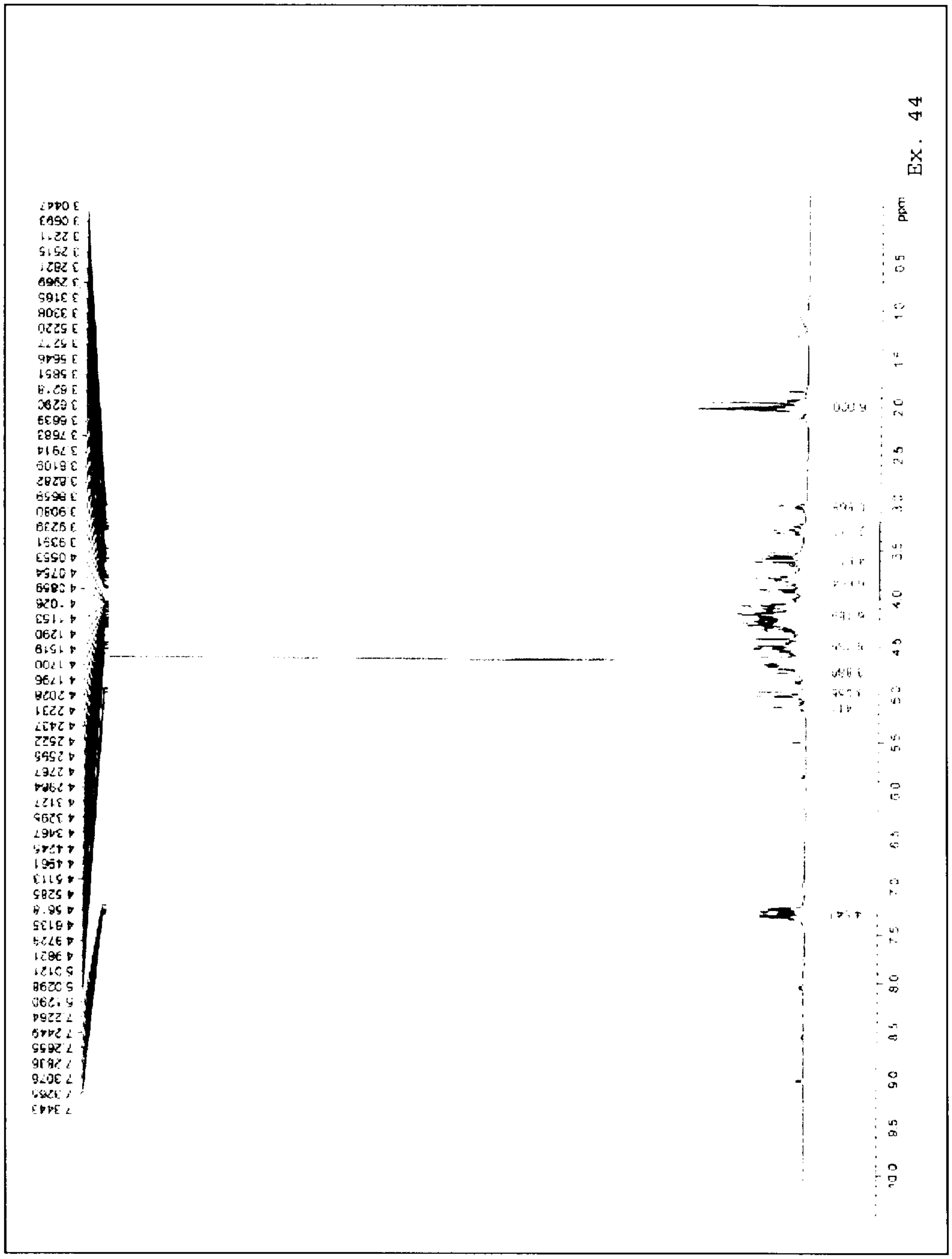
FIG. 94 is a $^1$H-NMR chart of Compound 44.

$^1$H-NMR: FIG. 94 illustrates the chart.

Example 45

The same process as that in Example 14 was performed except that the compound obtained in Production Example 51 (10 mg) was used instead as a material to yield Compound 45 (21 mg, white powder).

Figure 95:
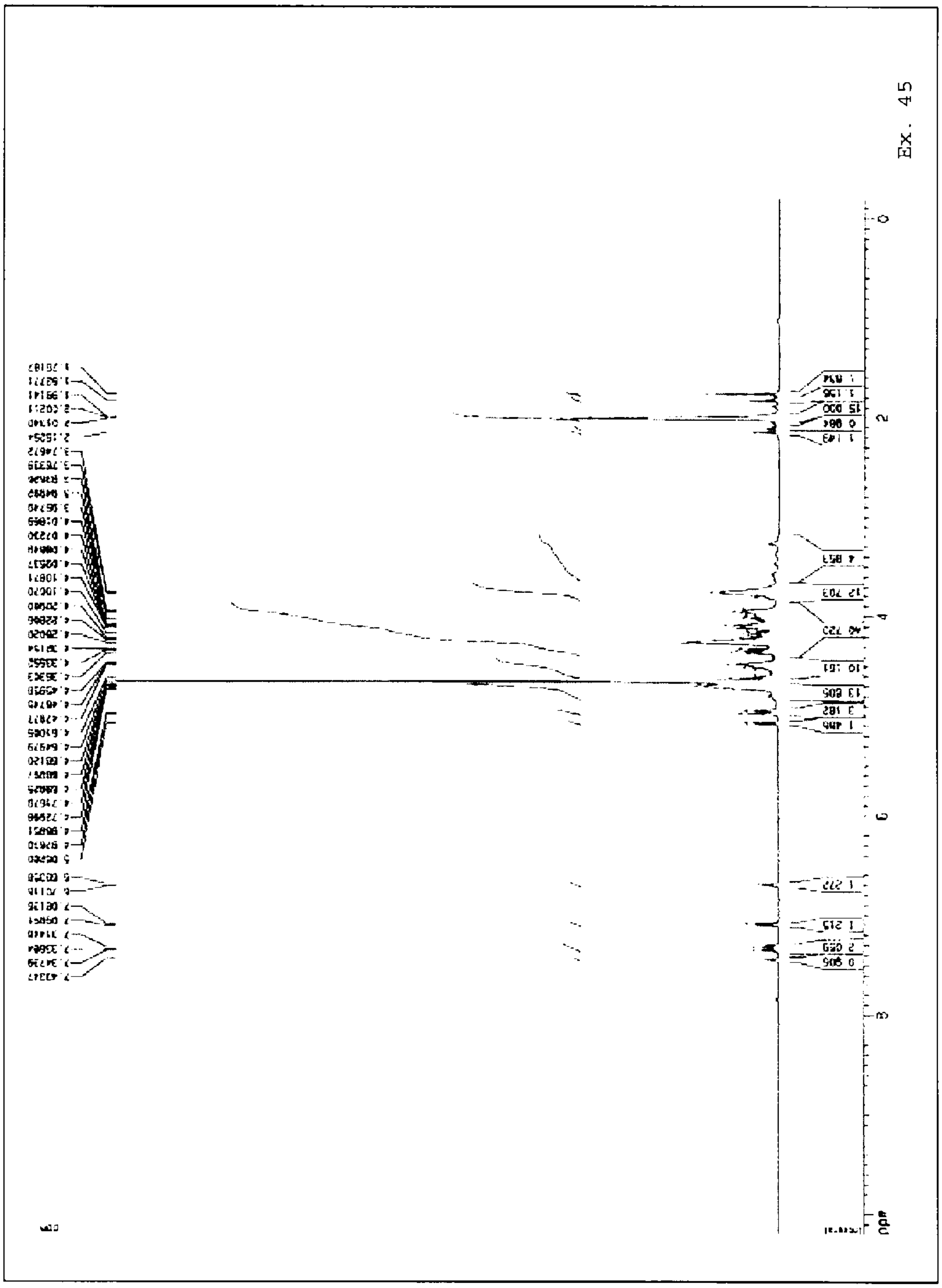
FIG. 95 is a $^1$H-NMR chart of Compound 45.

$^1$H-NMR: FIG. 95 illustrates the chart.

Example 46

The same process as that in Example 14 was performed except that the compound obtained in Production Example 52 (12 mg) was used instead as a material to yield Compound 46 (15 mg, white powder).

Figure 96:
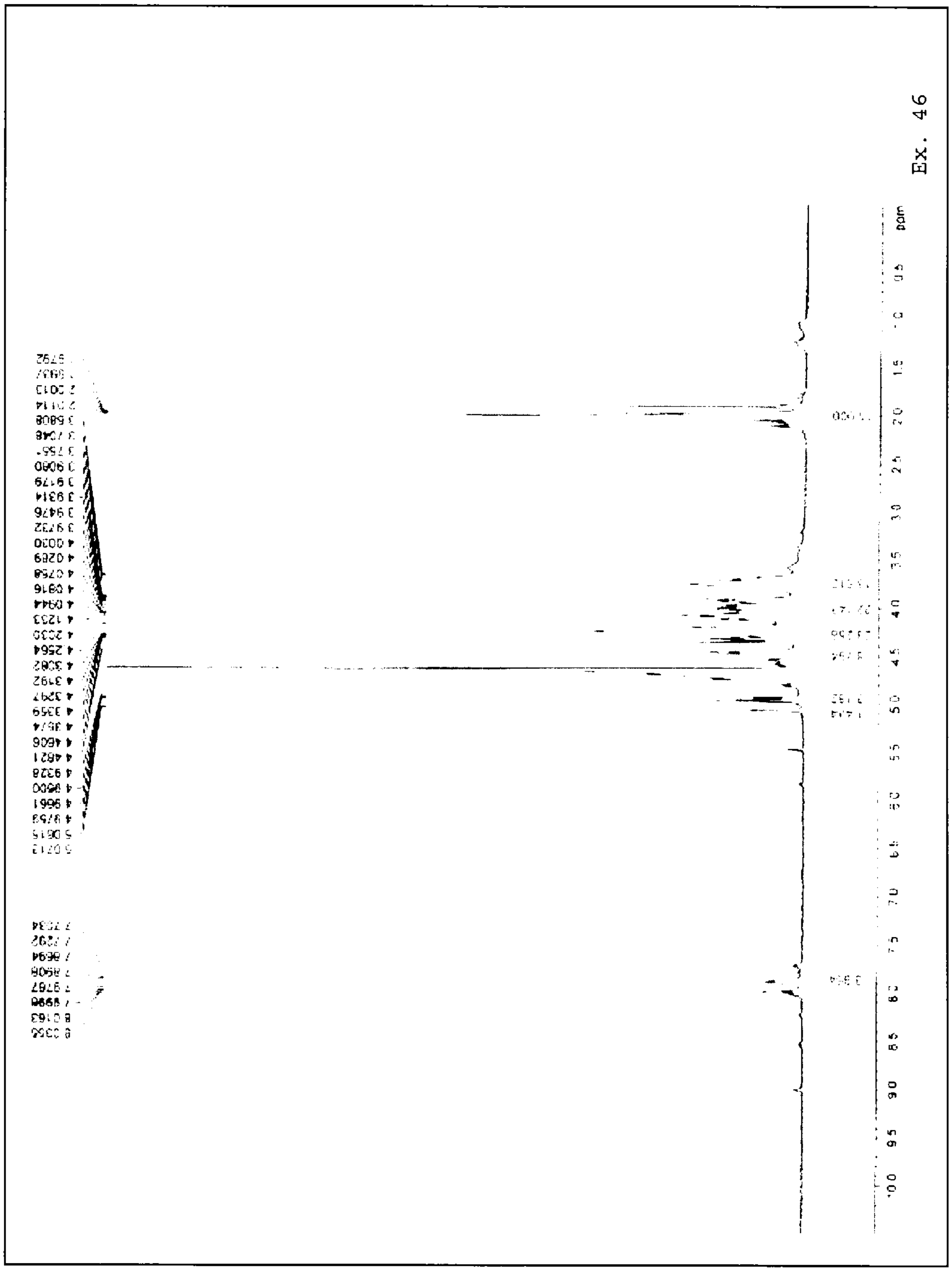
FIG. 96 is a $^1$H-NMR chart of Compound 46.

$^1$H-NMR: FIG. 96 illustrates the chart.

Example 47

The same process as that in Example 14 was performed except that the compound obtained in Production Example 53 (5 mg) was used instead as a material to yield Compound 47 (9 mg, white powder).

Figure 97:
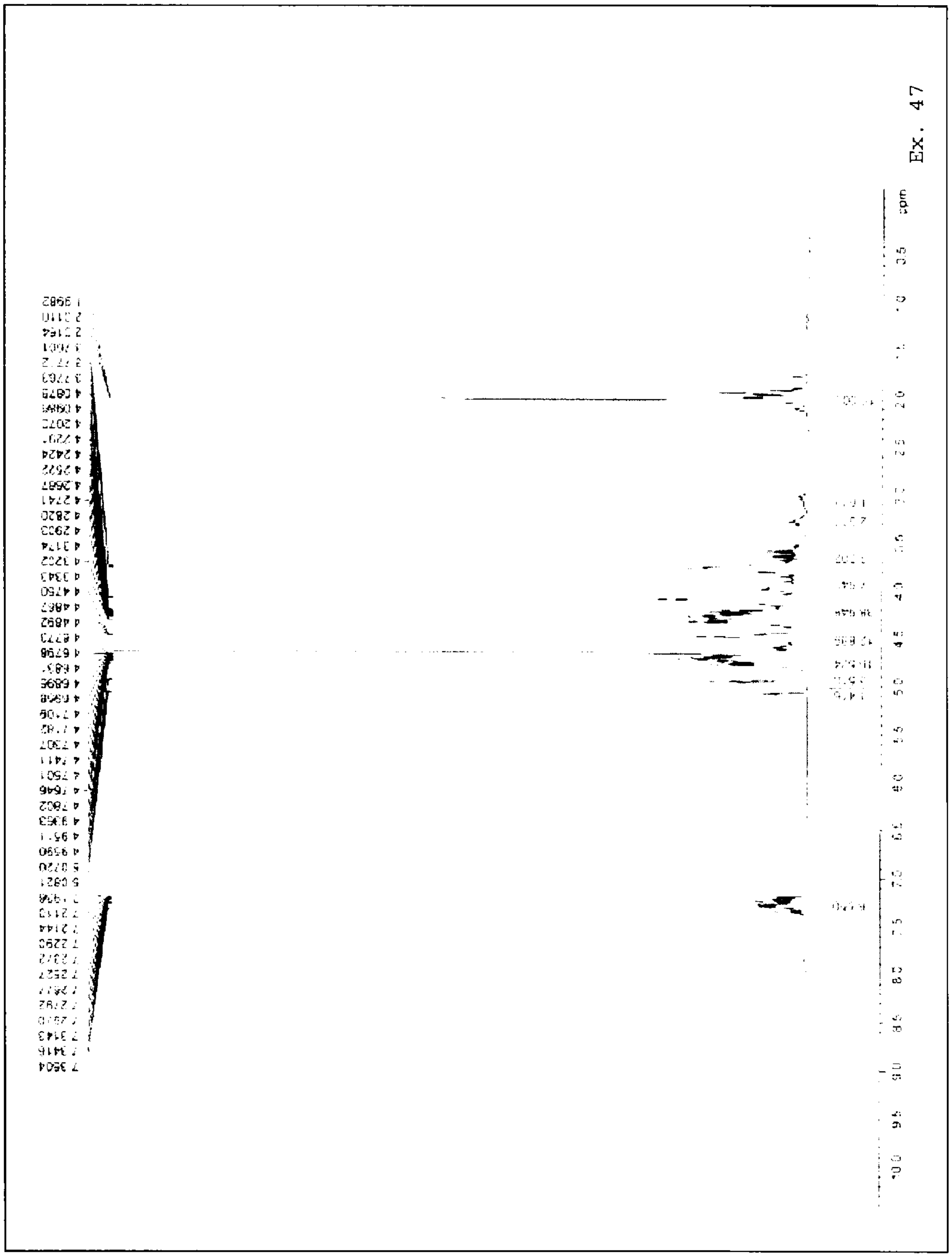
FIG. 97 is a $^1$H-NMR chart of Compound 47.

$^1$H-NMR: FIG. 97 illustrates the chart.

Example 48

The same process as that in Example 14 was performed except that the compound obtained in Production Example 54 (5 mg) was used instead as a material to yield Compound 48 (9 mg, white powder).

Figure 98:
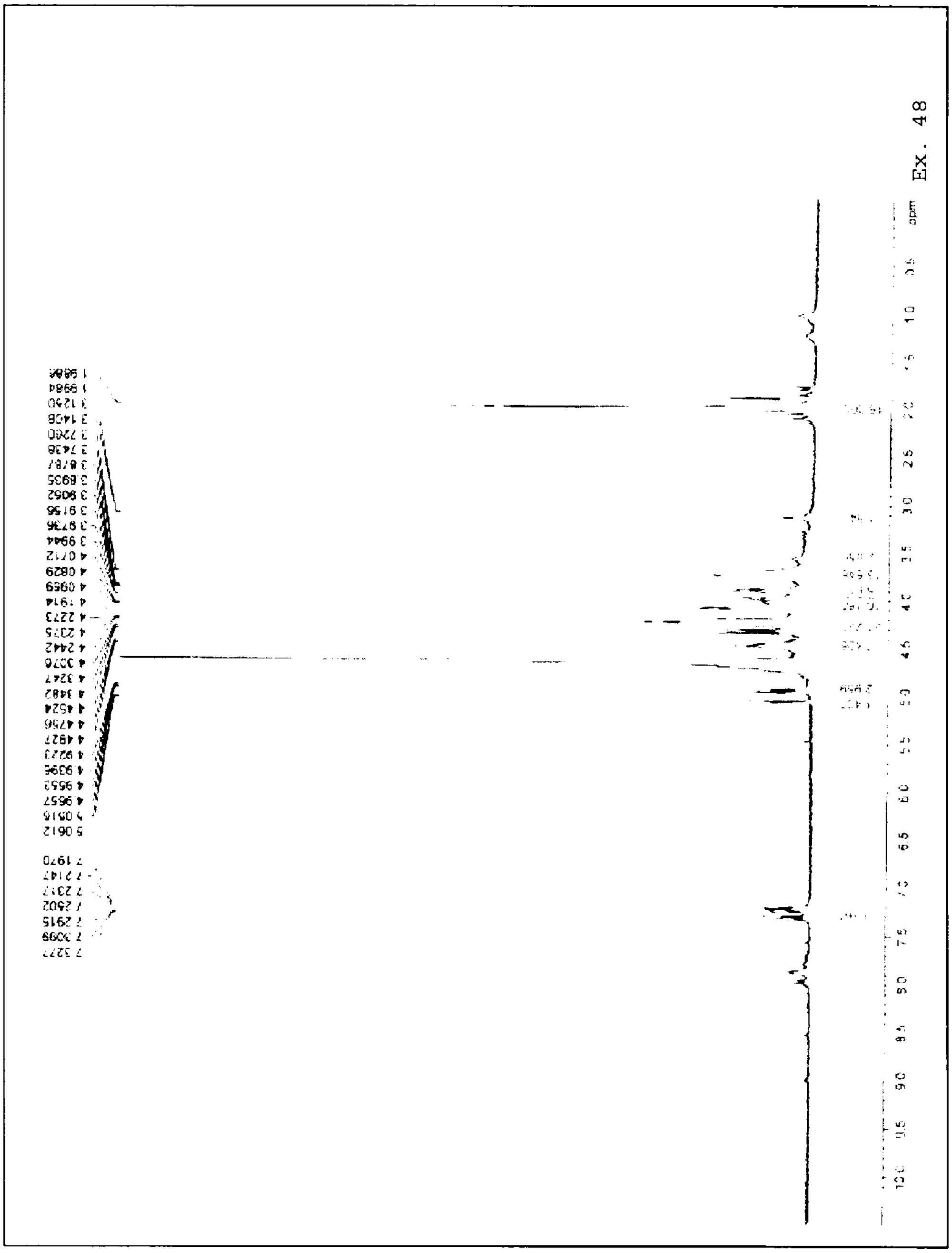
FIG. 98 is a $^1$H-NMR chart of Compound 48.

$^1$H-NMR: FIG. 98 illustrates the chart.

The structures of Compounds 39 to 48 are shown in Table 14 below.

TABLE 14

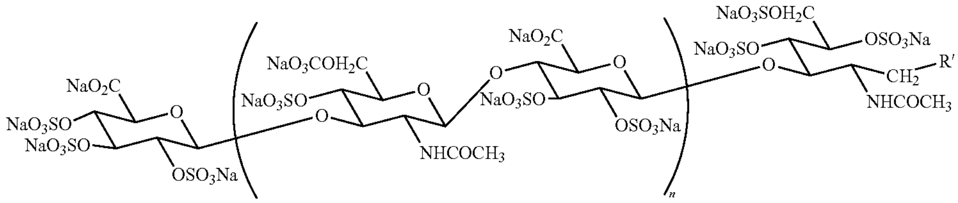

| Compound No. | n | R' |
|---|---|---|
| 39 | 1 | 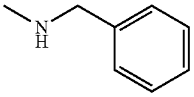 |
| 40 | 1 | 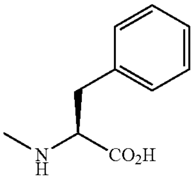 |
| 41 | 1 | 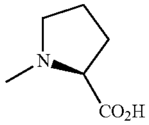 |
| 42 | 1 | 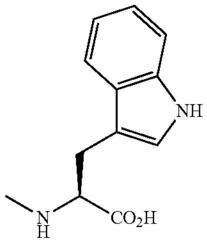 |
| 43 | 1 | 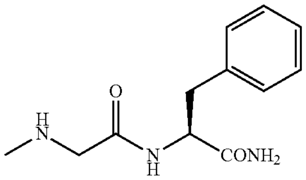 |

TABLE 14-continued

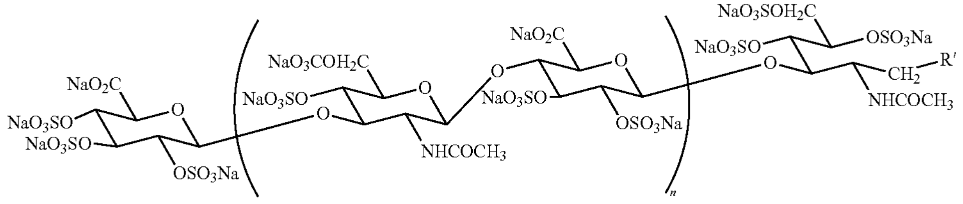

| Compound No. | n | R' |
|---|---|---|
| 44 | 1 | 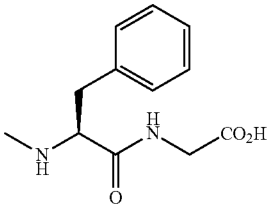 |
| 45 | 4 | 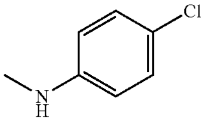 |
| 46 | 4 | 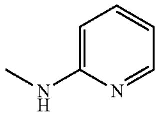 |
| 47 | 4 | 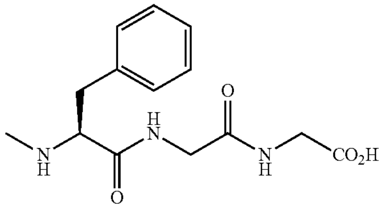 |
| 48 | 4 | 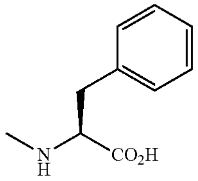 |

Reference Examples 1 to 7

The compounds (known compounds) of the present invention shown in Table 15 were produced according to a method described in the document, Glycobiology, vol. 11, No. 1, pp. 57 to 64, 2001.

Reference Example 1

Sodium hyaluronate (BIO Sodium Hyaluronate HA9, manufactured by Shiseido Co., Ltd.) and bovine testis-derived hyaluronidase (Hyaluronidase Bovine T 100KU, manufactured by Calbiochem Behring Corporation), which were each purchased, were subjected to separation in accordance with the document, Glycobiology, vol. 12, No. 7, pp. 421 to 426, 2002 to yield a hyaluronan oligosaccharide 4-mer. The hyaluronan oligosaccharide 4-mer (20 mg) was used as a material to perform production according to the above document, Glycobiology, vol. 11, No. 1, pp. 57 to 64, 2001 to yield Compound 49 (21 mg, white powder).

Reference Example 2

The same process as that in Reference Example 1 was performed except that a hyaluronan oligosaccharide 10-mer (43 mg) was used instead as a material to yield Compound 50 (86 mg, white powder).

Reference Example 3

The same process as that in Reference Example 1 was performed except that a hyaluronan oligosaccharide 16-mer (75 mg) was used instead as a material to yield Compound 51 (80 mg, white powder).

Reference Example 4

The same process as that in Reference Example 1 was performed except that a hyaluronan oligosaccharide 20-mer (23 mg) was used instead as a material to yield Compound 52 (42 mg, white powder).

Reference Example 5

The same process as that in Reference Example 1 was performed except that a hyaluronan oligosaccharide 22-mer (17 mg) was used instead as a material to yield Compound 53 (25 mg, white powder).

Reference Example 6

The same process as that in Reference Example 1 was performed except that a hyaluronan oligosaccharide 24-mer to 32-mer (20 mg) was used instead as a material to yield Compound 54 (18 mg, white powder).

Reference Example 7

The same process as that in Reference Example 1 was performed except that a hyaluronan oligosaccharide 34-mer to 46-mer (24 mg) was used instead as a material to yield Compound 55 (39 mg, white powder). The structures of Compounds 49 to 55 are shown in Table 15 below.

Grouping of the animals was performed using a two-dimensional stratified random sampling method based on their body weights on the day of completion of sensitization and body weight changes from the day of initiation of sensitization to the day of completion of sensitization as indices.

One week after the last sensitization, physiological saline containing 20 mg/ml OVA was administered into both nasal cavities of the animal at an amount of 10 μl each, inducing an antigen-antibody reaction. Likewise, to a control group (non-inducing group), physiological saline was administered.

10 μl each of test substances were administered into both nasal cavities of the animal 30 minutes before the start of the induction. Each of the test substances was dissolved in physiological saline to be used as a solution having a concentration of 500 μg/ml for administration. Likewise, to the control group (non-inducing group) and a saline group (solvent control group), physiological saline was administered. A "Flunase" (manufactured by GlaxoSmithKline K.K.) was used as a control agent (containing no compound).

Measurement of nasal airway resistance was conducted before induction, 10 minutes, 2 hours, 3 hours, 4 hours, 5 hours, 6 hours, and 7 hours after the induction on the date of the induction. Nasal airway resistance (nRaw) for 100 times of respiration was measured once in each of the measurement time periods, and the average value of the results was defined

TABLE 15

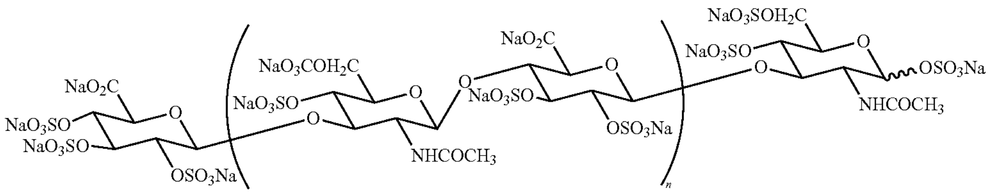

| Compound No. | n |
|---|---|
| 49 | 1 |
| 50 | 4 |
| 51 | 7 |
| 52 | 9 |
| 53 | 10 |
| 54 | 11-15 |
| 55 | 16-22 |

Test Example 1

Anti-Allergy Action; Guinea Pig Allergic Rhinitis Model (Nasal Obstruction Model)

Hartley guinea pigs (male, 6 or 7 weeks old at the time of the first sensitization) were used in experiments.

After the animals were supplied, they underwent seven days or more of preliminary breeding for quarantine and acclimation before being used in the experiments.

As the first sensitization, physiological saline containing ovalbumin (OVA, 1 mg) and an aluminum hydroxide gel (Alum, 10 mg) was administered subcutaneously to the back of each animal at an amount of 1 ml per animal. Then, physiological saline containing 10 mg/ml OVA was administered into both nasal cavities of the animal with a micropipette at an amount of 20 μl each, once (i.e., one week after the first sensitization) or twice (i.e., one week and two weeks after the first sensitization), to thereby perform local sensitization.

as nRaw in each measurement time period. The rate of increase of the nRaw was calculated to be used as an index for the nasal airway resistance.

The rate of increase (%) of the nasal airway resistance (nRaw) was calculated based on the following equation.

Rate of increase of nRaw in each measurement time period $$(\%) = \frac{(R_x - R_0)}{R_0} \times 100$$

$R_0$: nRaw before induction $R_x$: nRaw in each measurement time period (x hours later)

Evaluations were performed based on the rate of increase of nRaw 10 minutes after the induction (immediate-type nasal airway resistance) and the area under curve of the rate of increase of nRaw 3 to 7 hours after the induction ($AUC_{3\text{-}7\ hr}$, delayed nasal airway resistance).

$$AUC_{3\text{-}7\ hr} = \frac{(I_{3\ hr} + 2xI_{1\ hr} + 2xI_{5\ hr} + 2xI_{6\ hr} + I_{7\ hr})}{2}$$

$I_{3\text{-}7\ hr}$: rate of increase of nRaw 3 to 7 hours after induction

Figure 99:
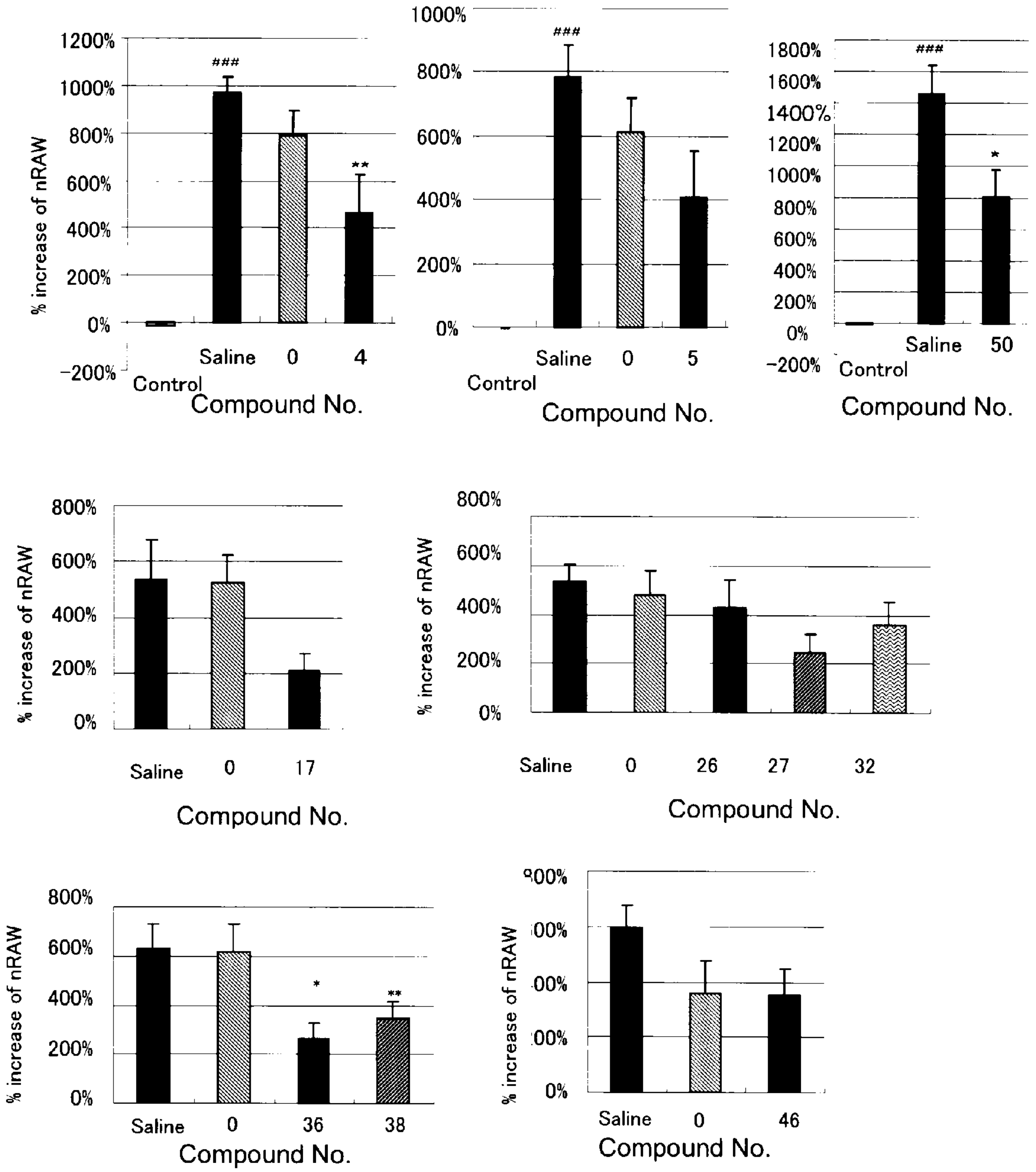
FIG. 99 is a graph illustrating an inhibiting effect on an immediate-type allergic response. ###: $p<0.01$, ##: $p<0.01$, †: $p<0.05$, *: $p<0.05$, **: $P<0.01$, N=8, mean+/−SE.
Figure 100:
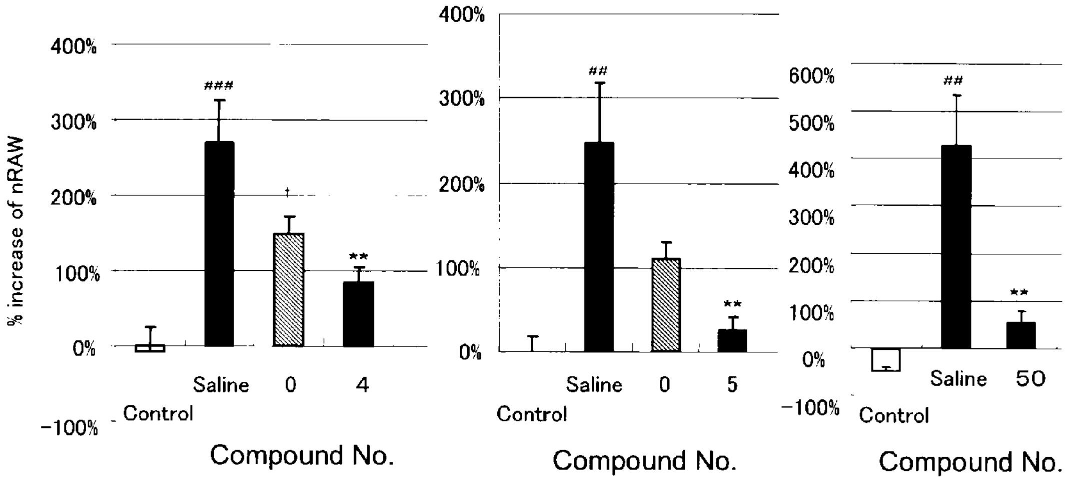
FIG. 100 is a graph illustrating an inhibiting effect on a delayed allergic response. ###: $p<0.01$, ##: $p<0.01$, †: $p<0.05$, *: $p<0.05$, **: $P<0.01$, N=8, mean+/−SE.
Figure 100:
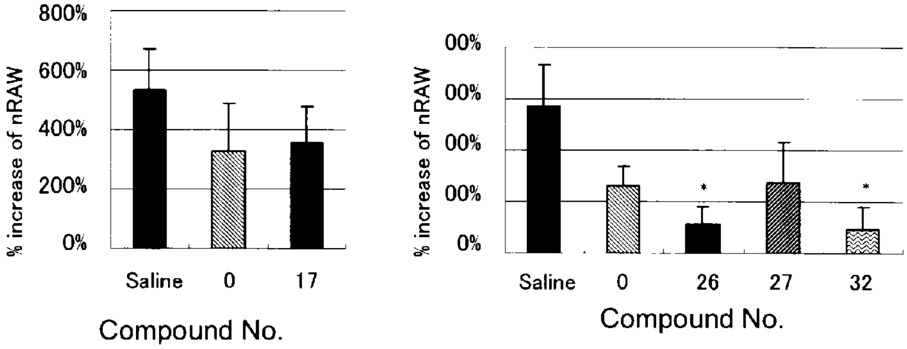
Figure 100:
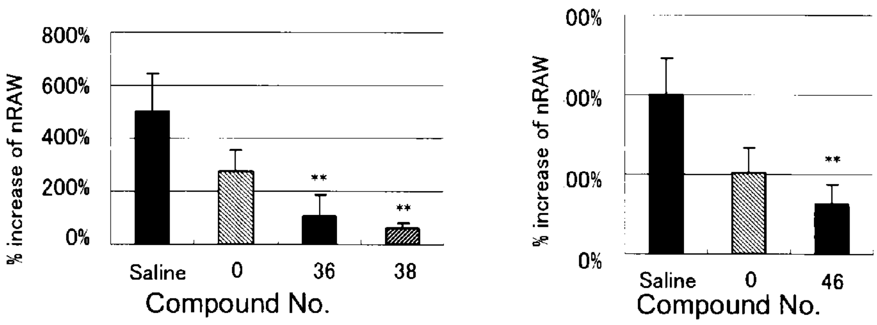

FIGS. 99 and 100 show the results.

FIGS. 99 and 100 show that the compounds of the present invention exert an inhibiting effect on an immediate-type allergic response and an inhibiting effect on a delayed allergic response.

Test Example 2

Inhibiting Effect on Passive Cutaneous Anaphylaxis (PCA)

Hartley guinea pigs (male, 5 weeks old or older) were used in experiments.

An anti-OVA serum obtained by immunizing a guinea pig with OVA was diluted by 500 fold with physiological saline (Solution A).

Each of the test substances listed in Table 16 below was diluted to 200 μg/ml with physiological saline (Solution B).

Solution B was mixed with a solution obtained by diluting a guinea pig anti-OVA serum by 250 fold in an equivalent amount, and the final concentration of the mixture was adjusted to 100 μg/ml for the test substance and 500 fold for the anti-OVA serum (Solution C).

After etherization, a guinea pig was intradermally injected with 100 μl of physiological saline, Solution A, or Solution C per spot on the back where hair had been shaved.

About 3 hours later, a 0.5% Evans blue physiological saline containing 0.2 to 0.4% OVA was intravenously administered to the guinea pig at 0.8 to 1 ml/body.

Within 30 minutes, bleeding was conducted, and the guinea pig was peeled. Then, the amount of pigment at each spot was determined by image processing. In the image processing, the amount of pigment at a spot where only the anti-OVA serum was administered was defined as 100%, and based on the definition, the degree of suppression caused by the test substance was examined. Table 16 shows the results (N=3 or 6).

TABLE 16

| Test substance | Suppression of PCA reaction |
|---|---|
| Anti-OVA serum alone | D |
| Compound 3 | B |
| Compound 4 | A |
| Compound 5 | B |
| Compound 7 | A |
| Compound 12 | C |
| Compound 13 | A |
| Compound 50 | A |
| Compound 51 | A |
| Compound 53 | A |
| Compound 54 | A |
| Compound 55 | A |

The case where pigment leakage is 80% or more, indicating no inhibiting effect on the PCA, was denoted by “D”; the case where the pigment leakage is between 60 to 80% was denoted by “C” (suppression percentage: 20 to 40%); the case where the pigment leakage is between 30 to 60% (suppression percentage: 40 to 70%) was denoted by “B”; and the case where the pigment leakage is less than 30% was denoted by “A”.

Table 16 above shows that the compounds of the present invention show suppression effect on the PCA.

Test Example 3

Test on Vascular Permeability Increasing Activity

Hartley guinea pigs (male, 5 weeks old or older) were used in experiments.

Test substance was diluted to 100 μg/ml with physiological saline.

Further, there was used, as a control, sulfated hyaluronic acid (a mixture of a tetrasaccharide to a near heptacontasaccharide synthesized according to the example (Production Example 1) of JP-A-1999-147901, or the like).

After etherization, a guinea pig was intradermally injected with 100 μl per spot of physiological saline or physiological saline containing the test substance on the back where hair had been shaved.

A 0.5% Evans blue physiological saline was intravenously administered to the guinea pig at 1 ml/body.

Within 30 minutes, bleeding was conducted, and the guinea pig was peeled. Then, the amount of pigment at each spot was determined by image processing.

Figure 101:
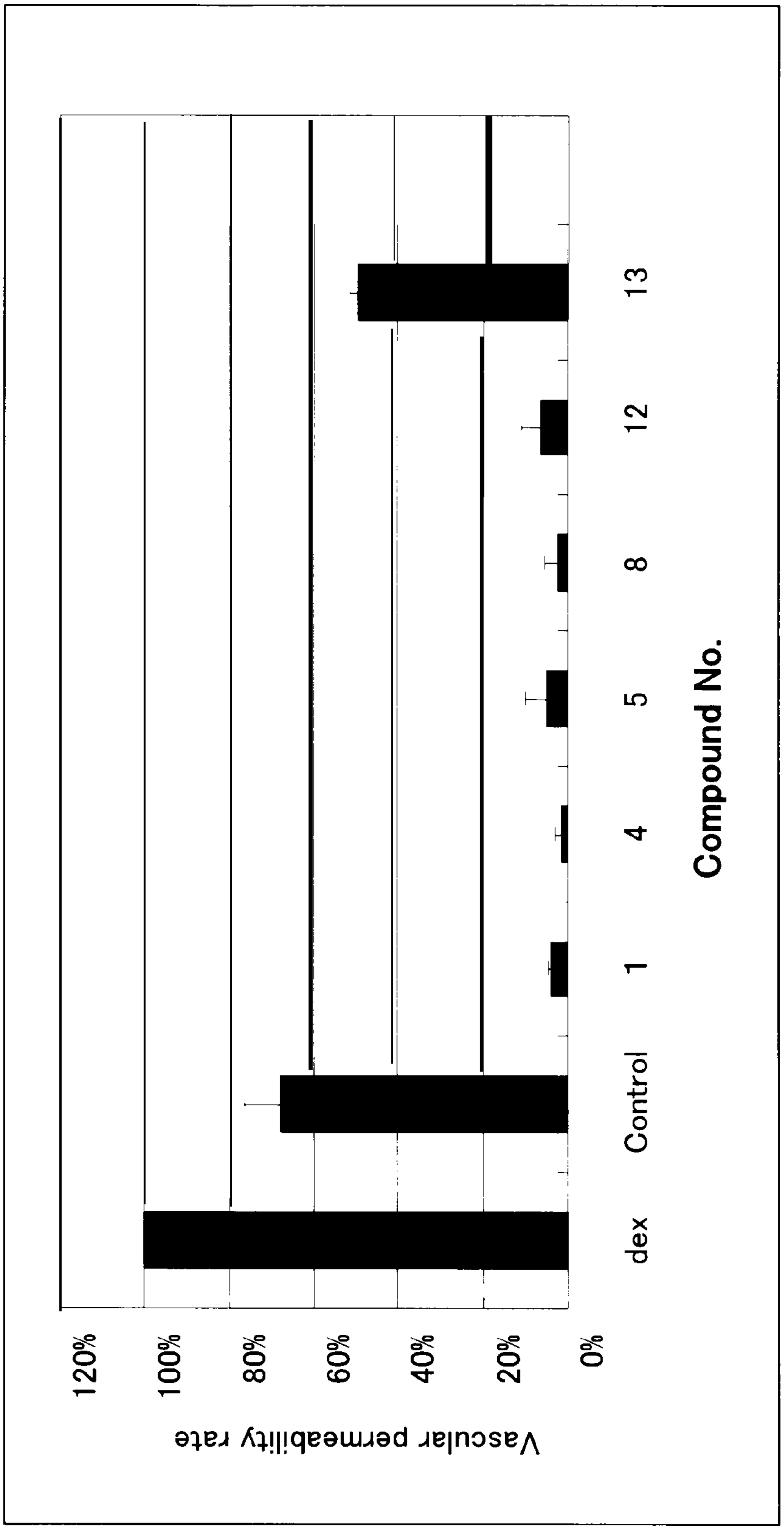
FIG. 101 is a graph illustrating a vascular permeability increasing activity. dex: spot of dextran administration, Control: spot of sulfated hyaluronic acid administration.
Figure 102:
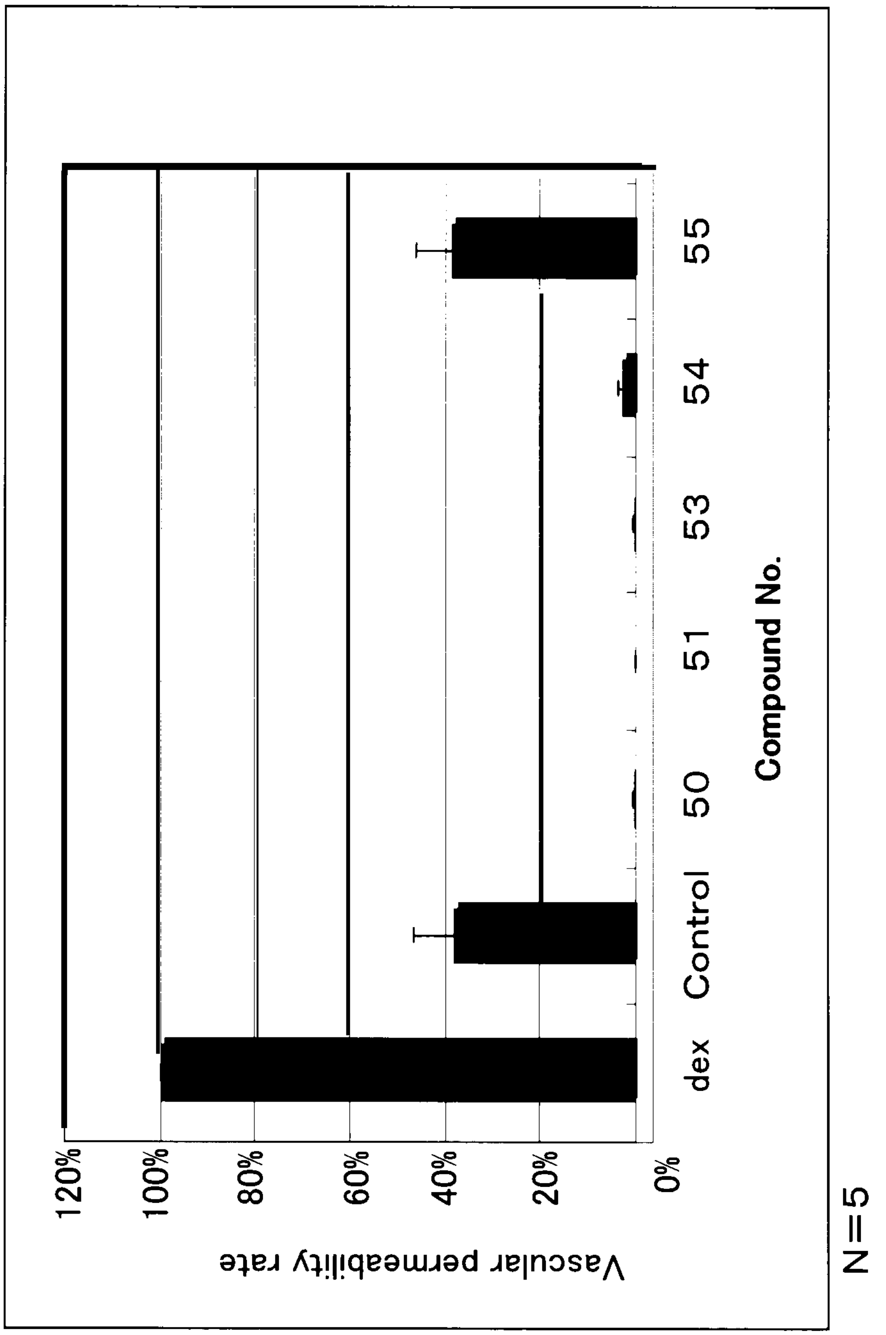
FIG. 102 is a graph illustrating a vascular permeability increasing activity. dex: spot of dextran administration, Control: spot of sulfated hyaluronic acid administration.
Figure 103:
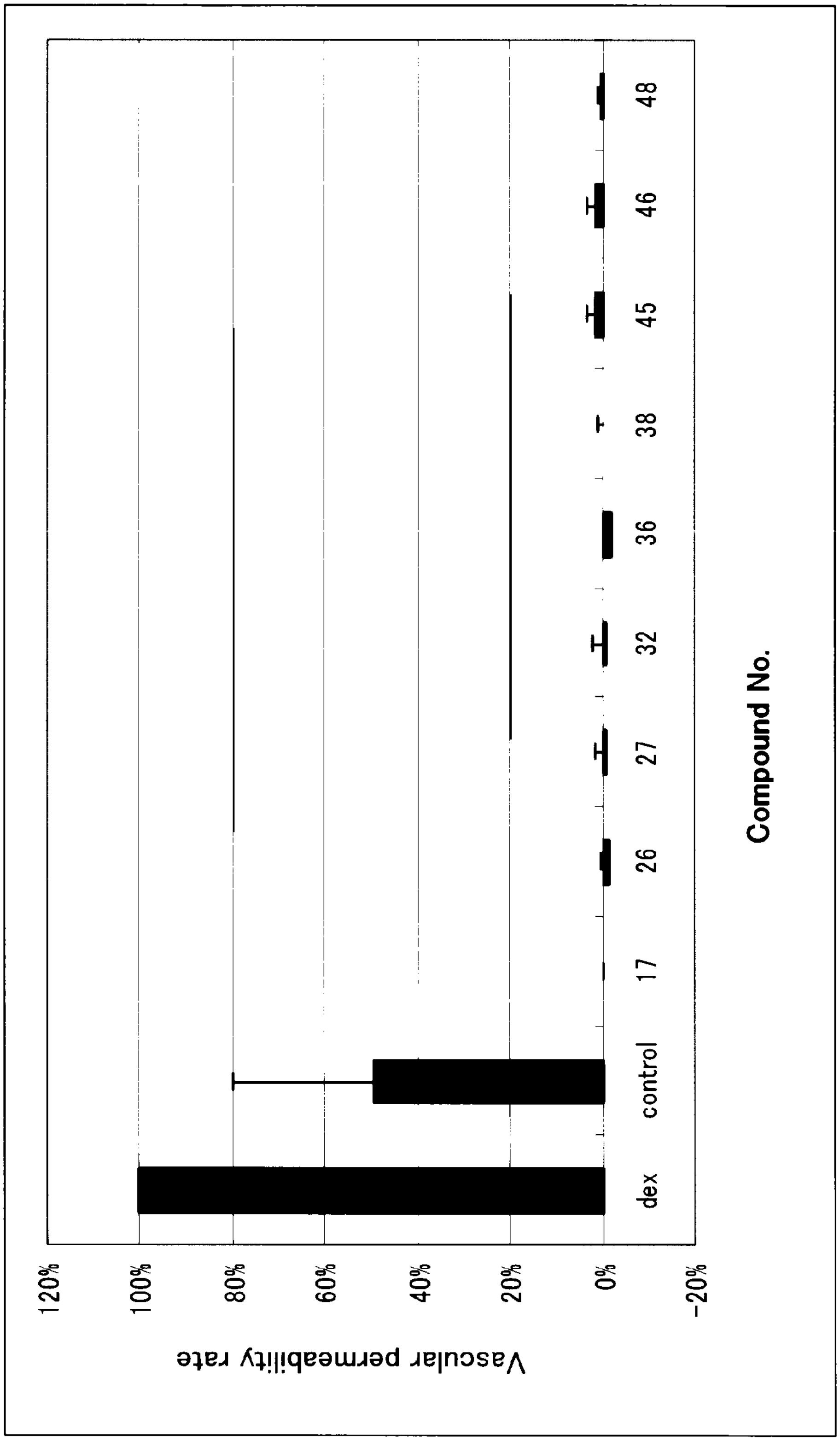
FIG. 103 is a graph illustrating a vascular permeability increasing activity. dex: spot of dextran administration, Control: spot of sulfated hyaluronic acid administration.

The amount of pigment at a spot where dextran sulfate 10000 was administered was defined as 100%, and based on the definition, the results of the image processing are shown as a vascular permeability rate of the test substance in FIGS. 101 to 103.

FIGS. 101 to 103 show that the compounds of the present invention, unlike known polymeric polysulfated hyaluronic acid, do not have a vascular permeability increasing activity and do not exhibit a stimulating action that itself is a side effect.

Test Example 4

Long-Term Stability (In Aqueous Solution)

Aqueous solutions containing Compound 4 and Compound 50 at 1 mg/ml were adjusted to perform HPLC analysis.

Those solutions were each stored in a cold place (2 to 8° C.) and at room temperature, and were subjected to time-dependent HPLC analysis up to 4 months to check the change in the pattern of the peaks of each solution.

HPLC Condition:

Column: Mightysil RP-18 GP (3 μm, 4.6 mm×50 mm)

Column temperature: 40° C.

Mobile phase A: 20 mM $KH_2PO_4$/MeCN (70:30) containing 2 mM TBAP

Mobile phase B: 20 mM $KH_2PO_4$ (80:20) containing MeCN/2 mM TBAP

Gradient condition: Initial; A: 100%, B: 0% 0 to 20 minutes; A: 100 to 95%, B:

0 to 5%, linear

Flow rate: 1 ml/min

Detection: UV (210 nm)

Injected amount: about 5 μg/5 μl (TBAP: tetrabutylammonium phosphate)

Table 17 below shows the results.

TABLE 17

| Storing condition and storing period | Compound 4 | Compound 50 |
|---|---|---|
| At start of test | One main peak and shoulder peaks were observed, and the area ratio of the main peak to the shoulder peaks was about 5 to 1. | Three peaks were mainly observed, and the area ratio of the second peak to the third peak was about 1 to 4. |
| In cold place, for 4 months | There was no change in the pattern of the peaks compared with that at the start of the test. | The area ratio of the second peak to the third peak was about 1 to 1. |
| At room temperature, for 10 days | —* | The area ratio of the second peak to the third peak was about 3 to 2. |
| At room temperature, for 4 months | There was no change in the pattern of the peaks compared with that at the start of the test. | —** |

—: No test was performed.

*There was no change in the pattern of the peaks compared with that at the start of the test when the solution was stored at room temperature for 7 days.

**When the solution was stored at room temperature for 10 days, the solution was observed to be clearly unstable, and hence, the test was terminated immediately.

The above Table 17 shows that no change in the pattern of the peaks for Compound 4 was observed after storage at room temperature for 4 months, and hence, Compound 4 is stable in an aqueous solution, while time-dependent increase in the area of the second peak and time-dependent decrease in the area of the third peak among three main peaks for Compound 50 were observed even though it was stored in the cold place, and hence, Compound 50 is unstable in an aqueous solution.

Among low-molecular-weight polysulfated hyaluronic acid derivatives, a compound group represented by the general formula (IA) wherein Y represents the formula (d) or (e), or a compound group represented by the general formula (IB) is particularly useful as a compound being stable in an aqueous solution.

INDUSTRIAL APPLICABILITY

The low-molecular-weight polysulfated hyaluronic acid derivative or the pharmaceutically acceptable salt thereof of the present invention shows weak vascular permeability increasing activity (causing an inflammatory side effect to a small extent), and hence can be used as a significantly safe agent for prevention and/or treatment of an allergic disease.

The invention claimed is:

1. A method for treating an allergic disease, the method comprising:

administering, to a human or an animal in need thereof, an effective dose of a low-molecular-weight polysulfated hyaluronic acid derivative of formula (IA) or (IB), or a pharmaceutically acceptable salt thereof:

(I A)

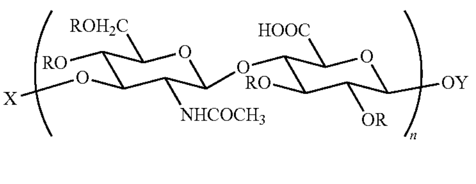

-continued (I B)

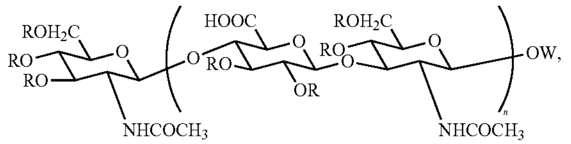

wherein n is from 1 to 15;

X is of formula (a) or (b):

(a)

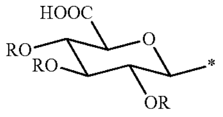

(b)

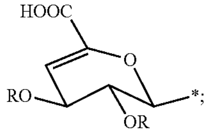

Y is of formula (c), (d), or (e):

(c)

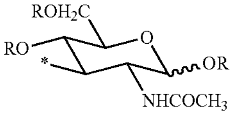

(d)

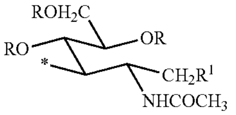

(e)

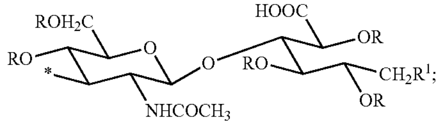

each R is independently a hydrogen atom or an $SO_3H$ group, provided that $SO_3H$ groups account for from 80 to 100% of a total number of R groups;

$R^1$ is —OH, —$OSO_3H$, or —$NZ_1Z_2$;

$Z_1$ and $Z_2$ are each independently a hydrogen atom, —$SO_3H$, an optionally substituted lower alkyl group, an optionally substituted aryl group, an optionally substituted aralkyl group, or an optionally substituted heteroaryl group, or —$NZ_1Z_2$ is an amino acid residue or a peptide residue, wherein when said lower alkyl group is substituted, the substituent is selected from the group consisting of a halogen atom, a carboxy group, an aryl group, a lower alkoxyl group, and an acyl group, wherein when said aryl group is substituted, the substituent is selected from the group consisting of a halogen atom, a carboxy group, a lower alkyl group, a lower alkoxyl group, and an acyl group, wherein when said aralkyl group is substituted, the substituent is selected from the group consisting of a halogen atom, a carboxy group, an aryl group, a lower alkoxyl group, an acyl group, and a lower alkyl group, and wherein when said heteroaryl group is substituted, the substituent is selected from the group consisting of a halogen atom, a carboxy group, a lower alkyl group, a lower alkoxyl group, and an acyl group;

each * is a bonding site with an oxygen atom; and

W is of formula (f) or (g):

(f)

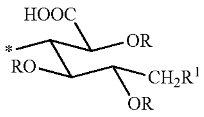

(g)

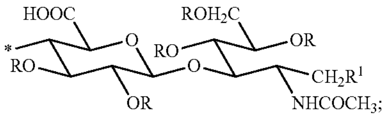

wherein the allergic disease is at least one selected from the group consisting of pollinosis, allergic rhinitis, allergic conjunctivitis, atopic dermatitis, and asthma; and wherein when X is (a), Y is not (c).

2. The method according to claim 1, wherein Y in formula (IA) is of formula (d) or (e).

3. The method according to claim 2, wherein X is of formula (a).

4. The method according to claim 3, wherein n is 3, 4, or 5.

5. The method according to claim 3, wherein n is 4 or 5.

6. The method according to claim 1, wherein the low-molecular-weight polysulfated hyaluronic acid derivative is of formula (IB).

7. The method according to claim 6, wherein n is 3, 4, or 5.

8. The method according to claim 6, wherein n is 4 or 5.

9. A low-molecular-weight polysulfated hyaluronic acid derivative of formula (IA') or (IB), or a pharmaceutically acceptable salt thereof:

(IA')

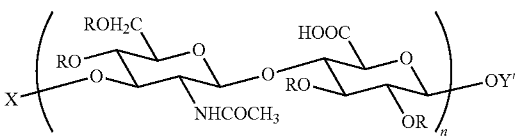

wherein n is from 1 to 15;

X is of formula (a) or (b);

(a)

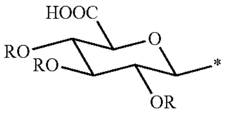

(b)

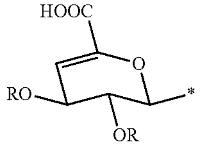

Y' is of formula (d) or (e);

(d)

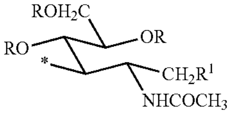

(e)

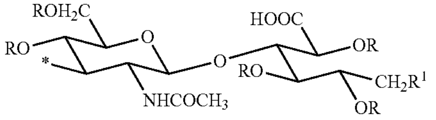

each R is independently a hydrogen atom or an $SO_3H$ group, provided that $SO_3H$ groups account for from 80 to 100% of a total number of R groups;

$R^1$ is —OH, —$OSO_3H$, or —$NZ_1Z_2$;

$Z_1$ and $Z_2$ are each independently a hydrogen atom, —$SO_3H$, an optionally substituted lower alkyl group, an optionally substituted aryl group, an optionally substituted aralkyl group, or an optionally substituted heteroaryl group, or —$NZ_1Z_2$ is an amino acid residue or a peptide residue, wherein when said lower alkyl group is substituted, the substituent is selected from the group consisting of a halogen atom, a carboxy group, an aryl group, a lower alkoxyl group, and an acyl group, wherein when said aryl group is substituted, the substituent is selected from the group consisting of a halogen atom, a carboxy group, a lower alkyl group, a lower alkoxyl group, and an acyl group, wherein when said aralkyl group is substituted, the substituent is selected from the group consisting of a halogen atom, a carboxy group, an aryl group, a lower alkoxyl group, an acyl group, and a lower alkyl group, and wherein when said heteroaryl group is substituted, the substituent is selected from the group consisting of a (IB)

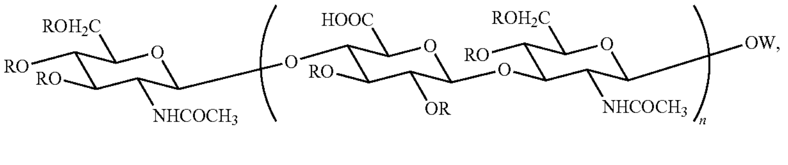

halogen atom, a carboxy group, a lower alkyl group, a lower alkoxyl group, and an acyl group;

each * is a bonding site with an oxygen atom; and

W is of formula (f) or (g):

(f)

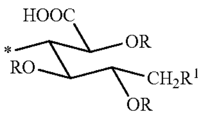

(g)

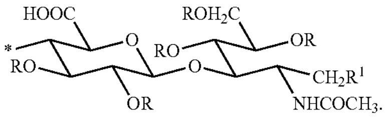

10. The low-molecular-weight polysulfated hyaluronic acid derivative or pharmaceutically acceptable salt thereof according to claim 9, wherein X is of formula (a).

11. The low-molecular-weight polysulfated hyaluronic acid derivative or pharmaceutically acceptable salt thereof according to claim 9, wherein the low-molecular-weight polysulfated hyaluronic acid derivative is of formula (TB).

12. The low-molecular-weight polysulfated hyaluronic acid derivative or pharmaceutically acceptable salt thereof according to claim 10, wherein n is 3, 4, or 5.

13. A pharmaceutical composition, comprising:

the low-molecular-weight polysulfated hyaluronic acid derivative or pharmaceutically acceptable salt thereof according to claim 9, and a pharmaceutically acceptable excipient.

14. The low-molecular-weight polysulfated hyaluronic acid derivative or pharmaceutically acceptable salt thereof according to claim 11, wherein n is 3, 4, or 5.

15. A pharmaceutical composition, comprising:

the low-molecular-weight polysulfated hyaluronic acid derivative or pharmaceutically acceptable salt thereof according to claim 10, and a pharmaceutically acceptable excipient.

16. A pharmaceutical composition, comprising:

the low-molecular-weight polysulfated hyaluronic acid derivative or pharmaceutically acceptable salt thereof according to claim 11, and a pharmaceutically acceptable excipient.

17. A pharmaceutical composition, comprising:

the low-molecular-weight polysulfated hyaluronic acid derivative or pharmaceutically acceptable salt thereof according to claim 12, and a pharmaceutically acceptable excipient.

18. A pharmaceutical composition, comprising:

the low-molecular-weight polysulfated hyaluronic acid derivative or pharmaceutically acceptable salt thereof according to claim 14, and a pharmaceutically acceptable excipient.

19. The method according to claim 1, wherein X is (b) and Y is of formula (c), (d), or (e).

20. The method according to claim 1, wherein X is (a) or (b) and Y is of formula (d) or (e).

* * * * *

UNITED STATES PATENT AND TRADEMARK OFFICE

CERTIFICATE OF CORRECTION

PATENT NO. : 8,993,536 B2
APPLICATION NO. : 13/143129
DATED : March 31, 2015
INVENTOR(S) : Kazuaki Kakehi et al.

It is certified that error appears in the above-identified patent and that said Letters Patent is hereby corrected as shown below:

In the Claims

At column 61, line 24 delete in it's entirety and replace with the following:

--polysulfated hyaluronic acid derivative is of formula (IB)--

Signed and Sealed this
Fifteenth Day of September, 2015

Michelle K. Lee
*Director of the United States Patent and Trademark Office*